US011142587B2

(12) United States Patent
Igawa et al.

(10) Patent No.: US 11,142,587 B2
(45) Date of Patent: Oct. 12, 2021

(54) METHOD FOR PRODUCING POLYPEPTIDE HETERO-OLIGOMER

(71) Applicant: CHUGAI SEIYAKU KABUSHIKI KAISHA, Tokyo (JP)

(72) Inventors: Tomoyuki Igawa, Shizuoka (JP); Hitoshi Katada, Shizuoka (JP); Yuji Hori, Shizuoka (JP); Shojiro Kadono, Kanagawa (JP)

(73) Assignee: Chugai Seiyaku Kabushiki Kaisha, Tokyo (JP)

(*) Notice: Subject to any disclaimer, the term of this patent is extended or adjusted under 35 U.S.C. 154(b) by 298 days.

(21) Appl. No.: 15/562,186

(22) PCT Filed: Mar. 31, 2016

(86) PCT No.: PCT/JP2016/060616
§ 371 (c)(1),
(2) Date: Sep. 27, 2017

(87) PCT Pub. No.: WO2016/159213
PCT Pub. Date: Oct. 6, 2016

(65) Prior Publication Data
US 2018/0057607 A1    Mar. 1, 2018

(30) Foreign Application Priority Data
Apr. 1, 2015    (JP) .............................. JP2015-075448

(51) Int. Cl.
C07K 16/46      (2006.01)
G01N 33/50      (2006.01)
C07K 16/28      (2006.01)
C07K 16/00      (2006.01)
G01N 33/15      (2006.01)
G01N 33/53      (2006.01)

(52) U.S. Cl.
CPC ............ C07K 16/464 (2013.01); C07K 16/00 (2013.01); C07K 16/2866 (2013.01); C07K 16/468 (2013.01); G01N 33/15 (2013.01); G01N 33/50 (2013.01); G01N 33/53 (2013.01); C07K 2317/31 (2013.01); C07K 2317/526 (2013.01); C07K 2317/53 (2013.01); C07K 2317/55 (2013.01); C07K 2317/56 (2013.01); C07K 2317/565 (2013.01); C07K 2317/624 (2013.01)

(58) Field of Classification Search
CPC .......................... C07K 16/464; C07K 16/2866; C07K 16/468; C07K 16/00; C07K 2317/56; C07K 2317/53; C07K 2317/31; C07K 2317/526; C07K 2317/55; C07K 2317/565; C07K 2317/624; G01N 33/50; G01N 33/53; G01N 33/15
See application file for complete search history.

(56) References Cited

U.S. PATENT DOCUMENTS

| | | | |
|---|---|---|---|
| 4,208,479 A | 6/1980 | Zuk et al. |
| 4,444,878 A | 4/1984 | Paulus |
| 4,474,893 A | 10/1984 | Reading |
| 5,126,250 A | 6/1992 | McDonough et al. |
| 5,322,678 A | 6/1994 | Morgan et al. |
| 5,496,549 A | 3/1996 | Yamazaki et al. |
| 5,591,828 A | 1/1997 | Bosslet et al. |
| 5,639,641 A | 6/1997 | Pedersen et al. |
| 5,670,373 A | 9/1997 | Kishimoto |
| 5,744,446 A | 4/1998 | Lollar et al. |
| 5,795,965 A | 8/1998 | Tsuchiya et al. |
| 5,859,205 A | 1/1999 | Adair et al. |
| 5,945,311 A | 8/1999 | Lindhofer et al. |
| 5,990,286 A | 11/1999 | Khawli et al. |
| 6,005,091 A | 12/1999 | Blackburn et al. |
| 6,010,902 A | 1/2000 | Ledbetter et al. |
| 6,126,980 A | 10/2000 | Smith et al. |
| 6,129,914 A | 10/2000 | Weiner |
| 6,329,511 B1 | 12/2001 | Vasquez et al. |
| 6,485,943 B2 | 11/2002 | Stevens et al. |
| 6,677,436 B1 | 1/2004 | Sato et al. |
| 6,723,319 B1 | 4/2004 | Ito et al. |
| 6,737,056 B1 | 5/2004 | Presta |
| 6,884,879 B1 | 4/2005 | Baca et al. |
| 6,913,747 B1 | 7/2005 | Co et al. |
| 7,018,632 B2 | 3/2006 | Lindhofer et al. |
| 7,033,590 B1 | 4/2006 | Scheiflinger et al. |

(Continued)

FOREIGN PATENT DOCUMENTS

| | | |
|---|---|---|
| CA | 2 203 182 | 5/1996 |
| CA | 2 331 641 | 11/1999 |

(Continued)

OTHER PUBLICATIONS

Lund et al., The Journal of Immunology 157:4963-4969 (Year: 1996).*
Wu et al., J Mol Biol 294: 151-162, 1999 (Year: 1999).*
Labrijn et al., PNAS 110(13): 5145-5150 (Year: 2013).*
Schuurman et al., Molecular Immunology 38: 1-8 (Year: 2001).*
Wenigetal., PNAS 101: 17371-17376 (Year: 2004).*
Amann et al., "Therapeutic window of an EpCAM/CD3-specific BiTE antibody in mice is determined by a subpopulation of EpCAM-expressing lymphocytes that is absent in humans," Cancer Immunol Immunother. Jan. 2009: 58(1):95-109. Epub Jul. 2, 2008.
Buque et al., "Trial Watch: Immunomodulatory monoclonal antibodies for oncological indications," Oncoimmunology, Mar. 2, 2015:4(4):e1008814. eCollection 2015.

(Continued)

Primary Examiner — Phuong Huynh
(74) Attorney, Agent, or Firm — Fish & Richardson P.C.

(57) ABSTRACT

It is intended to provide a method for efficiently and stably producing a heteromultimer by incubating homo variants of plural types of heavy chain constant region-containing polypeptides differing in antigen-binding activity under a reducing condition that reorganize the inter-polypeptide disulfide bond between cysteine residues outside of core hinge regions. A feature of the production method of the present invention is that amino acid residues in the core hinge regions do not form any disulfide bond.

14 Claims, 17 Drawing Sheets

Specification includes a Sequence Listing.

(56) References Cited

U.S. PATENT DOCUMENTS

| | | | |
|---|---|---|---|
| 7,052,873 B2 | 5/2006 | Tsuchiya | |
| 7,122,637 B2 | 10/2006 | Presta | |
| 7,217,797 B2 | 5/2007 | Hinton et al. | |
| 7,276,585 B2 | 10/2007 | Lazar et al. | |
| 7,538,196 B2 | 5/2009 | Jung | |
| 7,732,149 B2 | 6/2010 | Kojima et al. | |
| 8,062,635 B2 | 11/2011 | Hattori et al. | |
| 8,217,147 B2 | 7/2012 | Stavenhagen et al. | |
| 8,597,911 B2 | 12/2013 | Miyazaki et al. | |
| 8,637,641 B2 | 1/2014 | Dahiyat et al. | |
| 9,096,651 B2 | 8/2015 | Igawa et al. | |
| 9,228,017 B2 | 1/2016 | Igawa et al. | |
| 9,334,331 B2 | 5/2016 | Igawa et al. | |
| 9,527,926 B2 | 12/2016 | Ho et al. | |
| 9,556,279 B2 | 1/2017 | Niwa et al. | |
| 9,637,557 B2 | 5/2017 | Scheer et al. | |
| 9,670,269 B2 | 6/2017 | Igawa et al. | |
| 9,688,762 B2 | 6/2017 | Igawa et al. | |
| 9,828,429 B2 | 11/2017 | Igawa et al. | |
| 9,975,966 B2 | 5/2018 | Nezu et al. | |
| 10,011,858 B2 | 7/2018 | Igawa et al. | |
| 10,066,018 B2 | 9/2018 | Igawa et al. | |
| 10,150,808 B2 | 12/2018 | Kuramochi et al. | |
| 10,253,091 B2 | 4/2019 | Igawa et al. | |
| 10,435,458 B2 | 10/2019 | Kuramochi et al. | |
| 10,450,381 B2 | 10/2019 | Igawa et al. | |
| 2001/0001663 A1 | 5/2001 | Kishimoto et al. | |
| 2002/0062010 A1 | 5/2002 | Arathoon et al. | |
| 2002/0142374 A1 | 10/2002 | Gallo et al. | |
| 2002/0147326 A1 | 10/2002 | Chaiklin et al. | |
| 2002/0164339 A1 | 11/2002 | Do et al. | |
| 2002/0164668 A1 | 11/2002 | Durham et al. | |
| 2002/0187150 A1 | 12/2002 | Mihara et al. | |
| 2003/0187225 A1 | 10/2003 | Penichet et al. | |
| 2003/0190311 A1 | 10/2003 | Dall'Acqua et al. | |
| 2003/0207346 A1 | 11/2003 | Arathoon et al. | |
| 2003/0219441 A1 | 11/2003 | Thorpe et al. | |
| 2003/0224397 A1 | 12/2003 | Lowman et al. | |
| 2004/0071706 A1 | 4/2004 | Ito et al. | |
| 2004/0081651 A1 | 4/2004 | Karpusas et al. | |
| 2004/0236080 A1 | 11/2004 | Aburatani et al. | |
| 2005/0095243 A1 | 5/2005 | Chan et al. | |
| 2005/0130224 A1 | 6/2005 | Saito et al. | |
| 2005/0142133 A1 | 6/2005 | Lazar et al. | |
| 2005/0142635 A1 | 6/2005 | Tsuchiya et al. | |
| 2005/0164352 A1 | 7/2005 | Lauder et al. | |
| 2005/0191293 A1 | 9/2005 | Deshpande et al. | |
| 2005/0261229 A1 | 11/2005 | Gillies | |
| 2005/0266425 A1 | 12/2005 | Zauderer et al. | |
| 2006/0019342 A1 | 1/2006 | Dall'Acqua et al. | |
| 2006/0024298 A1 | 2/2006 | Lazar et al. | |
| 2006/0057149 A1 | 3/2006 | Johnson et al. | |
| 2006/0063228 A1 | 3/2006 | Kasaian et al. | |
| 2006/0074225 A1 | 4/2006 | Chamberlain | |
| 2006/0134105 A1 | 6/2006 | Lazar et al. | |
| 2006/0134709 A1 | 6/2006 | Stavenhagen et al. | |
| 2006/0134805 A1 | 6/2006 | Berg et al. | |
| 2006/0159673 A1 | 7/2006 | Kojima | |
| 2006/0160184 A1 | 7/2006 | Hoogenboom et al. | |
| 2006/0194280 A1 | 8/2006 | Dillon et al. | |
| 2006/0204493 A1* | 9/2006 | Huang | C07K 16/00 424/133.1 |
| 2006/0275282 A1 | 12/2006 | Moore et al. | |
| 2006/0292147 A1 | 12/2006 | Yoshizaki et al. | |
| 2007/0036785 A1 | 2/2007 | Kishimoto et al. | |
| 2007/0041978 A1 | 2/2007 | Hattori et al. | |
| 2007/0054354 A1 | 3/2007 | Humphreys et al. | |
| 2007/0059312 A1 | 3/2007 | Baca et al. | |
| 2007/0087381 A1 | 4/2007 | Kojima | |
| 2007/0110757 A1 | 5/2007 | Wei et al. | |
| 2007/0134234 A1 | 6/2007 | Smith et al. | |
| 2007/0148163 A1 | 6/2007 | Takahashi et al. | |
| 2007/0148164 A1 | 6/2007 | Farrington et al. | |
| 2007/0212357 A1 | 9/2007 | Pons et al. | |
| 2008/0063635 A1 | 3/2008 | Takahashi et al. | |
| 2008/0075712 A1 | 3/2008 | Hattori et al. | |
| 2008/0166756 A1 | 7/2008 | Tsuchiya et al. | |
| 2009/0208416 A1 | 8/2009 | Moretta et al. | |
| 2009/0221803 A1 | 9/2009 | Dall'Acqua et al. | |
| 2009/0263392 A1 | 10/2009 | Igawa et al. | |
| 2009/0324589 A1 | 12/2009 | Igawa et al. | |
| 2010/0003254 A1 | 1/2010 | Hattori et al. | |
| 2010/0004429 A1 | 1/2010 | Kai et al. | |
| 2010/0008907 A1 | 1/2010 | Nishimoto et al. | |
| 2010/0015133 A1* | 1/2010 | Igawa | A61P 35/00 424/133.1 |
| 2010/0239577 A1 | 9/2010 | Igawa et al. | |
| 2010/0286374 A1 | 11/2010 | Kannan et al. | |
| 2010/0291072 A1 | 11/2010 | Lowman et al. | |
| 2010/0298542 A1 | 11/2010 | Igawa et al. | |
| 2010/0331527 A1 | 12/2010 | Davis et al. | |
| 2011/0076275 A1 | 3/2011 | Igawa et al. | |
| 2011/0129459 A1 | 6/2011 | Kuramochi et al. | |
| 2011/0236374 A1 | 9/2011 | Shitara et al. | |
| 2011/0245473 A1 | 10/2011 | Igawa et al. | |
| 2012/0009188 A1 | 1/2012 | Behrens | |
| 2012/0071634 A1 | 3/2012 | Igawa et al. | |
| 2012/0149876 A1 | 6/2012 | Kreudenstein et al. | |
| 2012/0237517 A1 | 9/2012 | Hattori et al. | |
| 2012/0238729 A1 | 9/2012 | Kuramochi et al. | |
| 2013/0011866 A1 | 1/2013 | Igawa et al. | |
| 2013/0018174 A1 | 1/2013 | Igawa et al. | |
| 2013/0030156 A1 | 1/2013 | Apostolou et al. | |
| 2013/0039913 A1* | 2/2013 | Labrijn | C07K 16/1063 424/136.1 |
| 2013/0052196 A1 | 2/2013 | Apostolou et al. | |
| 2013/0085199 A1 | 4/2013 | Tamori et al. | |
| 2013/0101581 A1 | 4/2013 | Kuramochi et al. | |
| 2013/0195849 A1 | 8/2013 | Spreter et al. | |
| 2014/0037632 A1 | 2/2014 | Igawa et al. | |
| 2014/0051833 A1 | 2/2014 | Fischer et al. | |
| 2014/0112883 A1 | 4/2014 | Ponath et al. | |
| 2014/0112914 A1 | 4/2014 | Nezu et al. | |
| 2014/0154270 A1 | 6/2014 | Wang et al. | |
| 2014/0303356 A1 | 10/2014 | Gramer et al. | |
| 2014/0370018 A1 | 12/2014 | Igawa et al. | |
| 2014/0370020 A1 | 12/2014 | Kuramochi et al. | |
| 2014/0377253 A1 | 12/2014 | Harding et al. | |
| 2015/0118184 A1 | 4/2015 | Kawai | |
| 2015/0274809 A1 | 10/2015 | Igawa et al. | |
| 2015/0284465 A1 | 10/2015 | Igawa et al. | |
| 2015/0315278 A1 | 11/2015 | Igawa et al. | |
| 2016/0024147 A1 | 1/2016 | Tustian et al. | |
| 2016/0159915 A1 | 6/2016 | Igawa et al. | |
| 2016/0168259 A1 | 6/2016 | Igawa et al. | |
| 2016/0222129 A1 | 8/2016 | Igawa et al. | |
| 2016/0229915 A1 | 8/2016 | Igawa | |
| 2017/0022287 A1 | 1/2017 | Igawa et al. | |
| 2017/0022293 A1 | 1/2017 | Igawa et al. | |
| 2017/0145111 A1 | 5/2017 | Hattori et al. | |
| 2017/0267783 A1 | 9/2017 | Nezu et al. | |
| 2017/0275332 A1 | 9/2017 | Igawa | |
| 2017/0283483 A1 | 10/2017 | Igawa et al. | |
| 2017/0342154 A1 | 11/2017 | Igawa et al. | |
| 2018/0051307 A1 | 2/2018 | Igawa et al. | |
| 2018/0142027 A1 | 5/2018 | Igawa et al. | |
| 2018/0162902 A1 | 6/2018 | Igawa et al. | |
| 2018/0244800 A1 | 8/2018 | Hattori et al. | |
| 2019/0062368 A1 | 2/2019 | Igawa et al. | |
| 2019/0112390 A1 | 4/2019 | Hattori et al. | |
| 2019/0211081 A1 | 7/2019 | Igawa et al. | |
| 2019/0315884 A1 | 10/2019 | Igawa et al. | |
| 2019/0330268 A1 | 10/2019 | Tanaka et al. | |
| 2019/0352334 A1 | 11/2019 | Igawa et al. | |
| 2019/0359728 A1 | 11/2019 | Hattori et al. | |
| 2020/0087380 A1 | 3/2020 | Kuramochi et al. | |
| 2020/0207805 A1 | 7/2020 | Igawa et al. | |
| 2020/0277402 A1 | 9/2020 | Hattori et al. | |

FOREIGN PATENT DOCUMENTS

| | | |
|---|---|---|
| CA | 2 019 559 | 1/2002 |
| CA | 2 443 294 | 10/2002 |
| CA | 2 523 577 | 11/2004 |

(56) References Cited

FOREIGN PATENT DOCUMENTS

| | | |
|---|---|---|
| CA | 2 531 482 | 1/2005 |
| CA | 2 549 467 | 7/2005 |
| CA | 2 560 953 | 9/2005 |
| CA | 2 603 264 | 10/2006 |
| CA | 2 625 773 | 4/2007 |
| CA | 2 626 688 | 4/2007 |
| CA | 2 647 846 | 10/2007 |
| CA | 2 700 986 | 4/2009 |
| CA | 2 819 530 | 6/2012 |
| CN | 101198698 | 6/2008 |
| CN | 102471378 | 5/2012 |
| CN | 102782131 | 11/2012 |
| CN | 102946906 | 2/2013 |
| CN | 103429737 | 12/2013 |
| CN | 103833852 | 6/2014 |
| CN | 101874042 | 9/2018 |
| EP | 0 369 566 | 5/1990 |
| EP | 0 329 185 | 4/1994 |
| EP | 0 637 593 | 2/1995 |
| EP | 0 404 097 | 9/1996 |
| EP | 0 783 893 | 7/1997 |
| EP | 0 811 691 | 12/1997 |
| EP | 1 069 185 | 1/2001 |
| EP | 1 220 923 | 7/2002 |
| EP | 1 327 681 | 7/2003 |
| EP | 1 510 943 | 3/2005 |
| EP | 0 979 281 | 7/2005 |
| EP | 1 605 058 | 12/2005 |
| EP | 1 693 448 | 8/2006 |
| EP | 1 701 979 | 9/2006 |
| EP | 1 773 391 | 4/2007 |
| EP | 1 847 602 | 10/2007 |
| EP | 1 870 458 | 12/2007 |
| EP | 1 870 459 | 12/2007 |
| EP | 1 876 236 | 1/2008 |
| EP | 1 900 814 | 3/2008 |
| EP | 2 006 381 | 12/2008 |
| EP | 2 009 101 | 12/2008 |
| EP | 2 031 064 | 3/2009 |
| EP | 1 505 148 | 4/2009 |
| EP | 2 107 115 | 10/2009 |
| EP | 2 194 066 | 6/2010 |
| EP | 2 196 541 | 6/2010 |
| EP | 2 202 245 | 6/2010 |
| EP | 2 206 775 | 7/2010 |
| EP | 2 236 604 | 10/2010 |
| EP | 1 688 488 | 8/2011 |
| EP | 2 409 991 | 1/2012 |
| EP | 2 238 985 | 8/2012 |
| EP | 2 522 724 | 11/2012 |
| EP | 2 526 963 | 11/2012 |
| EP | 2 543 727 | 1/2013 |
| EP | 2 644 698 | 10/2013 |
| EP | 2 647 707 | 10/2013 |
| EP | 2 905 290 | 8/2015 |
| EP | 2 914 634 | 9/2015 |
| EP | 3 199 628 | 8/2017 |
| JP | S63-52890 | 3/1988 |
| JP | 2-028200 | 1/1990 |
| JP | H02-145187 | 6/1990 |
| JP | H03-500644 | 2/1991 |
| JP | H05-184383 | 7/1993 |
| JP | H05-199894 | 8/1993 |
| JP | H05-203652 | 8/1993 |
| JP | H05-213775 | 8/1993 |
| JP | H05-304992 | 11/1993 |
| JP | 07-67688 | 3/1995 |
| JP | 8-500979 | 2/1996 |
| JP | 8-510555 | 11/1996 |
| JP | 09-506001 | 6/1997 |
| JP | 10-165184 | 6/1998 |
| JP | 10-511085 | 10/1998 |
| JP | 11-500915 | 1/1999 |
| JP | 11-500916 | 1/1999 |
| JP | 11-71288 | 3/1999 |
| JP | 11-506310 | 6/1999 |
| JP | 3032287 | 4/2000 |
| JP | 2001-523971 | 11/2001 |
| JP | 2002-514406 | 5/2002 |
| JP | 2002-518041 | 6/2002 |
| JP | 2003-055398 | 2/2003 |
| JP | 2003-509049 | 3/2003 |
| JP | 2004-086682 | 3/2004 |
| JP | 2004-086862 | 3/2004 |
| JP | 2004-511426 | 4/2004 |
| JP | 2004-321100 | 11/2004 |
| JP | 2005-501514 | 1/2005 |
| JP | 2005-101105 | 3/2005 |
| JP | 2005-535341 | 11/2005 |
| JP | 2005-378266 | 12/2005 |
| JP | 2005-537009 | 12/2005 |
| JP | 2008-512995 | 5/2008 |
| JP | 2008-523140 | 7/2008 |
| JP | 2008-538920 | 11/2008 |
| JP | 2009-500458 | 1/2009 |
| JP | 2010-522701 | 7/2010 |
| JP | 2011-508604 | 3/2011 |
| JP | 2012-504970 | 3/2012 |
| JP | 2012-510281 | 5/2012 |
| JP | 2012-515160 | 7/2012 |
| JP | 2012-522527 | 9/2012 |
| JP | 2012-531439 | 12/2012 |
| JP | 5144499 | 2/2013 |
| JP | 2013-515509 | 5/2013 |
| JP | 2013-529084 | 7/2013 |
| JP | 2013-529190 | 7/2013 |
| JP | 2013-165716 | 8/2013 |
| JP | 5334319 | 11/2013 |
| JP | 5484060 | 5/2014 |
| JP | 2015-510764 | 4/2015 |
| JP | 5717624 | 5/2015 |
| JP | 2015-130883 | 7/2015 |
| JP | 5787446 | 9/2015 |
| JP | 5912436 | 4/2016 |
| JP | 2016-69329 | 5/2016 |
| JP | 6175590 | 8/2017 |
| JP | 6534615 | 6/2019 |
| KR | 2009/0107091 | 10/2009 |
| KR | 2010/0056467 | 5/2010 |
| KR | 2010/0074221 | 7/2010 |
| KR | 2012/0123055 | 11/2012 |
| KR | 2013/0102113 | 9/2013 |
| KR | 2013/0102640 | 9/2013 |
| KR | 2013/0130765 | 12/2013 |
| NO | 20062087 | 7/2006 |
| RU | 94028282 | 7/1996 |
| RU | 2232773 | 7/2004 |
| RU | 2266298 | 12/2005 |
| RU | 2339696 | 11/2008 |
| RU | 2009/149451 | 7/2011 |
| RU | 2427588 | 8/2011 |
| RU | 2012/112067 | 10/2013 |
| SG | 11201701119 R | 3/2017 |
| TW | 2007/14313 | 4/2007 |
| TW | 2007/22517 | 6/2007 |
| TW | 2012/49872 | 12/2012 |
| TW | I452135 | 9/2014 |
| TW | I452136 | 9/2014 |
| TW | 2016/19193 | 6/2016 |
| WO | WO 89/01343 | 2/1989 |
| WO | WO 91/01335 | 2/1991 |
| WO | WO 91/08770 | 6/1991 |
| WO | WO 92/019759 | 11/1992 |
| WO | WO 93/11161 | 6/1993 |
| WO | WO 94/05690 | 3/1994 |
| WO | WO 94/13804 | 6/1994 |
| WO | WO 95/01571 | 1/1995 |
| WO | WO 95/33844 | 12/1995 |
| WO | WO 96/01653 | 1/1996 |
| WO | WO 96/07754 | 3/1996 |
| WO | WO 96/11020 | 4/1996 |
| WO | WO 96/12503 | 5/1996 |
| WO | WO 96/16673 | 6/1996 |
| WO | WO 96/26964 | 9/1996 |

(56) References Cited

FOREIGN PATENT DOCUMENTS

| | | |
|---|---|---|
| WO | WO 96/27011 | 9/1996 |
| WO | WO 97/09351 | 3/1997 |
| WO | WO 97/10354 | 3/1997 |
| WO | WO 98/03546 | 1/1998 |
| WO | WO 98/50431 | 11/1998 |
| WO | WO 99/10494 | 3/1999 |
| WO | WO 99/018212 | 4/1999 |
| WO | WO 99/51743 | 10/1999 |
| WO | WO 99/58572 | 11/1999 |
| WO | WO 99/67359 | 12/1999 |
| WO | WO 01/19992 | 3/2001 |
| WO | WO 01/30854 | 5/2001 |
| WO | WO 01/82899 | 11/2001 |
| WO | WO 01/90192 | 11/2001 |
| WO | WO 02/06838 | 1/2002 |
| WO | WO 02/30463 | 4/2002 |
| WO | WO 02/33072 | 4/2002 |
| WO | WO 02/33073 | 4/2002 |
| WO | WO 02/060919 | 8/2002 |
| WO | WO 02/072605 | 9/2002 |
| WO | WO 03/000883 | 1/2003 |
| WO | WO 03/012069 | 2/2003 |
| WO | WO 03/020949 | 3/2003 |
| WO | WO 03/035835 | 5/2003 |
| WO | WO 03/042231 | 5/2003 |
| WO | WO-03074679 A2 * | 9/2003 ......... C07K 16/2893 |
| WO | WO 03/087163 | 10/2003 |
| WO | WO 03/091424 | 11/2003 |
| WO | WO 2004/009618 | 1/2004 |
| WO | WO 2004/016740 | 2/2004 |
| WO | WO 2004/020579 | 3/2004 |
| WO | WO 2004/060919 | 7/2004 |
| WO | WO 2004/065611 | 8/2004 |
| WO | WO 2004/068931 | 8/2004 |
| WO | WO 2004/096273 | 11/2004 |
| WO | WO 2004/097041 | 11/2004 |
| WO | WO 2004/111233 | 12/2004 |
| WO | WO 2004/113387 | 12/2004 |
| WO | WO 2005/000900 | 1/2005 |
| WO | WO 2005/005604 | 1/2005 |
| WO | WO 2005/025615 | 3/2005 |
| WO | WO 2005/035753 | 4/2005 |
| WO | WO 2005/035754 | 4/2005 |
| WO | WO 2005/035756 | 4/2005 |
| WO | WO 2005/047327 | 5/2005 |
| WO | WO 2005/056606 | 6/2005 |
| WO | WO 2005/059106 | 6/2005 |
| WO | WO 2005/062916 | 7/2005 |
| WO | WO 2005/067620 | 7/2005 |
| WO | WO 2005/092925 | 10/2005 |
| WO | WO 2005/112564 | 12/2005 |
| WO | WO 2005/121180 | 12/2005 |
| WO | WO 2005/123126 | 12/2005 |
| WO | WO 2006/004663 | 1/2006 |
| WO | WO 2006/019447 | 2/2006 |
| WO | WO 2006/029879 | 3/2006 |
| WO | WO 2006/030200 | 3/2006 |
| WO | WO 2006/030220 | 3/2006 |
| WO | WO 2006/033386 | 3/2006 |
| WO | WO 2006/047340 | 5/2006 |
| WO | WO 2006/047350 | 5/2006 |
| WO | WO 2006/050491 | 5/2006 |
| WO | WO 2006/065208 | 6/2006 |
| WO | WO 2006/067913 | 6/2006 |
| WO | WO 2006/071877 | 7/2006 |
| WO | WO 2006/075668 | 7/2006 |
| WO | WO 2006/106903 | 10/2006 |
| WO | WO 2006/106905 | 10/2006 |
| WO | WO 2006/109592 | 10/2006 |
| WO | WO 2006/113767 | 10/2006 |
| WO | WO 2006/116260 | 11/2006 |
| WO | WO 2006/121852 | 11/2006 |
| WO | WO 2007/009065 | 1/2007 |
| WO | WO 2007/024535 | 3/2007 |
| WO | WO 2007/060411 | 5/2007 |
| WO | WO 2007/108559 | 9/2007 |
| WO | WO 2007/110205 | 10/2007 |
| WO | WO 2007/114319 | 10/2007 |
| WO | WO 2007/114325 | 10/2007 |
| WO | WO 2007/147901 | 12/2007 |
| WO | WO 2008/090960 | 7/2008 |
| WO | WO 2008/092117 | 7/2008 |
| WO | WO 2008/118970 | 10/2008 |
| WO | WO 2008/119353 | 10/2008 |
| WO | WO 2008/145141 | 12/2008 |
| WO | WO 2008/145142 | 12/2008 |
| WO | WO 2009/012394 | 1/2009 |
| WO | WO 2009/036209 | 3/2009 |
| WO | WO 2009/041062 | 4/2009 |
| WO | WO 2009/041613 | 4/2009 |
| WO | WO 2009/041621 | 4/2009 |
| WO | WO 2009/041643 | 4/2009 |
| WO | WO 2009/041734 | 4/2009 |
| WO | WO 2009/052439 | 4/2009 |
| WO | WO 2009/053368 | 4/2009 |
| WO | WO 2009/072604 | 6/2009 |
| WO | WO 2009/079649 | 6/2009 |
| WO | WO 2009/084659 | 7/2009 |
| WO | WO 2009/089004 | 7/2009 |
| WO | WO-2009089004 A1 * | 7/2009 .............. A61P 35/00 |
| WO | WO 2009/100309 | 8/2009 |
| WO | WO 2009/125825 | 10/2009 |
| WO | WO 2010/042904 | 4/2010 |
| WO | WO 2010/063746 | 6/2010 |
| WO | WO 2010/064090 | 6/2010 |
| WO | WO 2010/080065 | 7/2010 |
| WO | WO 2010/106180 | 9/2010 |
| WO | WO 2010/107109 | 9/2010 |
| WO | WO 2010/107110 | 9/2010 |
| WO | WO 2010/115589 | 10/2010 |
| WO | WO 2010/129304 | 11/2010 |
| WO | WO 2010/151792 | 12/2010 |
| WO | WO 2011/090088 | 2/2011 |
| WO | WO 2011/025964 | 3/2011 |
| WO | WO 2011/037158 | 3/2011 |
| WO | WO 2011/078332 | 6/2011 |
| WO | WO 2011/090754 | 7/2011 |
| WO | WO 2011/090762 | 7/2011 |
| WO | WO 2011/091177 | 7/2011 |
| WO | WO 2011/091181 | 7/2011 |
| WO | WO 2011/108502 | 9/2011 |
| WO | WO 2011/108714 | 9/2011 |
| WO | WO 2011/111007 | 9/2011 |
| WO | WO 2011/125674 | 10/2011 |
| WO | WO 2011/131746 | 10/2011 |
| WO | WO 2011/133886 | 10/2011 |
| WO | WO 2011/143545 | 11/2011 |
| WO | WO 2012/020096 | 2/2012 |
| WO | WO 2012/067176 | 5/2012 |
| WO | WO 2012/073985 | 6/2012 |
| WO | WO 2012/131555 | 10/2012 |
| WO | WO 2012/145238 | 10/2012 |
| WO | WO 2013/060867 | 5/2013 |
| WO | WO 2013/065708 | 5/2013 |
| WO | WO 2013/124450 | 8/2013 |
| WO | WO 2013/131866 | 9/2013 |
| WO | WO 2013/136186 | 9/2013 |
| WO | WO 2013/157954 | 10/2013 |
| WO | WO 2013/158856 | 10/2013 |
| WO | WO 2013/181543 | 12/2013 |
| WO | WO 2014/028354 | 2/2014 |
| WO | WO 2014/051433 | 4/2014 |
| WO | WO 2014/054804 | 4/2014 |
| WO | WO 2014/067011 | 5/2014 |
| WO | WO 2015/046467 | 4/2015 |
| WO | WO 2015/046554 | 4/2015 |
| WO | WO 2015/063339 | 5/2015 |
| WO | WO 2015/156268 | 10/2015 |
| WO | WO 2015/174439 | 11/2015 |
| WO | WO 2015/194233 | 12/2015 |
| WO | WO 2016/047722 | 3/2016 |
| WO | WO 2016/159213 | 10/2016 |
| WO | WO 2016/166014 | 10/2016 |
| WO | WO 2016/171202 | 10/2016 |

(56) References Cited

FOREIGN PATENT DOCUMENTS

| WO | WO 2017/115773 | 7/2017 |
|---|---|---|
| WO | WO 2017/129585 | 8/2017 |
| WO | WO 2017/159287 | 9/2017 |
| WO | WO 2017/188356 | 11/2017 |
| WO | WO 2018/181870 | 10/2018 |

OTHER PUBLICATIONS

Campoli et al., "Immunotherapy of Malignant Disease with Tumor Antigen-Specific Monoclonal Antibodies," Clin Cancer Res. Jan. 1, 2010:16(1):11-20. doi: 10.1158/1078-0432. CCR-09-2345. Epub Dec. 22, 2009.

Chan et al., "Therapeutic antibodies for autoimmunity and inflammation," Nat Rev Immunol. May 2010;10(5):301-16. doi: 10.1038/nri2761.

Hattori, Introduction of ART-Ig and application to hemophilia A treatment, Chugai Seiyaku ni Okeru Dokuji no Kakushinteki Kotai Gijutsu. Dec. 2012; 18: 42-57 (with English translation).

Hess et al., "Cancer therapy with trifunctional antibodies: linking innate and adaptive immunity," Future Oncol. Jan. 2012: 8(1):73-85. doi: 10.2217/fon.11.138.

Iwai et al., "Therapeutic Agents for Gastric Cancer," Igan Chiryoyaku, Yakkyoku, Jan. 5, 2016:67(1)138-41 (with English translation).

Jefferis et al., "Interaction sites on human IgG-Fc for FcγR: current models," Immunol Lett. Jun. 3, 2002:82(1-2):57-65.

Jones et al., "Growth factor receptor interplay and resistance in cancer," Endocr Relat Cancer. Dec. 2006 :13 Supp 1 1:S45-51.

Klein et al., "Progress in overcoming the chain association issue in bispecific heterodimeric IgG antibodies," MAbs., Nov.-Dec. 2012;4(6):653-63. doi: 10.4161/mabs.21379. Epub Aug. 27, 2012.

Klinger et al., "Harnessing T cells to fight cancer with BiTE((R)) antibody constructs—past developments and future directions," Immunol. Rev., Mar. 2016 :270(1):193-208. doi:10.1111/imr.12393.

Kontermann, "Dual targeting strategies with bispecific antibodies," MAbs. Mar.-Apr. 2012;4(2):182-97. doi: 10.4161/mabs.4.2.19000. Epub Mar. 1, 2012.

Labrijn et al., "Controlled Fab-arm exchange for the generation of stable bispecific IgG1," Nat Protoc. Oct. 2014; 9(10): 2450-63. doi: 10.1038/nprot.2014.169. Epub Sep. 25, 2014.

Labrijn et al., "Efficient generation of stable bispecific IgG1 by controlled Fab-arm exchange," Pro Natl Acad Sci U S A., Mar. 26, 2013;110(13):5145-50. doi: 10.1073/pnas.1220145110. Epub Mar. 11, 2013.

Larkin et al., "Combined Nivolumab and Ipilimumab or Monotherapy in Untreated Melanoma," N. Engl. J. Med., Jul. 2, 2015:373(1):23-34. doi:10.1056/NEJMoa1504030. Epub May 31, 2015.

Merchant et al., "An efficient route to human bispecific IgG," Nat Biotechnol., Jul. 1998;16(7):677-81.

Mezzanzanica et al., "Human Ovarian Carcinoma Lysis by Cytotoxic T Cells Targeted by Bispecific Monoclonal Antibodies: Analysis of the Antibody Components," Int J Cancer. Apr. 15, 1988:41(4):609-15.

Natsume et al., "National Haemophilia Foundation (NHF) Medical and Scientific Advisory Council (MASAC) Recommendations Concerning Prophylaxis," Medical Bulletin, No. 193, 1 page (1994)

Improving effector functions of antibodies for cancer treatment: Enhancing ADCC and CDC, Drug Des Devel Ther. Sep. 21, 2009:3:7-16.

Nimmerjahn et al., "Fcγ receptors as regulators of immune responses," Nat Rev Immunol. Jan. 2008; 8(1):34-47.

Pavlou et al., "The therapeutic antibodies market to 2008," Eur. J. Pharm. Biopharm., Apr. 30, 2005, 59:389-396.

Peters et al., "Engineering an improved IgG4 molecule with reduced disulfide bond heterogeneity and increased Fab domain thermal stability," J Biol Chem. Jul. 13, 2012; 287(29): 24525-33. doi:. 10.1074/jbc.M112.369744. Epub May 18, 2012.

Radaev et al., "The Structure of a Human Type III Fcγ Receptor in Complex with Fc," J Biol Chem. May 11, 2001 :276 (19) :16469-77. Epub Jan. 31, 2001.

Reichert et al., "Monoclonal antibody successes in the clinic," Nat. Biotechnol., Sep. 1, 2005, 23:1073-78.

Ridgway et al., "'Knobs-into-holes' engineering of antibody $C_H3$ domains for heavy chain heterodimerization," Protein Eng., Jul. 1, 1996, 9:617-621.

Riechelmann et al., "Adoptive therapy of head and neck squamous cell carcinoma with antibody coated immune cells: a pilot clinical trial," Cancer Immunol Immunother. Sep. 2007:56(9):1397-406. Epub Feb. 2, 2007.

Rispens et al., "Dynamics of inter-heavy chain interactions in human immunoglobulin G (IgG) subclasses studied by kinetic Fab arm exchange," J Biol Chem., Feb. 28, 2014;289(9):6098-109. doi: 10.1074/jbc.M113.541813. Epub Jan. 14, 2014.

Rothe et al., Recombinant proteins in rheumatology—recent advances, N Biotechnol. Sep. 2011;28(5):502-10.doi:10.1016/ j.nbt.2011.03.019. Epub Apr. 5, 2011.

Schaefer et al., "Immunoglobulin domain crossover as a generic approach for the production of bispecific IgG antibodies," Proc Natl Acad Sci U S A., Jul. 5, 2011;108(27):11187-92. doi: 10.1073/pnas.1019002108. Epub Jun. 20, 2011.

Schlereth et al., "T-cell activation and B-cell depletion in chimpanzees treated with a bispecific anti-CD19/anti-CD3 single-chain antibody construct," Cancer Immunol Immunother. May 2006:55(5):503-14. Epub Jul. 20, 2005.

Schuurman et al., "Normal human immunoglobulin G4 is bispecific: it has two different antigen-combining sites," Immunology, Aug. 1999;97(4):693-8.

Schuurman et al., "The inter-heavy chain disulfide bonds of IgG4 are in equilibrium with intra-chain disulfide bonds," Mol Immunol., Jan. 2001;38(1):1-8.

Sebastian et al., "Treatment of non-small cell lung cancer patients with the trifunctional monoclonal antibody catumaxomab (anti-EpCAM x anti-CD3): a phase I study," Cancer Immunol Immunother. Oct. 2007 :56 (10) :1637-44. Epub Apr. 5, 2007.

Seimetz et al., "Development and approval of the trifunctional antibody catumaxomab (anti-EpCAM x anti-CD3) as a targeted cancer immunotherapy," Cancer Treat Rev. Oct. 2010 :36(6):458-67.doi:10.1016/j.ctrv.2010.03.001 Epub Mar. 27, 2010.

Staerz et al., "Hybrid antibodies can target sites for attack by T cells," Nature. Apr. 18-24, 1985:314(6012):628-31.

Staerz et al., "Hybrid hybridoma producing a bispecific monoclonal antibody that can focus effector T-cell activity," Proc Natl Acad Sci U.S.A., Mar. 1, 1986, 83:1453-7.

Unkeless et al., "Structure and Function of Human and Murine Receptors for IgG," Annu Rev Immunol., Apr. 1988, 6:251-81.

Van Der Neut Kolfschoten et al., "Anti-inflammatory activity of human IgG4 antibodies by dynamic Fab arm exchange," Science, Sep. 14, 2007;317(5844):1554-7.

Wozniak-Knopp et al., "Introducing antigen-binding sites in structural loops of immunoglobulin constant domains: Fc fragments with engineered HER2/neu-binding sites and antibody properties," Protein Eng Des Sel. Apr. 2010; 23(4):289-97.doi:10.1093/protein/gzq005. Epub Feb. 11, 2010.

Zeidler et al., "Simultaneous Activation of T Cells and Accessory Cells by a New Class of Intact Bispecific Antibody Results in Efficient Tumor Cell Killing," J Immunol. Aug. 1, 1999;163(3):1246-52.

International Preliminary Report on Patentability for App. Ser. No. PCT/JP2016/060616, dated Mar. 31, 2016, 11 pages.

U.S. Appl. No. 16/448,088, filed Jun. 21, 2019, Igawa et al.
U.S. Appl. No. 16/459,791, filed Jul. 2, 2019, Igawa et al.
U.S. Appl. No. 16/496,089, filed Sep. 20, 2019, Shima et al.
U.S. Appl. No. 16/536,385, filed Aug. 9, 2019, Hattori et al.

Barrabes et al., "Effect of sialic acid content on glycoprotein p/ analyzed by two-dimensional electrophoresis," Electrophoresis, Sep. 2010, 31(17):2903-12. doi: 10.1002/elps.200900764.

Davie, "A Brief Historical Review of the Waterfall/Cascade of Blood Coagulation," J Biol Chem, Dec. 19, 2003, 278(51):50819-32. Epub Oct. 21, 2003.

(56) References Cited

OTHER PUBLICATIONS

Decision of the Opposition Division in EP 2 275 443, dated Apr. 26, 2018 (submitted on May 24, 2019 by the Patentee during EPO Opposition Procedure for EP 2 202 245), 29 pages.
Declaration of Taichi Kuramochi, signed May 23, 2019 (submitted on May 24, 2019 by the Patentee during EPO Opposition Procedure for EP 2 202 245), 11 pages.
Do et al., "A rapid method for determining dynamic binding capacity of resins for the purification of proteins," Protein Expr Purif, Aug. 2008, 60(2):147-50. doi: 10.1016/j.pep.2008.04.009. Epub May 3, 2008.
Granted claims of EP 2 275 443 (submitted on May 24, 2019 by the Patentee during EPO Opposition Procedure for EP 2 202 245), 1 page.
Mariuzza, "The Structural Basis of Antigen-Antibody Recognition," Annu Rev Biophys Biophys Chem, Jun. 1987, 16:139-159.
Pabst et al., "Engineering of novel Staphylococcal Protein A ligands to enable milder elution pH and high dynamic binding capacity," J Chromatogr A, Oct. 3, 2014, 1362:180-5. doi: 10.1016/j.chroma.2014.08.046. Epub Aug. 19, 2014.
Pabst et al., "Evaluation of recent Protein A stationary phase innovations for capture of biotherapeutics," J Chromatogr A, Jun. 15, 2018, 1554:45-60. doi: 10.1016/j.chroma.2018.03.060. Epub Apr. 7, 2018.
Supplemental Material to Raposo et al., "Epitope-specific antibody response is controlled by immunoglobulin VH polymorphisms," J Exp Med, Mar. 10, 2014, 211(3):405-11. doi: 10.1084/jem.20130968. Epub Feb. 17, 2014 (submitted on May 24, 2019 by the Patentee during EPO Opposition Procedure for EP 2 202 245), 4 pages.
U.S. Appl. No. 14/921,590, filed Oct. 23, 2015, Hattori et al.
U.S. Appl. No. 15/172,727, filed Apr. 3, 2016, Hattori et al.
U.S. Appl. No. 15/701,630, filed Sep. 12, 2017, Hattori et al.
U.S. Appl. No. 15/725,692, filed Oct. 5, 2017, Igawa et al.
U.S. Appl. No. 15/782,256, filed Oct. 12, 2017, Igawa et al.
U.S. Appl. No. 15/875,847, filed Jan. 19, 2018, Igawa et al.
"Hemophilia and von Willebrand's disease: 2. Management. Association of Hemophilia Clinic Directors of Canada," CMAJ., 153(2):147-157, Jul. 15, 1995.
"National Haemophilia Foundation (NHF) Medical and Scientific Advisory Council (MASAC) Recommendations Concerning Prophylaxis," MedicalBulletin, No. 193, 1 page (1994).
Abe et al., "Purification of monoclonal antibodies with light-chain heterogeneity produced by mouse hybridomas raised with NS-1 myelomas: application of hydrophobic interaction high-performance liquid chromatography," J. Biochem. Biophys. Methods, Oct. 1993, 27:215-227.
Adams et al., "Humanization of a recombinant monoclonal antibody to produce a therapeutic HER dimerization inhibitor, pertuzumab," Cancer Immunol. Immunother., Jun. 2006, 55:717-727. Epub Sep. 3, 2005.
Algonomics—Tripole® applications [online] [retrieved on Feb. 29, 2012]. Retrieved from the Internet: http://web.archive.org/web20090221052902/http://www.algonomics.com/proteinengineering/tripole_applications.php, 2 pages (Feb. 21, 2009).
Allard et al., "Antigen binding properties of highly purified bispecific antibodies," Mol Immunol., Oct. 1992;29(10):1219-27.
Allen et al., "Interchain disulfide bonding in human IgG2 antibodies probed by site-directed mutagenesis," Biochemistry, Apr. 15, 2009, 48(17):3755-66.
Almagro et al., "Humanization of antibodies," Front Biosci., Jan. 1, 2008, 13:1619-33.
Amersdorfer et al., GenPept Accession No. AAC26541, "anti BoNT/A Hc scFv antibody [synthetic construct]," Aug. 1, 2001, 1 page.
Amersham Biosciences, "Protein Purification Handbook," Edition AC, 98 pages (2001).
Armour et al., "Recombinant human IgG molecules lacking Fcgamma receptor I binding and monocyte triggering activities," Eur. J. Immunol., Aug. 1, 1999, 29(8):2613-24.

Arndt et al., "Factors influencing the dimer to monomer transition of an antibody single-chain Fv fragment," Biochemistry, Sep. 15, 1998, 37(37):12918-26.
Arndt et al., "Helix-stabilized Fv (hsFv) antibody fragments: substituting the constant domains of a Fab fragment for a heterodimeric coiled-coil domain," J. Mol. Biol., Sep. 7, 2001, 312:221-228.
Aslan et al., "Engineering a novel, stable dimeric streptavidin with lower isoelectric point," J. Biotechnol., Feb. 1, 2007, 128(2):213-25. Epub Sep. 26, 2006.
Asselta et al., "Factor V Deficiency," Semin. Thromb. Hemost., Jun. 2009, 35:382-389.
Atwell et al., "Stable heterodimers from remodeling the domain interface of a homodimer using a phage display library," J. Mol. Biol., Jul. 1997, 270:26-35.
Baerga-Ortiz et al., "Two different proteins that compete for binding to thrombin have opposite kinetic and thermodynamic profiles," Protein Sci., Jan. 1, 2004, 13(1):166-76.
Bajaj et al., "A Monoclonal Antibody to Factor IX That Inhibits the Factor VIII:Ca Potentiation of Factor X Activation," J. Biol. Chem., Sep. 25, 1985;260(21):11574-11580.
Baker et al., "Conversion of a T cell antagonist into an agonist by repairing a defect in the TCR/peptide/MHC interface: implications for TCR signaling," Immunity, Oct. 1, 2000, 13:475-484.
Bartelds et al., "Clinical response to adalimumab: relationship to anti-adalimumab antibodies and serum adalimumab concentrations in rheumatoid arthritis," Ann Rheum. Dis., Feb. 14, 2007, 66:921-926. Epub Feb. 14, 2007.
Batra et al., "Pharmacokinetics and biodistribution of genetically engineered antibodies," Curr Opin Biotechnol., Dec. 2002;13(6):603-8.
Bebbington et al., "High-Level Expression of a Recombinant Antibody from Myeloma Cells Using a Glutamine Synthetase Gene as an Amplifiable Selectable Marker," Biotechnology (N Y), Feb. 1992;10:169-175.
Bender et al., "Immunogenicity, efficacy and adverse events of adalimumab in RA patients," Rheumatol. Int., Jan. 1, 2007, 27:269-274. Epub Sep. 28, 2006.
Bendig M. M., "Humanization of Rodent Monoclonal Antibodies by CDR Grafting," Methods: A Companion to Methods in Enzymology, 1995; 8:83-93.
Bessos et al., "The characterization of a panel of monoclonal antibodies to human coagulation factor IX," Thrombosis Research, Dec. 15, 1985;40:863-867.
Bian et al., "Discovery of promiscuous HLA-II-restricted T cell epitopes with TEPITOPE," Methods, Dec. 2004;34(4):468-75.
Binz et al., "Engineering novel binding proteins from nonimmunoglobulin domains," Nat. Biotechnol., Oct. 1, 2005, 23:1257-68.
Blazar, "Infusion of Anti-B7.1 (CD80) and Anti-B7.2 (CD86) Monoclonal Antibodies Inhibits Murine Graft-Versus-Host Disease Lethality in Part Via Direct Effects on CD4+ and CD8+ T Cells," J. Immunol., Oct. 15, 1996, 157:3250-59.
Bolton-Maggs et al., "Haemophilias A and B," The Lancet, May 24, 2003;361:1801-9.
Borrebaeck et al., "Antibody evolution beyond Nature," Nat Biotechnol., Dec. 2002;20(12):1189-90.
Bos et al., "Enhanced Transfection of a Bacterial Plasmid into Hybridoma Cells by Electroporation: Application for the Selection of Hybrid Hybridoma (Quadroma) Cell Lines," Hybridoma, Feb. 1992;11:41-51.
Bowen, Haemophilia A and haemophilia B: molecular insights, Mol Pathol., Feb. 2002;55(1):1-18.
Bowie et al., "Deciphering the Message in Protein Sequences: Tolerance to Amino Acid Substitutions," Science, Mar. 16, 1990, 247:1306-1310.
Branden and Tooze, "Recognition of Foreign Molecules by the Immune System," Introduction to Protein Structure, 2d Ed., Garland Publishing, pp. 299-323 (1999).
Brandstetter et al., "X-ray structure of clotting factor IXa: active site and module structure related to Xase activity and hemophilia B," Proc Natl Acad Sci U S A, Oct. 10, 1995;92(21):9796-800.

(56) References Cited

OTHER PUBLICATIONS

Brennan et al., "Preparation of Bispecific Antibodies by Chemical Recombination of Monoclonal Immunoglobulin G1 Fragments," Science, Jul. 5, 1985;229:81-3.
Brenner et al., "Errors in genome annotation," Trends in Genetics, Apr. 1999;15:132-133.
Brinkman et al. "Phospholipid-binding domain of factor VIII is involved in endothelial cell-mediated activation of factor X by factor IXa," Arterioscler. Thromb. Vasc. Biol., Mar. 1, 2002;22(3):511-6.
Brown et al., "Tolerance of single, but not multiple, amino acid replacements in antibody VH CDR2: a means of minimizing B cell wastage from somatic hypermutation?," J. Immunol., May 1, 1996, 156(9):3285-91.
Burges et al., "Effective relief of malignant ascites in patients with advanced ovarian cancer by a trifunctional anti-EpCAM x anti-CD3 antibody: a phase I/II study," Clin. Cancer Res., Jul. 1, 2007, 13(13):3899-905.
Burgess et al., "Possible dissociation of the heparin-binding and mitogenic activities of heparin-binding (acidic fibroblast) growth factor-1 from its receptor-binding activities by site-directed mutagenesis of a single lysine residue," J Cell Biol., Nov. 1990;111(5 Pt 1):2129-38.
CALBIOCHEM® Buffers, "A guide for the preparation and use of buffers in biological systems," by Chandra Mohan, Ph.D., Copyright© 2003 EMD Biosciences, Inc., an Affiliate of Merck KGaA, Darmstadt, Germany, 37 pages.
Carter, "Bispecific human IgG by design," J. Immunol. Methods, Feb. 1, 2001, 248:7-15.
Chamow et al., "A humanized, bispecific immunoadhesin-antibody that retargets CD3+ effectors to kill HIV-1-infected cells," J. Immunol., Nov. 1, 1994, 153(9):4268-80.
Chappel et al., "Identification of a secondary Fc gamma RI binding site within a genetically engineered human IgG antibody," J Biol Chem., Nov. 25, 1993;268(33):25124-31.
Chappel et al., "Identification of the Fc gamma receptor class I binding site in human IgG through the use of recombinant IgG1/IgG2 hybrid and point-mutated antibodies," Proc Natl Acad Sci U S A., Oct. 15, 1991;88(20):9036-40.
Chatellier et al., "Functional mapping of conserved residues located at the VL and VH domain interface of a Fab," J. Mol. Biol., Nov. 22, 1996, 264(1):1-6.
Chau et al., "HuM291(Nuvion), a humanized Fc receptor-nonbinding antibody against CD3, anergizes peripheral blood T cells as partial agonist of the T cell receptor," Transplantation., Apr. 15, 2001, 71(7):941-50.
Chen et al., "Defective secretion of an immunoglobulin caused by mutations in the heavy chain complementarity determining region 2," J. Exp. Med., Aug. 1, 1994, 180(2):577-86.
Chen et al., "Generation and analysis of random point mutations in an antibody CDR2 sequence: many mutated antibodies lose their ability to bind antigen," J. Exp. Med., Sep. 1, 1992, 176(3):855-66.
Chen et al., "Selection and analysis of an optimized anti-VEGF antibody: crystal structure of an affinity-matured Fab in complex with antigen," Journal of Molecular Biology, Nov. 5, 1999, 293:865-881.
Chirino et al., "Minimizing the immunogenicity of protein therapeutics," Drug Discov. Today., Jan. 15, 2004, 9:82-90.
Choi et al., "Engineering of Immunoglobulin Fc Heterodimers Using Yeast Surface-Displayed Combinatorial Fc Library Screening," PLoS One, Dec. 16, 2015;10(12):e0145349. doi: 10.1371/journal.pone.0145349. eCollection 2015.
Chu et al., "Accumulation of succinimide in a recombinant monoclonal antibody in mildly acidic buffers under elevated temperatures," Pharm. Res., Jun. 1, 2007, 24(6):1145-56.
Chugai Seiyaku Kabushiki Kaisha's letter dated Jun. 12, 2013, regarding oral proceedings scheduled on Jun. 26, 2013, in App. Ser. No. EP 06730769.4 (Annex A submitted with patentee's letter dated Jun. 12, 2013).
Cole et al., "Human IgG2 variants of chimeric anti-CD3 are nonmitogenic to T cells," J. Immunol., Oct. 1, 1997, 159(7):3613-21.
Coloma et al., "Position effects of variable region carbohydrate on the affinity and in vivo behavior of an anti-(1-->6) dextran antibody," J Immunol., Feb. 15, 1999;162(4):2162-70.
Comper et al., "Charge selectivity in kidney ultrafiltration," Kidney Int., May 1, 1995, 47:1242-51.
Cordoba et al., "Non-enzymatic hinge region fragmentation of antibodies in solution," J. Chromatogr. B. Analyt. Technol. Biomed. Life Sci., Apr. 25, 2005, 818(2):115-21.
Couto et al., "Anti-BA46 Monoclonal Antibody Mc3. Humanization Using a Novel Positional Consensus and in Vivo and in Vitro Characterization," Cancer Research, Apr. 15, 1995, 55:1717-1722.
Dahlback, "Blood coagulation," Lancet, May 6, 2000, 355(9215):1627-32.
Dall'Acqua et al., "Antibody humanization by framework shuffling," Methods, May 31, 2005, 36(1):43-60.
Dall'Acqua et al., "Increasing the affinity of a human IgG1 for the neonatal Fc receptor: biological consequences," J. Immunol., Nov. 1, 2002;169(9):5171-80.
Dall'Acqua et al., "Modulation of the effector functions of a human IgG1 through engineering of its hinge region," J. Immunol., Jul. 15, 2006, 177(2):1129-38.
Damschroder et al., "Framework shuffling of antibodies to reduce immunogenicity and manipulate functional and biophysical properties," Mol. Immunol., Apr. 30, 2007, 44(11):3049-60. Epub Jan. 22, 2007.
Datta-Mannan et al., "Monoclonal antibody clearance. Impact of modulating the interaction of IgG with the neonatal Fc receptor," J Biol Chem., Jan. 19, 2007, 282(3):1709-17. Epub Nov. 29, 2006.
Davie et al., "The coagulation cascade: Initiation, maintenance, and regulation," Biochemistry, Oct. 29, 1991;30(43):10363-70.
Davies et al., "Antibody VH domains as small recognition units," Biotechnology (N.Y.), May 1, 1995, 13(5):475-9.
De Groot et al., "De-immunization of therapeutic proteins by T-cell epitope modification," Dev. Biol. (Basel), Jan. 2005, 122:171-94.
Deen et al., "Structural determinants of glomerular permeability," Am. J. Physiol. Renal. Physiol., Oct. 1, 2001, 281:F579-F596.
Del Rio et al., "An Engineered Penicillin Acylase with Altered Surface Charge Is More Stable in Alkaline pH," Ann. NY Acad. Sci., Oct. 1, 1996, 799:61-64.
Deng et al., "An Agonist Murine Monoclonal Antibody to the Human c-Mpl Receptor Stimulates Megakaryocytopoiesis," Blood, Sep. 15, 1998, 92:1981-1988.
Depascalis et al., "Grafting of "abbreviated" complementarity-determining regions containing specificity-determining residues essential for ligand contact to engineer a less immunogenic humanized monoclonal antibody," J Immunol., Sep. 15, 2002;169(6):3076-84.
Dhiman et al., "Gene expression microarrays: a 21st century tool for directed vaccine design," Vaccine, Oct. 12, 2001;20(1-2):22-30.
Diaz et al., "Effects of engineering charged amino acids in the CH3 domains on antibody heavy chain dimerization," Philippine Science Letters. 2011;4(1):48-55.
Dillon et al., "Structural and functional characterization of disulfide isoforms of the human IgG2 subclass," J. Biol. Chem., Jun. 6, 2008, 283(23):16206-15. Epub Mar. 12, 2008.
Dumont et al., "Monomeric Fc fusions: impact on pharmacokinetic and biological activity of protein therapeutics," BioDrugs., May 1, 2006, 20(3):151-60.
Edelman et al., "The covalent structure of an entire gammaG immunoglobulin molecule," Proc Natl Acad Sci U S A., May 1969;63(1):78-85.
Ejima et al, "Effects of Acid Exposure on the Conformation, Stability, and Aggregation of Monoclonal Antibodies," Proteins. Mar. 1, 2007;66(4):954-62.
Elliott et al., "Activation of the Erythropoietin (EPO) Receptor by Bivalent Anti-EPO Receptor Antibodies," J. Biol. Chem., Oct. 4, 1996, 271:24691-24697.
Ewert et al., "Stability improvement of antibodies for extracellular and intracellular applications: CDR grafting to stable frameworks and structure-based framework engineering," Methods, Oct. 31, 2004, 34:184-199.

(56) References Cited

OTHER PUBLICATIONS

Fay et al., "Chapter 2B Nonenzymatic cofactors: factor VIII," Comprehensive Biochemistry, Jun. 23, 1986, 13:35-37.
Fay et al., "The size of human factor VIII heterodimers and the effects produced by thrombin," Biochim Biophys Acta., Jun. 23, 1986, 871(3):268-78.
Fay, "Activation of factor VIII and mechanisms of cofactor action," Blood Rev., Mar. 2004;18(1):1-15.
Figini et al., "In vitro assembly of repertoires of antibody chains on the surface of phage by renaturation," J Mol Biol., May 27, 1994;239(1):68-78.
Francois et al., "Construction of a Bispecific Antibody Reacting with the α- and β-Chains of the Human IL-2 Receptor," J. Immunol., May 15, 1993;150:4610-9.
Fujii, "Antibody affinity maturation by random mutagenesis," Methods Mol. Biol., 248:345-59 (2004).
Gelderman et al., "The inhibitory effect of CD46, CD55, and CD59 on complement activation after immunotherapeutic treatment of cervical carcinoma cells with monoclonal antibodies or bispecific monoclonal antibodies," Lab Invest., Apr. 1, 2002, 82(4):483-93.
Gen Bank Accession No. AAG00910.2, "recombinant IgG2 heavy chain, partial [*Homo sapiens*]," May 14, 2001, 1 page.
Gerstner et al., "Sequence plasticity in the antigen-binding site of a therapeutic anti-HER2 antibody," J. Mol. Biol., Aug. 30, 2002, 321(5):851-62.
Gessner et al., "The IgG Fc receptor family," Ann. Hematol., Jun. 1, 1998, 76:231-248.
Ghetie et al., "FcRn: the MHC class I-related receptor that is more than an IgG transporter," Immunol. Today, Dec. 1, 1997, 18:592-598.
Ghetie et al., "Increasing the serum persistence of an IgG fragment by random mutagenesis," Nature Biotechnology, Jul. 1, 1997, 15:637-640.
Ghetie et al., "Multiple roles for the major histocompatibility complex class I-related receptor FcRn," Annu. Rev. Immunol., Apr. 18, 2000, 18:739-766.
Gobburu et al., "Pharmacokinetics/dynamics of 5c8, a monoclonal antibody to CD154 (CD40 ligand) suppression of an immune response in monkeys," J. Pharmacol. Exp. Ther., Aug. 1, 1998, 286:925-930.
Gonzales et al., "Minimizing the immunogenicity of antibodies for clinical application," Tumour Biol., Jan.-Feb. 2005;26(1):31-43.
Goode et al., "The glomerular basement membrane charge-selectivity barrier: an oversimplified concept?," Nephrol. Dial. Transplant., Sep. 1996, 11:1714-16.
Gramer et al., "Production of stable bispecific IgG1 by controlled Fab-arm exchange: scalability from bench to large-scale manufacturing by application of standard approaches," MAbs., Nov.-Dec. 2013;5(6):962-73. doi: 10.4161/mabs.26233. Epub Aug. 22, 2013.
Graves et al., "Molecular modeling and preclinical evaluation of the humanized NR-LU-13 antibody," Clin. Cancer Res., Apr. 1, 1999, 5(4):899-908.
Greenwood et al., "Structural motifs involved in human IgG antibody effector functions," Eur J Immunol., May 1993;23(5):1098-104.
Griffin et al., "Analysis of heavy and light chain sequences of conventional camelid antibodies from *Camelus dromedarius* and *Camelus bactrianus* species," J Immunol Methods, Mar. 2014;405:35-46. doi: 10.1016/j.jim.2014.01.003. Epub Jan. 18, 2014.
Grosse-Hovest et al., "A recombinant bispecific single-chain antibody induces targeted, supra-agonistic CD28-stimulation and tumor cell killing", European Journal of Immunology, May 2003;33(5):1334-40.
Gunasekaran et al., "Enhancing antibody Fc heterodimer formation through electrostatic steering effects: applications to bispecific molecules and monovalent IgG," J. Biol. Chem., Jun. 18, 2010;285(25):19637-46. doi: 10.1074/jbc.M110.117382. Epub Apr. 16, 2010.
Gunawardane et al., "Agonistic Human Antibodies Binding to Lecithin-Cholesterol Acyltransferase Modulate High Density Lipoprotein Metabolism," J Biol Chem. Feb. 5, 2016;291(6):2799-811. doi: 10.1074/jbc.M115.672790. Epub Dec. 7, 2015.
Gupta et al., "Affinity chromatography and co-chromatography of bispecific monoclonal antibody immunoconjugates," J. Biochem. Biophys. Methods, May 31, 2002, 51(3):203-216.
Guyre et al., "Increased potency of Fc-receptor-targeted antigens," Cancer Immunol. Immunother., Nov. 1, 1997, 45(3-4):146-8.
Haagen et al., "Unprimed CD4+ and CD8+ T cells can be rapidly activated by a CD3 x CD19 bispecific antibody to proliferate and become cytotoxic," Cancer Immunol Immunother., Dec. 1994;39(6):391-6.
Hamers-Casterman et al., "Naturally occurring antibodies devoid of light chains," Nature, Jun. 3, 1993;363(6428):446-8.
Hämmerling et al., "Use of Hybrid Antibody with Anti-γG and Anti-Ferritin Specificities in Locating Cell Surface Antigens by Electron Microscopy," J. Exp. Med., Dec. 1, 1968;128:1461-73.
He et al., "Humanization and pharmacokinetics of a monoclonal antibody with specificity for both E- and P-selectin," J. Immunol., Jan. 15, 1998, 160(2):1029-35.
Helfrich et al., "A rapid and versatile method for harnessing scFv antibody fragments with various biological effector functions," J. Immunol. Methods, Apr. 3, 2000, 237(1-2):131-45.
Hinton et al., "An engineered human IgG1 antibody with longer serum half-life," J. Immunol., Jan. 1, 2006;176:346-56.
Hinton et al., "Engineered human IgG antibodies with longer serum half-lives in primates," J Biol Chem., Feb. 20, 2004;279(8):6213-6. Epub Dec. 29, 2003.
Hird et al., "Tumour localisation with a radioactively labelled reshaped human monoclonal antibody," Br J Cancer, Nov. 1991;64(5):911-4.
Hoad et al. "Characterization of monoclonal antibodies to human factor X.Xa: Initial observations with a quantitative ELISA procedure," J. Immunol. Methods, Feb. 15, 1991;136(2):269-78.
Holliger et al., "'Diabodies': Small bivalent and bispecific antibody fragments," Proc. Natl. Acad. Sci. USA, Jul. 15, 1993, 90(14):6444-6448.
Hombach et al., "A CD16/CD30 bispecific monoclonal antibody induces lysis of Hodgkin's cells by unstimulated natural killer cells in vitro and in vivo," Int J Cancer, Nov. 11, 1993, 55:830-6.
Hong et al., "Enhanced cellular uptake and transport of polyclonal immunoglobulin G and fab after their cationization," J Drug Target., Jan. 1, 2000;8(2):67-77.
Hoyer, L.W., "The factor VIII complex: structure and function," Blood, Jul. 1, 1981, 58(1):1-13.
Hozumi et al., "Evidence for somatic rearrangement of immunoglobulin genes coding for variable and constant regions," Proc. Natl. Acad. Sci. USA, Oct. 1, 1976, 73(10):3628-3632.
Hsia et al., "Treatment of acquired factor X inhibitor by plasma exchange with concomitant intravenous immunoglobulin and corticosteroids," Am. J. Hematol., Apr. 2008;83:318-20.
Hu et al., "Development and characterization of a novel fusion protein composed of a human IgG1 heavy chain constant region and a single-chain fragment variable antibody against Venezuelan equine encephalitis virus," J Biochem., Jan. 1, 2003, 133(1):59-66.
Huse et al., "Generation of a Large Combinatorial Library of the Immunoglobulin Repertoire in Phage Lambda," Science, Dec. 8, 1989;246:1275-81.
Hwang et al., "Use of human germline genes in a CDR homology-based approach to antibody humanization," Methods, May 31, 2005, 36:35-42.
Ibragimova et al., "Stability of the beta-sheet of the WW domain: A molecular dynamics simulation study," Biophys J., Oct. 1999;77(4):2191-8.
Igawa et al., "VH/VL interface engineering to promote selective expression and inhibit conformational isomerization of thrombopoietin receptor agonist single-chain diabody," Protein Eng Des Sel., Aug. 2010;23(8):667-77. doi: 10.1093/protein/gzq034. Epub Jun. 24, 2010.
IMGT Scientific charts depicting the correspondence between Eu and Kabat numberings for the human IgG constant region, created May 17, 2001 and last updated Aug. 13, 2014.
Ito et al., "The His-probe method: effects of histidine residues introduced into the complementarity-determining regions of anti-

(56) References Cited

OTHER PUBLICATIONS bodies on antigen-antibody interactions at different pH values," FEBS Lett., Aug. 31, 1992, 309:85-88.
Iwahashi et al., "CDR substitutions of a humanized monoclonal antibody (CC49): contributions of individual CDRs to antigen binding and immunogenicity," Mol Immunol., Oct.-Nov. 1999;36(15-16):1079-91.
Jackman et al., "Development of a two-part strategy to identify a therapeutic human bispecific antibody that inhibits IgE receptor signaling," J Biol Chem., Jul. 2, 2010;285(27): 20850-9. doi: 10.1074/jbc.M110.113910. Epub May 5, 2010.
Jain et al., "Engineering antibodies for clinical applications," Trends Biotechnol., Jul. 31, 2007, 25(7):307-16.
Janeway et al., "Structure of the Antibody Molecule and Immunoglobulin Genes," Immunobiology, 3$^{rd}$ Edition, Garland Press, 3:1-3:11 (1997).
Janeway et al., Immunobiology, 5th edition. 2001 :Extract from Chapter 3, pp. 93-122.
Janeway et al., Immunobiology, 5th edition. 2001 :Extract from Chapter 4, pp. 123-154.
Jefferis et al., "Recognition sites on human IgG for Fc gamma receptors: the role of glycosylation," Immunol. Lett., Jan. 2, 1995, 44(2-3):111-7.
Jendeberg et al., "Engineering of Fc(1) and Fc(3) from human immunoglobulin G to analyse subclass specificity for staphylococcal protein A," J. Immunol. Methods., Feb. 14, 1997, 201(1):25-34.
Jirholt et al., "Exploiting sequence space: shuffling in vivo formed complementarity determining regions into a master framework," Gene., Jul. 30, 1998;215(2):471-6.
Johnson et al., "Cation exchange—HPLC and mass spectrometry reveal C-terminal amidation of an IgG1 heavy chain," Anal. Biochem., Jan. 1, 2007, 360:75-83. Epub Oct. 30, 2006.
Johnson et al., "Kabat database and its applications: 30 years after the first variability plot," Nucleic Acids Res., Jan. 1, 2000;28(1):214-8.
Jones et al., "Identification and removal of a promiscuous CD4+ T cell epitope from the C1 domain of factor VIII," Thromb. Haemost., May 1, 2005, 3:991-1000.
Ju et al., "Conversion of the interleukin 1 receptor antagonist into an agonist by site-specific mutagenesis," Proc. Natl. Acad. Sci. U.S.A., Apr. 1, 1991, 88:2658-2662.
JHung et al., "The importance of framework residues H6, H7 and H10 in antibody heavy chains: experimental evidence for a new structural subclassification of antibody V(H) domains," J. Mol. Biol., Jun. 8, 2001;309(3):701-16.
Kabat et al., Sequence of Proteins of Immunological Interest, 5$^{th}$ Edition 1991, p. 690 and p. 693.
Kabat et al., Sequences of Proteins of Immunological Interest, National Institute of Health, Publ'n No. 91-3242, vol. 1 p. 647-60 (5th ed. 1991).
Kabsch et al., "On the use of sequence homologies to predict protein structure: identical pentapeptides can have completely different conformations," Proc Natl Acad Sci U S A., Feb. 1984;81(4):1075-8.
Kai et al., "Switching constant domains enhances agonist activities of antibodies to a thrombopoietin receptor," Nat. Biotechnol., Feb. 1, 2008, 26(2):209-11. Epub Dec. 23, 2007.
Kang et al., "Linkage of recognition and replication functions by assembling combinatorial antibody Fab libraries along phage surfaces," Proc. Natl. Acad. Sci.USA, May 15, 1991;88:4363-6.
Karpovsky et al., "Production of Target-Specific Effector Cells Using Hetero-Cross-Linked Aggregates Containing Anti-Target Cell and Anti-Fcγ Receptor Antibodies," J. Exp. Med., Dec. 1, 1984;160:1686-701.
Kashmiri et al., "Generation, characterization, and in Vivo studies of humanized anticarcinoma antibody CC49," Hybridoma, Oct. 1995, 14:461-473.
Katayose et al., "MUC1-specific targeting immunotherapy with bispecific antibodies: inhibition of xenografted human bile duct carcinoma growth," Cancer Res., Sep. 15, 1996, 56(18):4205-12.

Kenanova et al., "Tailoring the pharmacokinetics and positron emission tomography imaging properties of anti-carcinoembryonic antigen single-chain Fv-Fc antibody fragments," Cancer Res., Jan. 15, 2005;65(2):622-31.
Kerschbaumer et al., "An antibody specific for coagulation factor IX enhances the activity of the intrinsic factor X-activating complex," J. Biol. Chem., Sep. 24, 2004, 279(39):40445-50. Epub Jul. 20, 2004.
Khalifa et al., "Effects on interaction kinetics of mutations at the VH-VL interface of Fabs depend on the structural context," J. Mol. Recognit., May-Jun. 2000;13(3):127-39.
Khawli et al., "Improved tumor localization and radio imaging with chemically modified monoclonal antibodies," Cancer Biother. Radiopharm., Jun. 1996, 11:203-215.
Kim et al., "Antibody Engineering for the Development of Therapeutic Antibodies," Mol. Cells, Aug. 1, 2005, 20:17-29.
Kim et al., "Chemical modification to reduce renal uptake of disulfide-bonded variable region fragment of anti-tac monoclonal antibody labeled with 99mTc," Bioconjugate Chem., May 17, 1999, 10(3):447-453.
Kim et al., "Lowering of pI by acylation improves the renal uptake of 99mTc-labeled anti-Tac dsFv: effect of different acylating reagents," Nucl. Med. Biol., Nov. 30, 2002, 29:795-801.
Kim et al., "Mammalian type I interferon receptors consists of two subunits: IFNaR1 and IFNaR2," Gene, Sep. 1, 1997;196:279-86.
Kim et al., "Mapping the site on human IgG for binding of the MHC class I-related receptor, FcRn," Eur. J. Immunol., Sep. 1999;29(9):2819-25.
Kipriyanov et al., "Bispecific tandem diabody for tumor therapy with improved antigen binding and pharmacokinetics," J Mol Biol., Oct. 15, 1999;293(1):41-56.
Kipriyanov et al., "Effect of Domain Order on the Activity of Bacterially Produced Bispecific Single-chain Fv Antibodies," J. Mol. Biol., Jun. 27, 2003;330(1):99-111.
Kitazawa et al., "A bispecific antibody to factors IXa and X restores factor VIII hemostatic activity in a hemophilia A model," Nat. Med., Oct. 2012;18(10):1570□4. doi:10.1038/nm.2942. Epub Sep. 30, 2012.
Kobayashi et al., "The pharmacokinetic characteristics of glycolated humanized anti-Tac Fabs are determined by their isoelectric points," Cancer Res., Jan. 15, 1999, 59:422-430.
Komissarov et al., "Site-specific mutagenesis of a recombinant anti-single-stranded DNA Fab. Role of heavy chain complementarity-determining region 3 residues in antigen interaction," J. Biol. Chem., Oct. 24, 1997, 272(43):26864-70.
Kontermann, R., "Recombinant bispecific antibodies for cancer therapy," Acta Pharmacol Sin., Jan. 2005;26(1):1-9.
Korn et al., "Recombinant bispecific antibodies for the targeting of adenoviruses to CEA-expressing tumour cells: a comparative analysis of bacterially expressed single-chain diabody and tandem scFv," J Gene Med., Jun. 2004;6(6):642-651.
Kranenborg et al., "Development and characterization of anti-renal cell carcinoma x antichelate bispecific monoclonal antibodies for two-phase targeting of renal cell carcinoma," Cancer Res., Dec. 1, 1995, 55:5864s-5867s.
Kreutz et al., "Efficient bispecific monoclonal antibody purification using gradient thiophilic affinity chromatography," J. Chromatogr. B, Sep. 4, 1998, 714:161-170.
Kroesen et al., "Phase I study of intravenously applied bispecific antibody in renal cell cancer patients receiving subcutaneous interleukin 2," Br. J. Cancer, Oct. 1994;70:652-61.
Kufer et al., "A revival of bispecific antibodies," Trends Biotechnol., May 1, 2004, 22(5):238-44.
Kumar et al., "The second PDZ domain of INAD is a type I domain involved in binding to eye protein kinase C. Mutational analysis and naturally occurring variants," J Biol Chem., Jul. 6, 2001;276(27):24971-7. Epub May 7, 2001.
Kurfis et al., "Role of Arg182 in the second extracellular loop of angiotensin II receptor AT2 in ligand binding," Biochem Biophys Res Commun., Oct. 5, 1999;263:816-9.
Kurokawa et al., "Enhanced Fibrinolysis by a Bispecific Monoclonal Antibody Reactive to Fibrin and Tissue Plasminogen Activator," Bio/Technology, Nov. 1989;7:1163-7.

(56) References Cited

OTHER PUBLICATIONS

Labrijn et al., "Species-specific determinants in the IgG CH3 domain enable Fab-arm exchange by affecting the noncovalent CH3—CH3 interaction strength," J Immunol., Sep. 15, 2011;187(6):3238-46. doi: 10.4049/jimmunol.1003336. Epub Aug. 12, 2011.
Lacroix-Desmazes et al, "Dynamics of factor VIII interactions determine its immunologic fate in hemophilia A," Blood. Jul. 15, 2008;112(2):240-9. doi: 10.1182/blood-2008-02-124941. Epub May 9, 2008.
Lansdorp et al., "Purification and analysis of bispecific tetrameric antibody complexes," Mol. Immunol., Jul. 31, 1990, 27:659-666.
Lapan et al., "Interaction of the A1 Subunit of Factor VIIIa and the Serine Protease Domain of Factor X Identified by Zero-length Cross-linking," Thromb. Haemost., Sep. 1998;80:418-22.
Lazar et al., "Transforming growth factor alpha: mutation of aspartic acid 47 and leucine 48 results in different biological activities," Mol Cell Biol., Mar. 1988;8(3):1247-52.
Le Doussal et al., "Bispecific Monoclonal Antibody-Mediated Targeting of an Indium-111-Labeled DTPA Dimer to Primary Colorectal Tumors: Pharmacokinetics, Biodistribution, Scintigraphy and Immune Response," J. Nucl. Med., Oct. 1993;34:1662-71.
Le Gall et al., "Effect of linker sequences between the antibody variable domains on the formation, stability and biological activity of a bispecific tandem diabody," Protein Eng Des Sel., Apr. 2004;17(4):357-66. Epub May 4, 2004.
Lebégue et al., "Production and characterization of hybrid monoclonal antibodies with IgG1/IgG3 double isotype," C R Acad Sci III., 1990;310(9):377-82.
Lenting et al., "The life cycle of coagulation factor VIII in view of its structure and function", Blood, Dec. 1, 1998;92(11):3983-96.
Leong et al., "Adapting pharmacokinetic properties of a humanized anti-interleukin-8 antibody for therapeutic applications using site-specific pegylation," Cytokine, Nov. 1, 2001, 16(3):106-19.
Li et al., "Construction and characterization of a humanized anti-human CD3 monoclonal antibody 12F6 with effective immunoregulation functions," Immunology, Dec. 2005;116(4):487-98.
Life Technologies (Invitrogen: "ecdysone analogue" and pIND plasmid), Aug. 10, 2012, 2 pages.
Lin et al., "Preclinical pharmacokinetics, interspecies scaling, and tissue distribution of a humanized monoclonal antibody against vascular endothelial growth factor," J Pharmacol Exp Ther., Jan. 1, 1999, 288(1):371-8.
Lin et al., "Structure-function relationships in glucagon: properties of highly purified des-His-1-, monoiodo-, and (des-Asn-28, Thr-29)(homoserine lactone-27)-glucagon," Biochemistry, Apr. 22, 1975;14(8):1559-63.
Lindhofer et al., "Preferential Species-Restricted Heavy/Light Chain Pairing in Rat/Mouse Quadromas," J. Immunol., Jul. 1, 1995, 155:219-225.
Lindsay, "Chapter 4: Determination of the Kinetics and Mechanism of tg-FIX Activation by Factor XIa," 49-75 (2004).
Link et al., "Production and Characterization of a Bispecific IgG Capable of Inducing T-Cell-Mediated Lysis of Malignant B Cells," Blood, Jun. 15, 1993;81:3343-9.
Liu et al., "Functional interactions between arginine-133 and aspartate-88 in the human reduced folate carrier: evidence for a charge-pair association," Biochem J., Sep. 1, 2001;358(Pt 2):511-6.
Liu et al., "Heterogeneity of monoclonal antibodies," J. Pharm. Sci., Jul. 1, 2008, 97(7):2426-47.
Lloyd et al., "The production of a bispecific anti-CEA, anti-hapten (4-amino-phthalate) hybrid-hybridoma," J Natl Med Assoc., Oct. 1991;83(10):901-4.
Lobo et al., "Antibody pharmacokinetics and pharmacodynamics," J. Pharm. Sci., Nov. 1, 2004, 93:2645-68.
Löfqvist et al., "Haemophilia prophylaxis in young patients—a long-term follow-up," J. Intern. Med., May 1997;241:395-400.
Lu et al., "Di-diabody: a novel tetravalent bispecific antibody molecule by design," J. Immunol. Methods, Aug. 2003;279:219-32.
Lu et al., "Fab-scFv fusion protein: an efficient approach to production of bispecific antibody fragments," J. Immunol. Methods, Sep. 15, 2002;267:213-26.
Lund et al., "Expression and characterization of truncated forms of humanized L243 IgG1. Architectural features can influence synthesis of its oligosaccharide chains and affect superoxide production triggered through human Fcgamma receptor I," Eur. J. Biochem., Dec. 2000, 267(24):7246-57.
MacCallum et al., "Antibody-antigen interactions: contact analysis and binding site topography," J. Mol. Biol., Oct. 11, 1996, 262:732-45.
Maini et al., "Double-blind randomized controlled clinical trial of the interleukin-6 receptor antagonist, tocilizumab, in European patients with rheumatoid arthritis who had an incomplete response to methotrexate," Arthritis Rheum., Sep. 1, 2006, 54:2817-29.
Maity et al., "Equilibrium unfolding of dimeric and engineered monomeric forms of Cro (F58W) repressor and the effect of added salts: evidence for the formation of folded monomer induced by sodium perchlorate," Arch Biochem Biophys., Feb. 1, 2005;434(1):93-107.
Male et al., "Antibodies" Immunology, 7th Edition (2006), published by Elsevier Ltd., pp. 59-86.
Manz et al., Bioanalytical Chemistry, World Scientific Publishing Co., 1 page (2003).
Manzke et al., "Single-step purification of bispecific monoclonal antibodies for immunotherapeutic use by hydrophobic interaction chromatography," J. Immunol. Methods, Oct. 13, 1997;208:65-73.
Marshall et al., "Rational design and engineering of therapeutic proteins," Drug Discov Today, Mar. 1, 2003;8(5):212-21.
Marti et al., "Inverse electrostatic effect: electrostatic repulsion in the unfolded state stabilizes a leucine zipper," Biochemistry, Oct. 5, 2004, 43(39):12436-47.
Martin et al., "Crystal structure at 2.8 A of an FcRn/heterodimeric Fc complex: mechanism of pH-dependent binding," Mol. Cell, Apr. 30, 2001, 7:867-877.
Martinez et al., "Disulfide connectivity of human immunoglobulin G2 structural isoforms," Jul. 15, 2008;47(28):7496-508. doi: 10.1021/bi800576c. Epub Jun. 13, 2008.
Marvin et al., "Recombinant approaches to IgG-like bispecific antibodies," Acta Pharmacol Sin., Jun. 2005;26:649-58.
Marvin et al., "Redesigning an antibody fragment for faster association with its antigen," Biochemistry, Jun. 17, 2003, 42:7077-83.
Massino et al., "Quantitative analysis of the products of IgG chain recombination in hybrid hybridomas based on affinity chromatography and radioimmunoassay," J. Immunol. Methods, Feb. 14, 1997;201:57-66.
McCafferty et al., "Phage antibodies: filamentous phage displaying antibody variable domains," Nature, Dec. 6, 1990;348:552-4.
McPhee et al., "Engineering human immunodeficiency virus 1 protease heterodimers as macromolecular inhibitors of viral maturation," Proc Natl Acad Sci U S A., Oct. 15, 1996;93(21):11477-81.
Medesan et al., "Delineation of the amino acid residues involved in transcytosis and catabolism of mouse IgG1," J Immunol., Mar. 1, 1997;158(5):2211-7.
Menegatti et al., "Factor X Deficiency," Semin. Thromb. Hemost., Jun. 2009;35:407-15.
Mertens et al., "Factor VIII-Factor IX Interactions: Molecular Sites Involved in Enzyme-Cofactor Complex Assembly," Thromb. Haemost., Aug. 1999;82:209-17.
Michaelsen et al., "A mutant human IgG molecule with only one C1q binding site can activate complement and induce lysis of target cells," Eur J Immunol., Jan. 2006;36(1):129-38.
Milstein et al., "Hybrid hybridomas and their use in immunohistochemistry," Nature, Oct. 6-12, 1983;305:537-40.
Miyazaki et al., "Generation of bispecific IgG, which mimics the cofactor function of blood coagulation factor VIII," Seikagaku, Poster sessions (2P-B-161) (2006).
Morell et al., "Metabolic properties of IgG subclasses in man," J. Clin. Invest., Apr. 1970, 49(4):673-80.
Morimoto et al., "Single-step purification of F(ab')2 fragments of mouse monoclonal antibodies (immunoglobulins G1) by hydropho-

(56) References Cited

OTHER PUBLICATIONS bic interaction high performance liquid chromatography using TSKgel Phenyl-5PW," J. Biochem. Biophys. Methods, Jan. 1, 1992, 24:107-117.

Morrison, "Two heads are better than one," Nat Biotechnol. Nov. 2007;25(11):1233-4.

Murata et al., "Anti-Digoxin Fab Variants Generated by Phage Display," Mol Biotechnol. Jun. 2013:54(2):269-77. doi:10.1007/s12033-012-9564-1.

Nakano et al. "Anti-glypican 3 antibodies cause ADCC against human hepatocellular carcinoma cells," Biochem Biophys Res Conrnun. Jan. 9, 2009:378(2):279-84. doi:10.1016/j.bbrc.2008.11.033. Epub Nov. 18, 2008.

Narhi et al., "Asn to Lys mutations at three sites which are N-glycosylated in the mammalian protein decrease the aggregation of *Escherichia coli*-derived erythropoietin," Protein Eng., Feb. 2001;14(2):135-40.

Nesterova et al., "Glypican-3 as a novel target for an antibody-drug conjugate," AACR Abstract No. 656, Los Angeles, CA (Apr. 4-18, 2007).

Newman et al, "Modification of the Fc Region of a Primatized IgG Antibody to Human CD4 Retains Its Ability to Modulate CD4 Receptors but Does Not Deplete CD4 T Cells in Chimpanzees," Clin Immunol. Feb. 2001;98(2):164-74.

Nieba et al., "Disrupting the hydrophobic patches at the antibody variable/constant domain interface: improved in vivo folding and physical characterization of an engineered scFv fragment," Protein Eng., Apr. 1997;10(4):435-44.

Nilsson et al., "Induction of split tolerance and clinical cure in high-responding hemophiliacs with factor IX antibodies," Proc. Natl. Acad. Sci. U S A., Dec. 1986;83:9169-73.

Nilsson et al., "Twenty-five years' experience of prophylactic treatment in severe haemophilia A and B," J. Intern. Med., Jul. 1992;232:25-32.

Nishimoto et al., "Humanized anti-interleukin-6 receptor antibody treatment of multicentric Castleman disease," Blood, Oct. 15, 2005, 106:2627-32. Epub Jul. 5, 2005.

Nishimoto et al., "Interleukin 6: from bench to bedside," Nat. Clin. Pract. Rheumatol., Nov. 1, 2006, 2:619-626.

Nitta et al., "Preliminary trial of specific targeting therapy against malignant glioma," Lancet, Feb. 17, 1990;335:368-371.

Nohaile et al., "Altering dimerization specificity by changes in surface electrostatics," Pro Natl Acad Sci U S A., Mar. 13, 2001;98(6):3109-14. Epub Feb. 27, 2001.

O'Shea et al., "Peptide 'Velcro': design of a heterodimeric coiled coil," Curr Biol., Oct. 1, 1993;3(10):658-67.

Okubo et al. "The production and characterization of four monoclonal antibodies to human factor X," Nara Med Assoc., Sep. 1987;38(1):20-28.

Onda et al., "Lowering the Isoelectric Point of the Fv Portion of Recombinant Immunotoxins Leads to Decreased Nonspecific Animal Toxicity without Affecting Antitumor Activity," Cancer Res., Jul. 1, 2001, 61:5070-77.

Ono et al., "The humanized anti-HM1.24 antibody effectively kills multiple myeloma cells by human effector cell-mediated cytotoxicity," Mol. Immunol., Apr. 30, 1999, 36:387-395.

Ozhegov et al., Tolkovyi Slovar Russkogo iazyka: 2004, p. 292 (with an English translation of the relevant passage defining "control").

Padlan et al., "Antibody Fab assembly: the interface residues between CH1 and CL," Mol Immunol., Sep. 1, 1986, 23(9):951-60.

Pakula et al., "Genetic Analysis of Protein Stability and Function," Annu. Rev. Genet., Dec. 1989, 23:289-310.

Pan et al., "Blocking neuropilin-1 function has an additive effect with anti-VEGF to inhibit tumor growth," Cancer Cell, Jan. 2007;11(1):53-67.

Panka et al., "Variable region framework differences result in decreased or increased affinity of variant anti-digoxin antibodies," Proc. Natl. Acad. Sci. U.S.A., May 1, 1988, 85(9):3080-4.

Pardridge et al., "Enhanced cellular uptake and in vivo biodistribution of a monoclonal antibody following cationization," J Pharm Sci., Aug. 1995;84(8):943-8.

Pardridge et al., "Enhanced endocytosis in cultured human breast carcinoma cells and in vivo biodistribution in rats of a humanized monoclonal antibody after cationization of the protein," J. Pharmacol. Exp. Ther., Jul. 1, 1998, 286(1):548-54.

Paul et al., "Immunologiya", M.:Mir, 1987-1988, vol. 1, p. 231 (with English translation).

Paul, "Structure and function of immunoglobulins," Fundamental Immunology, Third Edition, 292-295 (1993).

Paul, William ed., Fundamental Immunology, $3^{rd}$ edition, p. 242 (1993).

Pavlinkova et al., "Charge-modified single chain antibody constructs of monoclonal antibody CC49: Generation, characterization, pharmacokinetics, and biodistribution analysis," Nucl. Med. Biol., Jan. 31, 1999, 26:27-34.

Peipp et al., "Bispecific antibodies targeting cancer cells," Biochem. Soc. Trans., Aug. 2002, 30:507-511.

Pejchal et al., "A Conformational Switch in Human Immunodeficiency Virus gp41 Revealed by the Structures of Overlapping Epitopes Recognized by Neutralizing Antibodies," J Virol. Sep. 2009;83(17):8451-62. doi:10.1128/JVI.00685-09. Epub Jun. 10, 2009.

Petkova et al., "Enhanced half-life of genetically engineered human lgG1 antibodies in a humanized FcRn mouse model: potential application in humorally mediated autoimmune disease," Int. Immunol. Dec. 2006;18(12):1759☐69. Epub 2006.

Piper et al., "Interferon therapy in primary care," Primary Care Update for Ob/Gyns, Jul. 2001;8(4):163-69.

Poduslo et al., "Polyamine modification increases the permeability of proteins at the blood—nerve and blood-brain barriers," J. Neurochem., Apr. 1, 1996, 66:1599-1609.

Pokkuluri et al., "A domain flip as a result of a single amino-acid substitution," Structure, Aug. 15, 1998;6(8):1067-73.

Pons et al., "Energetic analysis of an antigen/antibody interface: alanine scanning mutagenesis and double mutant cycles on the HyHEL-10/lysozyme interaction," Protein Sci., May 1999, 8(5):958-68.

Portolano et al., "Lack of Promiscuity in Autoantigen-Specific H and L Chain Combinations as Revealed by Human H and L Chain "Roulette"," J. Immunol., Feb. 1, 1993, 150(3):880-887.

Presta et al., "Molecular engineering and design of therapeutic antibodies," Curr. Opin. Immunol., Aug. 31, 2008, 20(4):460-70. doi: 10.1016/j.coi.2008.06.012.

Presta, "Engineering of therapeutic antibodies to minimize immunogenicity and optimize function," Adv. Drug Deliv. Rev., Aug. 7, 2006, 58(5-6):640-56.

Price et al., "Tissue factor and tissue factor pathway inhibitor," Anaesthesia, May 2004;59:483-92.

Pritsch et al., "Can Immunoglobulin CH1 Constant Region Domain Modulate Antigen Binding Affinity of Antibodies?," J Clin Invest. Nov. 15, 1996;98(10):2235-43.

Queen et al., "A humanized antibody that binds to the interleukin 2 receptor," Proc. Natl. Acad. Sci. U.S.A., Dec. 1, 1989, 86(24):10029-10033.

Raffen et al., "Reengineering immunoglobulin domain interactions by introduction of charged residues," Protein Eng. Apr. 1998;11:303-9.

Rajpal et al., A general method for greatly improving the affinity of antibodies by using combinatorial libraries, Proc. Natl. Acad. Sci. USA, Jun. 14, 2005, 102:8466-71. Epub Jun. 6, 2005.

Raposo et al., "Epitope-specific antibody response is controlled by immunoglobulin Vh polymorphisms," J Exp Med. Mar. 10, 2014:211(3):405-11.doi:10.1084/jem.20130968. Epub Feb. 17, 2014.

Reddy et al., "Elimination of Fc receptor-dependent effector functions of a modified IgG4 monoclonal antibody to human CD4," J. Immunol., Feb. 15, 2000, 164(4):1925-33.

Reichert et al., "Development trends for monoclonal antibody cancer therapeutics," Nat. Rev. Drug Discov., May 1, 2007, 6(5):349-56.

Reimann et al., "A humanized form of a CD4-specific monoclonal antibody exhibits decreased antigenicity and prolonged plasma

(56) References Cited

OTHER PUBLICATIONS half-life in rhesus monkeys while retaining its unique biological and antiviral properties," AIDS Res Hum Retroviruses, Jul. 20, 1997;13(11):933-43.
Reist et al., "Human IgG2 constant region enhances in vivo stability of anti-tenascin antibody 81C6 compared with its murine parent," Clin Cancer Res., Oct. 1998;4(10):2495-502.
Roguska et al., "Humanization of murine monoclonal antibodies through variable domain resurfacing," Proc Natl Acad Sci U.S.A., Feb. 1, 1994, 91:969-73.
Roitt et al., Immunology, M., Mir, (2000), pp. 110-111 (in Russian, with what is believed to be a published English equivalent of those pages taken from Roitt et al., "Antibody Structure and Function," Immunology, Fifth Ed., (1998), pp. 80-81).
Roitt et al., Immunology, M., Mir, 5th Edition (2000), pp. 97-113 (In Russian. What are believed to be corresponding pages from an English language edition of Immunology are cited as Desig. ID 559 (Male et al.).
Roopenian et al., "FcRn: the neonatal Fc receptor comes of age," Nat Rev Immunol., 7(9):715-25 (Sep. 2007), Epub Aug. 17, 2007.
Rothe et al., "Ribosome display for improved biotherapeutic molecules," Expert Opin. Biol. Ther., Feb. 1, 2006, 6:177-187.
Rothlisberger et al., "Domain interactions in the Fab fragment: a comparative evaluation of the single-chain Fv and Fab format engineered with variable domains of different stability," J Mol Biol., Apr. 8, 2005, 347(4):773-89.
Rudikoff et al., "Single amino acid substitution altering antigen-binding specificity," Proc. Natl. Acad. Sci. U.S.A., Mar. 1, 1982, 79(6):1979-83.
Ruef et al., "A bispecific antifibrin-antiplatelet urokinase conjugate (BAAUC) induces enhanced clot lysis and inhibits platelet aggregation," Thromb. Haemost., Jul. 1999;82(1):109-14.
Ruf et al., "Pharmacokinetics and in vivo stability of intraperitoneally administered therapeutic antibody catumaxomab," J. Clin. Oncol., 26 (May 20 suppl) (2008), abstr 14006.
Ruggeri et al., "von Willebrand factor and von Willebrand disease," Blood. Oct. 1987;70(4):895☐904.
Saito et al., "Establishment of Factor VIII Mimetic Antibodies and Their In Vitro Activities in Hemophilia A," 2006 National Hemophilia Foundation Symposia.
Saito et al., "Factor VIII Mimetic Antibody: (1) Establishment and Characterization of Anti-factor IX/anti-factor X Bispecific Antibodies," 2005 International Society of Thrombosis and Haemostasis, vol. 3, Issue Supplement s1, p. #OR160.
Salfeld et al., "Isotype selection in antibody engineering," Nat. Biotechnol., Dec. 1, 2007, 25:1369-72.
Sal-Man et al., "Arginine mutations within a transmembrane domain of Tar, an *Escherichia coli* aspartate receptor, can drive homodimer dissociation and heterodimer association in vivo," Biochem J., Jan. 1, 2005;385(Pt 1):29-36.
Sampei et al., "Identification and multidimensional optimization of an asymmetric bispecific IgG antibody mimicking the function of factor VIII cofactor activity," PLoS One, 2013;8(2):e57479. doi: 10.1371/journal.pone.0057479. Epub Feb. 28, 2013.
Sarkar et al., "Rational cytokine design for increased lifetime and enhanced potency using pH-activated "histidine switching"," Nat Biotechnol., Sep. 2002;20(9):908-13. Epub Aug. 5, 2002.
Sarmay et al., "Mapping and comparison of the interaction sites on the Fc region of IgG responsible for triggering antibody dependent cellular cytotoxicity (ADCC) through different types of human Fc gamma receptor," Mol. Immunol., May 1, 1992, 29(5):633-9.
Sato et al., "Properties of Two VEGF Receptors, Flt-1 and KDR, in Signal Transduction," Ann N.Y. Acad. Sci, May 2000;902:201-207, discussion 205-7.
Sato et al., "Reshaping a human antibody to inhibit the interleukin 6-dependent tumor cell growth," Cancer Res., Feb. 15, 1993, 53:851-856.
Schaeffer et al., "The Rat Glomerular Filtration Barrier Does Not Show Negative Charge Selectivity," Microcirculation, Jan. 1, 2002, 9:329-342.
Schmidt et al., "Structure-function relationships in factor IX and factor IXa," Trends Cardiovasc Med., Jan. 2003;13(1):39-45.
Schmidt et al., Human Physiology, Moscow, 2:431-436 (1996), and English equivalent: Schmidt et al., "Hemostatis and Coagulation," Human Physiology, R.F. Schmidt, G. Thews (Eds.), Second, Completely Revised Edition, 418-423, Springer-Verlag, 1989.
Schmidt et al., Human Physiology, Moscow, 3:764 (1996), and English equivalent: Schmidt et al., "Enzymes of the pancreatic juice," Human Physiology, R.F. Schmidt, G. Thews (Eds.), Second, Completely Revised Edition, 716, Springer-Verlag, 1989.
Schmitz et al., "Phage display: a molecular tool for the generation of antibodies—a review," Placenta., Mar. 1, 2000, 21 Suppl A:S106-12.
Schwartz et al., "A superactive insulin: [B10-aspartic acid]insulin(human)," Proc Natl Acad Sci. U S A., Sep. 1987;84(18):6408-11.
Segal et al., "Bispecific antibodies in cancer therapy," Curr Opin Immunol., Oct. 1999;11(5):558-62.
Segal et al., "Introduction: bispecific antibodies," J. Immunol. Methods, Feb. 1, 2001;248:1-6.
Shalaby et al., "Development of Humanized Bispecific Antibodies Reactive with Cytotoxic Lymphocytes and Tumor Cells Overexpressing the HER2 Protooncogene," J. Exp. Med., Jan. 1, 1992, 175:217-225.
Sharifi et al., "Improving monoclonal antibody pharmacokinetics via chemical modification," Q J Nucl Med., Dec. 1998;42(4):242-9.
Shaul, "Exploring the charge space of protein-protein association: a proteomic study," Proteins, Aug. 15, 2005, 60:341-352.
Shields et al., "High resolution mapping of the binding site on human IgG1 for Fc gamma RI, Fc gamma RII, Fc gamma RIII, and FcRn and design of IgG1 variants with improved binding to the Fc gamma R," J. Biol. Chem., Mar. 2, 2001, 276:6591-6604 (Epub Nov. 28, 2000).
Shima et al., "Factor VIII Mimetic Antibody: (2) In Vitro Assessment of Cofactor Activity in Hemophilia A," 2005 International Society of Thrombosis and Haemostasis, vol. 3, Issue Supplement s1, p. #P0038.
Shima et al., "Factor VIII Taitei Kotai (2), Ketsuyubyo A Kanja Katsueki ni okeru in vitro Gyoko Kassei no Kento", Rinsho Ketsueki, Aug. 30, 2005;46(8):777 (#WS-36-5) (with English translation).
Shima, M., "Bispecific antibodies to coagulation factors IXa and X mimic the function of factor VIII," 2006 World Federation of Haemophilia (Haemophilia, 12(Suppl. 2):98 (2006)).
Shirahata, Minna ni yakudatsu ketsuyubyo no kiso to rinsho. Iyaku (Medicine and Drug) Journal Co., Ltd., 280-9 (2009) (including English translation).
Shire et al., "Challenges in the development of high protein concentration formulations," Journal of Pharmaceutical Sciences, Jun. 1, 2004, 93(6):1390-1402.
Singer et al., Genes & Genomes, 1991; Chapter 1, pp. 67-69.
Singer et al., Genes & Genomes, 1998; Chapter 1, pp. 63-64.
Sinha et al., "Electrostatics in protein binding and function," Curr Protein Pept Sci., Dec. 2002;3(6):601-14.
Sinha et al., "Molecular dynamics simulation of a high-affinity antibody-protein complex: the binding site is a mosaic of locally flexible and preorganized rigid regions," Cell Biochem Biophys., Oct. 1, 2005, 43:253-273.
Skerra, "Use of the tetracycline promoter for the tightly regulated production of a murine antibody fragment in *Escherichia coli*," Gene, Dec. 30, 1994, 151:131-135.
Smans et al., "Bispecific antibody-mediated lysis of primary cultures of ovarian carcinoma cells using multiple target antigens," Int. J. Cancer, Oct. 8, 1999, 83:270-277.
Smith et al., "The challenges of genome sequence annotation or 'the devil is in the details'," Nature Biotechnology, Nov. 1997;15:1222-1223.
Smith, "Creative Expression: Mammalian Expression Vectors and Systems," The Scientist Magazine, Feb. 2, 1998, 3 pages.
Smolen et al., "Interleukin-6: a new therapeutic target," Arthritis Res Ther., 2006;8 Suppl 2:S5. Epub Jul. 28, 2006.
Soeda et al., "Factor VIII Taitei Kotai (1) Ko FIXa/FX bispecific Kotai no Sakusei oyobi characterization," Rinsho Ketsueki, Aug. 30, 2005, 46(8):728 (including English translation).

(56) References Cited

OTHER PUBLICATIONS

Soeda et al., "Phage library-ho ni yori Sakusei shita Ko-FIXa/Ko-FX bispecific Kotai no FVIII Taitei Sayo," Jpn J Thromb Hemost., Oct. 1, 2005, 16(5):526 (including English translation).
Spiess et al., "Bispecific antibodies with natural architecture produced by co-culture of bacteria expressing two distinct half-antibodies," Nat Biotechnol., Aug. 2013; 31(8):753-8. doi: 10.1038/nbt.2621. Epub Jul. 7, 2013.
Stickney et al., "Bifunctional Antibody: A Binary Radiopharmaceutical Delivery System for Imaging Colorectal Carcinoma," Cancer Res., Dec. 15, 1991;51:6650-5.
Strand et al., "Biologic therapies in rheumatology: lessons learned, future directions," Nat. Rev. Drug Discov., Jan. 1, 2007, 6:75-92.
Suresh et al., "Advantages of bispecific hybridomas in one-step immunocytochemistry and immunoassays," Proc. Natl. Acad. Sci. U S A., Oct. 1986;83:7989-93.
Suresh et al., "Bispecific monoclonal antibodies from hybrid hybridomas," Methods Enzymol., Dec. 31, 1986;121:210-228.
Tabrizi et al., "Elimination mechanisms of therapeutic monoclonal antibodies," Drug Discov Today, Jan. 2006;11(1-2):81-8.
Taki, The Journal of Japanese Society on Thrombosis and Hemostasis, Feb. 2, 2002;13:109-113.
Tamura et al., "Structural correlates of an anticarcinoma antibody: identification of specificity-determining residues (SDRs) and development of a minimally immunogenic antibody variant by retention of SDRs only," J Immunol., Feb. 1, 2000;164(3):1432-41.
Tan et al., "Contributions of a highly conserved $V_H/V_L$ hydrogen bonding interaction to scFv folding stability and refolding efficiency," Biophys J., Sep. 1998; 75(3):1473-82.
Tan et al., "Engineering the isoelectric point of a renal cell carcinoma targeting antibody greatly enhances scFv solubility," Immunotechnology, Oct. 31, 1998, 4(2):107-114.
Tarditi et al., "Selective high-performance liquid chromatographic purification of bispecific monoclonal antibodies," J. Chromatogr., May 2, 1992, 599:13-20.
Teeling et al., "The biological activity of human CD20 monoclonal antibodies is linked to unique epitopes on CD20," J. Immunol., Jul. 1, 2006, 177(1):362-71.
Teerinen et al., "Structure-based stability engineering of the mouse IgG1 Fab fragment by modifying constant domains," J Mol Biol., Aug. 25, 2006, 361(4):687-97.
Ten Kate et al., "Effect of isoelectric point on biodistribution and inflammation: imaging with indium-111-labelled IgG," Eur. J. Nucl. Med., Jun. 1, 1990, 17:305-309.
Thies et al., "The alternatively folded state of the antibody C(H)3 domain," J Mol Biol., Jun. 22, 2001;309(5):1077-85.
Tsubaki et al., "C-terminal modification of monoclonal antibody drugs: amidated species as a general product-related substance," Int J Biol Macromol., 52:139-47. doi: 10.1016/j.ijbiomac.2012.09.016. Epub Sep. 25, 2012.
Tsurushita et al., "Design of humanized antibodies: From anti-Tac to Zenapax," Methods, May 31, 2005, 36:69-83.
Vaccaro et al., "Divergent activities of an engineered antibody in murine and human systems have implications for therapeutic antibodies," Proc Natl Acad Sci U S A. Dec. 5, 2006;103(49):18709□14. Epub Nov. 20, 2006.
Vaisitti et al., "Cationization of monoclonal antibodies: another step towards the "magic bullet"?," J. Biol. Regul. Homeost. Agents., Jul. 1, 2005, 19(3-4):105-12.
Vajdos et al., "Comprehensive functional maps of the antigen-binding site of an anti-ErbB2 antibody obtained with shotgun scanning mutagenesis," J. Mol. Biol., Jul. 5, 2002, 320(2):415-28.
Van Loghem et al., "Staphylococcal protein A and human IgG subclasses and allotypes," Scand. J. Immunol., Mar. 1, 1982, 15(3):275-8.
Van Walle et al., "Immunogenicity screening in protein drug development," Expert Opin. Biol. Ther., Mar. 1, 2007, 7(3):405-18.
Vargas-Madrazo et al., "An improved model of association for VH-VL immunoglobulin domains: asymmetries between VH and VL in the packing of some interface residues," J Mol Recognit., May-Jun. 2003;16(3):113-20.
Vaughan et al., "Human antibodies with sub-nanomolar affinities isolated from a large non-immunized phage display library," Nat Biotechnol., Mar. 1996;14(3):309-14.
Vehar et al., "Structure of human factor VIII," Nature, Nov. 22, 1984, 312(5992):337-42.
Verhoeyen et al., "Construction of a reshaped HMFG1 antibody and comparison of its fine specificity with that of the parent mouse antibody," Immunology, Mar. 1993;78(3):364-70.
Verhoeyen et al., "Monoclonal Antibodies in Clinical Oncology," 1991, Edited by AA Epenetos, Chapter 5, pp. 37-43, Chapman and Hall.
Wally et al., "Identification of a novel substitution in the constant region of a gene coding for an amyloidogenic kappal light chain," Biochim Biophys Acta., May 31, 1999;1454(1):49-56.
Wang et al., "Conserved amino acid networks involved in antibody variable domain interactions," Proteins, Jul. 2009;76(1):99-114. doi: 10.1002/prot.22319.
Wang et al., "Polyethylene Glycol-modified Chimeric Toxin Composed of Transforming Growth Factor alpha and Pseudomonas Exotoxin," Cancer. Res., Oct. 1, 1993, 53:4588-4594.
Ward et al., "Binding activities of a repertoire of single immunoglobulin variable domains secreted from *Escherichia coli*," Nature, Oct. 12, 1989;341:544-546.
Ward et al., "Effects of engineering complementary charged residues into the hydrophobic subunit interface of tyrosyl-tRNA synthetase. Appendix: Kinetic analysis of dimeric enzymes that reversibly dissociate into inactive subunits," Biochemistry, Jun. 30, 1987;26(13):4131-8.
Warnaar et al., "Purification of bispecific F(ab')2 from murine trinoma OC/TR with specificity for CD3 and ovarian cancer," Hybridoma, Dec. 13, 1994, 13:519-526.
Weiner et al., "A Human Tumor Xenograft Model of Therapy with a Bispecific Monoclonal Antibody Targeting c-erbB-2 and CD16," Cancer Res., Jan. 1, 1993;53:94-100.
Weiner et al., "The Role of T Cell Activation in Anti-CD3 × Antitumor Bispecific Antibody Therapy," J. Immunol., Mar. 1, 1994;152:2385-92.
Wiens et al., "Mutation of a single conserved residue in VH complementarity-determining region 2 results in a severe Ig secretion defect," J. Immunol., Aug. 15, 2001, 167(4):2179-86.
Wiens et al., "Somatic mutation in VH complementarity-determining region 2 and framework region 2: differential effects on antigen binding and Ig secretion," J. Immunol., Aug. 1, 1997, 159(3):1293-302.
Wood et al., "Expression of active human factor VIII from recombinant DNA clones," Nature, Nov. 22, 1984, 312(5992):330-7.
Worn et al., "Stability engineering of antibody single-chain Fv fragments," J Mol Biol., Feb. 2, 2001;305(5):989-1010.
Wu et al., "Development of motavizumab, an ultra-potent antibody for the prevention of respiratory syncytial virus infection in the upper and lower respiratory tract," J. Mol. Biol., May 4, 2007, 368(3):652-65.
Wu et al., "Multimerization of a chimeric anti-CD20 single-chain Fv-Fc fusion protein is mediated through variable domain exchange," Protein Eng., Dec. 2001;14(12):1025-33.
Wypych et al., "Human IgG2 antibodies display disulfide-mediated structural isoforms," J. Biol. Chem., Jun. 6, 2008, 283(23):16194-16205. Epub Mar. 13, 2008.
Xiang et al., "Production of murine V-human Cr1 chimeric anti-TAG72 antibody using V region cDNA amplified by PCR," Mol Immunol., Aug. 1990;27(8):809-817.
Xiang et al., "Study of B72.3 combining sites by molecular modeling and site-directed mutagenesis," Protein Eng., May 1, 2000, 13(5):339-44.
Yamasaki et al., "Pharmacokinetic analysis of in vivo disposition of succinylated proteins targeted to liver nonparenchymal cells via scavenger receptors: importance of molecular size and negative charge density for in vivo recognition by receptors," J. Pharmacol. Exp. Ther., May 1, 2002, 301:467-477.

(56) References Cited

OTHER PUBLICATIONS

Yang et al., "CDR Walking Mutagenesis for the Affinity Maturation of a Potent Human Anti-HIV-1 Anitbody into the Picomolar Range," J Mol. Biol., 254(3):392-403 (Dec. 1995).
Yang et al., "Tailoring structure-function and pharmacokinetic properties of single-chain Fv proteins by site-specific PEGylation," Protein Eng., Oct. 1, 2003, 16:761-770.
Yasukawa et al., "Structure and expression of human B cell stimulatory factor-2 (BSF-2/IL-6) gene," EMBO J., Oct. 1987;6(10):2939-45.
Zhu et al., "An efficient route to the production of an IgG-like bispecific antibody", Protein Eng., May 1, 2000, 13:361-367.
Zhu et al., "Remodeling domain interfaces to enhance heterodimer formation," Protein Sci., Apr. 1997;6(4):781-8.
Zuckier et al., "Chimeric human-mouse IgG antibodies with shuffled constant region exons demonstrate that multiple domains contribute to in vivo half-life," Cancer Res., Sep. 1, 1998, 58:3905-08.
Zuo et al., "An efficient route to the production of an IgG-like bispecific antibody," Protein Eng., May 1, 2000, 13(5):361-7.
Zwick et al., "The long third complementarity-determining region of the heavy chain is important in the activity of the broadly neutralizing anti-human immunodeficiency virus type 1 antibody 2F5," J. Virol., 78(6):3155-61 (Mar. 15, 2004).
U.S. Appl. No. 16/298,032, filed Mar. 11, 2019, Igawa et al.
Choi et al., "Crystal structures of immunoglobulin Fc heterodimers reveal the molecular basis for heterodimer formation," Mol Immunol, Jun. 2015, 65(2):377-83. doi: 10.1016/j.molimm.2015.02.017. Epub Mar. 2, 2015.
Goulet et al., "Kinetic mechanism of controlled Fab-arm exchange for the formation of bispecific immunoglobulin G1 antibodies," J Biol Chem, Jan. 12, 2018, 293(2):651-661. doi:10.1074/jbc.RA117.000303. Epub Nov. 17, 2017.
Rispens et al., "Mechanism of Immunoglobulin G4 Fab-arm Exchange," J Am Chem Soc, Jul. 6, 2011, 133(26):10302-11. doi: 10.1021/ja203638y. Epub Jun. 15, 2011.
Declaration of Dr. Anette Henriksen, signed Apr. 17, 2019 (submitted by the Opponent during EPO opposition procedure for EP 2 006 381).
Feige et al., "An Unfolded $C_H1$ Domain Controls the Assembly and Secretion of IgG Antibodies," Mol Cell, Jun. 12, 2009, 34(5):569-79. doi: 10.1016/j.molcel.2009.04.028.
Horne et al., "Noncovalent Association of Heavy and Light Chains of Human Immunoglobulins," J Immunol, Aug. 1982, 129(2):660-4.
Kabat et al., "Sequences of proteins of immunological interest," 1991, vol. 1, 5$^{th}$ edition, Diane Publishing, pp. 647-652 and 661-669.
Moiseenko, "Monoclonal Antibodies in the Treatment of Malignant Tumors," Practical Oncology, 2003, 4(3):148-56 (with English translation).
Muller et al., "The first constant domain ($C_H1$ and $C_L$) of an antibody used as heterodimerization domain for bispecific miniantibodies," FEBS Lett, Jan. 30, 1998, 422(2):259-64.
U.S. Appl. No. 16/093,495, filed Oct. 12, 2018, Saeki et al.
Abe et al., "Novel Protein A Resin: Synthetic Polymer Matrix Design Impact on Antibody Binding Capacity," JSR Technical Review No. 119, 2012, p. 1-5 [online], [retrieved on Feb. 17, 2017], retrieved from the internet: http://www.jsr.co.jp/pdf/rd/tec119-1.pdf (with English translation).
Cruse et al., Atlas of Immunology, CRC Press LLC, 2004, excerpt from Chapter 3 "Antigens and Immunogens", p. 109.
Decision of the EPO Opposition Division for EP 2 006 381 on Jul. 25, 2018, 17 pages.
GE Healthcare Life Sciences, Dynamic binding capacity study on MabSelect SuRe™ LX for capturing high-titer monoclonal antibodies, Application note 28-9875-25-AA, 2011, [online], [retrieved on Feb. 17, 2017], retrieved from the internet: http://www.processdevelopmentforum.com/images/articles/28/9875-25_AA_AN_DBC_study_on_MabSelect_SuRe_LX_final.pdf.
Geneseq Accession No. ARZ17615, Aug. 21, 2008, "Human antibody IgG2 heavy chain constant region SEQ ID No. 36".
Sequence alignments and modification scheme (document filed during Oral Proceedings in EPO opposition for EP 2 006 381 mentioned in minutes of the Oral Proceedings posted by EPO on Jul. 25, 2018); 3 pages.
Van Den Abbeele et al., "Antigen-Binding Site Protection During Radiolabeling Leads to a Higher Immunoreactive Fraction," J Nucl Med, Jan. 1991, 32(1):116-22.
U.S. Appl. No. 16/155,673, filed Oct. 9, 2018, Igawa et al.
Geneseq Accession No. AEM45140, Feb. 22, 2007, "Light chain constant region of therapeutic human IgG antibody" 1 page.
Golay et al., "Mechanism of action of therapeutic monoclonal antibodies: Promises and pitfalls of in vitro and in vivo assays," Archives of Biochemistry and Biophysics 526: 146-153, Feb. 25, 2012.
Kabat et al., "Identical V Region Amino Acid Sequences and Segments of Sequences in Antibodies of Different Specificities," Journal of Immunology. Sep. 1, 1991; 147(5):1709-19.
Kim et al., "Antibody light chain variable domains and their biophysically improved versions for human immunotherapy," mAbs. Jan.-Feb. 2014; 6(1):219-35. doi: 10.4161/mabs.26844.
Li et al., "Framework selection can influence pharmacokinetics of a humanized therapeutic antibody through differences in molecule charge," mAbs. 2014;6(5):1255-64. doi: 10.4161/mabs.29809. Epub Oct. 30, 2014.
Stancovski et al., "Mechanistic Aspects of the Opposing Effects of Monoclonal Antibodies to the ERBB2 Receptor on Tumor Growth," Proceedings of the National Academy of Sciences, USA 88:8691-8695, Oct. 1, 1991.
U.S. Appl. No. 16/226,798, filed Dec. 20, 2018, Hattori et al.
Feige et al., "How antibodies fold," Trends Biochem Sci. Apr. 2010;35(4):189-98. doi: 10.1016/j.tibs.2009.11.005. Epub Dec. 21, 2009.
Roitt et al., Immunology, M., Mir, (2000), pp. 110, 150, and 537-9 (in Russian, with what is believed to be a published English equivalent of those pages).
U.S. Appl. No. 15/963,221, filed Apr. 26, 2018, Nezu et al.
U.S. Appl. No. 15/963,345, filed Apr. 26, 2018, Hattori et al.
U.S. Appl. No. 16/061,454, filed Jun. 12, 2018, Tanaka et al.
U.S. Appl. No. 16/083,975, filed Sep. 11, 2018, Kinoshita et al.
Canfield et al., "The Binding Affinity of Human IgG for its High Affinity Fc Receptor Is Determined by Multiple Amino Acids in the $C_H2$ Domain and Is Modulated by the Hinge Region," J Exp Med, Jun. 1, 1991, 173(6):1483-91.
Dall'Acqua et al., "Properties of Human IgG1s Engineered for Enhanced Binding to the Neonatal Fc Receptor (FcRn)," J Biol Chem., Aug. 18, 2006, 281(33):23514-24. Epub Jun. 21, 2006.
EPO Register Extract EP 1915397 (document submitted in EP opposition and posted by EPO on Feb. 2, 2018); 4 pages.
Hotzel et al., "A strategy for risk mitigation of antibodies with fast clearance," mAbs., Nov.-Dec. 2012, 4(6):753-60. doi: 10.4161/mabs.22189.
Jaeger, "Clinical Immunology and Allergology," 2nd edition, M.: Medicina, 1990, 2:484-5 (with English translation).
Ryman et al., "Pharmacokinetics of Monoclonal Antibodies," CPT Pharmacometrics Syst Pharmacol., Sep. 2017, 6(9):576-588. doi: 10.1002/psp4.12224. Epub Jul. 29, 2017.
Sampei et al, "Non-antigen-contacting region of an asymmetric bispecific antibody to factors IXa/X significantly affects factor VIII-mimetic activity," mAbs, 2015, 7(1):120-8. doi: 10.4161/19420862.2015.989028.
Summary of information about antibodies in Examples of patent (document submitted in EP opposition and posted by EPO on Apr. 13, 2018); 3 pages.
Written Submissions by Opponent 1 (Alexion Pharmaceuticals, Inc.) in Opposition of EP 2006381 dated Apr. 13, 2018, 19 pages.
Written Submissions by Opponent 2 (Novo Nordisk A/S) in Opposition of EP 2006381 dated Apr. 13, 2018, 14 pages.
Written Submissions by Opponent 3 (name Unknown) in Opposition of EP 2006381 dated Apr. 13, 2018, 16 pages.
Wu et al., "Ultra-potent Antibodies Against Respiratory Syncytial Virus: Effects of Binding Kinetics and Binding Valence on Viral Neutralization," J Mol Biol., Jul. 1, 2005, 350(1):126-44.

(56) References Cited

OTHER PUBLICATIONS

Yarilin, Fundamentals of Immunology, M: Medicina, 1999, pp. 169-174 (with English translation).
Yarilin, Fundamentals of Immunology, M: Medicina, 1999, pp. 169-172, 354-358 (with English translation).
U.S. Appl. No. 16/692,676, filed Nov. 22, 2019, Kuramochi et al.
U.S. Appl. No. 16/815,089, filed Mar. 11, 2020, Igawa et al.
U.S. Appl. No. 16/825,513, filed Mar. 20, 2020, Hattori et al.
U.S. Appl. No. 61/467,727, filed Mar. 25, 2011, Blein et al.
"Hemostatic Therapy Guideline for Inhibitor-negative Hemophilia Patients," Japanese Journal of Thrombosis and Hemostasis, 2013, 24(6):619-639 (with English translation).
"Hemostatic Therapy Guideline for Inhibitor-positive Hemophilia Patients," Japanese Journal of Thrombosis and Hemostasis, 2013, 24(6):640-658 (with English translation).
ALPROLIX® Intravenous, May 2019, 16 pages (with English translation).
Annex I. Analysis of the Examples of EP 2 787 078 (document submitted in opposition of EP 2 787 078 on Feb. 28, 2020).
Arguments filed on Oct. 12, 2016 in U.S. Appl. No. 14/351,654 (document submitted in opposition of EP 2 787 078 on Feb. 25, 2020).
Astermark et al., "A randomized comparison of bypassing agents in hemophilia complicated by an inhibitor: the FEIBA NovoSeven Comparative (FENOC) Study," Blood, Jan. 15, 2007, 109(2):546-51. Epub Sep. 21, 2006.
Claims filed on Sep. 5, 2018 in U.S. Appl. No. 14/351,654 (document submitted in opposition of EP 2 787 078 on Feb. 28, 2020).
Collins et al., "Implications of coagulation factor VIII and IX pharmaco-kinetics in the prophylactic treatment of haemophilia," Haemophilia, Jan. 2011, 17(1):2-10. doi: 10.1111/j.1365-2516.2010.02370.x. Epub Aug. 22, 2010.
Coppola et al., "Acquired Inhibitors of Coagulation Factors: Part I—Acquired Hemophilia A," Semin Thromb Hemost, Jul. 2012, 38(5):433-46. doi: 10.1055/s-0032-1315757. Epub Jun. 27, 2012.
Franchini et al., "Acquired haemophilia A: A 2013 update," Thromb Haemost, Dec. 2013, 110(6):1114-20. doi:10.1160/TH13-05-0363. Epub Sep. 5, 2013.
Guidelines for the management of hemophilia, 2005, World Federation of Hemophilia, 52 pages.
Hagiwara et al., "Effect of Emicizumab in improving coagulation ability in the presence of minor amount of Factor IX," Japanese Journal of Thrombosis and Hemostasis, 2017, 28(2):190 0-012 (with English translation).
Kruse-Jarres, "Inhibitors: our greatest challenge. Can we minimize the incidence?," Haemophilia, Jan. 2013, 19 Suppl 1:2-7. doi: 10.1111/hae. 12049.
Lillicrap, "von Willebrand disease: advances in pathogenetic understanding, diagnosis, and therapy," Blood, Nov. 28, 2013, 122(23):3735-40. doi: 10.1182/blood-2013-06-498303. Epub Sep. 24, 2013.
Minami et al., "Bispecific Antibody ACE910 Improves Coagulation Function in Plasma of Patients with Factor XI Deficiency," Japanese Journal of Thrombosis and Hemostasis, 2015, 26(2):188 0-024 (with English translation).
Miyata, "Factor IX Abnormality—Molecular defects of Factor IX," Japanese Journal of Thrombosis and Hemostasis, 1991, 2(1):1-11 (with English translation).
Muto et al., "Anti-factor IXa/X bispecific antibody (ACE910): hemostatic potency against ongoing bleeds in a hemophilia A model and the possibility of routine supplementation," J Thromb Haemost. Feb. 2014, 12(2):206-213. doi: 10. 1111/jth.12474.
Muto et al., "Anti-factor IXa/X bispecific antibody ACE910 prevents joint bleeds in a long-term primate model of acquired hemophilia A," Blood, Nov. 13, 2014, 124(20):3165-71. doi: 10. 1182/blood-2014-07-585737. Epub Oct. 1, 2014.
Nishimura et al., "Factor IX Fukuoka—Substitution of ASN[92] by His in the second epidermal growth factor-like domain results in defective interaction with factors VIIIa/X," Journal of Biological Chemistry, Nov. 15, 1993, 268(32):24041-24046.
Nogami, "Bispecific Antibody that Substitutes for Factor VIII in the Treatment of Childhood Hemophilia A," The Japanese Journal of Pediatric Hematology/Oncology, 2016, 53(2):69-74 (with English translation).
Shima et al., "Factor VIII—Mimetic Function of Humanized Bispecific Antibody in Hemophilia A," The New England Journal of Medicine, May 26, 2016, 374(21):2044-2053. doi: 10.1052/NEJMoa1511769.
Shima, "The Forefront and Prospects of Hemophilia Treatment," J Jpn Pediatr Soc, Mar. 1, 2017, 121(3):543-552 (with English translation).
Tarantino et al., "Safety of human plasma-derived clotting factor products and their role in haemostasis in patients with haemophilia meeting report," Haemophilia, Sep. 2007, 13(5):663-9.
Uchida et al., "A first-in-human phase 1 study of ACE910, a novel factor VIII-mimetic bispecific antibody, in healthy subjects," Blood, Mar. 2016, 127(13):1633-1641. doi: 10.1182/blood-2015-06-650226. Epub Dec. 1, 2015.
USPTO Final Office Action in U.S. Appl. No. 14/351,654, dated Apr. 14, 2016, 11 pages (document submitted in opposition of EP 2 787 078 on Feb. 28, 2020).
U.S. Appl. No. 17/076,938, filed Oct. 22, 2020, Igawa et al.
U.S. Appl. No. 17/130,736, filed Dec. 22, 2020, Hattori et al.
Adlersberg et al., "The Immunoglobulin Hinge (Interdomain) Region," Ric Clin Lab, Jul.-Sep. 1976, 6(3):191-205.
Dall'Acqua et al., "Contribution of Domain Interface Residues to the Stability of Antibody CH3 Domain Homodimers," Biochemistry, Jun. 30, 1998, 37(26):9266-9273. doi: 10.1021/bi980270i. PMID: 9649307.
Declaration of Christian Beil, signed Jun. 18, 2020, submitted by the opponent in Opposition of EP 3 050 963, 6 pages.
Filmus et al., "Glypicans," Genome Biol, May 22, 2008, 9(5):224, 6 pages. doi:10.1186/gb-2008-9-5-224.
Helguera et al., "Antibody-Cytokine Fusion Proteins for the Therapy of Cancer," Methods Mol Med, 2005, 109:347-374. doi: 10.1385/1-59259-862-5:347. PMID: 15585931.
Hugo et al., "Functional aspects of co-variant surface charges in an antibody fragment," Protein Sci, Nov. 2002, 11(11):2697-2705. doi: 10.1110/ps.0209302. PMID: 12381851; PMCID: PMC2373727.
Ogiwara et al., "Effect of Emicizumab in improving coagulation ability in the presence of minor amount of Factor IX," Japanese Journal of Thrombosis and Hemostasis, 2017, 28(2):190 0-012.
Otomo et al., "Structure of the heterodimeric complex between CAD domains of CAD and ICAD," Nat Struct Biol, Aug. 2000, 7(8):658-662. doi: 10.1038/77957. PMID: 10932250.
Raghavan et al., "Fc Receptors and Their Interactions with Immunoglobulins," Annu Rev Cell Dev Biol, Nov. 1996, 12:181-220.
Reference table: IMGT exon, EU and Kabat numbering of residues within the human IgG1 sequence; retrieved from http://www.imgt.org/IMGTScientificChart/Numbering/Hu_IGHGnber.html on Jun. 1, 2020, 4 pages (cited by the opponents in the Opposition procedure in the corresponding European Patent No. 3 050 963, which was notified to the patentee on Jul. 3, 2020).
Singer et al., Chapter 1.3 "Structure of Proteins," Genes & Genomes, 1998, pp. 63-64 (in Russian, with what are believed to be corresponding pages from an English version of Genes & Genomes, pp. 67-70).
USPTO Non-Final Office Action in U.S. Appl. No. 11/910,128, dated Nov. 28, 2016, 17 pages.
U.S. Appl. No. 15/963,345, Hattori et al., filed Apr. 26, 2018.
U.S. Appl. No. 15/132,996, Igawa et al., filed Apr. 19, 2016.
U.S. Appl. No. 15/288,965, Igawa et al., filed Oct. 7, 2016.
U.S. Appl. No. 14/680,250, Igawa et al., filed Apr. 7, 2015.
U.S. Appl. No. 14/962,293, Igawa et al., filed Dec. 8, 2015.
U.S. Appl. No. 13/497,269, Kuramochi et al., filed Jun. 1, 2012.
U.S. Appl. No. 13/582,073, Kuramochi et al., filed Dec. 20, 2012.
U.S. Appl. No. 15/617,008, Igawa et al., filed Jun. 8, 2017.
U.S. Appl. No. 15/875,847, Igawa et al., filed Jan. 19, 2018.
U.S. Appl. No. 15/467,654, Nezu et al., filed Mar. 23, 2017.
U.S. Appl. No. 15/024,063, Igawa et al., filed Mar. 23, 2016.
U.S. Appl. No. 10/575,905, Hattori et al., filed Apr. 30, 2007 (abandoned).
U.S. Appl. No. 11/910,836, Hattori et al., filed Jan. 12, 2009 (abandoned).

(56) References Cited

OTHER PUBLICATIONS

U.S. Appl. No. 13/434,643, Hattori et al., filed Mar. 29, 2012 (abandoned).
U.S. Appl. No. 14/921,590, Hattori et al., filed Oct. 23, 2015 (abandoned).
U.S. Appl. No. 15/172,727, Hattori et al., filed Jun. 3, 2016 (abandoned).
U.S. Appl. No. 15/402,580, Hattori et al., filed Jan. 10, 2017 (abandoned).
U.S. Appl. No. 15/701,630, Hattori et al., filed Sep. 12, 2017 (abandoned).
U.S. Appl. No. 15/963,345, Hattori et al., filed Apr. 26, 2018 (abandoned).
U.S. Appl. No. 16/226,798, Hattori et al., filed Dec. 20, 2018 (abandoned).
U.S. Appl. No. 16/536,385, Hattori et al., filed Aug. 9, 2019 (abandoned).
U.S. Appl. No. 16/825,513, Hattori et al., filed Mar. 20, 2020 (abandoned).
U.S. Appl. No. 17/130,736, Hattori et al., filked Dec. 22, 2020.
U.S. Appl. No. 14/019,117, Igawa et al., filed Sep. 5, 2013 (abandoned).
U.S. Appl. No. 14/019,712, Igawa et al., filed Sep. 6, 2013 (abandoned).
U.S. Appl. No. 15/288,965, Igawa et al., filed Oct. 7, 2016 (abandoned).
U.S. Appl. No. 16/459,791, Igawa et al., filed Jul. 2, 2019.
U.S. Appl. No. 12/295,039, Igawa et al., filed Jan. 20, 2009.
U.S. Appl. No. 15/725,692, Igawa et al., filed Oct. 5, 2017.
U.S. Appl. No. 15/614,842, Igawa et al., filed Jun. 6, 2017.
U.S. Appl. No. 13/257,145, Igawa et al., filed Nov. 22, 2011 (abandoned).
U.S. Appl. No. 16/298,032, Igawa et al., filed Mar. 11, 2019.
U.S. Appl. No. 15/490,936, Igawa et al., filed Apr. 19, 2017.
U.S. Appl. No. 13/518,861, Igawa et al., filed Oct. 4, 2012.
U.S. Appl. No. 15/617,008, Igawa et al., filed Jun. 8, 2017 (abandoned).
U.S. Appl. No. 15/875,847, Igawa et al., filed Jan. 19, 2018 (abandoned).
U.S. Appl. No. 16/155,673, Igawa et al., filed Oct. 9, 2018 (abaondoned).
U.S. Appl. No. 16/448,088, Igawa et al., filed Jun. 21, 2019 (abandoned).
U.S. Appl. No. 16/815,089, Igawa et al., filed Mar. 11, 2020 (abandoned).
U.S. Appl. No. 17/076,938, Igawa et al., filed Oct. 22, 2020.
U.S. Appl. No. 14/351,654, Kuramochi et al., filed Apr. 14, 2014.
U.S. Appl. No. 16/692,676, Kuramochi et al., filed Nov. 22, 2019.
U.S. Appl. No. 15/782,256, Igawa et al., filed Oct. 12, 2017.
U.S. Appl. No. 16/061,454, Tanaka et al., filed Jun. 12, 2018.
U.S. Appl. No. 16/093,495, Saeki et al., filed Oct. 12, 2018.
U.S. Appl. No. 16/496,089, Shima et al., filed Sep. 20, 2019.
U.S. Appl. No. 15/963,221, Nezu et al., filed Apr. 26, 2018.
U.S. Appl. No. 16/083,975, Kinoshita et al., filed Sep. 11, 2018.

* cited by examiner

[Figure 1]
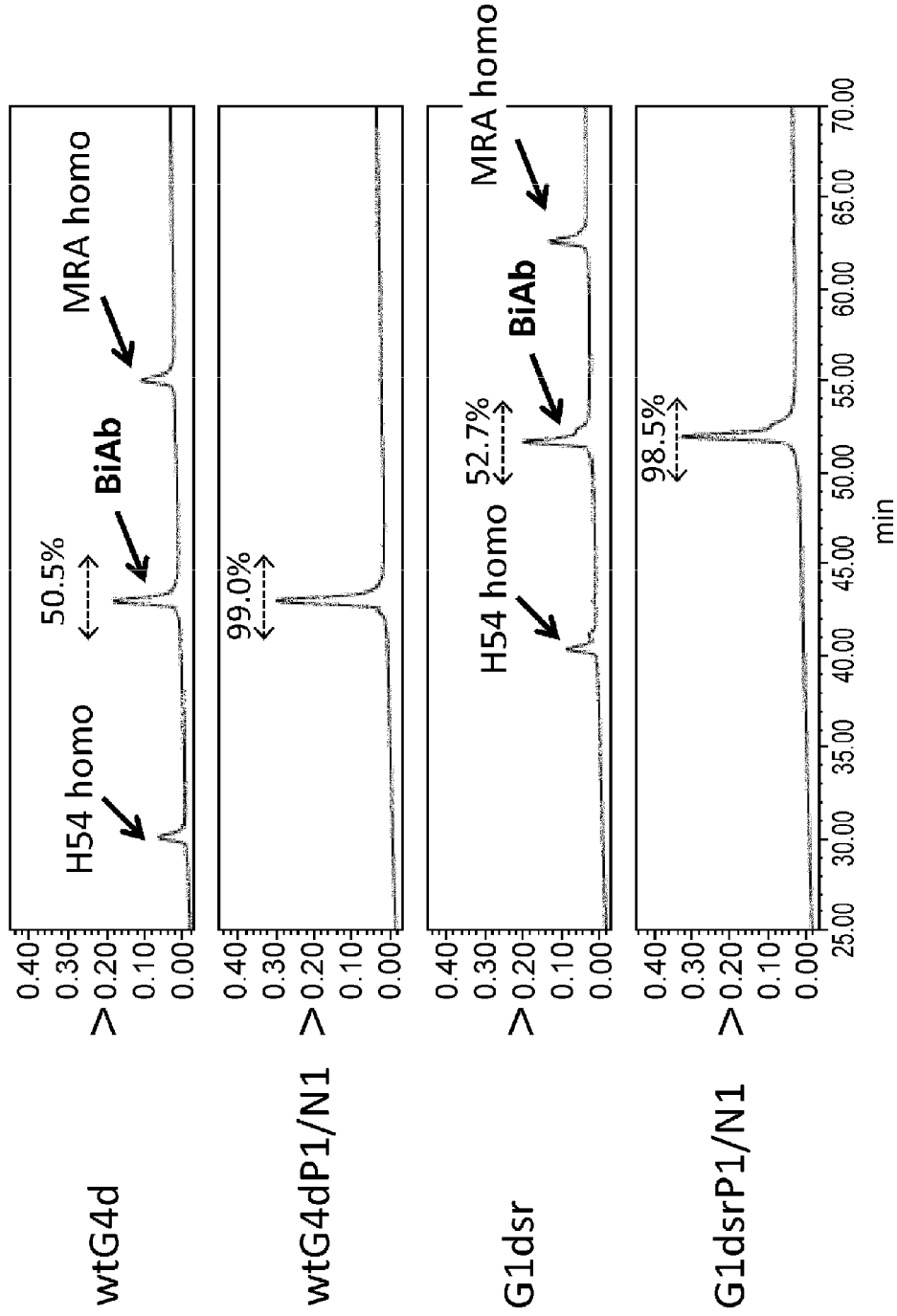

[Figure 2]
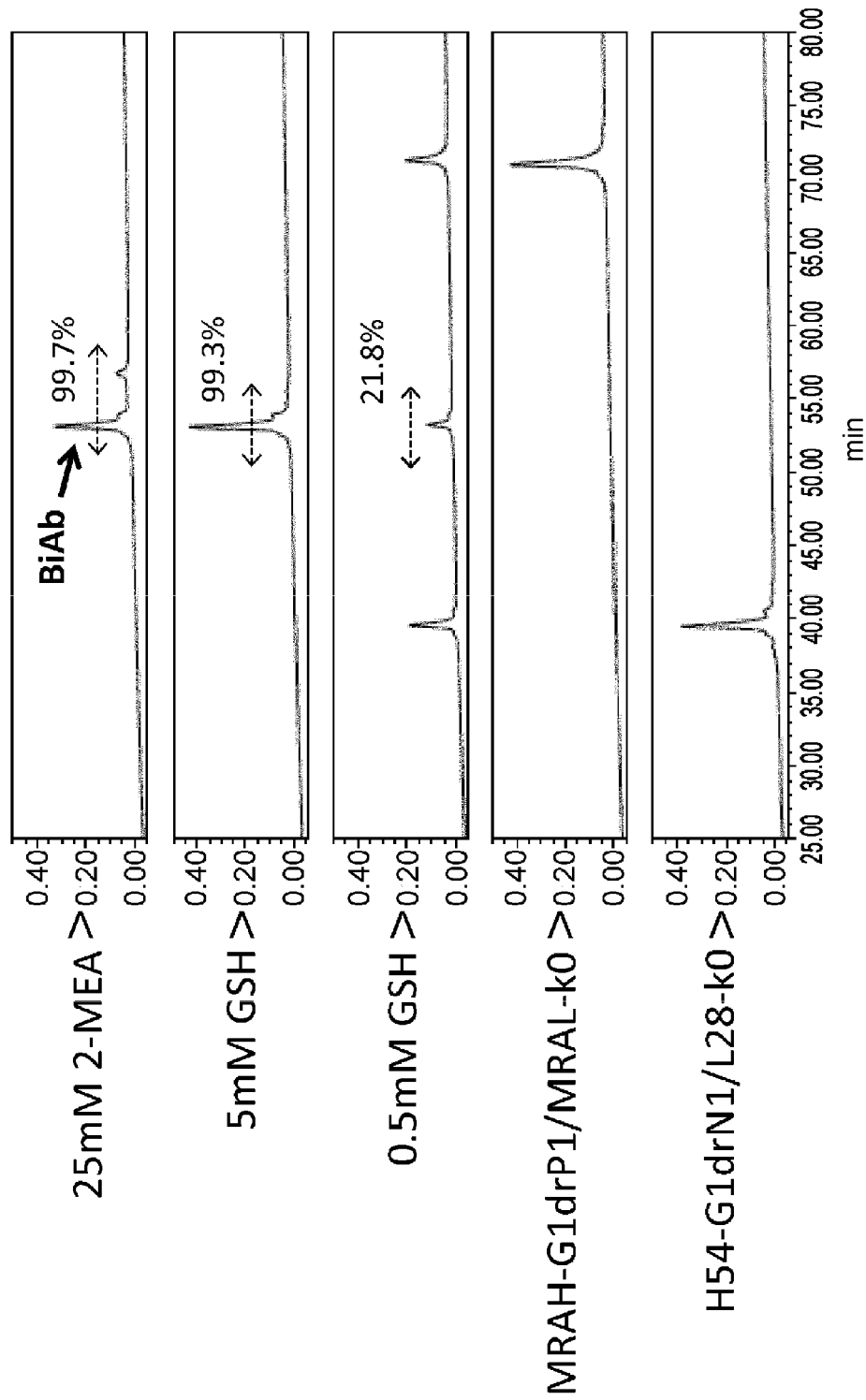

[Figure 3]
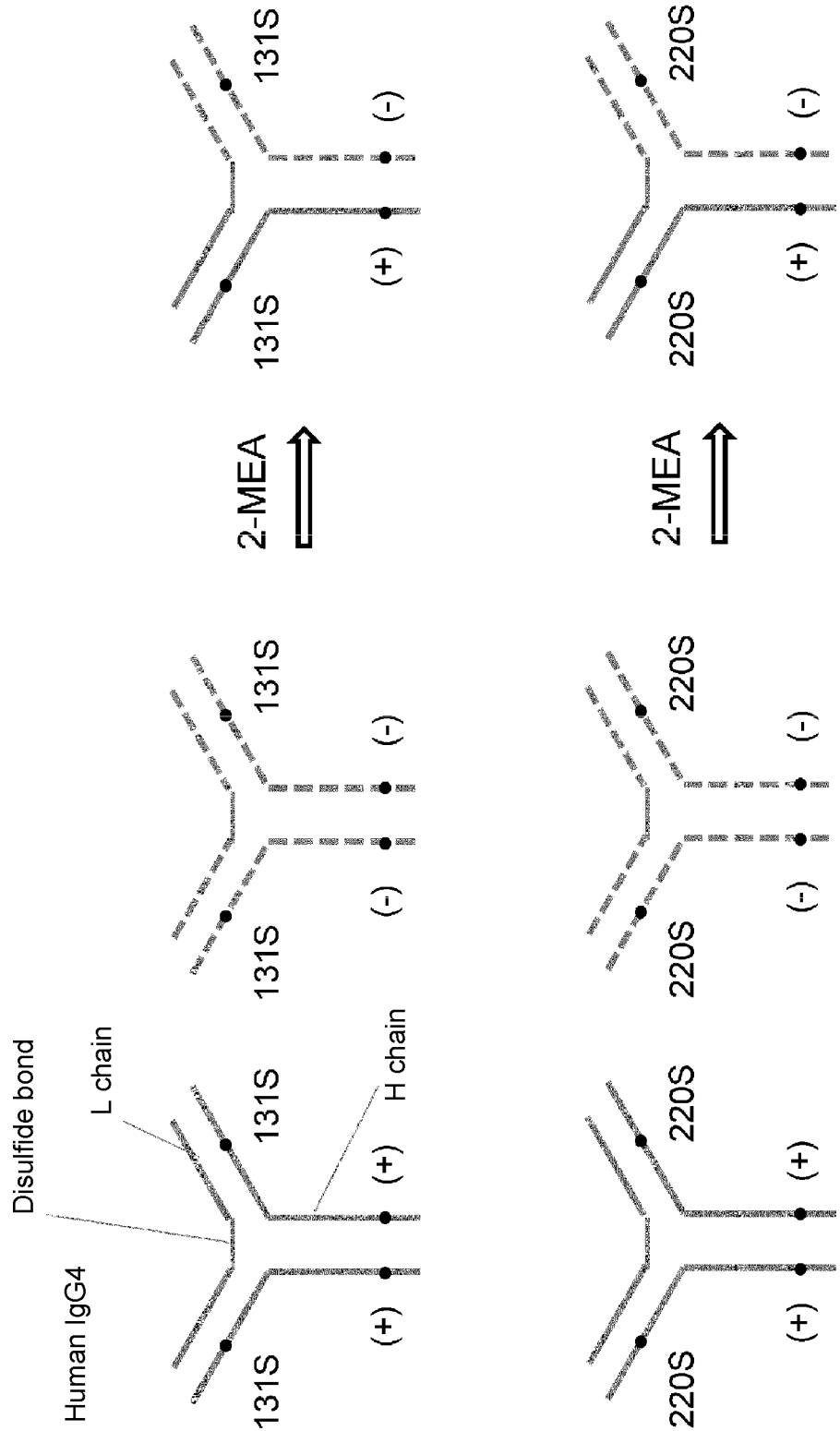

[Figure 4]
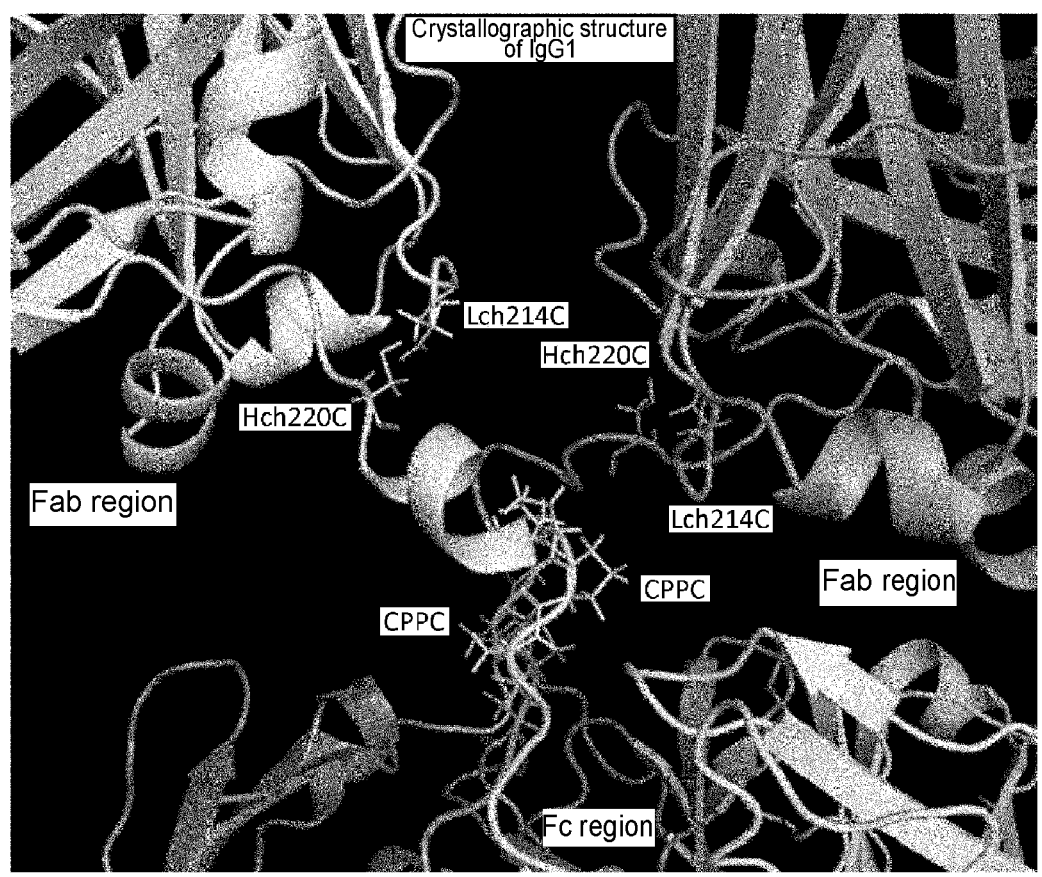

[Figure 5-1]
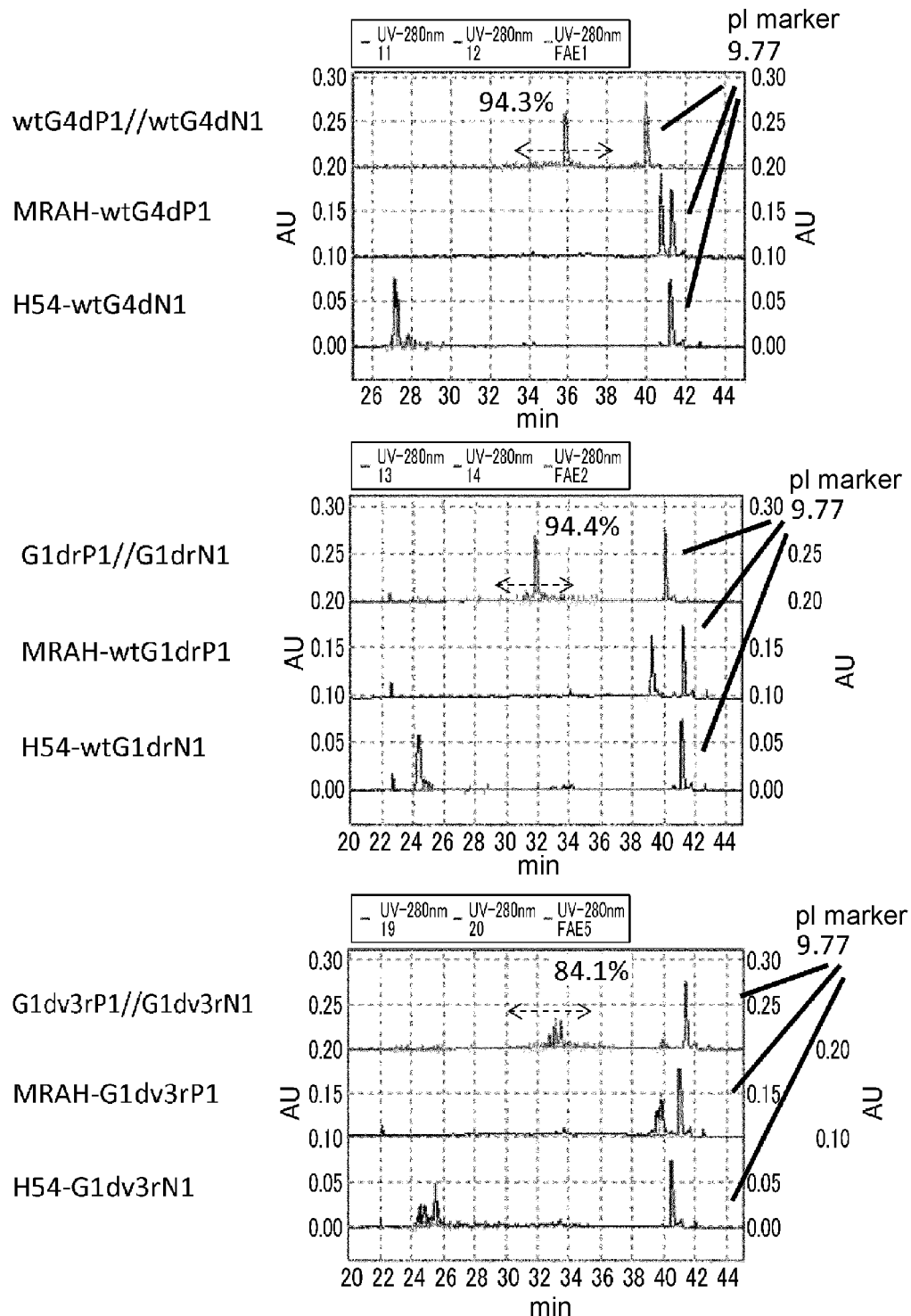

[Figure 5-2]
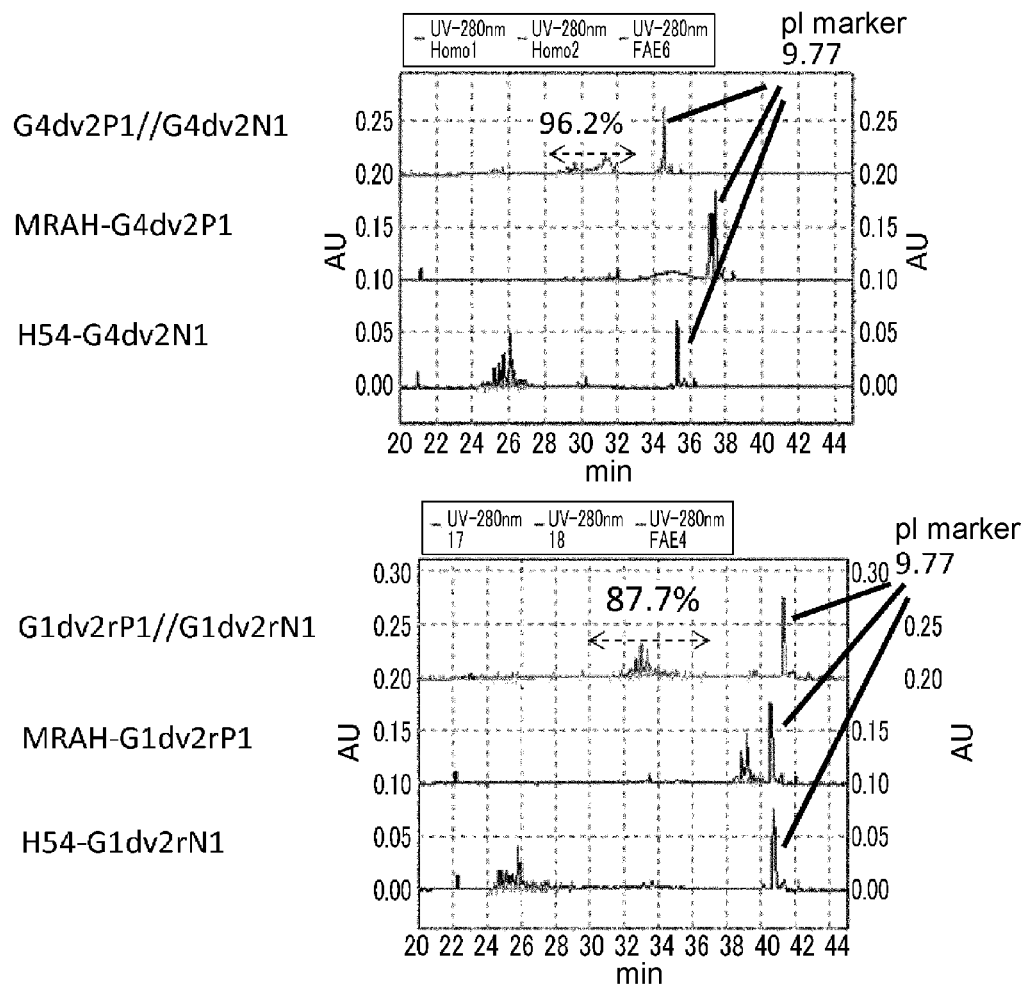

[Figure 6]
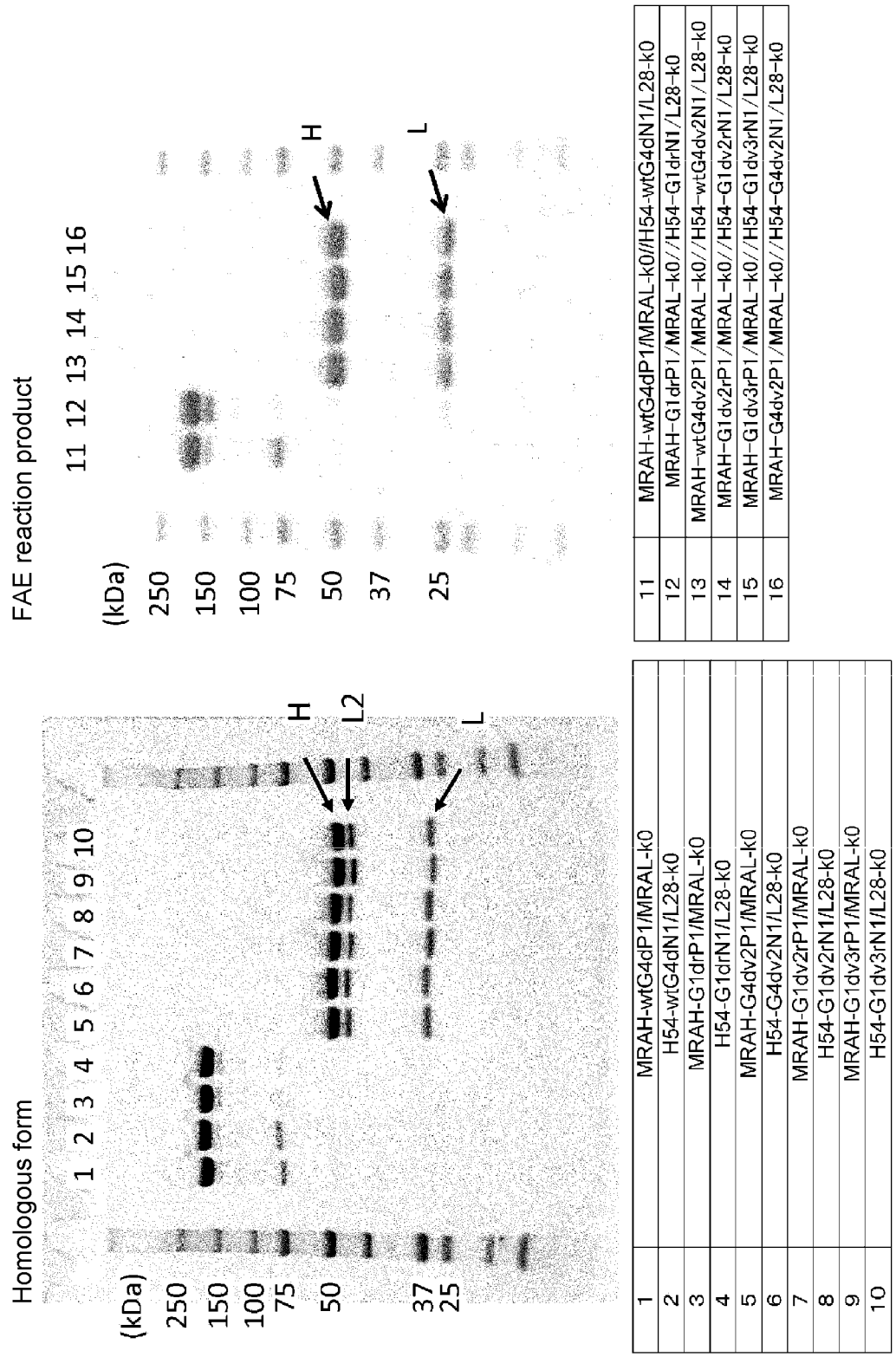

[Figure 7-1]
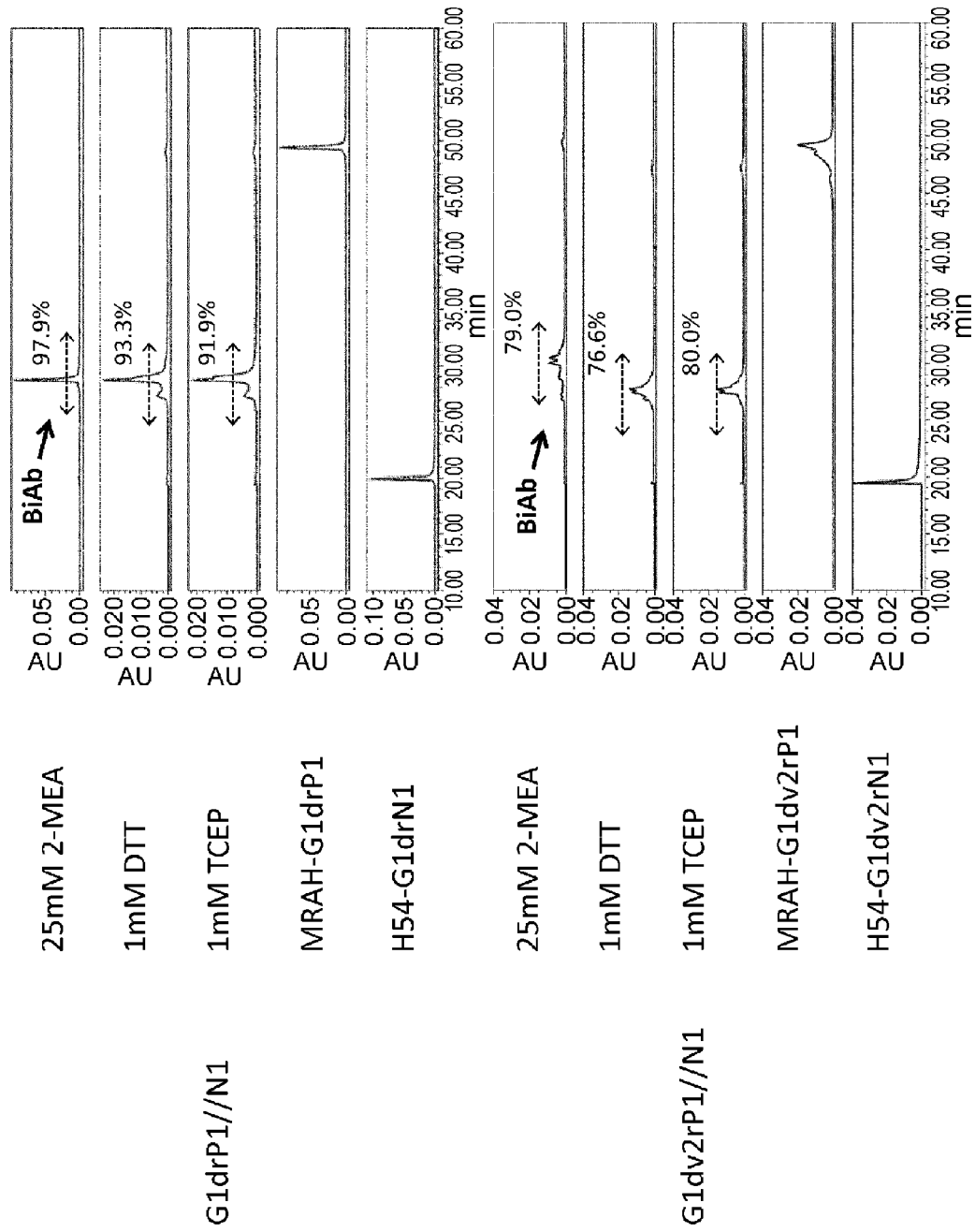

[Figure 7-2]
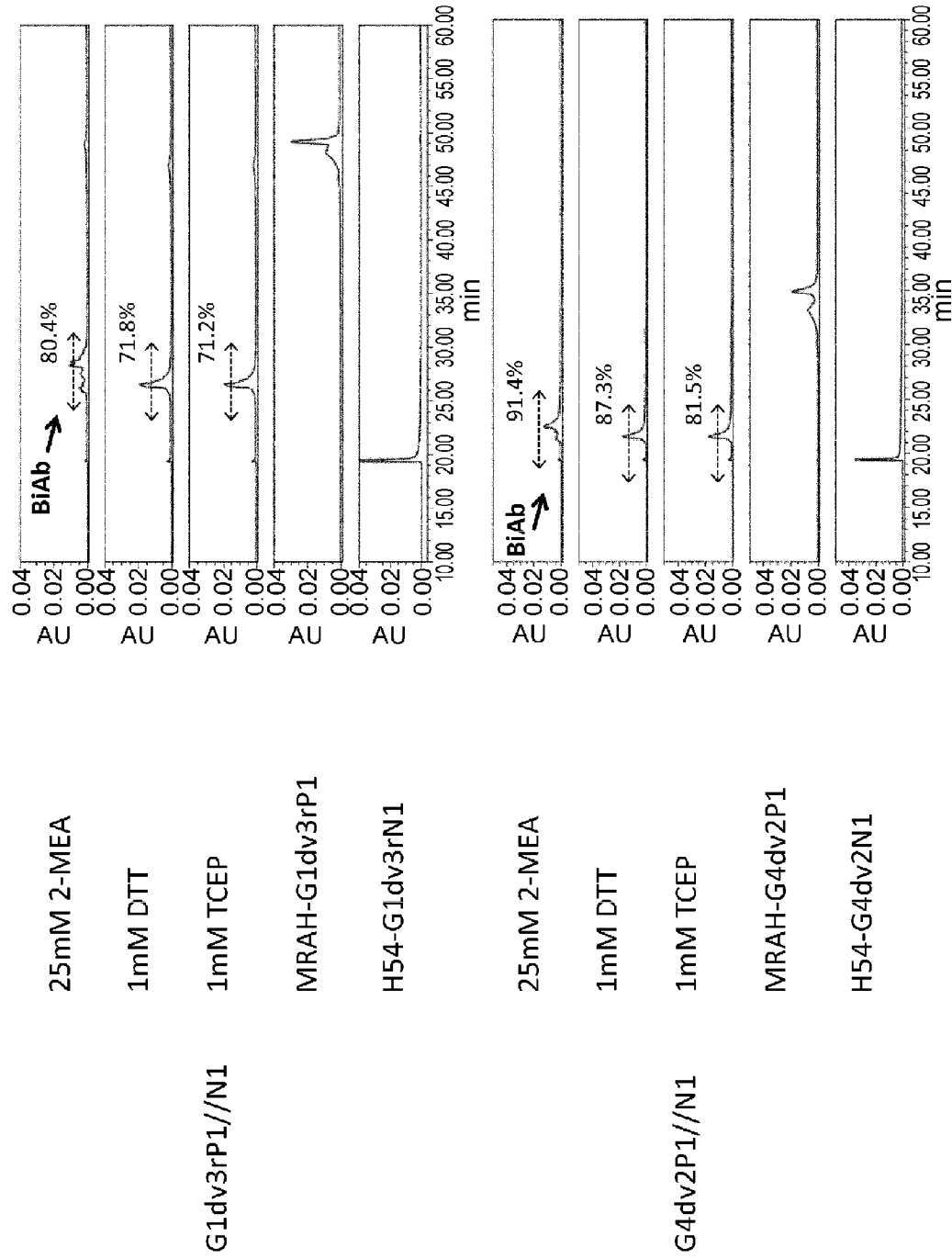

[Figure 8]
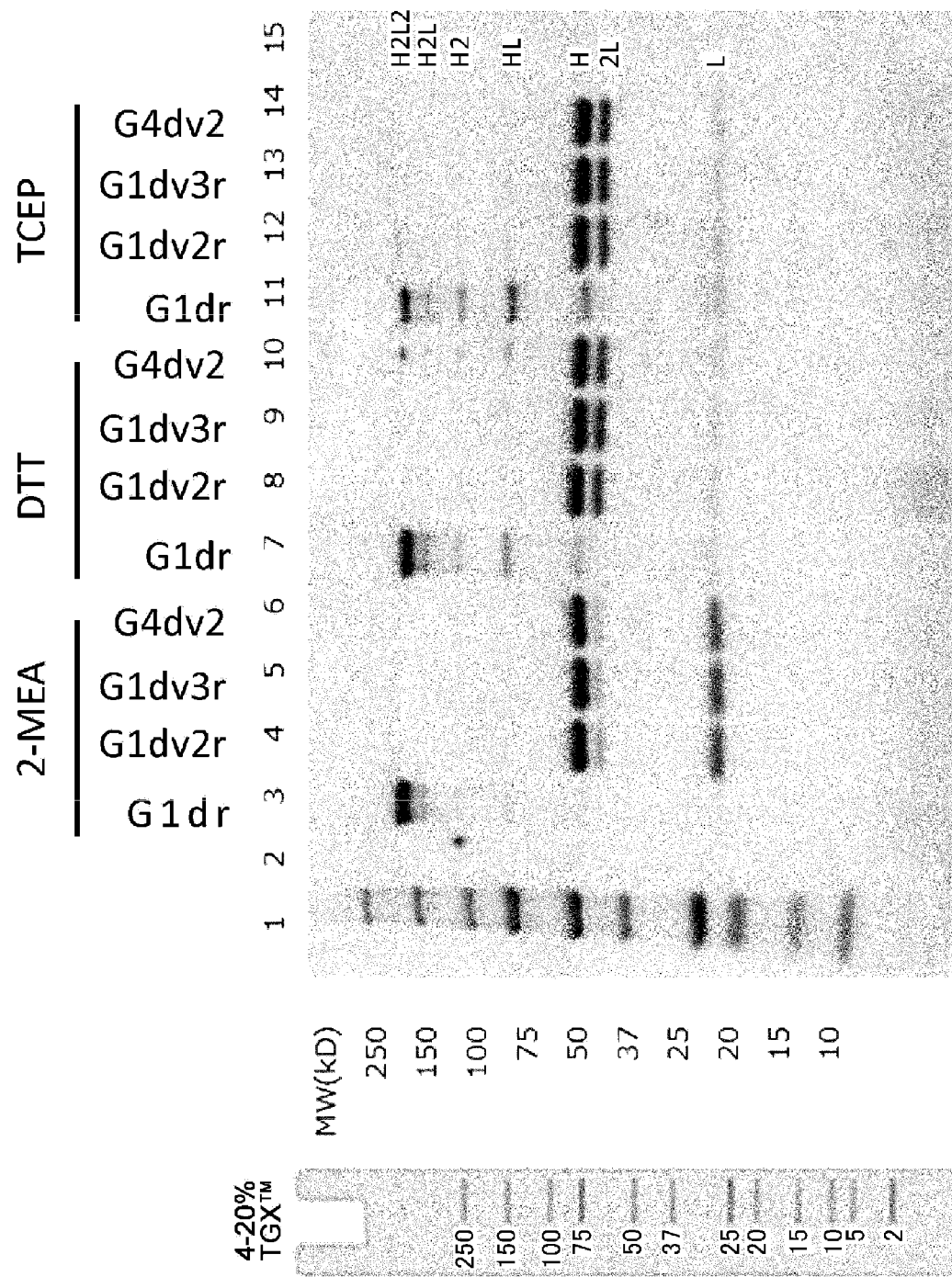

[Figure 9]
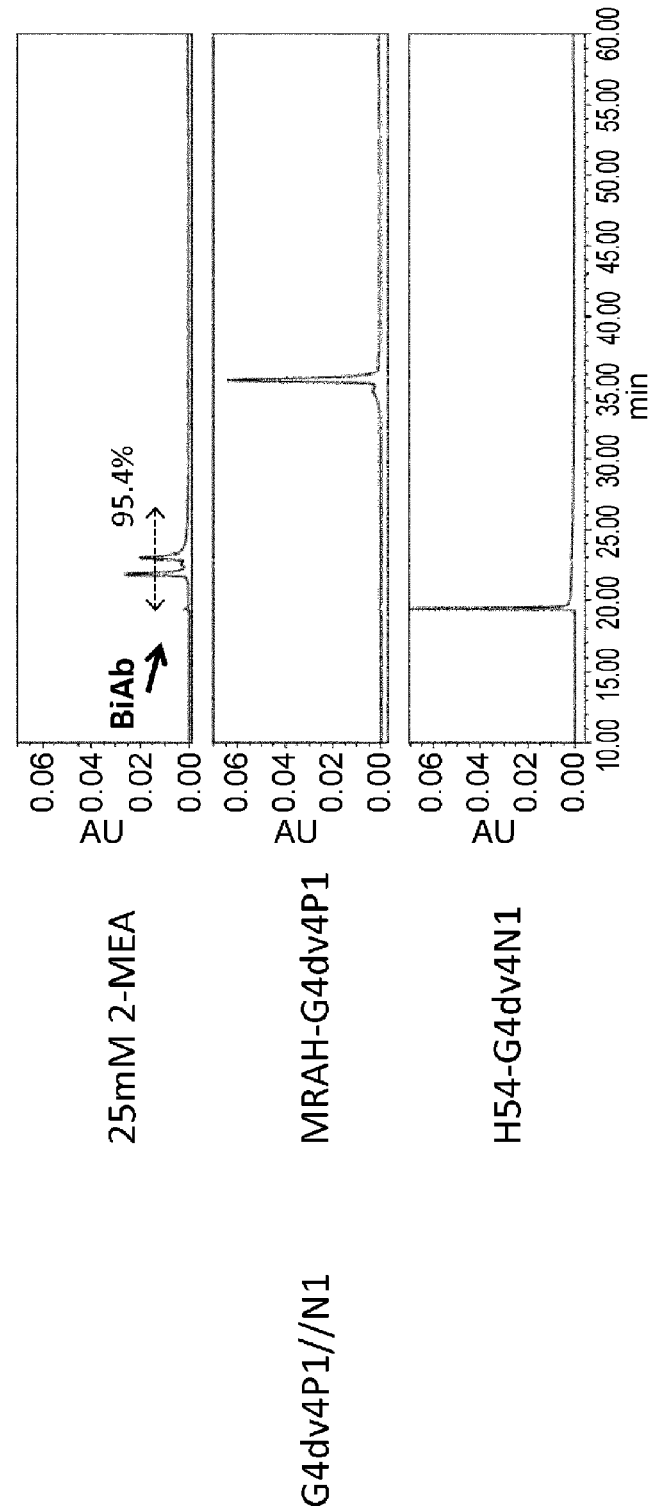

[Figure 10]
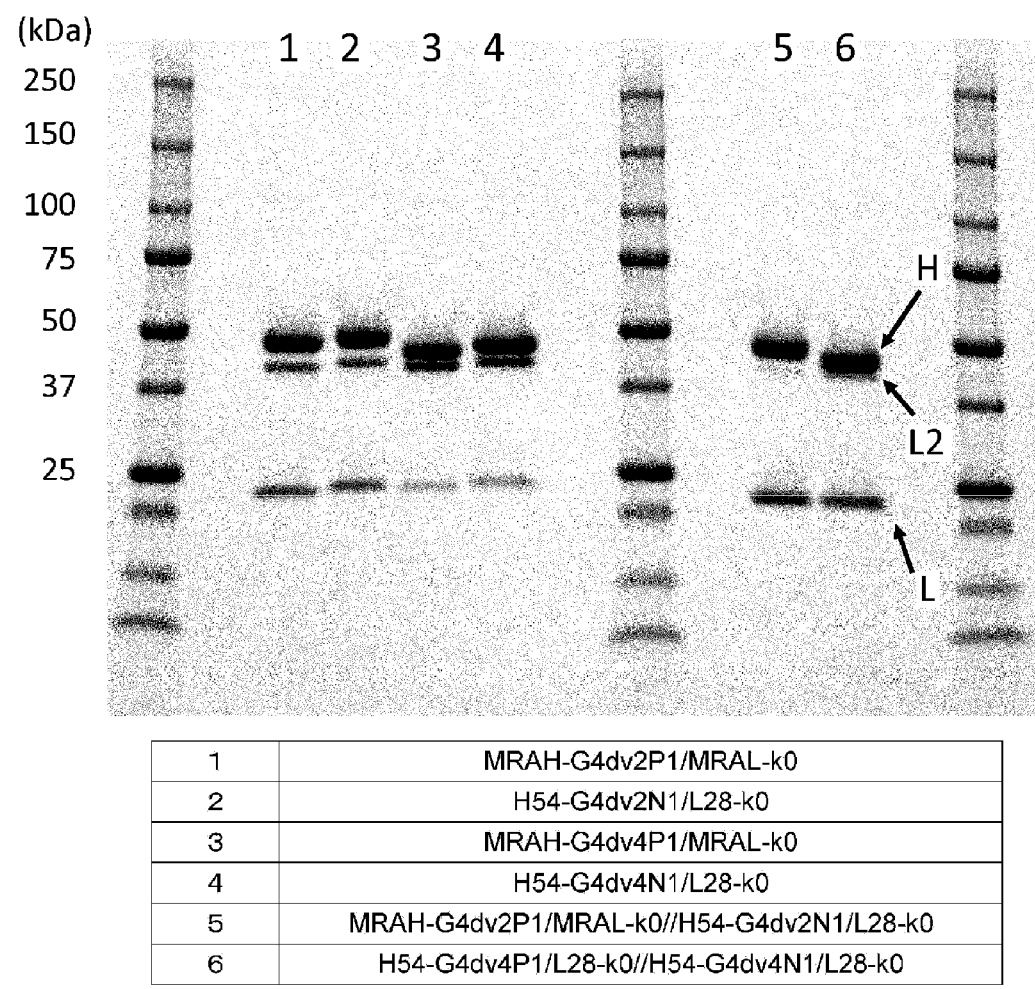
| 1 | MRAH-G4dv2P1/MRAL-k0 |
| 2 | H54-G4dv2N1/L28-k0 |
| 3 | MRAH-G4dv4P1/MRAL-k0 |
| 4 | H54-G4dv4N1/L28-k0 |
| 5 | MRAH-G4dv2P1/MRAL-k0//H54-G4dv2N1/L28-k0 |
| 6 | H54-G4dv4P1/L28-k0//H54-G4dv4N1/L28-k0 |

[Figure 11]
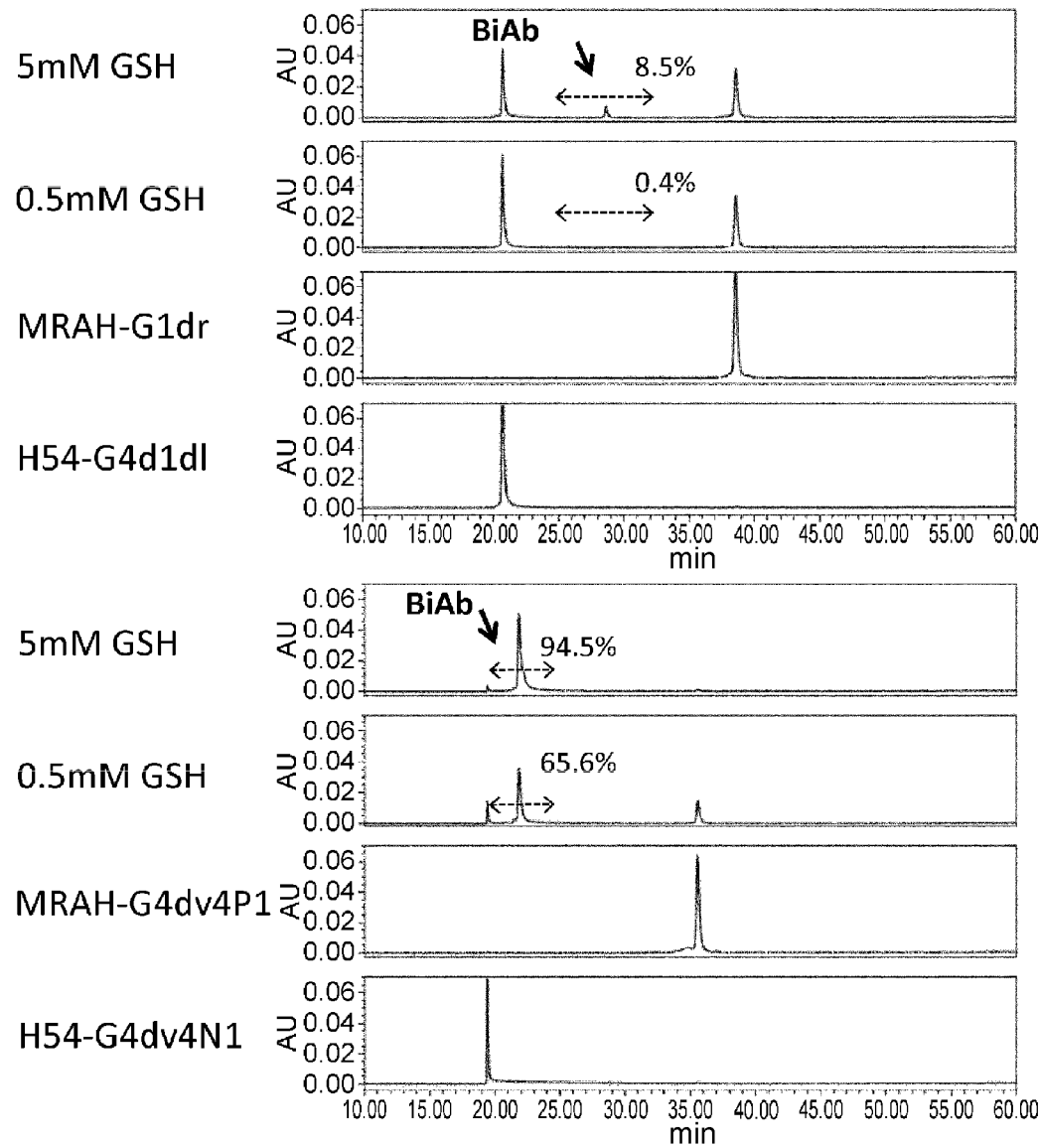

[Figure 12-1]
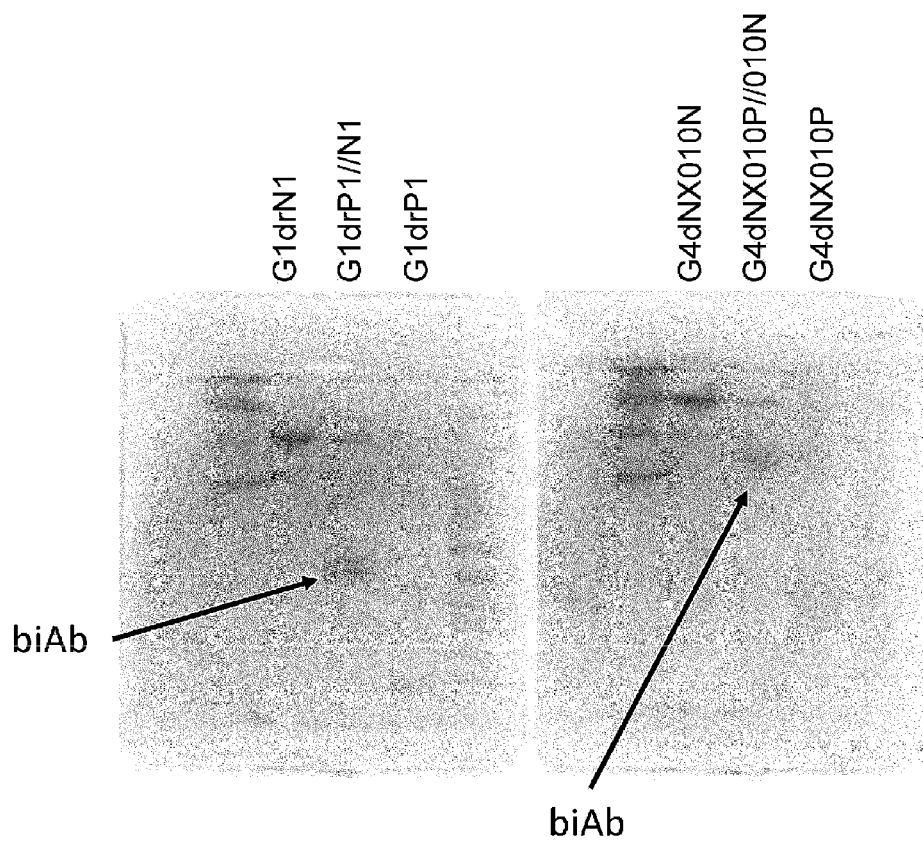

[Figure 12-2]
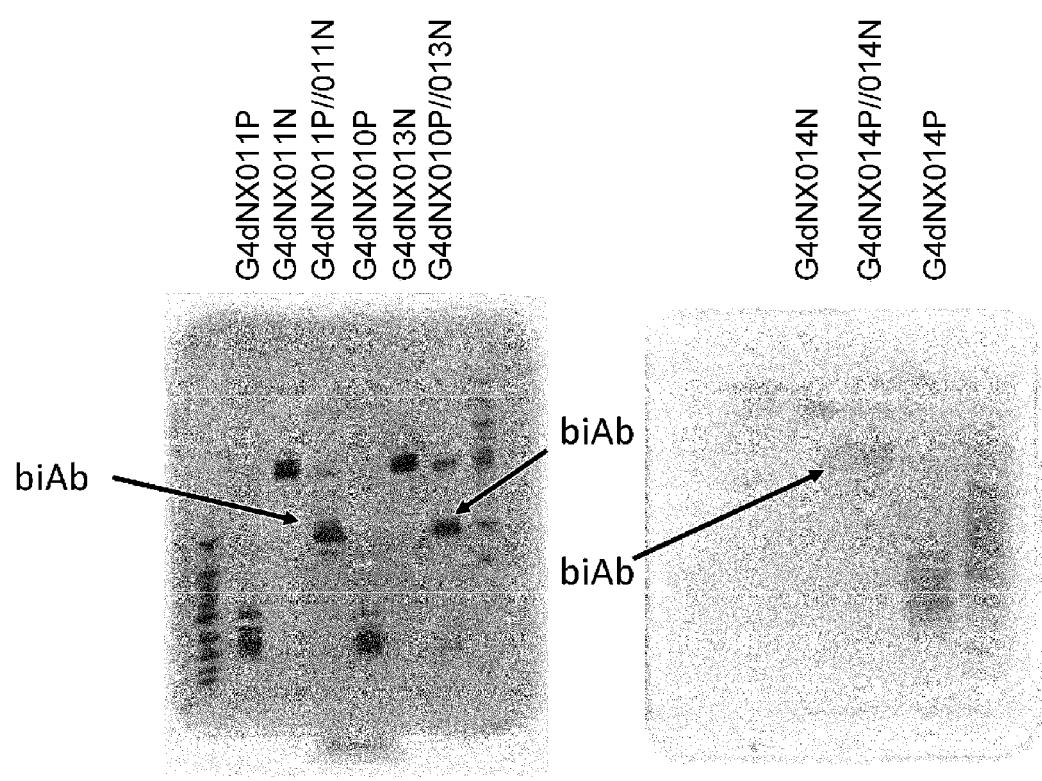

[Figure 13-1]
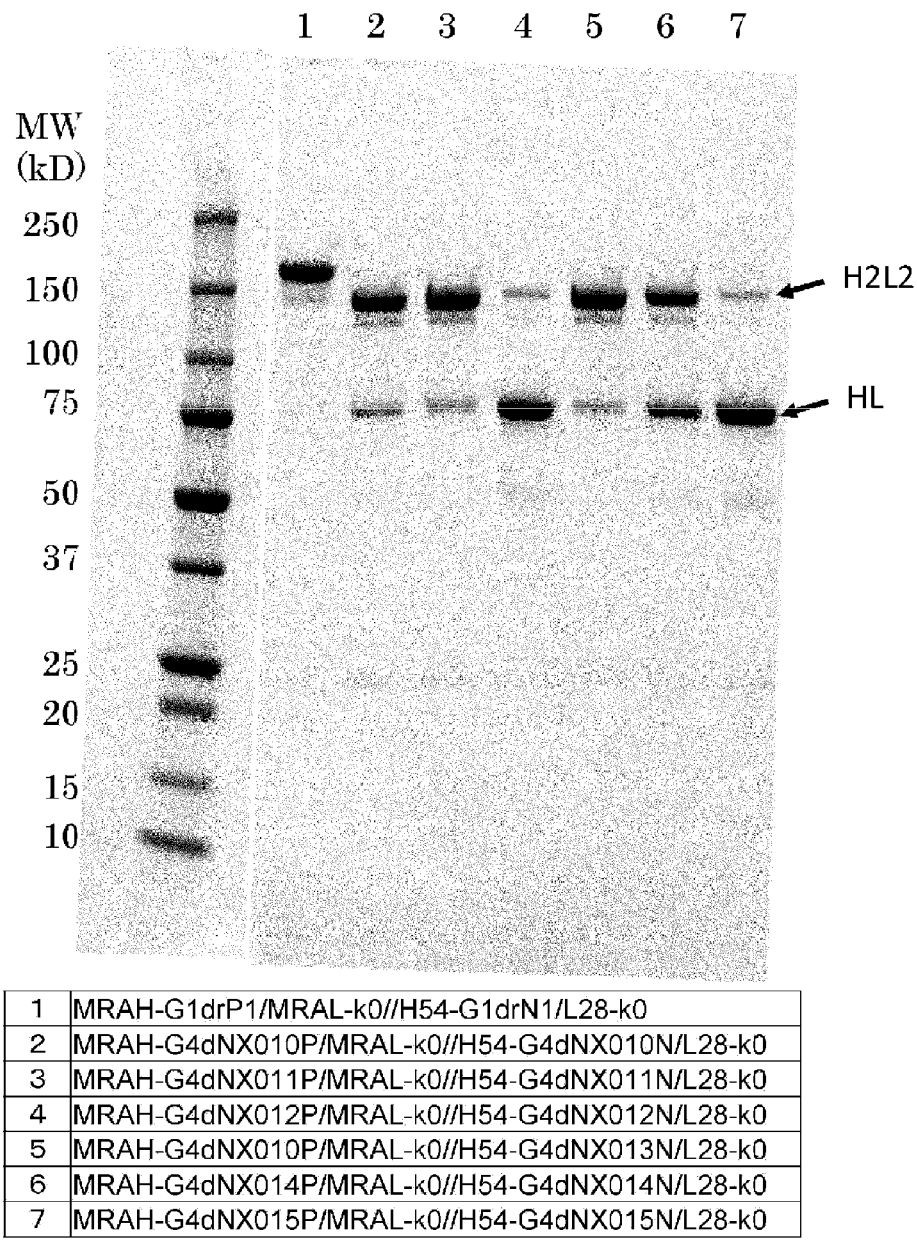

[Figure 13-2]
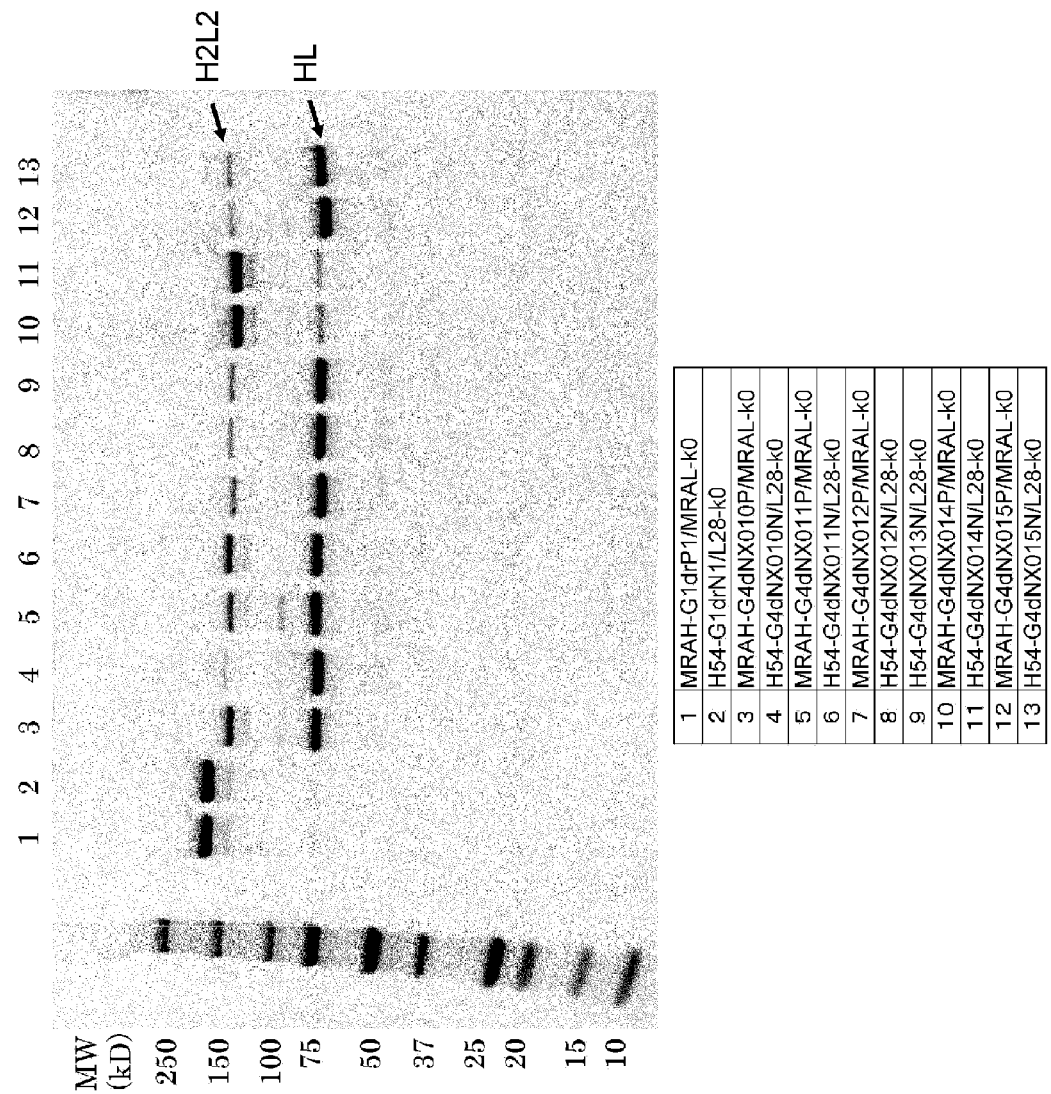

SEQUENCE LISTING

```
<160> NUMBER OF SEQ ID NOS: 47

<210> SEQ ID NO 1
<211> LENGTH: 119
<212> TYPE: PRT
<213> ORGANISM: Artificial sequence
<220> FEATURE:
<223> OTHER INFORMATION: MRAH

<400> SEQUENCE: 1

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser
        115

<210> SEQ ID NO 2
<211> LENGTH: 119
<212> TYPE: PRT
<213> ORGANISM: Artificial sequence
<220> FEATURE:
<223> OTHER INFORMATION: H54

<400> SEQUENCE: 2

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

Gln Ala Trp Ser Trp Val Arg Gln Pro Pro Gly Glu Gly Leu Glu Trp
        35                  40                  45
```

```
Ile Gly Tyr Ile Ser Tyr Ser Gly Ile Thr Asn Tyr Asn Pro Ser Leu
         50                  55                  60

Lys Gly Arg Val Thr Ile Ser Arg Asp Thr Ser Lys Asn Gln Phe Ser
 65                  70                  75                  80

Leu Lys Leu Ser Ser Val Thr Ala Ala Asp Thr Ala Ala Tyr Tyr Cys
                 85                  90                  95

Ala Arg Ser Leu Ala Arg Thr Thr Ala Met Asp Tyr Trp Gly Glu Gly
                100                 105                 110

Thr Leu Val Thr Val Ser Ser
            115

<210> SEQ ID NO 3
<211> LENGTH: 447
<212> TYPE: PRT
<213> ORGANISM: Artificial sequence
<220> FEATURE:
<223> OTHER INFORMATION: MRAH-G1d

<400> SEQUENCE: 3

Gln Val Gln Leu Gln Glu Ser Gly Pro Gly Leu Val Arg Pro Ser Gln
 1               5                  10                  15

Thr Leu Ser Leu Thr Cys Thr Val Ser Gly Tyr Ser Ile Thr Ser Asp
                 20                  25                  30

His Ala Trp Ser Trp Val Arg Gln Pro Pro Gly Arg Gly Leu Glu Trp
             35                  40                  45

Ile Gly Tyr Ile Ser Tyr Ser Gly Ile Thr Thr Tyr Asn Pro Ser Leu
         50                  55                  60

Lys Ser Arg Val Thr Met Leu Arg Asp Thr Ser Lys Asn Gln Phe Ser
 65                  70                  75                  80

Leu Arg Leu Ser Ser Val Thr Ala Ala Asp Thr Ala Val Tyr Tyr Cys
                 85                  90                  95

Ala Arg Ser Leu Ala Arg Thr Thr Ala Met Asp Tyr Trp Gly Gln Gly
                100                 105                 110

Ser Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285
```

```
Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro
            435                 440                 445

<210> SEQ ID NO 4
<211> LENGTH: 447
<212> TYPE: PRT
<213> ORGANISM: Artificial sequence
<220> FEATURE:
<223> OTHER INFORMATION: H54-G1d

<400> SEQUENCE: 4

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
                20                  25                  30

Gln Ala Trp Ser Trp Val Arg Gln Pro Pro Gly Glu Gly Leu Glu Trp
            35                  40                  45

Ile Gly Tyr Ile Ser Tyr Ser Gly Ile Thr Asn Tyr Asn Pro Ser Leu
        50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Ser Leu Ala Arg Thr Thr Ala Met Asp Tyr Trp Gly Glu Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205
```

```
Ser Asn Thr Lys Val Asp Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445

<210> SEQ ID NO 5
<211> LENGTH: 444
<212> TYPE: PRT
<213> ORGANISM: Artificial sequence
<220> FEATURE:
<223> OTHER INFORMATION: MRAH-wtG4d

<400> SEQUENCE: 5

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125
```

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Ser Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu
        435                 440

<210> SEQ ID NO 6
<211> LENGTH: 444
<212> TYPE: PRT
<213> ORGANISM: Artificial sequence
<220> FEATURE:
<223> OTHER INFORMATION: H54-wtG4d

<400> SEQUENCE: 6

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

Gln Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
 50                  55                  60

Lys Gly Arg Val Thr Ile Ser Arg Asp Thr Ser Lys Asn Gln Phe Ser
 65                  70                  75                  80

Leu Lys Leu Ser Ser Val Thr Ala Ala Asp Thr Ala Ala Tyr Tyr Cys
                 85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Ser Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu
        435                 440

<210> SEQ ID NO 7
<211> LENGTH: 447

<212> TYPE: PRT
<213> ORGANISM: Artificial sequence
<220> FEATURE:
<223> OTHER INFORMATION: MRAH-G1dsr

<400> SEQUENCE: 7

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Ser Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

```
Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro
    435                 440                 445

<210> SEQ ID NO 8
<211> LENGTH: 447
<212> TYPE: PRT
<213> ORGANISM: Artificial sequence
<220> FEATURE:
<223> OTHER INFORMATION: H54-G1dsr

<400> SEQUENCE: 8

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

Gln Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
            85                  90                  95

Ala Arg Ser Leu Ala Arg Thr Thr Ala Met Asp Tyr Trp Gly Glu Gly
        100                 105                 110

Thr Leu Val Thr Val Ser Ser Ala Ser Thr Lys Gly Pro Ser Val Phe
    115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
    195                 200                 205

Ser Asn Thr Lys Val Asp Lys Lys Val Glu Pro Lys Ser Cys Asp Lys
210                 215                 220

Thr His Thr Cys Pro Ser Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
    275                 280                 285

Ala Lys Thr Lys Pro Arg Glu Glu Gln Tyr Asn Ser Thr Tyr Arg Val
    290                 295                 300
```

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445

<210> SEQ ID NO 9
<211> LENGTH: 447
<212> TYPE: PRT
<213> ORGANISM: Artificial sequence
<220> FEATURE:
<223> OTHER INFORMATION: MRAH-G1dsrP1

<400> SEQUENCE: 9

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

```
Thr His Thr Cys Pro Ser Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
    275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
        340                 345                 350

Leu Pro Pro Ser Arg Lys Glu Leu Thr Lys Asn Gln Val Ser Leu Thr
    355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro
    435                 440                 445

<210> SEQ ID NO 10
<211> LENGTH: 447
<212> TYPE: PRT
<213> ORGANISM: Artificial sequence
<220> FEATURE:
<223> OTHER INFORMATION: H54-G1dsrN1

<400> SEQUENCE: 10

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

Gln Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
    50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
            85                  90                  95

Ala Arg Ser Leu Ala Arg Thr Thr Ala Met Asp Tyr Trp Gly Glu Gly
        100                 105                 110

Thr Leu Val Thr Val Ser Ser Ala Ser Thr Lys Gly Pro Ser Val Phe
    115                 120                 125

Pro Leu Ala Pro Ser Ser Lys Ser Thr Ser Gly Gly Thr Ala Ala Leu
130                 135                 140
```

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Ser Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445

<210> SEQ ID NO 11
<211> LENGTH: 444
<212> TYPE: PRT
<213> ORGANISM: Artificial sequence
<220> FEATURE:
<223> OTHER INFORMATION: MRAH-wtG4dP1

<400> SEQUENCE: 11

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

```
Lys Ser Arg Val Thr Met Leu Arg Asp Thr Ser Lys Asn Gln Phe Ser
 65                  70                  75                  80

Leu Arg Leu Ser Ser Val Thr Ala Ala Asp Thr Ala Val Tyr Tyr Cys
             85                  90                  95

Ala Arg Ser Leu Ala Arg Thr Thr Ala Met Asp Tyr Trp Gly Gln Gly
        100                 105                 110

Ser Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
210                 215                 220

Cys Pro Ser Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Lys Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu
        435                 440

<210> SEQ ID NO 12
<211> LENGTH: 444
<212> TYPE: PRT
<213> ORGANISM: Artificial sequence
<220> FEATURE:
<223> OTHER INFORMATION: H54-wtG4dN1
```

<400> SEQUENCE: 12

```
Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

Gln Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
    50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Ser Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
```

-continued

```
                        405                 410                 415
Gln Glu Gly Asn Val Phe Ser Cys Ser Val Met His Glu Ala Leu His
            420                 425                 430

Asn His Tyr Thr Gln Glu Ser Leu Ser Leu
        435                 440

<210> SEQ ID NO 13
<211> LENGTH: 214
<212> TYPE: PRT
<213> ORGANISM: Artificial sequence
<220> FEATURE:
<223> OTHER INFORMATION: MRAL-k0

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 14
<211> LENGTH: 214
<212> TYPE: PRT
<213> ORGANISM: Artificial sequence
<220> FEATURE:
<223> OTHER INFORMATION: L28-k0

<400> SEQUENCE: 14

Asp Ile Gln Met Thr Gln Ser Pro Ser Ser Leu Ser Ala Ser Val Gly
1               5                   10                  15

Asp Ser Val Thr Ile Thr Cys Gln Ala Ser Gln Asp Ile Ser Ser Tyr
            20                  25                  30

Leu Asn Trp Tyr Gln Gln Lys Pro Gly Lys Ala Pro Glu Leu Leu Ile
        35                  40                  45
```

```
Tyr Tyr Gly Ser Glu Leu His Ser Gly Val Pro Ser Arg Phe Ser Gly
     50                   55                  60

Ser Gly Ser Gly Thr Asp Phe Thr Phe Thr Ile Ser Ser Leu Glu Ala
 65              70                  75                      80

Glu Asp Ala Ala Thr Tyr Tyr Cys Gln Gln Gly Asn Ser Leu Pro Tyr
                 85                  90                  95

Thr Phe Gly Gln Gly Thr Lys Val Glu Ile Glu Arg Thr Val Ala Ala
            100                 105                 110

Pro Ser Val Phe Ile Phe Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
210

<210> SEQ ID NO 15
<211> LENGTH: 447
<212> TYPE: PRT
<213> ORGANISM: Artificial sequence
<220> FEATURE:
<223> OTHER INFORMATION: MRAH-G1drP1

<400> SEQUENCE: 15

Gln Val Gln Leu Gln Glu Ser Gly Pro Gly Leu Val Arg Pro Ser Gln
 1               5                  10                  15

Thr Leu Ser Leu Thr Cys Thr Val Ser Gly Tyr Ser Ile Thr Ser Asp
             20                  25                  30

His Ala Trp Ser Trp Val Arg Gln Pro Pro Gly Arg Gly Leu Glu Trp
         35                  40                  45

Ile Gly Tyr Ile Ser Tyr Ser Gly Ile Thr Thr Tyr Asn Pro Ser Leu
     50                  55                  60

Lys Ser Arg Val Thr Met Leu Arg Asp Thr Ser Lys Asn Gln Phe Ser
 65                  70                  75                  80

Leu Arg Leu Ser Ser Val Thr Ala Ala Asp Thr Ala Val Tyr Tyr Cys
                 85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190
```

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Lys Glu Leu Thr Lys Asn Gln Val Ser Leu Thr
    355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
    435                 440                 445

<210> SEQ ID NO 16
<211> LENGTH: 447
<212> TYPE: PRT
<213> ORGANISM: Artificial sequence
<220> FEATURE:
<223> OTHER INFORMATION: H54-G1drN1

<400> SEQUENCE: 16

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

Gln Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
    50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445

<210> SEQ ID NO 17
<211> LENGTH: 444
<212> TYPE: PRT
<213> ORGANISM: Artificial sequence
<220> FEATURE:
<223> OTHER INFORMATION: MRAH-G4d

<400> SEQUENCE: 17

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

-continued

His Ala Trp Ser Trp Val Arg Gln Pro Pro Gly Arg Gly Leu Glu Trp
                35                  40                  45
Ile Gly Tyr Ile Ser Tyr Ser Gly Ile Thr Thr Tyr Asn Pro Ser Leu
 50                  55                  60
Lys Ser Arg Val Thr Met Leu Arg Asp Thr Ser Lys Asn Gln Phe Ser
 65                  70                  75                  80
Leu Arg Leu Ser Ser Val Thr Ala Ala Asp Thr Ala Val Tyr Tyr Cys
                 85                  90                  95
Ala Arg Ser Leu Ala Arg Thr Thr Ala Met Asp Tyr Trp Gly Gln Gly
                100                 105                 110
Ser Leu Val Thr Val Ser Ser Ala Ser Thr Lys Gly Pro Ser Val Phe
                115                 120                 125
Pro Leu Ala Pro Cys Ser Arg Ser Thr Ser Glu Ser Thr Ala Ala Leu
130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
                180                 185                 190
Ser Ser Leu Gly Thr Lys Thr Tyr Thr Cys Asn Val Asp His Lys Pro
                195                 200                 205
Ser Asn Thr Lys Val Asp Lys Arg Val Glu Ser Lys Tyr Gly Pro Pro
                210                 215                 220
Cys Pro Pro Cys Pro Ala Pro Glu Phe Leu Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser Gln Glu Asp Pro Glu Val
                260                 265                 270
Gln Phe Asn Trp Tyr Val Asp Gly Val Glu Val His Asn Ala Lys Thr
                275                 280                 285
Lys Pro Arg Glu Glu Gln Phe Asn Ser Thr Tyr Arg Val Val Ser Val
290                 295                 300
Leu Thr Val Leu His Gln Asp Trp Leu Asn Gly Lys Glu Tyr Lys Cys
305                 310                 315                 320
Lys Val Ser Asn Lys Gly Leu Pro Ser Ser Ile Glu Lys Thr Ile Ser
                325                 330                 335
Lys Ala Lys Gly Gln Pro Arg Glu Pro Gln Val Tyr Thr Leu Pro Pro
                340                 345                 350
Ser Gln Glu Glu Met Thr Lys Asn Gln Val Ser Leu Thr Cys Leu Val
                355                 360                 365
Lys Gly Phe Tyr Pro Ser Asp Ile Ala Val Glu Trp Glu Ser Asn Gly
                370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Arg Leu Thr Val Asp Lys Ser Arg Trp
                405                 410                 415
Gln Glu Gly Asn Val Phe Ser Cys Ser Val Met His Glu Ala Leu His
                420                 425                 430
Asn His Tyr Thr Gln Lys Ser Leu Ser Leu Ser Leu
                435                 440

-continued

```
<210> SEQ ID NO 18
<211> LENGTH: 444
<212> TYPE: PRT
<213> ORGANISM: Artificial sequence
<220> FEATURE:
<223> OTHER INFORMATION: H54-G4d

<400> SEQUENCE: 18
```

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

Gln Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
    50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly

```
                    370                 375                 380
Gln Pro Glu Asn Asn Tyr Lys Thr Thr Pro Val Leu Asp Ser Asp
385                 390                 395                 400

Gly Ser Phe Phe Leu Tyr Ser Arg Leu Thr Val Asp Lys Ser Arg Trp
            405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu
            435                 440

<210> SEQ ID NO 19
<211> LENGTH: 444
<212> TYPE: PRT
<213> ORGANISM: Artificial sequence
<220> FEATURE:
<223> OTHER INFORMATION: MRAH-G4dv1

<400> SEQUENCE: 19

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
```

```
                    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                    325                 330                 335

Lys Ala Lys Gly Gln Pro Arg Glu Pro Gln Val Tyr Thr Leu Pro Pro
                    340                 345                 350

Ser Gln Glu Glu Met Thr Lys Asn Gln Val Ser Leu Thr Cys Leu Val
                    355                 360                 365

Lys Gly Phe Tyr Pro Ser Asp Ile Ala Val Glu Trp Glu Ser Asn Gly
                    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                    405                 410                 415

Gln Glu Gly Asn Val Phe Ser Cys Ser Val Met His Glu Ala Leu His
                    420                 425                 430

Asn His Tyr Thr Gln Lys Ser Leu Ser Leu
                    435                 440

<210> SEQ ID NO 20
<211> LENGTH: 444
<212> TYPE: PRT
<213> ORGANISM: Artificial sequence
<220> FEATURE:
<223> OTHER INFORMATION: H54-G4dv1

<400> SEQUENCE: 20

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
                20                  25                  30

Gln Ala Trp Ser Trp Val Arg Gln Pro Pro Gly Glu Gly Leu Glu Trp
            35                  40                  45

Ile Gly Tyr Ile Ser Tyr Ser Gly Ile Thr Asn Tyr Asn Pro Ser Leu
50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
            115                 120                 125

Pro Leu Ala Pro Ser Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
            195                 200                 205

Ser Asn Thr Lys Val Asp Lys Arg Val Glu Ser Lys Tyr Gly Pro Pro
```

```
            210                 215                 220
Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
                260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
                420                 425                 430

Asn His Tyr Thr Gln Lys Ser Leu Ser Leu Ser Leu
            435                 440
```

<210> SEQ ID NO 21
<211> LENGTH: 444
<212> TYPE: PRT
<213> ORGANISM: Artificial sequence
<220> FEATURE:
<223> OTHER INFORMATION: MRAH-G4dv2P1

<400> SEQUENCE: 21

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Arg Ser Thr Ser Glu Ser Thr Ala Ala Leu
```

```
        130                 135                 140
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Lys Thr Tyr Thr Cys Asn Val Asp His Lys Pro
                195                 200                 205

Ser Asn Thr Lys Val Asp Lys Arg Val Glu Ser Lys Tyr Gly Pro Pro
210                 215                 220

Ser Pro Pro Ser Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
                260                 265                 270

Gln Phe Asn Trp Tyr Val Asp Gly Val Glu Val His Asn Ala Lys Thr
                275                 280                 285

Lys Pro Arg Glu Glu Gln Phe Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Gln Lys Glu Met Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
                420                 425                 430

Asn His Tyr Thr Gln Lys Ser Leu Ser Leu Ser Leu
                435                 440

<210> SEQ ID NO 22
<211> LENGTH: 444
<212> TYPE: PRT
<213> ORGANISM: Artificial sequence
<220> FEATURE:
<223> OTHER INFORMATION: H54-G4dv2N1

<400> SEQUENCE: 22

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
                20                  25                  30

Gln Ala Trp Ser Trp Val Arg Gln Pro Pro Gly Glu Gly Leu Glu Trp
                35                  40                  45

Ile Gly Tyr Ile Ser Tyr Ser Gly Ile Thr Asn Tyr Asn Pro Ser Leu
```

```
              50                  55                  60
Lys Gly Arg Val Thr Ile Ser Arg Asp Thr Ser Lys Asn Gln Phe Ser
 65                  70                  75                  80

Leu Lys Leu Ser Ser Val Thr Ala Ala Asp Thr Ala Ala Tyr Tyr Cys
                 85                  90                  95

Ala Arg Ser Leu Ala Arg Thr Thr Ala Met Asp Tyr Trp Gly Glu Gly
                100                 105                 110

Thr Leu Val Thr Val Ser Ser Ala Ser Thr Lys Gly Pro Ser Val Phe
                115                 120                 125

Pro Leu Ala Pro Ser Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Lys Thr Tyr Thr Cys Asn Val Asp His Lys Pro
                195                 200                 205

Ser Asn Thr Lys Val Asp Lys Arg Val Glu Ser Lys Tyr Gly Pro Pro
210                 215                 220

Ser Pro Pro Ser Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
                260                 265                 270

Gln Phe Asn Trp Tyr Val Asp Gly Val Glu Val His Asn Ala Lys Thr
                275                 280                 285

Lys Pro Arg Glu Glu Gln Phe Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Gln Glu Glu Met Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
                370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
                420                 425                 430

Asn His Tyr Thr Gln Glu Ser Leu Ser Leu Ser Leu
                435                 440

<210> SEQ ID NO 23
<211> LENGTH: 447
<212> TYPE: PRT
<213> ORGANISM: Artificial sequence
```

```
<220> FEATURE:
<223> OTHER INFORMATION: MRAH-G1dv1

<400> SEQUENCE: 23

Gln Val Gln Leu Gln Glu Ser Gly Pro Gly Leu Val Arg Pro Ser Gln
  1               5                  10                  15

Thr Leu Ser Leu Thr Cys Thr Val Ser Gly Tyr Ser Ile Thr Ser Asp
             20                  25                  30

His Ala Trp Ser Trp Val Arg Gln Pro Pro Gly Arg Gly Leu Glu Trp
         35                  40                  45

Ile Gly Tyr Ile Ser Tyr Ser Gly Ile Thr Thr Tyr Asn Pro Ser Leu
     50                  55                  60

Lys Ser Arg Val Thr Met Leu Arg Asp Thr Ser Lys Asn Gln Phe Ser
 65                  70                  75                  80

Leu Arg Leu Ser Ser Val Thr Ala Ala Asp Thr Ala Val Tyr Tyr Cys
                 85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Ser Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400
```

Asp Ser Asp Gly Ser Phe Phe Leu Tyr Ser Lys Leu Thr Val Asp Lys
              405                 410                 415

Ser Arg Trp Gln Gln Gly Asn Val Phe Ser Cys Ser Val Met His Glu
              420                 425                 430

Ala Leu His Asn His Tyr Thr Gln Lys Ser Leu Ser Leu Ser Pro
              435                 440                 445

<210> SEQ ID NO 24
<211> LENGTH: 447
<212> TYPE: PRT
<213> ORGANISM: Artificial sequence
<220> FEATURE:
<223> OTHER INFORMATION: H54-G1dv1

<400> SEQUENCE: 24

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
              20                  25                  30

Gln Ala Trp Ser Trp Val Arg Gln Pro Pro Gly Glu Gly Leu Glu Trp
              35                  40                  45

Ile Gly Tyr Ile Ser Tyr Ser Gly Ile Thr Asn Tyr Asn Pro Ser Leu
       50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
              85                  90                  95

Ala Arg Ser Leu Ala Arg Thr Thr Ala Met Asp Tyr Trp Gly Glu Gly
              100                 105                 110

Thr Leu Val Thr Val Ser Ser Ala Ser Thr Lys Gly Pro Ser Val Phe
              115                 120                 125

Pro Leu Ala Pro Ser Ser Lys Ser Thr Ser Gly Gly Thr Ala Ala Leu
       130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
              165                 170                 175

Gln Ser Ser Gly Leu Tyr Ser Leu Ser Ser Val Val Thr Val Pro Ser
              180                 185                 190

Ser Ser Leu Gly Thr Gln Thr Tyr Ile Cys Asn Val Asn His Lys Pro
              195                 200                 205

Ser Asn Thr Lys Val Asp Lys Lys Val Glu Pro Lys Ser Ser Asp Lys
       210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
              245                 250                 255

Arg Thr Pro Glu Val Thr Cys Val Val Val Asp Val Ser His Glu Asp
              260                 265                 270

Pro Glu Val Lys Phe Asn Trp Tyr Val Asp Gly Val Glu Val His Asn
              275                 280                 285

Ala Lys Thr Lys Pro Arg Glu Glu Gln Tyr Asn Ser Thr Tyr Arg Val
       290                 295                 300

Val Ser Val Leu Thr Val Leu His Gln Asp Trp Leu Asn Gly Lys Glu
305                 310                 315                 320

-continued

```
Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445

<210> SEQ ID NO 25
<211> LENGTH: 447
<212> TYPE: PRT
<213> ORGANISM: Artificial sequence
<220> FEATURE:
<223> OTHER INFORMATION: MRAH-G1dv2rP1

<400> SEQUENCE: 25

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Ser Asp Lys
    210                 215                 220

Thr His Thr Ser Pro Pro Ser Pro Ala Pro Glu Leu Leu Gly Gly Pro
225                 230                 235                 240
```

```
Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Lys Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445

<210> SEQ ID NO 26
<211> LENGTH: 447
<212> TYPE: PRT
<213> ORGANISM: Artificial sequence
<220> FEATURE:
<223> OTHER INFORMATION: H54-G1dv2rN1

<400> SEQUENCE: 26

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

Gln Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
    50                  55                  60

Lys Gly Arg Val Thr Ile Ser Arg Asp Thr Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160
```

```
Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Ser Asp Lys
        210                 215                 220

Thr His Thr Ser Pro Pro Ser Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445

<210> SEQ ID NO 27
<211> LENGTH: 445
<212> TYPE: PRT
<213> ORGANISM: Artificial sequence
<220> FEATURE:
<223> OTHER INFORMATION: MRAH-G1dv3rP1

<400> SEQUENCE: 27

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
            35                  40                  45

Ile Gly Tyr Ile Ser Tyr Ser Gly Ile Thr Thr Tyr Asn Pro Ser Leu
        50                  55                  60

Lys Ser Arg Val Thr Met Leu Arg Asp Thr Ser Lys Asn Gln Phe Ser
65                  70                  75                  80
```

```
Leu Arg Leu Ser Ser Val Thr Ala Ala Asp Thr Ala Val Tyr Tyr Cys
                85                  90                  95
Ala Arg Ser Leu Ala Arg Thr Thr Ala Met Asp Tyr Trp Gly Gln Gly
            100                 105                 110
Ser Leu Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Tyr Gly Pro
    210                 215                 220
Pro Ser Pro Pro Ser Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
        275                 280                 285
Thr Lys Pro Arg Glu Glu Gln Tyr Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Lys Glu Leu Thr Lys Asn Gln Val Ser Leu Thr Cys Leu
        355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Arg Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro
        435                 440                 445

<210> SEQ ID NO 28
<211> LENGTH: 445
<212> TYPE: PRT
<213> ORGANISM: Artificial sequence
<220> FEATURE:
<223> OTHER INFORMATION: H54-G1dv3rN1

<400> SEQUENCE: 28
```

```
Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

Gln Ala Trp Ser Trp Val Arg Gln Pro Pro Gly Glu Gly Leu Glu Trp
            35                  40                  45

Ile Gly Tyr Ile Ser Tyr Ser Gly Ile Thr Asn Tyr Asn Pro Ser Leu
50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Tyr Gly Pro
210                 215                 220

Pro Ser Pro Pro Ser Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415
```

Trp Gln Gln Gly Asn Val Phe Ser Cys Ser Val Met His Glu Ala Leu
            420                 425                 430

His Asn His Tyr Thr Gln Glu Ser Leu Ser Leu Ser Pro
            435                 440                 445

<210> SEQ ID NO 29
<211> LENGTH: 436
<212> TYPE: PRT
<213> ORGANISM: Artificial sequence
<220> FEATURE:
<223> OTHER INFORMATION: MRAH-G4dv4

<400> SEQUENCE: 29

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Pro Ala Pro Glu
    210                 215                 220

Phe Leu Gly Gly Pro Ser Val Phe Leu Phe Pro Pro Lys Pro Lys Asp
225                 230                 235                 240

Thr Leu Met Ile Ser Arg Thr Pro Glu Val Thr Cys Val Val Val Asp
                245                 250                 255

Val Ser Gln Glu Asp Pro Glu Val Gln Phe Asn Trp Tyr Val Asp Gly
            260                 265                 270

Val Glu Val His Asn Ala Lys Thr Lys Pro Arg Glu Glu Gln Phe Asn
        275                 280                 285

Ser Thr Tyr Arg Val Val Ser Val Leu Thr Val Leu His Gln Asp Trp
    290                 295                 300

Leu Asn Gly Lys Glu Tyr Lys Cys Lys Val Ser Asn Lys Gly Leu Pro
305                 310                 315                 320

Ser Ser Ile Glu Lys Thr Ile Ser Lys Ala Lys Gly Gln Pro Arg Glu
                325                 330                 335

```
Pro Gln Val Tyr Thr Leu Pro Pro Ser Gln Glu Glu Met Thr Lys Asn
                340                 345                 350

Gln Val Ser Leu Thr Cys Leu Val Lys Gly Phe Tyr Pro Ser Asp Ile
            355                 360                 365

Ala Val Glu Trp Glu Ser Asn Gly Gln Pro Glu Asn Asn Tyr Lys Thr
        370                 375                 380

Thr Pro Pro Val Leu Asp Ser Asp Gly Ser Phe Phe Leu Tyr Ser Arg
385                 390                 395                 400

Leu Thr Val Asp Lys Ser Arg Trp Gln Glu Gly Asn Val Phe Ser Cys
                405                 410                 415

Ser Val Met His Glu Ala Leu His Asn His Tyr Thr Gln Lys Ser Leu
            420                 425                 430

Ser Leu Ser Leu
        435

<210> SEQ ID NO 30
<211> LENGTH: 436
<212> TYPE: PRT
<213> ORGANISM: Artificial sequence
<220> FEATURE:
<223> OTHER INFORMATION: H54-G4dv4

<400> SEQUENCE: 30

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

Gln Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
    50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Pro Ala Pro Glu
    210                 215                 220

Phe Leu Gly Gly Pro Ser Val Phe Leu Phe Pro Pro Lys Pro Lys Asp
225                 230                 235                 240

Thr Leu Met Ile Ser Arg Thr Pro Glu Val Thr Cys Val Val Val Asp
                245                 250                 255
```

Val Ser Gln Glu Asp Pro Glu Val Gln Phe Asn Trp Tyr Val Asp Gly
            260                 265                 270

Val Glu Val His Asn Ala Lys Thr Lys Pro Arg Glu Glu Gln Phe Asn
        275                 280                 285

Ser Thr Tyr Arg Val Val Ser Val Leu Thr Val Leu His Gln Asp Trp
    290                 295                 300

Leu Asn Gly Lys Glu Tyr Lys Cys Lys Val Ser Asn Lys Gly Leu Pro
305                 310                 315                 320

Ser Ser Ile Glu Lys Thr Ile Ser Lys Ala Lys Gly Gln Pro Arg Glu
                325                 330                 335

Pro Gln Val Tyr Thr Leu Pro Pro Ser Gln Glu Glu Met Thr Lys Asn
            340                 345                 350

Gln Val Ser Leu Thr Cys Leu Val Lys Gly Phe Tyr Pro Ser Asp Ile
        355                 360                 365

Ala Val Glu Trp Glu Ser Asn Gly Gln Pro Glu Asn Asn Tyr Lys Thr
    370                 375                 380

Thr Pro Pro Val Leu Asp Ser Asp Gly Ser Phe Phe Leu Tyr Ser Arg
385                 390                 395                 400

Leu Thr Val Asp Lys Ser Arg Trp Gln Glu Gly Asn Val Phe Ser Cys
                405                 410                 415

Ser Val Met His Glu Ala Leu His Asn His Tyr Thr Gln Lys Ser Leu
            420                 425                 430

Ser Leu Ser Leu
        435

<210> SEQ ID NO 31
<211> LENGTH: 436
<212> TYPE: PRT
<213> ORGANISM: Artificial sequence
<220> FEATURE:
<223> OTHER INFORMATION: MRAH-G4dv4P1

<400> SEQUENCE: 31

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                    180                 185                 190

Ser Ser Leu Gly Thr Lys Thr Tyr Thr Cys Asn Val Asp His Lys Pro
            195                 200                 205

Ser Asn Thr Lys Val Asp Lys Arg Val Glu Ser Lys Pro Ala Pro Glu
        210                 215                 220

Phe Leu Gly Gly Pro Ser Val Phe Leu Phe Pro Pro Lys Pro Lys Asp
225                 230                 235                 240

Thr Leu Met Ile Ser Arg Thr Pro Glu Val Thr Cys Val Val Val Asp
                245                 250                 255

Val Ser Gln Glu Asp Pro Glu Val Gln Phe Asn Trp Tyr Val Asp Gly
            260                 265                 270

Val Glu Val His Asn Ala Lys Thr Lys Pro Arg Glu Glu Gln Phe Asn
        275                 280                 285

Ser Thr Tyr Arg Val Val Ser Val Leu Thr Val Leu His Gln Asp Trp
290                 295                 300

Leu Asn Gly Lys Glu Tyr Lys Cys Lys Val Ser Asn Lys Gly Leu Pro
305                 310                 315                 320

Ser Ser Ile Glu Lys Thr Ile Ser Lys Ala Lys Gly Gln Pro Arg Glu
                325                 330                 335

Pro Gln Val Tyr Thr Leu Pro Pro Ser Gln Lys Glu Met Thr Lys Asn
            340                 345                 350

Gln Val Ser Leu Thr Cys Leu Val Lys Gly Phe Tyr Pro Ser Asp Ile
        355                 360                 365

Ala Val Glu Trp Glu Ser Asn Gly Gln Pro Glu Asn Asn Tyr Lys Thr
370                 375                 380

Thr Pro Pro Val Leu Asp Ser Asp Gly Ser Phe Phe Leu Tyr Ser Arg
385                 390                 395                 400

Leu Thr Val Asp Lys Ser Arg Trp Gln Glu Gly Asn Val Phe Ser Cys
                405                 410                 415

Ser Val Met His Glu Ala Leu His Asn His Tyr Thr Gln Lys Ser Leu
            420                 425                 430

Ser Leu Ser Leu
        435

<210> SEQ ID NO 32
<211> LENGTH: 436
<212> TYPE: PRT
<213> ORGANISM: Artificial sequence
<220> FEATURE:
<223> OTHER INFORMATION: H54-G4dv4N1

<400> SEQUENCE: 32

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

Gln Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
    50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Pro Ala Pro Glu
    210                 215                 220

Phe Leu Gly Gly Pro Ser Val Phe Leu Phe Pro Pro Lys Pro Lys Asp
225                 230                 235                 240

Thr Leu Met Ile Ser Arg Thr Pro Glu Val Thr Cys Val Val Val Asp
                245                 250                 255

Val Ser Gln Glu Asp Pro Glu Val Gln Phe Asn Trp Tyr Val Asp Gly
            260                 265                 270

Val Glu Val His Asn Ala Lys Thr Lys Pro Arg Glu Glu Gln Phe Asn
        275                 280                 285

Ser Thr Tyr Arg Val Val Ser Val Leu Thr Val Leu His Gln Asp Trp
    290                 295                 300

Leu Asn Gly Lys Glu Tyr Lys Cys Lys Val Ser Asn Lys Gly Leu Pro
305                 310                 315                 320

Ser Ser Ile Glu Lys Thr Ile Ser Lys Ala Lys Gly Gln Pro Arg Glu
                325                 330                 335

Pro Gln Val Tyr Thr Leu Pro Pro Ser Gln Glu Glu Met Thr Lys Asn
            340                 345                 350

Gln Val Ser Leu Thr Cys Leu Val Lys Gly Phe Tyr Pro Ser Asp Ile
        355                 360                 365

Ala Val Glu Trp Glu Ser Asn Gly Gln Pro Glu Asn Asn Tyr Lys Thr
    370                 375                 380

Thr Pro Pro Val Leu Asp Ser Asp Gly Ser Phe Phe Leu Tyr Ser Arg
385                 390                 395                 400

Leu Thr Val Asp Lys Ser Arg Trp Gln Glu Gly Asn Val Phe Ser Cys
                405                 410                 415

Ser Val Met His Glu Ala Leu His Asn His Tyr Thr Gln Glu Ser Leu
            420                 425                 430

Ser Leu Ser Leu
        435

<210> SEQ ID NO 33
<211> LENGTH: 447
<212> TYPE: PRT
<213> ORGANISM: Artificial sequence
<220> FEATURE:
<223> OTHER INFORMATION: MRAH-G1dr

<400> SEQUENCE: 33

Gln Val Gln Leu Gln Glu Ser Gly Pro Gly Leu Val Arg Pro Ser Gln
1               5                   10                  15

```
Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
            35                  40                  45

Ile Gly Tyr Ile Ser Tyr Ser Gly Ile Thr Thr Tyr Asn Pro Ser Leu
 50                  55                  60

Lys Ser Arg Val Thr Met Leu Arg Asp Thr Ser Lys Asn Gln Phe Ser
 65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
```

<210> SEQ ID NO 34
<211> LENGTH: 447
<212> TYPE: PRT
<213> ORGANISM: Artificial sequence
<220> FEATURE:
<223> OTHER INFORMATION: H54-G1d1

<400> SEQUENCE: 34

```
Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

Gln Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
    50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
```

```
                    355                 360                 365
Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Leu Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
                435                 440                 445

<210> SEQ ID NO 35
<211> LENGTH: 444
<212> TYPE: PRT
<213> ORGANISM: Artificial sequence
<220> FEATURE:
<223> OTHER INFORMATION: MRAH-G4dNX010P

<400> SEQUENCE: 35

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Ser Pro Pro Ser Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
```

```
                275                 280                 285
Lys Pro Arg Glu Glu Gln Phe Asn Ser Thr Tyr Arg Val Ser Val
            290                 295                 300
Leu Thr Val Leu His Gln Asp Trp Leu Asn Gly Lys Glu Tyr Lys Cys
305                 310                 315                 320
Lys Val Ser Asn Lys Gly Leu Pro Ser Ser Ile Glu Lys Thr Ile Ser
                325                 330                 335
Lys Ala Lys Gly Gln Pro Arg Glu Pro Gln Val Cys Thr Leu Pro Pro
                340                 345                 350
Ser Gln Lys Glu Met Thr Lys Asn Gln Val Ser Leu Thr Cys Leu Val
                355                 360                 365
Lys Gly Phe Tyr Pro Ser Asp Ile Ala Val Glu Trp Glu Ser Asn Gly
                370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Arg Leu Thr Val Asp Lys Ser Arg Trp
                405                 410                 415
Gln Glu Gly Asn Val Phe Ser Cys Ser Val Met His Glu Ala Leu His
                420                 425                 430
Asn His Tyr Thr Gln Lys Ser Leu Ser Leu Ser Leu
                435                 440

<210> SEQ ID NO 36
<211> LENGTH: 444
<212> TYPE: PRT
<213> ORGANISM: Artificial sequence
<220> FEATURE:
<223> OTHER INFORMATION: H54-G4dNX010N

<400> SEQUENCE: 36

Gln Val Gln Leu Gln Glu Ser Gly Pro Gly Leu Val Lys Pro Ser Glu
1               5                   10                  15
Thr Leu Ser Leu Thr Cys Ala Val Ser Gly Tyr Ser Ile Ser Asp Asp
                20                  25                  30
Gln Ala Trp Ser Trp Val Arg Gln Pro Pro Gly Glu Gly Leu Glu Trp
            35                  40                  45
Ile Gly Tyr Ile Ser Tyr Ser Gly Ile Thr Asn Tyr Asn Pro Ser Leu
        50                  55                  60
Lys Gly Arg Val Thr Ile Ser Arg Asp Thr Ser Lys Asn Gln Phe Ser
65                  70                  75                  80
Leu Lys Leu Ser Ser Val Thr Ala Ala Asp Thr Ala Ala Tyr Tyr Cys
                85                  90                  95
Ala Arg Ser Leu Ala Arg Thr Thr Ala Met Asp Tyr Trp Gly Glu Gly
                100                 105                 110
Thr Leu Val Thr Val Ser Ser Ala Ser Thr Lys Gly Pro Ser Val Phe
                115                 120                 125
Pro Leu Ala Pro Cys Ser Arg Ser Thr Ser Glu Ser Thr Ala Ala Leu
                130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
                180                 185                 190
Ser Ser Leu Gly Thr Lys Thr Tyr Thr Cys Asn Val Asp His Lys Pro
```

```
                    195                 200                 205
Ser Asn Thr Lys Val Asp Lys Arg Val Glu Ser Lys Tyr Gly Pro Pro
210                 215                 220

Ser Pro Pro Ser Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
                260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Cys Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Glu Ser Leu Ser Leu Ser Leu
            435                 440

<210> SEQ ID NO 37
<211> LENGTH: 444
<212> TYPE: PRT
<213> ORGANISM: Artificial sequence
<220> FEATURE:
<223> OTHER INFORMATION: MRAH-G4dNX011P

<400> SEQUENCE: 37

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
                20                  25                  30

His Ala Trp Ser Trp Val Arg Gln Pro Pro Gly Arg Gly Leu Glu Trp
            35                  40                  45

Ile Gly Tyr Ile Ser Tyr Ser Gly Ile Thr Thr Tyr Asn Pro Ser Leu
        50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
```

```
            115                 120                 125
Pro Leu Ala Pro Cys Ser Arg Ser Thr Ser Glu Ser Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Ser Pro Pro Ser Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Cys Thr Leu Pro Pro
            340                 345                 350

Ser Gln Lys Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Tyr Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu
        435                 440

<210> SEQ ID NO 38
<211> LENGTH: 444
<212> TYPE: PRT
<213> ORGANISM: Artificial sequence
<220> FEATURE:
<223> OTHER INFORMATION: H54-G4dNX011N

<400> SEQUENCE: 38

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

Gln Ala Trp Ser Trp Val Arg Gln Pro Pro Gly Glu Gly Leu Glu Trp
```

```
            35                  40                  45
Ile Gly Tyr Ile Ser Tyr Ser Gly Ile Thr Asn Tyr Asn Pro Ser Leu
 50                  55                  60

Lys Gly Arg Val Thr Ile Ser Arg Asp Thr Ser Lys Asn Gln Phe Ser
 65                  70                  75                  80

Leu Lys Leu Ser Ser Val Thr Ala Ala Asp Thr Ala Ala Tyr Tyr Cys
                 85                  90                  95

Ala Arg Ser Leu Ala Arg Thr Thr Ala Met Asp Tyr Trp Gly Glu Gly
                100                 105                 110

Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
210                 215                 220

Ser Pro Pro Ser Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Cys Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Tyr Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Glu Ser Leu Ser Leu Ser Leu
        435                 440

<210> SEQ ID NO 39
```

<211> LENGTH: 444
<212> TYPE: PRT
<213> ORGANISM: Artificial sequence
<220> FEATURE:
<223> OTHER INFORMATION: MRAH-G4dNX012P

<400> SEQUENCE: 39

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
            85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Ser Pro Pro Ser Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Lys Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380
```

```
Gln Pro Glu Asn Asn Tyr Lys Thr Cys Pro Pro Val Leu Asp Ser Asp
385                 390                 395                 400

Gly Ser Phe Phe Leu Tyr Ser Arg Leu Thr Val Asp Lys Ser Arg Trp
            405                 410                 415

Gln Glu Gly Asn Val Phe Ser Cys Ser Val Met His Glu Ala Leu His
        420                 425                 430

Asn His Tyr Thr Gln Lys Ser Leu Ser Leu Ser Leu
        435                 440

<210> SEQ ID NO 40
<211> LENGTH: 444
<212> TYPE: PRT
<213> ORGANISM: Artificial sequence
<220> FEATURE:
<223> OTHER INFORMATION: H54-G4dNX012N

<400> SEQUENCE: 40

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

Gln Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
    50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Ser Pro Pro Ser Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300
```

```
Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Cys Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Glu Ser Leu Ser Leu Ser Leu
        435                 440

<210> SEQ ID NO 41
<211> LENGTH: 444
<212> TYPE: PRT
<213> ORGANISM: Artificial sequence
<220> FEATURE:
<223> OTHER INFORMATION: H54-G4dNX013N

<400> SEQUENCE: 41

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

Gln Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
    50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220
```

Ser Pro Pro Ser Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser Gln Glu Asp Pro Glu Val
        260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Cys Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Glu Ser Leu Ser Leu Ser Leu
            435                 440

<210> SEQ ID NO 42
<211> LENGTH: 444
<212> TYPE: PRT
<213> ORGANISM: Artificial sequence
<220> FEATURE:
<223> OTHER INFORMATION: MRAH-G4dNX014P

<400> SEQUENCE: 42

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
        130                 135                 140

```
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Lys Thr Tyr Thr Cys Asn Val Asp His Lys Pro
    195                 200                 205

Ser Asn Thr Lys Val Asp Lys Arg Val Glu Ser Lys Tyr Gly Pro Pro
210                 215                 220

Ser Pro Pro Ser Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser Gln Glu Asp Pro Glu Val
        260                 265                 270

Gln Phe Asn Trp Tyr Val Asp Gly Val Glu Val His Asn Ala Lys Thr
    275                 280                 285

Lys Pro Arg Glu Glu Gln Phe Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
            325                 330                 335

Lys Ala Lys Gly Gln Pro Arg Glu Pro Gln Val Tyr Thr Cys Pro Pro
        340                 345                 350

Ser Gln Lys Glu Met Thr Lys Asn Gln Val Ser Leu Thr Cys Leu Val
    355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
            405                 410                 415

Gln Glu Gly Asn Val Phe Ser Cys Ser Val Met His Glu Ala Leu His
        420                 425                 430

Asn His Tyr Thr Gln Lys Ser Leu Ser Leu Ser Leu
    435                 440

<210> SEQ ID NO 43
<211> LENGTH: 444
<212> TYPE: PRT
<213> ORGANISM: Artificial sequence
<220> FEATURE:
<223> OTHER INFORMATION: H54-G4dNX014N

<400> SEQUENCE: 43

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

Gln Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
    50                  55                  60
```

```
Lys Gly Arg Val Thr Ile Ser Arg Asp Thr Ser Lys Asn Gln Phe Ser
 65                  70                  75                  80

Leu Lys Leu Ser Ser Val Thr Ala Ala Asp Thr Ala Ala Tyr Tyr Cys
                 85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
            195                 200                 205

Ser Asn Thr Lys Val Asp Lys Arg Val Glu Ser Lys Tyr Gly Pro Pro
210                 215                 220

Ser Pro Pro Ser Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Cys Pro Pro
            340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Glu Ser Leu Ser Leu Ser Leu
            435                 440
```

<210> SEQ ID NO 44
<211> LENGTH: 444
<212> TYPE: PRT
<213> ORGANISM: Artificial sequence
<220> FEATURE:

<223> OTHER INFORMATION: MRAH-G4dNX015P

<400> SEQUENCE: 44

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Ser Pro Pro Ser Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Lys Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

```
Gly Ser Phe Phe Leu Cys Ser Arg Leu Thr Val Asp Lys Ser Arg Trp
                405                 410                 415
Gln Glu Gly Asn Val Phe Ser Cys Ser Val Met His Glu Ala Leu His
            420                 425                 430
Asn His Tyr Thr Gln Lys Ser Leu Ser Leu Ser Leu
        435                 440

<210> SEQ ID NO 45
<211> LENGTH: 444
<212> TYPE: PRT
<213> ORGANISM: Artificial sequence
<220> FEATURE:
<223> OTHER INFORMATION: H54-G4dNX015N

<400> SEQUENCE: 45

Gln Val Gln Leu Gln Glu Ser Gly Pro Gly Leu Val Lys Pro Ser Glu
1               5                   10                  15
Thr Leu Ser Leu Thr Cys Ala Val Ser Gly Tyr Ser Ile Ser Asp Asp
            20                  25                  30
Gln Ala Trp Ser Trp Val Arg Gln Pro Pro Gly Glu Gly Leu Glu Trp
        35                  40                  45
Ile Gly Tyr Ile Ser Tyr Ser Gly Ile Thr Asn Tyr Asn Pro Ser Leu
50                  55                  60
Lys Gly Arg Val Thr Ile Ser Arg Asp Thr Ser Lys Asn Gln Phe Ser
65                  70                  75                  80
Leu Lys Leu Ser Ser Val Thr Ala Ala Asp Thr Ala Ala Tyr Tyr Cys
                85                  90                  95
Ala Arg Ser Leu Ala Arg Thr Thr Ala Met Asp Tyr Trp Gly Glu Gly
            100                 105                 110
Thr Leu Val Thr Val Ser Ser Ala Ser Thr Lys Gly Pro Ser Val Phe
        115                 120                 125
Pro Leu Ala Pro Cys Ser Arg Ser Thr Ser Glu Ser Thr Ala Ala Leu
130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Lys Thr Tyr Thr Cys Asn Val Asp His Lys Pro
        195                 200                 205
Ser Asn Thr Lys Val Asp Lys Arg Val Glu Ser Lys Tyr Gly Pro Pro
210                 215                 220
Ser Pro Pro Ser Pro Ala Pro Glu Phe Leu Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser Gln Glu Asp Pro Glu Val
            260                 265                 270
Gln Phe Asn Trp Tyr Val Asp Gly Val Glu Val His Asn Ala Lys Thr
        275                 280                 285
Lys Pro Arg Glu Glu Gln Phe Asn Ser Thr Tyr Arg Val Val Ser Val
290                 295                 300
Leu Thr Val Leu His Gln Asp Trp Leu Asn Gly Lys Glu Tyr Lys Cys
305                 310                 315                 320
```

Lys Val Ser Asn Lys Gly Leu Pro Ser Ser Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Cys Ser Arg Leu Thr Val Asp Lys Ser Arg Trp
            405                 410                 415

Gln Glu Gly Asn Val Phe Ser Cys Ser Val Met His Glu Ala Leu His
            420                 425                 430

Asn His Tyr Thr Gln Glu Ser Leu Ser Leu Ser Leu
            435                 440

<210> SEQ ID NO 46
<211> LENGTH: 444
<212> TYPE: PRT
<213> ORGANISM: Artificial sequence
<220> FEATURE:
<223> OTHER INFORMATION: MRAH-wtG4dv2P1

<400> SEQUENCE: 46

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
            35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
            85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
            115                 120                 125

Pro Leu Ala Pro Ser Ser Arg Ser Thr Ser Glu Ser Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
            195                 200                 205

Ser Asn Thr Lys Val Asp Lys Arg Val Glu Ser Lys Tyr Gly Pro Pro
            210                 215                 220

Ser Pro Ser Ser Pro Ala Pro Glu Phe Leu Gly Gly Pro Ser Val Phe
225                 230                 235                 240

```
Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Lys Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu
        435                 440

<210> SEQ ID NO 47
<211> LENGTH: 444
<212> TYPE: PRT
<213> ORGANISM: Artificial sequence
<220> FEATURE:
<223> OTHER INFORMATION: H54-wtG4dv2N1

<400> SEQUENCE: 47

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
                20                  25                  30

Gln Ala Trp Ser Trp Val Arg Gln Pro Pro Gly Glu Gly Leu Glu Trp
            35                  40                  45

Ile Gly Tyr Ile Ser Tyr Ser Gly Ile Thr Asn Tyr Asn Pro Ser Leu
        50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160
```

```
Asn Ser Gly Ala Leu Thr Ser Gly Val His Thr Phe Pro Ala Val Leu
            165                 170                 175
Gln Ser Ser Gly Leu Tyr Ser Leu Ser Ser Val Val Thr Val Pro Ser
            180                 185                 190
Ser Ser Leu Gly Thr Lys Thr Tyr Thr Cys Asn Val Asp His Lys Pro
            195                 200                 205
Ser Asn Thr Lys Val Asp Lys Arg Val Glu Ser Lys Tyr Gly Pro Pro
            210                 215                 220
Ser Pro Ser Ser Pro Ala Pro Glu Phe Leu Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser Gln Glu Asp Pro Glu Val
                260                 265                 270
Gln Phe Asn Trp Tyr Val Asp Gly Val Glu Val His Asn Ala Lys Thr
            275                 280                 285
Lys Pro Arg Glu Glu Gln Phe Asn Ser Thr Tyr Arg Val Val Ser Val
            290                 295                 300
Leu Thr Val Leu His Gln Asp Trp Leu Asn Gly Lys Glu Tyr Lys Cys
305                 310                 315                 320
Lys Val Ser Asn Lys Gly Leu Pro Ser Ser Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Gln Glu Glu Met Thr Lys Asn Gln Val Ser Leu Thr Cys Leu Val
            355                 360                 365
Lys Gly Phe Tyr Pro Ser Asp Ile Ala Val Glu Trp Glu Ser Asn Gly
        370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Arg Leu Thr Val Asp Lys Ser Arg Trp
                405                 410                 415
Gln Glu Gly Asn Val Phe Ser Cys Ser Val Met His Glu Ala Leu His
            420                 425                 430
Asn His Tyr Thr Gln Glu Ser Leu Ser Leu Ser Leu
            435                 440
```

METHOD FOR PRODUCING POLYPEPTIDE HETERO-OLIGOMER

CROSS-REFERENCE TO RELATED APPLICATIONS

This application is the National Stage of International Application Serial No. PCT/JP2016/060616, filed on Mar. 31, 2016, which claims the benefit of Japanese Application Serial No. 2015-075448, filed on Apr. 1, 2015.

TECHNICAL FIELD

The present invention relates to, for example, a method for producing a polypeptide heteromultimer and a polypeptide heteromultimer having a modified amino acid in a heavy chain constant region so as to promote polypeptide heteromultimerization.

BACKGROUND ART

Antibodies have received attention as drugs because of having high stability in blood and few adverse reactions (Non-patent Documents 1 and 2). Among these antibodies, there exist bispecific antibodies that can each recognize two types of antigens or epitopes at the same time. These bispecific antibodies are expected to have high target specificity and the function of inhibiting a plurality of pathways at the same time (Non-patent Document 3). For example, already launched catumaxomab is a bispecific antibody binding to an endothelial cell adhesion factor EpCAM and CD3 expressed on T cells, and is used as a therapeutic drug for malignant ascites.

Some reports on the production of IgG-type bispecific antibodies give findings about the low efficiency of obtainment of a bispecific antibody of interest or efficient production, albeit with a high degree of difficulty due to difficult purification (Non-patent Document 3). In the case of transfecting, for example, 4 types in total of genes, i.e., genes of H chains and L chains constituting IgG having two types of variable regions, to cells and secreting these chains by coexpression, the covalent bond between the two types of H chains or the noncovalent bond between the H chain and the L chain occurs at random. Therefore, the ratio of the bispecific antibody of interest is exceedingly low with remarkably reduced production efficiency. A reported approach to solve this problem involves applying amino acid substitution to the CH3 regions of IgG H chains, whereby IgG having different types of H chains in combination can be preferentially secreted (Patent Document 1 and Non-patent Documents 4 and 5). This approach is a method which involves substituting an amino acid side chain present in the CH3 region of one H chain by a larger side chain (knob), and substituting its counterpart amino acid side chain present in the CH3 region of another H chain by a smaller side chain (hole) so that the knob is inserted into the hole to promote the heterodimerization of the H chains and to inhibit the homodimerization of H chains. Also, a method for introducing different charges to the respective CH3 regions of IgG H chains has been reported (Patent Document 2). Specifically, this method involves substituting an amino acid present in the CH3 region of one H chain by an amino acid having a positive charge, and substituting its counterpart amino acid present in the CH3 region of another H chain by an amino acid having a negative charge to promote the heterodimerization of the H chains and to inhibit the homodimerization of H chains. Meanwhile, a technique of controlling H and L chain pairing has also been reported (Non-patent Document 6). This approach involves using antibodies prepared by the exchange of a light chain constant region (CL) and an H chain CH1 region in one Fab to efficiently induce the H and L chain pairing of interest. In addition, there also exists an approach using common L chains in both Fabs. In this case, use of the common L chains allows only one type of L chain gene to be transfected to cells, and yields a bispecific antibody without the need of taking H and L chain pairing into consideration. Currently, bispecific antibodies can be formed with high efficiency by the combined use of the H chain heterodimerization technique and the H-L chain pairing control technique. Nevertheless, it is difficult to completely control H and L chain pairing, and a complicated molecular design is required. Another problem is a high degree of difficulty in maintaining the high affinity of the common L chains for two types of antigens.

Meanwhile, instead of the gene recombination methods described above, an approach called Fab arm exchange has been reported as a method for preparing a bispecific antibody using monoclonal antibodies separately prepared in advance. This technique has been developed on the basis of the finding that the in vivo exchange of IgG4 with endogenous IgG4 yields a bispecific antibody (Non-patent Document 7). According to the reports, two types of IgG4 are mixed in vitro to produce a bispecific antibody (Patent Document 3), and this reaction occurs more efficiently under a reducing condition (Non-patent Document 8). Two sites characteristic of IgG4, i.e., amino acid residues at position 228 in the hinge region and at position 409 in the CH3 region have been identified as amino acid residues important for this reaction. It has been found that even in IgG1, the substitution of these two sites by IgG4-type amino acids causes the reaction with efficiency equivalent to that of IgG4 (Patent Document 4). The Fab arm exchange produces a bispecific antibody of interest by merely mixing in vitro monoclonal antibodies prepared by a general method and is thus highly versatile. The half-molecule exchange reaction, however, occurs at random. Therefore, the bispecific antibody obtained by mixing two types of antibodies is theoretically 50% of the total amount of antibodies present in the system. Hence, a method for improving the rate of bispecific antibody formation has been studied. The reaction efficiency can be reportedly improved by introducing asymmetric amino acid modification to two types of antibodies, i.e., K409R modification to the H chains of one antibody and F405L modification to the H chains of the other antibody (Patent Document 5 and Non-patent Documents 9 and 10). Although this approach has previously succeeded in drastically improving reaction efficiency, the Fab arm exchange involves the reaction of antibodies under a reducing condition and might therefore result in cleavage of disulfide bonds in hinge regions other than the intended one, increase in heterogeneity caused by the reduction of sugar chains or amino acids, and decrease in binding activity in association with change in their physical properties. In actuality, Fab arm exchange performed under conditions of 37° C. and 24 hours in the presence of a reducing agent reportedly increases peaks derived from by-products in ion exchange chromatography (Non-patent Document 9). The efficient and stable production of bispecific antibodies inevitably requires convenient purification and minimized lot-to-lot variation. Thus, there has been a demand for the development of an excellent approach that achieves high reaction efficiency even under a milder reducing condition.

PRIOR ART DOCUMENTS

Patent Document

[Patent Document 1] WO1996/027011
[Patent Document 2] WO2006/106905
[Patent Document 3] WO2005/062916
[Patent Document 4] WO2008/119353
[Patent Document 5] WO2011/131746

Non-Patent Document

[Non-patent Document 1] Nat Biotechnol., 23, 1073-1078, 2005
[Non-patent Document 2] Eur J Pharm Biopharm, 59 (3), 389-396, 2005
[Non-patent Document 3] mAbs, 4, 653-663, 2012
[Non-patent Document 4] Protein Engineering, 9, 617-621, 1996
[Non-patent Document 5] Nature Biotechnol., 16, 677-681, 1998
[Non-patent Document 6] Proc. Natl. Acad. Sci., 108, 11187-11192, 2011
[Non-patent Document 7] Immunology, 97, 693-698, 1999
[Non-patent Document 8] Science, 317, 1554-1557, 2007
[Non-patent Document 9] Proc. Natl. Acad. Sci., 110, 5145-5150, 2013
[Non-patent Document 10] Nature Protocols, 9, 2450-2463, 2014

SUMMARY OF THE INVENTION

Problems to be Solved by the Invention

The present invention has been made in light of these circumstances, and an object of the present invention is to provide an excellent approach for the efficient and stable production of a heteromultimer with high reaction efficiency, whereby the desired heteromultimer is obtained through the promotion of polypeptide heteromultimerization under a reducing condition.

Means for Solving the Problems

The present inventors have conducted diligent studies on a method for controlling the dissociation and association of heavy chain constant regions by selecting polypeptides having the heavy chain constant regions as polypeptides to be included in a heteromultimer. As a result, the present inventors have found that: the promotion of the dissociation of heavy chain constant regions and the control of the association thereof under a reducing condition can be achieved by the substitution of a particular amino acid present in a heavy chain constant region; and a desired heteromeric molecule is formed efficiently as compared with the conventional techniques. The present inventors have also found a method for forming a stable heteromeric molecule by eliminating disulfide bonds formed in the core hinge regions of general antibodies and forming a disulfide bond between L chains or between CH3 regions.

The present invention is based on these findings and specifically provides the following [1] to [32].
[1] A method for producing a heteromultimer, comprising the steps of:
a) providing a homologous form of a first polypeptide having a first antigen-binding activity and comprising a heavy chain constant region;
b) providing a homologous form of a second polypeptide having a second antigen-binding activity that is different from the first antigen-binding activity and comprising a heavy chain constant region;
c) incubating the homologous form of the first polypeptide and the homologous form of the second polypeptide together under a reducing condition that allows cysteines outside of core hinge regions to cause disulfide bond isomerization; and
d) obtaining a heteromultimer comprising the first and second polypeptides, wherein amino acid residues in the core hinge regions do not form any disulfide bond.
[2] The production method according to [1], wherein step a) of [1] comprises the step of providing a third polypeptide that forms a multimer with the first polypeptide, and step b) comprises the step of providing a fourth polypeptide that forms a multimer with the second polypeptide.
[3] The production method according to [2], wherein the third polypeptide and the fourth polypeptide are antibody light chains.
[4] The production method according to any one of [1] to [3], wherein the outside of core hinge regions are light chain constant regions.
[5] The production method according to [4], wherein in the heavy chain constant region of the first and/or the second polypeptide, the cysteine residue at position 131 and/or 220 according to EU numbering is modified to another amino acid residue.
[6] The production method according to any one of [1] to [3], wherein the outside of core hinge regions are CH3 regions contained in the heavy chain constant regions.
[7] The production method according to [6], wherein in each of the CH3 regions contained in the heavy chain constant regions of the first and second polypeptides, at least one amino acid residue selected from amino acid residues at positions 349, 351, 354, 356, 394, and 407 according to EU numbering is cysteine.
[8] The production method according to [7], wherein a set of in which amino acid residues in the CH3 regions contained in the heavy chain constant regions of the first and second polypeptides are each cysteine is any one of the following sets (1) to (5):
 (1) amino acid residues at positions 349 and 356 according to EU numbering,
 (2) amino acid residues at positions 394 and 394 according to EU numbering,
 (3) amino acid residues at positions 351 and 351 according to EU numbering,
 (4) amino acid residues at positions 407 and 407 according to EU numbering, and
 (5) amino acid residues at positions 349 and 354 according to EU numbering.
[9] The production method according to any one of [1] to [8], wherein the cysteine residue at position 226 and/or 229 according to EU numbering is modified into another amino acid residue or is deleted, or wherein the core hinge regions are deleted.
[10] The production method according to [9], wherein further, amino acid residues at positions 220 to 225 according to EU numbering are substituted by Tyr (Y)-Gly (G)-Pro (P)-Pro (P), or amino acid residues at positions 219 to 229 according to EU numbering are deleted.
[11] The production method according to any one of [1] to [10], wherein in the first and/or the second polypeptide, an amino acid is modified so as to destabilize the stability of the CH3 region of the first and/or the second polypeptide.

[12] The production method according to [11], wherein in the first and/or the second polypeptide, at least one of amino acid residues at positions 392, 397, and 409 according to EU numbering is modified.

[13] The production method according to any one of [1] to [12], wherein 1 to 3 sets of amino acid residues selected from the following sets of amino acid residues in the CH3 region contained in the heavy chain constant region of the first and/or the second polypeptide have the same type of charge:
 (1) amino acid residues at positions 356 and 439 according to EU numbering,
 (2) amino acid residues at positions 357 and 370 according to EU numbering, and
 (3) amino acid residues at positions 399 and 409 according to EU numbering, and wherein
 when the amino acid residues in the same set among the sets of amino acid residues (1) to (3) have the same type of charge as each other in both the CH3 region of the first polypeptide and the CH3 region of the second polypeptide, the amino acid residues in the set in the CH3 region of the second polypeptide have a charge opposite to that of the amino acid residues in the set in the CH3 region of the first polypeptide.

[14] The production method according to [13], wherein the amino acid residues having the same type of charge are selected from one or more amino acid residues included in any of the following groups (A) and (B):
(A) glutamic acid (E) and aspartic acid (D); and
(B) lysine (K), arginine (R), and histidine (H).

[15] The production method according to [13] or [14], wherein the set(s) of the amino acid residues having the same type of charge as each other in each of the first and second polypeptides is any one of the following sets of amino acid residues (1) to (4):
 (1) amino acid residues at positions 356 and 439 according to EU numbering,
 (2) amino acid residues at positions 357 and 370 according to EU numbering,
 (3) amino acid residues at positions 399 and 409 according to EU numbering, and
 (4) (i) amino acid residues at positions 399 and 409 according to EU numbering and
 (ii) amino acid residues at positions 356 and 439 according to EU numbering.

[16] The production method according to any one of [1] to [15], wherein the heavy chain constant region of the first and/or the second polypeptide is IgG1, IgG2, IgG3, or IgG4 type.

[17] The production method according to any one of [1] to [12], wherein the heavy chain constant region of the first and/or the second polypeptide is a mouse-derived heavy chain constant region.

[18] The method for producing a heteromultimer according to [17], wherein 1 to 3 sets of amino acid residues selected from the following sets of amino acid residues in the CH3 region contained in the heavy chain constant region of the first and/or the second polypeptide have the same type of charge:
 (1) amino acid residues at positions 356 and 439 according to EU numbering,
 (2) amino acid residues at positions 360 and 371 according to EU numbering, and
 (3) amino acid residues at positions 399 and 409 according to EU numbering, and wherein
 when the amino acid residues in the same set among the sets of amino acid residues (1) to (3) have the same type of charge as each other in both the CH3 region of the first polypeptide and the CH3 region of the second polypeptide, the amino acid residues in the set in the CH3 region of the second polypeptide have a charge opposite to that of the amino acid residues in the set in the CH3 region of the first polypeptide.

[19] The production method according to any one of [1] to [18], wherein in the first and/or the second polypeptide,
 the amino acid at position 397 according to EU numbering is modified to Met (M), Phe (F), or Tyr (Y), and/or
 the amino acid at position 392 according to EU numbering is modified to Asp (D), Glu (E), Thr (T), Val (V), or Ile (I), and/or
 the amino acid at position 409 according to EU numbering is modified to Arg (R).

[20] A method for producing a heteromultimer, comprising the steps of:
a) providing a homologous form of a first polypeptide having a first antigen-binding activity and comprising a heavy chain constant region;
b) providing a homologous form of a second polypeptide having a second antigen-binding activity that is different from the first antigen-binding activity and comprising a heavy chain constant region; and
c) obtaining a heteromultimer comprising the first and second polypeptides, wherein
 the heavy chain constant regions of the first and second polypeptides are each modified as shown in any of the following (1) to (5):
(1) the first polypeptide has an amino acid residue other than Cys (C) at position 226 according to EU numbering, an amino acid residue other than Cys (C) at position 229 according to EU numbering, and Cys (C) at position 349 according to EU numbering, and the second polypeptide has an amino acid residue other than Cys (C) at position 226 according to EU numbering, an amino acid residue other than Cys (C) at position 229 according to EU numbering, and Cys (C) at position 356 according to EU numbering;
(2) the first and second polypeptides have an amino acid residue other than Cys (C) at position 226 according to EU numbering, an amino acid residue other than Cys (C) at position 229 according to EU numbering, and Cys (C) at position 394 according to EU numbering;
(3) the first and second polypeptides have an amino acid residue other than Cys (C) at position 226 according to EU numbering, an amino acid residue other than Cys (C) at position 229 according to EU numbering, and Cys (C) at position 351 according to EU numbering;
(4) the first and second polypeptides have an amino acid residue other than Cys (C) at position 226 according to EU numbering, an amino acid residue other than Cys (C) at position 229 according to EU numbering, and Cys (C) at position 407 according to EU numbering; and
(5) the first polypeptide has an amino acid residue other than Cys (C) at position 226 according to EU numbering, an amino acid residue other than Cys (C) at position 229 according to EU numbering, and Cys (C) at position 349 according to EU numbering, and the second polypeptide has an amino acid residue other than Cys (C) at position 226 according to EU numbering, an amino acid residue other than Cys (C) at position 229 according to EU numbering, and Cys (C) at position 354 according to EU numbering.

[21] A method for producing a heteromultimer, comprising the steps of:
a) providing a homologous form of a first polypeptide having a first antigen-binding activity and comprising a heavy chain constant region;

b) providing a homologous form of a second polypeptide having a second antigen-binding activity that is different from the first antigen-binding activity and comprising a heavy chain constant region; and c) obtaining a heteromultimer comprising the first and second polypeptides, wherein step a) comprises the step of providing an antibody light chain polypeptide as a third polypeptide that forms a multimer with the first polypeptide, and step b) comprises the step of providing an antibody light chain as a fourth polypeptide that forms a multimer with the second polypeptide, and wherein the heavy chain constant regions of the first and second polypeptides are each modified as shown in any of the following (1) to (6):

(1) the first and second polypeptides have an amino acid residue other than Cys (C) at position 131 according to EU numbering, an amino acid residue other than Cys (C) at position 226 according to EU numbering, and an amino acid residue other than Cys (C) at position 229 according to EU numbering;

(2) the first and second polypeptides have an amino acid residue other than Cys (C) at position 131 according to EU numbering, an amino acid residue other than Cys (C) at position 226 according to EU numbering, Pro (P) at position 228 according to EU numbering, and an amino acid residue other than Cys (C) at position 229 according to EU numbering;

(3) the first and second polypeptides have an amino acid residue other than Cys (C) at position 220 according to EU numbering, an amino acid residue other than Cys (C) at position 226 according to EU numbering, and an amino acid residue other than Cys (C) at position 229 according to EU numbering;

(4) the first and second polypeptides have an amino acid residue other than Cys (C) at position 131 according to EU numbering and deletion at positions 219 to 229 according to EU numbering;

(5) the first and second polypeptides have deletion at positions 219 to 229 according to EU numbering; and (6) the first and second polypeptides have an amino acid residue other than Cys (C) at position 226 according to EU numbering, an amino acid residue other than Cys (C) at position 229 according to EU numbering, and Tyr (Y)-Gly (G)-Pro (P)-Pro (P) at positions 220 to 225 according to EU numbering.

[22] The production method according to any one of [1] to [21], wherein step c) of [1], [20], and [21] comprises contacting with a reducing agent.

[23] The production method according to [22], wherein step c) comprises adding an active substance selected from the group consisting of glutathione, L-cysteine, dithiothreitol, β-mercapto-ethanol, TCEP, and 2-MEA.

[24] The production method according to any one of [1] to [23], wherein the heteromultimer is a multispecific antibody or a hetero-Fc fusion protein.

[25] The production method according to any one of [1] to [24], wherein the heteromultimer is a bispecific antibody.

[26] A heteromultimer or a bispecific antibody produced by a method according to any one of [1] to [25].

[27] A bispecific antibody comprising first, second, third, and fourth polypeptides as constituents in which the first polypeptide which is an antibody heavy chain and the third polypeptide which is an antibody light chain form a dimer, and the second polypeptide which is an antibody heavy chain and the fourth polypeptide which is an antibody light chain form a dimer, wherein in each of the CH3 region contained in the heavy chain constant region of the first and/or the second polypeptide, at least one amino acid residue selected from amino acid residues at positions 349, 351, 354, 356, 394, and 407 according to EU numbering is cysteine.

[28] A bispecific antibody comprising first, second, third, and fourth polypeptides as constituents in which the first polypeptide which is an antibody heavy chain and the third polypeptide which is an antibody light chain form a dimer, and the second polypeptide which is an antibody heavy chain and the fourth polypeptide which is an antibody light chain form a dimer, wherein the first and second polypeptides each have amino acid residues shown in any of the following (1) to (6):

(1) the first and second polypeptides have an amino acid residue other than Cys (C) at position 131 according to EU numbering, an amino acid residue other than Cys (C) at position 226 according to EU numbering, and an amino acid residue other than Cys (C) at position 229 according to EU numbering;

(2) the first and second polypeptides have an amino acid residue other than Cys (C) at position 131 according to EU numbering, an amino acid residue other than Cys (C) at position 226 according to EU numbering, Pro (P) at position 228 according to EU numbering, and an amino acid residue other than Cys (C) at position 229 according to EU numbering;

(3) the first and second polypeptides have an amino acid residue other than Cys (C) at position 220 according to EU numbering, an amino acid residue other than Cys (C) at position 226 according to EU numbering, and an amino acid residue other than Cys (C) at position 229 according to EU numbering;

(4) the first and second polypeptides have an amino acid residue other than Cys (C) at position 131 according to EU numbering and deletion at positions 219 to 229 according to EU numbering;

(5) the first and second polypeptides have deletion at positions 219 to 229 according to EU numbering; and (6) the first and second polypeptides have an amino acid residue other than Cys (C) at position 226 according to EU numbering, an amino acid residue other than Cys (C) at position 229 according to EU numbering, and Tyr (Y)-Gly (G)-Pro (P)-Pro (P) at positions 220 to 225 according to EU numbering.

[29] A composition comprising a heteromultimer or a bispecific antibody according to any one of [26] to [28] and a pharmaceutically acceptable carrier.

[30] A method for producing a bispecific antibody according to [27] or [28].

[31] A method for screening for a heteromultimer, comprising further performing the following steps after step d) of [1]:

e) measuring the activity of the heteromultimer; and
f) selecting a heteromultimer having a desired activity.

[32] A method for producing a heteromultimer, comprising further performing the following steps after step f) of [31]:

g) obtaining the CDRs or the variable regions of the first polypeptide, the second polypeptide, the third polypeptide, and the fourth polypeptide of the heteromultimer selected in step 0 of [31]; and h) grafting the obtained CDRs or variable regions to another heteromultimer.

Effects of the Invention

According to the present invention, the promotion of the dissociation of heavy chain constant regions and the control of the association thereof under a reducing condition can be achieved by the substitution of a particular amino acid present in a heavy chain constant region. A production method for efficiently forming a desired heteromeric molecule as compared with the conventional techniques can be provided.

By use of the method of the present invention, convenience in the purification of a bispecific antibody can be improved, and lot-to-lot variation can be minimized, as compared with the conventional techniques.

A feature of the method for producing a heteromultimer according to the present invention is to modify an amino acid residue in a heavy chain constant region. Dissociation and association between polypeptides are promoted by introducing the amino acid residue modification of the present invention into this region. As a result, a desired heteromultimer can be efficiently obtained as compared with the conventional techniques.

BRIEF DESCRIPTION OF THE DRAWINGS

FIG. 1 is a diagram showing results of analyzing a Fab arm exchange reaction product by ion-exchange chromatography. In the diagram, "BiAb" denotes purified bispecific antibody; "H54 homo" denotes a monoclonal antibody having variable regions H54/L28; and "MRA homo" denotes a monoclonal antibody having variable regions MRAH/MRAL. The numeric values indicated by percentage in the diagram represent the rate of bispecific antibody formation and were calculated by dividing the area of a peak corresponding to the bispecific antibody by the area of all antibodies present in the system, followed by multiplication by 100.

FIG. 2 is a diagram showing results of analyzing a Fab arm exchange reaction product by ion-exchange chromatography. This diagram shows results of carrying out the reaction under 3 types of reducing conditions using MRAH-G1drP1/MRAL-k0 and H54-G1drN1/L28-k0 as homologous forms. The numeric values indicated by percentage in the diagram represent the rate of bispecific antibody formation and were calculated by dividing the area of a peak corresponding to the bispecific antibody by the area of all antibodies present in the system, followed by multiplication by 100.

FIG. 3 is a diagram schematically showing the Fab arm exchange reaction of IgG variants lacking a disulfide bond between heavy and light chains. In the diagram, (+) and (−) represent the charges of association interface-controlling modification sites introduced to CH3 regions.

FIG. 4 is a diagram showing the conformation of naturally occurring human IgG1 in and around hinge regions.

FIG. 5-1 is a diagram showing results of analyzing a Fab arm exchange reaction product by CE-IEF in Example 3. The numeric values indicated by percentage in the diagram represent the rate of bispecific antibody formation and were calculated by dividing the area of a peak corresponding to the bispecific antibody by the area of all antibodies present in the system, followed by multiplication by 100.

FIG. 5-2 is a diagram showing a sequel to FIG. 5-1.

FIG. 6 is a diagram showing results of analyzing a Fab arm exchange reaction product and its parent homologous forms by non-reducing polyacrylamide gel electrophoresis (SDS-PAGE) in Example 3.

FIG. 7-1 is a diagram showing results of analyzing a Fab arm exchange reaction product by ion-exchange chromatography in Example 4. The numeric values indicated by percentage in the diagram represent the rate of bispecific antibody formation and were calculated by dividing the area of a peak corresponding to the bispecific antibody by the area of all antibodies present in the system, followed by multiplication by 100.

FIG. 7-2 is a diagram showing a sequel to FIG. 7-1.

FIG. 8 is a diagram showing results of analyzing a Fab arm exchange reaction product by non-reducing polyacrylamide gel electrophoresis (SDS-PAGE) in Example 4.

FIG. 9 is a diagram showing results of analyzing a Fab arm exchange reaction product by ion-exchange chromatography in Example 5.

FIG. 10 is a diagram showing results of analyzing a Fab arm exchange reaction product and its parent homologous forms by non-reducing polyacrylamide gel electrophoresis (SDS-PAGE) in Example 5.

FIG. 11 is a diagram showing results of analyzing a Fab arm exchange reaction product by ion-exchange chromatography in Example 6.

FIG. 12-1 is a diagram showing results of analyzing a Fab arm exchange reaction product and its parent homologous forms by IEF in Example 7.

FIG. 12-2 is a diagram showing a sequel to FIG. 12-1.

FIG. 13-1 is a diagram showing results of analyzing a Fab arm exchange reaction product by non-reducing polyacrylamide gel electrophoresis (SDS-PAGE) in Example 7.

FIG. 13-2 is a diagram showing results of analyzing a Fab arm exchange reaction product and its parent homologous forms by non-reducing polyacrylamide gel electrophoresis (SDS-PAGE) in Example 7.

MODE FOR CARRYING OUT THE INVENTION

The present invention relates to a method for producing a desired heteromultimer by modifying an amino acid residue in a heavy chain constant region in order to promote the dissociation under a reducing condition of the respective homologous forms of a polypeptide having a first antigen-binding activity and a polypeptide having a second antigen-binding activity that is different from the first antigen-binding activity and to control the hetero-association thereof under the reducing condition. The present invention further relates to a method for selecting a desired heteromultimer.

Definition of Terms

In the present invention, the "polypeptide" refers to a polypeptide (heavy chain constant region-containing polypeptide) or a protein (heavy chain constant region-containing protein) comprising a heavy chain constant region in the amino acid sequence. The polypeptide is usually an organism-derived polypeptide, though the polypeptide of the present invention is not particularly limited thereto. The polypeptide may be, for example, a polypeptide consisting of an artificially designed sequence. Alternatively, a natural polypeptide, a synthetic polypeptide, a recombinant polypeptide, or the like may be used. In addition, fragments of these polypeptides are also included in the polypeptide of the present invention. The polypeptide of the present invention may be a monomer or a multimer. The "polypeptide" described herein can exist in the form of a monomer or a (homo or hetero) multimer unless the term "polypeptide multimer" is used. In the present application, the "polypeptide" or the "polypeptide multimer" may be an antibody.

In the present specification, the "antibody" refers to a natural immunoglobulin or an immunoglobulin produced by partial or complete synthesis. The antibody may be isolated from a natural resource (e.g., plasma or serum containing naturally occurring antibodies) or the culture supernatant of antibody-producing hybridoma cells or may be partially or completely synthesized by use of an approach such as gene recombination. Preferred examples of the antibody include isotypes of immunoglobulins and subclasses of these isotypes. Nine types of classes (isotypes), i.e., IgG1, IgG2, IgG3, IgG4, IgA1, IgA2, IgD, IgE, and IgM, are known as human immunoglobulins. Four types of classes, i.e., IgG1, IgG2a, IgG2b, and IgG3, are known as mouse immunoglobulins. Of these isotypes, human immunoglobulins IgG1, IgG2, IgG3, and IgG4 and mouse immunoglobulins IgG1, IgG2a, IgG2b, and IgG3 can be included in the antibody of the present invention. IgG1 is preferred as a mouse immunoglobulin. A plurality of allotype sequences based on gene polymorphism are described as human IgG1, human IgG2, human IgG3, and human IgG4 constant regions in Sequences of proteins of immunological interest, NIH Publication No. 91-3242. Any of these sequences can be used in the present invention. Particularly, an amino acid sequence from positions 356 to 358 according to EU numbering in the sequence of human IgG1 may be DEL or may be EEM. A plurality of allotype sequences based on gene polymorphism are described as a human Igκ (kappa) constant region and a human Igλ (lambda) constant region in Sequences of proteins of immunological interest, NIH Publication No. 91-3242. Any of these sequences can be used in the present invention.

In the present specification, the "second antigen-binding activity different from the first antigen-binding activity" is not limited by the case where the first antigen and the second antigen are different from each other, and also includes the case where the first antigen and the second antigen are the same as each other, but differ in binding site or epitope.

The term "Fc region" is used for defining the C-terminal region of an immunoglobulin heavy chain and includes a natural Fc region sequence and a variant Fc region. Although the boundary of the Fc region of an immunoglobulin heavy chain may vary, the Fc region refers to a region comprising hinges or a portion thereof and CH2 and CH3 domains in an antibody molecule. The heavy chain Fc region of human IgG is usually defined as extending from the amino acid residue Cys226 to the carboxyl terminus of the Fc region, though the Fc region of the present invention is not limited thereto. The immunoglobulin Fc region contains two constant regions, i.e., CH2 and CH3. The "CH2" domain of the human IgG Fc region usually extends from amino acid 231 to amino acid 340. The "CH3" domain extends from the carboxyl terminus of the Fc region to before the CH2 region, i.e., extends from amino acid 341 to about amino acid 447 of IgG.

The Fc region can be preferably obtained by the partial digestion of an IgG monoclonal antibody or the like with a proteolytic enzyme such as pepsin followed by the re-elution of a fraction adsorbed on a protein A or protein G column. Such a proteolytic enzyme is not particularly limited as long as the enzyme is capable of digesting a whole antibody so as to restrictively form Fab or F(ab')2 under appropriately set reaction conditions (e.g., pH) of the enzyme. Examples thereof can include pepsin and papain.

The position of each modification site is represented using the EU numbering system (Kabat E A et al., 1991. Sequences of Proteins of Immunological Interest. NIH).

In the present invention, the "association" of polypeptides can refer to, for example, a state where two or more polypeptide regions interact with each other.

In the present invention, the phrase "controlling association" refers to control so as to attain a desired associated state and more specifically refers to control so as to prevent undesired association between polypeptides (preferably, association between polypeptides having identical amino acid sequences).

In the present invention, the "interface" usually refers to the location of association at which polypeptides associate (interact) with each other. Amino acid residues that form the interface are usually one or more amino acid residues contained in the polypeptide regions subjected to this association and are more preferably amino acid residues that are placed close during the association to participate in the interaction. The interaction specifically includes, for example, the case where the amino acid residues that are placed close during the association form a hydrogen bond, an electrostatic interaction, or a salt bridge therebetween.

In the present invention, the "homologous form" of a polypeptide refers to a polypeptide multimer where polypeptides having identical amino acid sequences associate with each other.

In the present invention, the "heteromer" of polypeptides refers to a polypeptide multimer where a first polypeptide and a second polypeptide differing in amino acid sequence by at least one amino acid residue from the first polypeptide associate with each other.

In the present invention, the "dissociation" between polypeptides refers to a state where the associated form of two or more polypeptides in the polypeptide homologous form is separated into the single polypeptides.

In the present invention, the "heteromultimer" refers to a polypeptide multimer that is constituted by plural types of polypeptides capable of associating with each other. More specifically, the "heteromultimer" has at least a first polypeptide and a second polypeptide. In this context, the second polypeptide is a molecule differing in amino acid sequence by at least one amino acid residue from the first polypeptide. The heteromultimer preferably has antigen-binding activities against at least two different types of ligands, antigens, receptors, or substrates, etc., though the heteromultimer of the present invention is not particularly limited thereto. The heteromultimer of the present invention also includes a heteromultimer having binding activities against different sites or epitopes in the same ligand, antigen, receptor, or substrate, etc. The heteromultimer may contain an additional type of polypeptide in addition to the "heterodimer" formed by the first and second polypeptides. Specifically, the "heteromultimer" of the present invention is not limited to the heterodimer and also includes, for example, a heterotrimer and a heterotetramer.

In the polypeptide multimer of the present invention comprising the first polypeptide, the second polypeptide, and one or two third polypeptides, the first polypeptide and the second polypeptide can respectively form multimers (dimers) with the third polypeptides. Furthermore, the formed dimers can form a multimer (tetramer) with each other. The two third polypeptides may have completely identical amino acid sequences (which may have a binding activity against the same antigen). Alternatively, the two third polypeptides may have identical amino acid sequences, but have two or more activities (which may have, for example, binding activities against two or more different antigens). In the case of one third polypeptide, this third polypeptide can form a dimer with any one of the first polypeptide and the second polypeptide to form a polypeptide multimer.

In the polypeptide multimer of the present invention, the first polypeptide and the second polypeptide preferably have binding activities against different antigens, though the polypeptide multimer of the present invention is not particularly limited thereto. The polypeptide multimer of the present invention may have binding activities against different sites or epitopes in the same antigen. On the other hand, the third polypeptide may be a polypeptide having a binding activity against the same antigen as that of either of the first polypeptide or the second polypeptide, or both. Alternatively, the third polypeptide may be a polypeptide having a binding activity against an antigen different from that of the first polypeptide and the second polypeptide.

Alternatively, the polypeptide multimer of the present invention may be a polypeptide multimer comprising the first polypeptide, the second polypeptide, the third polypeptide, and a fourth polypeptide. In such a polypeptide multimer, the first polypeptide and the second polypeptide can form multimers (dimers) with the third polypeptide and the fourth polypeptide, respectively. For example, a disulfide bond can be formed between the first polypeptide and the third polypeptide and between the second polypeptide and the fourth polypeptide to form dimers. The third polypeptide and the fourth polypeptide may be the same as each other.

In the polypeptide multimer of the present invention, the first polypeptide and the second polypeptide preferably have binding activities against different antigens, though the polypeptide multimer of the present invention is not particularly limited thereto. The polypeptide multimer of the present invention may have binding activities against different sites or epitopes in the same antigen. On the other hand, the third polypeptide may be a polypeptide having a binding activity against the same antigen as that of either of the first polypeptide or the second polypeptide, or both. Alternatively, the third polypeptide may be a polypeptide having a binding activity against an antigen different from that of the first polypeptide and the second polypeptide. The fourth polypeptide may be a polypeptide having a binding activity against the same antigen as that of either of the first polypeptide or the second polypeptide, or both. Alternatively, the fourth polypeptide may be a polypeptide having a binding activity against an antigen different from that of the first polypeptide and the second polypeptide. The third polypeptide and the fourth polypeptide may be the same as each other.

When the "heteromultimer" according to the present invention is a bispecific antibody, the first polypeptide and the second polypeptide may be, for example, a polypeptide comprising the amino acid sequence of an antibody heavy chain against antigen A and a polypeptide comprising the amino acid sequence of an antibody heavy chain against antigen B, respectively. In this case, the third polypeptide can be a polypeptide comprising the amino acid sequence of an antibody light chain against the antigen A, while the fourth polypeptide can be a polypeptide comprising the amino acid sequence of an antibody light chain against the antigen B. The third polypeptide and the fourth polypeptide may be the same as each other.

In the present invention, the "polypeptide having an antigen-binding activity" refers to a peptide or a protein of 5 or more amino acids in length having a domain (or region) capable of binding to a protein or a peptide such as an antigen or a ligand, and includes, for example, an antibody heavy chain or light chain variable region, a receptor, a fusion peptide of a receptor and an Fc region, a scaffold, and their fragments. Specifically, the polypeptide having an antigen-binding activity can comprise the amino acid sequence of an antibody variable region, a receptor, a fusion peptide of a receptor and an Fc region, a scaffold, or any of their fragments.

Any polypeptide can be used as the scaffold as long as the polypeptide is conformationally stable and can bind to at least one antigen. Examples of such a polypeptide include, but are not limited to, antibody variable region fragments, fibronectin, protein A domains, LDL receptor A domains, and lipocalin as well as molecules described in Nygren et al. (Current Opinion in Structural Biology, 7: 463-469 (1997); and Journal of Immunol Methods, 290: 3-28 (2004)), Binz et al. (Nature Biotech 23: 1257-1266 (2005)), and Hosse et al. (Protein Science 15: 14-27 (2006)).

Method for obtaining the antibody variable region, the receptor, the fusion peptide of a receptor and an Fc region, the scaffold, and their fragments are well known to those skilled in the art. A polypeptide comprising the amino acid sequence of a heavy chain constant region and the amino acid sequence of a light chain constant region can also be used.

In the present invention, the "reducing condition" refers to a condition or an environment where cysteine residues forming an inter-heavy chain disulfide bond in the heavy chain hinge regions, cysteine residues forming an inter-light chain disulfide bond, or cysteine residues introduced for the purpose of forming an inter-CH3 disulfide bond are more likely to be reduced than oxidized. The reducing condition preferably refers to a condition or an environment that allows these cysteine residues to cause disulfide bond isomerization, and particularly preferably refers to a condition or an environment that allows cysteine residues in heavy chain hinge regions, cysteine residues forming an inter-light chain disulfide bond, or cysteine residues introduced for the purpose of forming an inter-CH3 disulfide bond to cause disulfide bond isomerization without causing significant disulfide bond isomerization of cysteine residues other than these cysteine residues. In the present invention, for example, the time of incubating together the homologous form of the first polypeptide comprising a heavy chain constant region and the homologous form of the second polypeptide comprising a heavy chain constant region under the reducing condition can be appropriately set by those skilled in the art.

In the present invention, the "reducing agent" refers to a compound that reduces a molecule in the environment, i.e., a compound that shifts a molecule into a state where the molecule has been more reduced or is being more reduced in the environment. The reducing agent acts by donating an electron so that the reducing agent itself becomes an oxidized state after reduction of a substrate. Thus, the reducing agent is an active substance donating an electron. Examples of the reducing agent include dithiothreitol (DTT), mercaptoethanol, cysteine, thioglycolic acid, cysteamine (2-mercaptoethylamine: 2-MEA), glutathione (GSH), TCEP (tris (2-carboxyethyl)phosphine), and sodium borohydride.

In the present invention, the "disulfide bond isomerization" refers to the exchange of the disulfide bond, i.e., the reorganization of the disulfide bond, between cysteines contained in different polypeptides. For example, the "disulfide bond isomerization" in heavy chains refers to the exchange of the disulfide bond, i.e., the reorganization of the disulfide bond, between cysteines contained in different heavy chains. For example, the "disulfide bond isomerization" in light chains refers to the exchange of the disulfide bond, i.e., the reorganization of the disulfide bond, between cysteines contained in different light chains.

The "disulfide bond formation" refers to the process of forming a covalent bond between two cysteines present in one or two polypeptides. This bond is schematized by "—S—S—".

The "reduction of the disulfide bond" refers to the process of cleaving the disulfide bond into two thiol groups (—SH groups).

In the present invention, the term "FcγR" or "FcgR" refers to an Fcγ receptor which is a receptor capable of binding to the Fc region of an IgG1, IgG2, IgG3, or IgG4 monoclonal antibody, and means any member of the protein family substantially encoded by Fcγ receptor genes. In humans, this family includes, for example: FcγRI (CD64) including isoforms FcγRIa, FcγRIb, and FcγRIc; FcγRII (CD32) including isoforms FcγRIIa (including allotypes H131 (H type) and R131 (R type)), FcγRIIb (including FcγRIIb-1 and FcγRIIb-2), and FcγRIIc; and FcγRIII (CD16) including isoforms FcγRIIIa (including allotypes V158 and F158) and FcγRIIIb (including allotypes FcγRIIIb-NA1 and FcγRIIIb-NA2); and any yet-to-be-discovered human FcγR or FcγR isoform or allotype. The FcγR includes those derived from humans, mice, rats, rabbits, and monkeys. The FcγR is not limited to these molecules and may be derived from any organism. The mouse FcγRs include, for example, FcγRI (CD64), FcγRII (CD32), FcγRIII (CD16) and FcγRIII-2 (CD16-2), and FcγRIV, and any yet-to-be-discovered mouse FcγR or FcγR isoform or allotype.

In the present invention, the term "modification" or "substitution" can mean "modification" or "substitution" even if the amino acid is the same between before and after the modification or between before and after the substitution. The "modification" may also include "substitution".

Method for Producing Heteromultimer by Amino Acid Modification in Heavy Chain Constant Region In a preferred embodiment of the method for controlling dissociation and/or association between polypeptides according to the present invention, the method is a method comprising introducing a mutation of an amino acid residue to an antibody heavy chain constant region. This method may further comprise the optional steps of: introducing amino acid modification related to interface control using charge repulsion described below or the like; and introducing amino acid modification so as to destabilize the stability of a heavy chain CH3 region.

In one embodiment, the method is a method for producing a heteromultimer, comprising the following steps:
a) providing a homologous form of a first polypeptide having a first antigen-binding activity and comprising a heavy chain constant region;
b) providing a homologous form of a second polypeptide having a second antigen-binding activity that is different from the first antigen-binding activity and comprising a heavy chain constant region;
c) incubating the homologous form of the first polypeptide and the homologous form of the second polypeptide together under a reducing condition that allows cysteines outside of core hinge regions to cause disulfide bond isomerization; and
d) obtaining a heteromultimer comprising the first and second polypeptides, wherein amino acid residues in the core hinge regions do not form any disulfide bond.

The term "hinge region" or "hinge" means a region constituted by amino acids at positions 216 to 230 (EU numbering) in an antibody heavy chain.

The term "core hinge region" is a region flanked by at least two cysteine residues forming inter-heavy chain disulfide bonds, in a hinge region. Examples of the core hinge region in IgG1 and IgG4 include a region constituted by amino acids at positions 226 to 229 (EU numbering) in an antibody heavy chain. As an example, the core hinge region in human IgG1 refers to a region comprising Cys at position 226 (EU numbering), Pro at position 227 (EU numbering), Pro at position 228 (EU numbering), and Cys at position 229 (EU numbering) in an antibody heavy chain.

The term "outside of a hinge region" means a region or a site other than the hinge region and means, for example, a heavy chain variable region, a CH1 region, a CH2 region, a CH3 region, a light chain variable region, and a light chain constant region. The term "outside of a core hinge region" means the aforementioned region outside of the hinge region as well as a region other than the core hinge region in the hinge region.

The phrase "amino acid residues in the core hinge regions do not form any disulfide bond" means that because no disulfide bond is formed in the core hinge regions, for example, the first polypeptides cannot form a homologous form in their core hinge regions, the second polypeptides cannot form a homologous form in their core hinge regions, and the first polypeptide and the second polypeptide do not form a heteromer in their core hinge regions.

Specifically, the phrase means that, for example, the cysteine residue at position 226 and/or 229 according to EU numbering is modified into another amino acid residue or is deleted, or the core hinge regions are deleted, though the phrase is not limited thereto. Alternatively, the cysteine residues at positions 226 and 229 according to EU numbering may be modified into other amino acid residues or may be deleted, or the core hinge regions may be deleted. In this context, the another or other amino acid(s) is not particularly limited as long as this amino acid is not a cysteine residue. An amino acid residue forming no disulfide bond can be used. Further, amino acid residues at positions 220 to 225 according to EU numbering may be substituted by Tyr (Y)-Gly (G)-Pro (P)-Pro (P), or amino acid residues at positions 219 to 229 according to EU numbering may be deleted.

Disulfide Bond Reformation Between CH3 Regions by Fab Arm Exchange Reaction (CH3-FAE)

In one aspect, the present invention provides a method for producing a heteromultimer using the isomerization of a disulfide bond between cysteines in the CH3 regions of polypeptides comprising antibody heavy chain constant regions (inter-CH3 region disulfide bond). Each cysteine used in this method is not particularly limited as long as the cysteine is present in CH3. Preferably, one or more of amino acids at positions 349, 351, 354, 356, 394, and 407 according to EU numbering can be modified to cysteine for use. Alternatively, a polypeptide comprising CH3 having cysteine at one or more of positions 349, 351, 354, 356, 394, and 407 according to EU numbering may be used. For an IgG1 heavy chain constant region, one or more of amino acids at positions 355, 356, 409, 419, and 445 according to EU numbering may be further modified. For example, the amino acids may be modified to Gln (Q) at position 355 according to EU numbering, Glu (E) at position 356 according to EU numbering, Arg (R) at position 409 according to EU numbering, Glu (E) at position 419 according to EU numbering, and/or Leu (L) at position 445 according to EU numbering.

Specifically, the present invention provides a method for producing a heteromultimer comprising first and second polypeptides, wherein in a CH3 region contained in the heavy chain constant region of the first and/or second polypeptide, at least one amino acid residue selected from amino acid residues at positions 349, 351, 354, 356, 394, and 407 according to EU numbering is cysteine.

More specifically, the present invention provides a method for producing a heteromultimer comprising first and second polypeptides, wherein a set in which amino acid residues in the first and second polypeptides are each cysteine is any one of the following sets (1) to (5):

(1) amino acid residues at positions 349 and 356 according to EU numbering,
(2) amino acid residues at positions 394 and 394 according to EU numbering,
(3) amino acid residues at positions 351 and 351 according to EU numbering,
(4) amino acid residues at positions 407 and 407 according to EU numbering, and
(5) amino acid residues at positions 349 and 354 according to EU numbering.

The core hinge regions are preferably free from cysteine. For example, cysteine at position 226 and/or 229 according to EU numbering may be modified to another amino acid, and amino acid residues at positions 226 to 229 according to EU numbering may be SPPS or SPSS, though the core hinge region of the present invention is not particularly limited thereto. Alternatively, cysteine at position 226 and/or 229 according to EU numbering may be deleted.

Other amino acid residues contained in each hinge region may be modified or deleted, or other amino acids may be inserted thereto. For example, in IgG1, an amino acid residue at position 220 (EU numbering) may be substituted by serine, or amino acid residues at positions 220 to 225 (EU numbering) may be substituted by the sequence of IgG4, though the method of the present invention is not particularly limited thereto. In IgG1 or IgG4, amino acid residues at positions 219 to 229 (EU numbering) may be deleted, though the method of the present invention is not particularly limited thereto.

A portion or the whole of each hinge region may be deleted. For example, in IgG1 or IgG4, amino acid residues at positions 216 to 230 (EU numbering) may be deleted.

Still more specifically, the present invention provides a method for producing a heteromultimer comprising first and second polypeptides, wherein the heavy chain constant regions of the first and second polypeptides each have amino acid residues shown in any of the following (1) to (5):
(1) the first polypeptide has an amino acid residue other than Cys (C) at position 226 according to EU numbering, an amino acid residue other than Cys (C) at position 229 according to EU numbering, and Cys (C) at position 349 according to EU numbering, and the second polypeptide has an amino acid residue other than Cys (C) at position 226 according to EU numbering, an amino acid residue other than Cys (C) at position 229 according to EU numbering, and Cys (C) at position 356 according to EU numbering;
(2) the first and second polypeptides have an amino acid residue other than Cys (C) at position 226 according to EU numbering, an amino acid residue other than Cys (C) at position 229 according to EU numbering, and Cys (C) at position 394 according to EU numbering;
(3) the first and second polypeptides have an amino acid residue other than Cys (C) at position 226 according to EU numbering, an amino acid residue other than Cys (C) at position 229 according to EU numbering, and Cys (C) at position 351 according to EU numbering;
(4) the first and second polypeptides have an amino acid residue other than Cys (C) at position 226 according to EU numbering, an amino acid residue other than Cys (C) at position 229 according to EU numbering, and Cys (C) at position 407 according to EU numbering; and
(5) the first polypeptide has an amino acid residue other than Cys (C) at position 226 according to EU numbering, an amino acid residue other than Cys (C) at position 229 according to EU numbering, and Cys (C) at position 349 according to EU numbering, and the second polypeptide has an amino acid residue other than Cys (C) at position 226 according to EU numbering, an amino acid residue other than Cys (C) at position 229 according to EU numbering, and Cys (C) at position 354 according to EU numbering.

The present invention also provides a method for producing a heteromultimer comprising first and second polypeptides, wherein the heavy chain constant regions of the first and second polypeptides each have amino acid residues shown in any of the following (1) to (5):
(1) the first polypeptide has Ser (S) at position 226 according to EU numbering, Ser (S) at position 229 according to EU numbering, and Cys (C) at position 349 according to EU numbering, and the second polypeptide has Ser (S) at position 226 according to EU numbering, Ser (S) at position 229 according to EU numbering, and Cys (C) at position 356 according to EU numbering;
(2) the first and second polypeptides have Ser (S) at position 226 according to EU numbering, Ser (S) at position 229 according to EU numbering, and Cys (C) at position 394 according to EU numbering;
(3) the first and second polypeptides have Ser (S) at position 226 according to EU numbering, Ser (S) at position 229 according to EU numbering, and Cys (C) at position 351 according to EU numbering;
(4) the first and second polypeptides have Ser (S) at position 226 according to EU numbering, Ser (S) at position 229 according to EU numbering, and Cys (C) at position 407 according to EU numbering; and
(5) the first polypeptide has Ser (S) at position 226 according to EU numbering, Ser (S) at position 229 according to EU numbering, and Cys (C) at position 349 according to EU numbering, and the second polypeptide has Ser (S) at position 226, Ser (S) at position 229 according to EU numbering, and Cys (C) at position 354 according to EU numbering.

The present invention also provides a method for producing a heteromultimer comprising first and second polypeptides, wherein the heavy chain constant regions of the first and second polypeptides each have amino acid residues shown in any of the following (1) to (5):
(1) the first polypeptide has an amino acid residue other than Cys (C) at position 226 according to EU numbering, Pro (P) at position 228 according to EU numbering, an amino acid residue other than Cys (C) at position 229 according to EU numbering, and Cys (C) at position 349 according to EU numbering, and the second polypeptide has an amino acid residue other than Cys (C) at position 226 according to EU numbering, Pro (P) at position 228 according to EU numbering, an amino acid residue other than Cys (C) at position 229 according to EU numbering, and Cys (C) at position 356 according to EU numbering;
(2) the first and second polypeptides have an amino acid residue other than Cys (C) at position 226 according to EU numbering, Pro (P) at position 228 according to EU numbering, an amino acid residue other than Cys (C) at position 229 according to EU numbering, and Cys (C) at position 394 according to EU numbering;
(3) the first and second polypeptides have an amino acid residue other than Cys (C) at position 226 according to EU numbering, Pro (P) at position 228 according to EU numbering, an amino acid residue other than Cys (C) at position 229 according to EU numbering, and Cys (C) at position 351 according to EU numbering;
(4) the first and second polypeptides have an amino acid residue other than Cys (C) at position 226 according to EU numbering, Pro (P) at position 228 according to EU numbering, an amino acid residue other than Cys (C) at position 229 according to EU numbering, and Cys (C) at position 407 according to EU numbering; and (5) the first polypeptide has an amino acid residue other than Cys (C) at position 226 according to EU numbering, Pro (P) at position 228 according to EU numbering, an amino acid residue other than Cys (C) at position 229 according to EU numbering, and Cys (C) at position 349 according to EU numbering, and the second polypeptide has an amino acid residue other than Cys (C) at position 226 according to EU numbering, Pro (P) at position 228 according to EU numbering, an amino acid residue other than Cys (C) at position 229 according to EU numbering, and Cys (C) at position 354 according to EU numbering.

The present invention also provides a method for producing a heteromultimer comprising first and second polypeptides, wherein the heavy chain constant regions of the first and second polypeptides each have amino acid residues shown in any of the following (1) to (5):

(1) the first polypeptide has Ser (S) at position 226 according to EU numbering, Pro (P) at position 228 according to EU numbering, Ser (S) at position 229 according to EU numbering, and Cys (C) at position 349 according to EU numbering, and the second polypeptide has Ser (S) at position 226 according to EU numbering, Pro (P) at position 228 according to EU numbering, Ser (S) at position 229 according to EU numbering, and Cys (C) at position 356 according to EU numbering;

(2) the first and second polypeptides have Ser (S) at position 226 according to EU numbering, Pro (P) at position 228 according to EU numbering, Ser (S) at position 229 according to EU numbering, and Cys (C) at position 394 according to EU numbering;

(3) the first and second polypeptides have Ser (S) at position 226 according to EU numbering, Pro (P) at position 228 according to EU numbering, Ser (S) at position 229 according to EU numbering, and Cys (C) at position 351 according to EU numbering;

(4) the first and second polypeptides have Ser (S) at position 226 according to EU numbering, Pro (P) at position 228 according to EU numbering, Ser (S) at position 229 according to EU numbering, and Cys (C) at position 407 according to EU numbering; and (5) the first polypeptide has Ser (S) at position 226 according to EU numbering, Pro (P) at position 228 according to EU numbering, Ser (S) at position 229 according to EU numbering, and Cys (C) at position 349 according to EU numbering, and the second polypeptide has Ser (S) at position 226 according to EU numbering, Pro (P) at position 228 according to EU numbering, Ser (S) at position 229 according to EU numbering, and Cys (C) at position 354 according to EU numbering.

Still more specifically, the present invention provides a method for producing a heteromultimer comprising first and second polypeptides, wherein the heavy chain constant regions of the first and second polypeptides each have amino acid residues shown in any of the following (1) to (6):

(1) the first polypeptide has an amino acid residue other than Cys (C) at position 226 according to EU numbering, an amino acid residue other than Cys (C) at position 229 according to EU numbering, Cys (C) at position 349 according to EU numbering and any of Lys (K), Arg (R), and His (H) at position 356 according to EU numbering, and the second polypeptide has an amino acid residue other than Cys (C) at position 226 according to EU numbering, an amino acid residue other than Cys (C) at position 229 according to EU numbering, Cys (C) at position 356 according to EU numbering, and Glu (E) or Asp (D) at position 439 according to EU numbering;

(2) the first polypeptide has an amino acid residue other than Cys (C) at position 226 according to EU numbering, an amino acid residue other than Cys (C) at position 229 according to EU numbering, Cys (C) at position 349 according to EU numbering, Tyr (Y) at position 397 according to EU numbering, and any of Lys (K), Arg (R), and His (H) at position 356 according to EU numbering, and the second polypeptide has an amino acid residue other than Cys (C) at position 226, according to EU numbering an amino acid residue other than Cys (C) at position 229 according to EU numbering, Cys (C) at position 356 according to EU numbering, Tyr (Y) at position 397 according to EU numbering, and Glu (E) or Asp (D) at position 439 according to EU numbering;

(3) the first and second polypeptides have an amino acid residue other than Cys (C) at position 226 according to EU numbering, an amino acid residue other than Cys (C) at position 229 according to EU numbering, and Cys (C) at position 394 according to EU numbering, one of the polypeptides has any of Lys (K), Arg (R), and His (H) at position 356 according to EU numbering, and the other polypeptide has Glu (E) or Asp (D) at position 439 according to EU numbering;

(4) the first polypeptide has an amino acid residue other than Cys (C) at position 226 according to EU numbering, an amino acid residue other than Cys (C) at position 229 according to EU numbering, and Cys (C) at position 349 according to EU numbering, the second polypeptide has an amino acid residue other than Cys (C) at position 226 according to EU numbering, an amino acid residue other than Cys (C) at position 229 according to EU numbering, and Cys (C) at position 354 according to EU numbering, one of the polypeptides has any of Lys (K), Arg (R), and His (H) at position 356 according to EU numbering, and the other polypeptide has Glu (E) or Asp (D) at position 439 according to EU numbering;

(5) the first and second polypeptides have an amino acid residue other than Cys (C) at position 226 according to EU numbering, an amino acid residue other than Cys (C) at position 229 according to EU numbering, and one of the polypeptides has Cys (C) at position 351 according to EU numbering, any of Lys (K), Arg (R), and His (H) at position 356 according to EU numbering, and the other polypeptide has Glu (E) or Asp (D) at position 439 according to EU numbering; and (6) the first and second polypeptides have an amino acid residue other than Cys (C) at position 226 according to EU numbering, an amino acid residue other than Cys (C) at position 229 according to EU numbering, and Cys (C) at position 407 according to EU numbering, one of the polypeptides has any of Lys (K), Arg (R), and His (H) at position 356 according to EU numbering, and the other polypeptide has Glu (E) or Asp (D) at position 439 according to EU numbering.

More specifically, the present invention also provides a method for producing a heteromultimer comprising first and second polypeptides, wherein the heavy chain constant regions of the first and second polypeptides each have amino acid residues shown in any of the following (1) to (6):

(1) the first polypeptide has Ser (S) at position 226 according to EU numbering, Ser (S) at position 229 according to EU numbering, Cys (C) at position 349 according to EU numbering, and any of Lys (K), Arg (R), and His (H) at position 356 according to EU numbering, and the second polypeptide has Ser (S) at position 226 according to EU numbering, Ser (S) at position 229 according to EU numbering, Cys (C) at position 356 according to EU numbering, and Glu (E) or Asp (D) at position 439 according to EU numbering;
(2) the first polypeptide has Ser (S) at position 226 according to EU numbering, Ser (S) at position 229 according to EU numbering, Cys (C) at position 349 according to EU numbering, Tyr (Y) at position 397 according to EU numbering, and any of Lys (K), Arg (R), and His (H) at position 356 according to EU numbering, and the second polypeptide has Ser (S) at position 226 according to EU numbering, Ser (S) at position 229 according to EU numbering, Cys (C) at position 356 according to EU numbering, Tyr (Y) at position 397 according to EU numbering, and Glu (E) or Asp (D) at position 439 according to EU numbering;
(3) the first and second polypeptides have Ser (S) at position 226 according to EU numbering, Ser (S) at position 229 according to EU numbering, and Cys (C) at position 394 according to EU numbering, one of the polypeptides has any of Lys (K), Arg (R), and His (H) at position 356 according to EU numbering, and the other polypeptide has Glu (E) or Asp (D) at position 439 according to EU numbering;
(4) the first polypeptide has Ser (S) at position 226 according to EU numbering, Ser (S) at position 229 according to EU numbering, and Cys (C) at position 349 according to EU numbering, the second polypeptide has Ser (S) at position 226 according to EU numbering, Ser (S) at position 229 according to EU numbering, and Cys (C) at position 354 according to EU numbering, one of the polypeptides has any of Lys (K), Arg (R), and His (H) at position 356 according to EU numbering, and the other polypeptide has Glu (E) or Asp (D) at position 439 according to EU numbering;
(5) the first and second polypeptides have Ser (S) at position 226 according to EU numbering, Ser (S) at position 229 according to EU numbering, and Cys (C) at position 351 according to EU numbering, one of the polypeptides has any of Lys (K), Arg (R), and His (H) at position 356 according to EU numbering, and the other polypeptide has Glu (E) or Asp (D) at position 439 according to EU numbering; and
(6) the first and second polypeptides have Ser (S) at position 226 according to EU numbering, Ser (S) at position 229 according to EU numbering, and Cys (C) at position 407 according to EU numbering, one of the polypeptides has any of Lys (K), Arg (R), and His (H) at position 356 according to EU numbering, and the other polypeptide has Glu (E) or Asp (D) at position 439 according to EU numbering.

The present invention also provides a method for producing a heteromultimer comprising first and second polypeptides, wherein the heavy chain constant regions of the first and second polypeptides each have amino acid residues shown in any of the following (1) to (6):
(1) the first polypeptide has an amino acid residue other than Cys (C) at position 226 according to EU numbering, Pro (P) at position 228 according to EU numbering, an amino acid residue other than Cys (C) at position 229 according to EU numbering, Cys (C) at position 349 according to EU numbering, and any of Lys (K), Arg (R), and His (H) at position 356 according to EU numbering, and the second polypeptide has an amino acid residue other than Cys (C) at position 226 according to EU numbering, Pro (P) at position 228 according to EU numbering, an amino acid residue other than Cys (C) at position 229 according to EU numbering, Cys (C) at position 356 according to EU numbering, and Glu (E) or Asp (D) at position 439 according to EU numbering;
(2) the first polypeptide has an amino acid residue other than Cys (C) at position 226 according to EU numbering, Pro (P) at position 228 according to EU numbering, an amino acid residue other than Cys (C) at position 229 according to EU numbering, Cys (C) at position 349 according to EU numbering, Tyr (Y) at position 397 according to EU numbering, and any of Lys (K), Arg (R), and His (H) at position 356 according to EU numbering, and the second polypeptide has an amino acid residue other than Cys (C) at position 226 according to EU numbering, Pro (P) at position 228 according to EU numbering, an amino acid residue other than Cys (C) at position 229 according to EU numbering, Cys (C) at position 356 according to EU numbering, Tyr (Y) at position 397 according to EU numbering, and Glu (E) or Asp (D) at position 439 according to EU numbering;
(3) the first and second polypeptides have an amino acid residue other than Cys (C) at position 226 according to EU numbering, Pro (P) at position 228 according to EU numbering, an amino acid residue other than Cys (C) at position 229 according to EU numbering, and Cys (C) at position 394 according to EU numbering, one of the polypeptides any of Lys (K), Arg (R), and His (H) at position 356 according to EU numbering, and the other polypeptide has Glu (E) or Asp (D) at position 439 according to EU numbering;
(4) the first polypeptide has an amino acid residue other than Cys (C) at position 226 according to EU numbering, Pro (P) at position 228 according to EU numbering, an amino acid residue other than Cys (C) at position 229 according to EU numbering, and Cys (C) at position 349 according to EU numbering, the second polypeptide has an amino acid residue other than Cys (C) at position 226 according to EU numbering, Pro (P) at position 228 according to EU numbering, an amino acid residue other than Cys (C) at position 229 according to EU numbering, and Cys (C) at position 354 according to EU numbering, one of the polypeptides has any of Lys (K), Arg (R), and His (H) at position 356 according to EU numbering, and the other polypeptide has Glu (E) or Asp (D) at position 439 according to EU numbering;
(5) the first and second polypeptides have an amino acid residue other than Cys (C) at position 226 according to EU numbering, Pro (P) at position 228 according to EU numbering, an amino acid residue other than Cys (C) at position 229 according to EU numbering, and Cys (C) at position 351 according to EU numbering, one of the polypeptides has any of Lys (K), Arg (R), and His (H) at position 356 according to EU numbering, and the other polypeptide has Glu (E) or Asp (D) at position 439 according to EU numbering; and
(6) the first and second polypeptides have an amino acid residue other than Cys (C) at position 226 according to EU numbering, Pro (P) at position 228 according to EU numbering, an amino acid residue other than Cys (C) at position 229 according to EU numbering, and Cys (C) at position 407 according to EU numbering, one of the polypeptides has any of Lys (K), Arg (R), and His (H) at position 356 according to EU numbering, and the other polypeptide has Glu (E) or Asp (D) at position 439 according to EU numbering.

The present invention also provides a method for producing a heteromultimer comprising first and second polypeptides, wherein the heavy chain constant regions of the first and second polypeptides each have amino acid residues shown in any of the following (1) to (6): (1) the first polypeptide has Ser (S) at position 226 according to EU numbering, Pro (P) at position 228 according to EU numbering, Ser (S) at position 229 according to EU numbering, Cys (C) at position 349 according to EU numbering, and any of Lys (K), Arg (R), and His (H) at position 356 according to EU numbering, and the second polypeptide has Ser (S) at position 226 according to EU numbering, Pro (P) at position 228 according to EU numbering, Ser (S) at position 229 according to EU numbering, Cys (C) at position 356 according to EU numbering, and Glu (E) or Asp (D) at position 439 according to EU numbering;
(2) the first polypeptide has Ser (S) at position 226 according to EU numbering, Pro (P) at position 228 according to EU numbering, Ser (S) at position 229 according to EU numbering, Cys (C) at position 349 according to EU numbering, Tyr (Y) at position 397 according to EU numbering, and any of Lys (K), Arg (R), and His (H) at position 356 according to EU numbering, and the second polypeptide has Ser (S) at position 226 according to EU numbering, Pro (P) at position 228 according to EU numbering, Ser (S) at position 229 according to EU numbering, Cys (C) at position 356 according to EU numbering, Tyr (Y) at position 397 according to EU numbering, and Glu (E) or Asp (D) at position 439 according to EU numbering;
(3) the first and second polypeptides have Ser (S) at position 226 according to EU numbering, Pro (P) at position 228 according to EU numbering, Ser (S) at position 229 according to EU numbering, and Cys (C) at position 394 according to EU numbering, one of the polypeptides has any of Lys (K), Arg (R), and His (H) at position 356 according to EU numbering, and the other polypeptide has Glu (E) or Asp (D) at position 439 according to EU numbering;
(4) the first polypeptide has Ser (S) at position 226 according to EU numbering, Pro (P) at position 228 according to EU numbering, Ser (S) at position 229 according to EU numbering, and Cys (C) at position 349 according to EU numbering, the second polypeptide has Ser (S) at position 226 according to EU numbering, Pro (P) at position 228 according to EU numbering, Ser (S) at position 229 according to EU numbering, and Cys (C) at position 354 according to EU numbering, one of the polypeptides has any of Lys (K), Arg (R), and His (H) at position 356 according to EU numbering, and the other polypeptide has Glu (E) or Asp (D) at position 439 according to EU numbering;
(5) the first and second polypeptides have Ser (S) at position 226 according to EU numbering, Pro (P) at position 228 according to EU numbering, Ser (S) at position 229 according to EU numbering, and Cys (C) at position 351 according to EU numbering, one of the polypeptides has any of Lys (K), Arg (R), and His (H) at position 356 according to EU numbering, and the other polypeptide has Glu (E) or Asp (D) at position 439 according to EU numbering; and
(6) the first and second polypeptides have Ser (S) at position 226 according to EU numbering, Pro (P) at position 228 according to EU numbering, Ser (S) at position 229 according to EU numbering, and Cys (C) at position 407 according to EU numbering, one of the polypeptides has any of Lys (K), Arg (R), and His (H) at position 356 according to EU numbering, and the other polypeptide has Glu (E) or Asp (D) at position 439 according to EU numbering.

Still more specifically, the present invention provides a method for producing a heteromultimer comprising first and second polypeptides, wherein the heavy chain constant regions of the first and second polypeptides each have amino acid residues shown in any of the following (1) to (6):
(1) the first polypeptide has an amino acid residue other than Cys (C) at position 226 according to EU numbering, an amino acid residue other than Cys (C) at position 229 according to EU numbering, Cys (C) at position 349 according to EU numbering, and Lys (K) at position 356 according to EU numbering, and the second polypeptide has an amino acid residue other than Cys (C) at position 226 according to EU numbering, an amino acid residue other than Cys (C) at position 229 according to EU numbering, Cys (C) at position 356 according to EU numbering, and Glu (E) at position 439 according to EU numbering;
(2) the first polypeptide has an amino acid residue other than Cys (C) at position 226 according to EU numbering, an amino acid residue other than Cys (C) at position 229 according to EU numbering, Cys (C) at position 349 according to EU numbering, Lys (K) at position 356 according to EU numbering, and Tyr (Y) at position 397 according to EU numbering, and the second polypeptide has an amino acid residue other than Cys (C) at position 226 according to EU numbering, an amino acid residue other than Cys (C) at position 229 according to EU numbering, Cys (C) at position 356 according to EU numbering, Tyr (Y) at position 397 according to EU numbering, and Glu (E) at position 439 according to EU numbering;
(3) the first polypeptide has an amino acid residue other than Cys (C) at position 226 according to EU numbering, an amino acid residue other than Cys (C) at position 229 according to EU numbering, Cys (C) at position 394 according to EU numbering, and Lys (K) at position 356 according to EU numbering, and the second polypeptide has an amino acid residue other than Cys (C) at position 226 according to EU numbering, an amino acid residue other than Cys (C) at position 229 according to EU numbering, Cys (C) at position 394 according to EU numbering, and Glu (E) at position 439 according to EU numbering;
(4) the first polypeptide has an amino acid residue other than Cys (C) at position 226 according to EU numbering, an amino acid residue other than Cys (C) at position 229 according to EU numbering, Cys (C) at position 349 according to EU numbering, and Lys (K) at position 356 according to EU numbering, and the second polypeptide has an amino acid residue other than Cys (C) at position 226 according to EU numbering, an amino acid residue other than Cys (C) at position 229 according to EU numbering, Cys (C) at position 354 according to EU numbering, and Glu (E) at position 439 according to EU numbering;
(5) the first polypeptide has an amino acid residue other than Cys (C) at position 226 according to EU numbering, an amino acid residue other than Cys (C) at position 229 according to EU numbering, Cys (C) at position 351 according to EU numbering, and Lys (K) at position 356 according to EU numbering, and the second polypeptide has an amino acid residue other than Cys (C) at position 226 according to EU numbering, an amino acid residue other than Cys (C) at position 229 according to EU numbering, Cys (C) at position 351 according to EU numbering, and Glu (E) at position 439 according to EU numbering; and
(6) the first polypeptide has an amino acid residue other than Cys (C) at position 226 according to EU numbering, an amino acid residue other than Cys (C) at position 229 according to EU numbering, Cys (C) at position 407 according to EU numbering, and Lys (K) at position 356 according to EU numbering, and the second polypeptide has an amino acid residue other than Cys (C) at position 226 according to EU numbering, an amino acid residue other than Cys (C) at position 229 according to EU numbering, Cys (C) at position 407 according to EU numbering, and Glu (E) at position 439 according to EU numbering.

More specifically, the present invention also provides a method for producing a heteromultimer comprising first and second polypeptides, wherein the heavy chain constant regions of the first and second polypeptides each have amino acid residues shown in any of the following (1) to (6):
(1) the first polypeptide has Ser (S) at position 226 according to EU numbering, Ser (S) at position 229 according to EU numbering, Cys (C) at position 349 according to EU numbering, and Lys (K) at position 356 according to EU numbering, and the second polypeptide has Ser (S) at position 226 according to EU numbering, Ser (S) at position 229 according to EU numbering, Cys (C) at position 356 according to EU numbering, and Glu (E) at position 439 according to EU numbering;
(2) the first polypeptide has Ser (S) at position 226 according to EU numbering, Ser (S) at position 229 according to EU numbering, Cys (C) at position 349 according to EU numbering, Lys (K) at position 356 according to EU numbering, and Tyr (Y) at position 397 according to EU numbering, and the second polypeptide has Ser (S) at position 226 according to EU numbering, Ser (S) at position 229 according to EU numbering, Cys (C) at position 356 according to EU numbering, Tyr (Y) at position 397 according to EU numbering, and Glu (E) at position 439 according to EU numbering;
(3) the first polypeptide has Ser (S) at position 226 according to EU numbering, Ser (S) at position 229 according to EU numbering, Cys (C) at position 394 according to EU numbering, and Lys (K) at position 356 according to EU numbering, and the second polypeptide has Ser (S) at position 226 according to EU numbering, Ser (S) at position 229 according to EU numbering, Cys (C) at position 394 according to EU numbering, and Glu (E) at position 439 according to EU numbering;
(4) the first polypeptide has Ser (S) at position 226 according to EU numbering, Ser (S) at position 229 according to EU numbering, Cys (C) at position 349 according to EU numbering, and Lys (K) at position 356 according to EU numbering, and the second polypeptide has Ser (S) at position 226 according to EU numbering, Ser (S) at position 229 according to EU numbering, Cys (C) at position 354 according to EU numbering, and Glu (E) at position 439 according to EU numbering;
(5) the first polypeptide has Ser (S) at position 226 according to EU numbering, Ser (S) at position 229 according to EU numbering, Cys (C) at position 351 according to EU numbering, and Lys (K) at position 356 according to EU numbering, and the second polypeptide has Ser (S) at position 226 according to EU numbering, Ser (S) at position 229 according to EU numbering, Cys (C) at position 351 according to EU numbering, and Glu (E) at position 439 according to EU numbering; and
(6) the first polypeptide has Ser (S) at position 226 according to EU numbering, Ser (S) at position 229 according to EU numbering, Cys (C) at position 407 according to EU numbering, and Lys (K) at position 356 according to EU numbering, and the second polypeptide has Ser (S) at position 226 according to EU numbering, Ser (S) at position 229 according to EU numbering, Cys (C) at position 407 according to EU numbering, and Glu (E) at position 439 according to EU numbering.

The present invention also provides a method for producing a heteromultimer comprising first and second polypeptides, wherein the heavy chain constant regions of the first and second polypeptides each have amino acid residues shown in any of the following (1) to (6):
(1) the first polypeptide has an amino acid residue other than Cys (C) at position 226 according to EU numbering, Pro (P) at position 228 according to EU numbering, an amino acid residue other than Cys (C) at position 229 according to EU numbering, Cys (C) at position 349 according to EU numbering, and Lys (K) at position 356 according to EU numbering, and the second polypeptide has an amino acid residue other than Cys (C) at position 226 according to EU numbering, Pro (P) at position 228 according to EU numbering, an amino acid residue other than Cys (C) at position 229 according to EU numbering, Cys (C) at position 356 according to EU numbering, and Glu (E) at position 439 according to EU numbering;
(2) the first polypeptide has an amino acid residue other than Cys (C) at position 226 according to EU numbering, Pro (P) at position 228 according to EU numbering, an amino acid residue other than Cys (C) at position 229 according to EU numbering, Cys (C) at position 349 according to EU numbering, Lys (K) at position 356 according to EU numbering, and Tyr (Y) at position 397 according to EU numbering, and the second polypeptide has an amino acid residue other than Cys (C) at position 226 according to EU numbering, Pro (P) at position 228 according to EU numbering, an amino acid residue other than Cys (C) at position 229 according to EU numbering, Cys (C) at position 356 according to EU numbering, Tyr (Y) at position 397 according to EU numbering, and Glu (E) at position 439 according to EU numbering;
(3) the first polypeptide has an amino acid residue other than Cys (C) at position 226 according to EU numbering, Pro (P) at position 228 according to EU numbering, an amino acid residue other than Cys (C) at position 229 according to EU numbering, Cys (C) at position 394 according to EU numbering, and Lys (K) at position 356 according to EU numbering, and the second polypeptide has an amino acid residue other than Cys (C) at position 226 according to EU numbering, Pro (P) at position 228 according to EU numbering, an amino acid residue other than Cys (C) at position 229 according to EU numbering, Cys (C) at position 394 according to EU numbering, and Glu (E) at position 439 according to EU numbering;
(4) the first polypeptide has an amino acid residue other than Cys (C) at position 226 according to EU numbering, Pro (P) at position 228 according to EU numbering, an amino acid residue other than Cys (C) at position 229 according to EU numbering, Cys (C) at position 349 according to EU numbering, and Lys (K) at position 356 according to EU numbering, and the second polypeptide has an amino acid residue other than Cys (C) at position 226 according to EU numbering, Pro (P) at position 228 according to EU numbering, an amino acid residue other than Cys (C) at position 229 according to EU numbering, Cys (C) at position 354 according to EU numbering, and Glu (E) at position 439 according to EU numbering;
(5) the first polypeptide has an amino acid residue other than Cys (C) at position 226 according to EU numbering, Pro (P) at position 228 according to EU numbering, an amino acid residue other than Cys (C) at position 229 according to EU numbering, Cys (C) at position 351 according to EU numbering, and Lys (K) at position 356 according to EU numbering, and the second polypeptide has an amino acid residue other than Cys (C) at position 226 according to EU numbering, Pro (P) at position 228 according to EU numbering, an amino acid residue other than Cys (C) at position 229 according to EU numbering, Cys (C) at position 351 according to EU numbering, and Glu (E) at position 439 according to EU numbering; and
(6) the first polypeptide has an amino acid residue other than Cys (C) at position 226 according to EU numbering, Pro (P) at position 228 according to EU numbering, an amino acid residue other than Cys (C) at position 229 according to EU numbering, Cys (C) at position 407 according to EU numbering, and Lys (K) at position 356 according to EU numbering, and the second polypeptide has an amino acid residue other than Cys (C) at position 226 according to EU numbering, Pro (P) at position 228 according to EU numbering, an amino acid residue other than Cys (C) at position 229 according to EU numbering, Cys (C) at position 407 according to EU numbering, and Glu (E) at position 439 according to EU numbering.

The present invention also provides a method for producing a heteromultimer comprising first and second polypeptides, wherein the heavy chain constant regions of the first and second polypeptides each have amino acid residues shown in any of the following (1) to (6):

(1) the first polypeptide has Ser (S) at position 226 according to EU numbering, Pro (P) at position 228 according to EU numbering, Ser (S) at position 229 according to EU numbering, Cys (C) at position 349 according to EU numbering, and Lys (K) at position 356 according to EU numbering, and the second polypeptide has Ser (S) at position 226 according to EU numbering, Pro (P) at position 228 according to EU numbering, Ser (S) at position 229 according to EU numbering, Cys (C) at position 356 according to EU numbering, and Glu (E) at position 439 according to EU numbering;

(2) the first polypeptide has Ser (S) at position 226 according to EU numbering, Pro (P) at position 228 according to EU numbering, Ser (S) at position 229 according to EU numbering, Cys (C) at position 349 according to EU numbering, Lys (K) at position 356 according to EU numbering, and Tyr (Y) at position 397 according to EU numbering, and the second polypeptide has Ser (S) at position 226 according to EU numbering, Pro (P) at position 228 according to EU numbering, Ser (S) at position 229 according to EU numbering, Cys (C) at position 356 according to EU numbering, Tyr (Y) at position 397 according to EU numbering, and Glu (E) at position 439 according to EU numbering;

(3) the first polypeptide has Ser (S) at position 226 according to EU numbering, Pro (P) at position 228 according to EU numbering, Ser (S) at position 229 according to EU numbering, Cys (C) at position 394 according to EU numbering, and Lys (K) at position 356 according to EU numbering, and the second polypeptide has Ser (S) at position 226 according to EU numbering, Pro (P) at position 228 according to EU numbering, Ser (S) at position 229 according to EU numbering, Cys (C) at position 394 according to EU numbering, and Glu (E) at position 439 according to EU numbering;

(4) the first polypeptide has Ser (S) at position 226 according to EU numbering, Pro (P) at position 228 according to EU numbering, Ser (S) at position 229 according to EU numbering, Cys (C) at position 349 according to EU numbering, and Lys (K) at position 356 according to EU numbering, and the second polypeptide has Ser (S) at position 226 according to EU numbering, Pro (P) at position 228 according to EU numbering, Ser (S) at position 229 according to EU numbering, Cys (C) at position 354 according to EU numbering, and Glu (E) at position 439 according to EU numbering;

(5) the first polypeptide has Ser (S) at position 226 according to EU numbering, Pro (P) at position 228 according to EU numbering, Ser (S) at position 229 according to EU numbering, Cys (C) at position 351 according to EU numbering, and Lys (K) at position 356 according to EU numbering, and the second polypeptide has Ser (S) at position 226 according to EU numbering, Pro (P) at position 228 according to EU numbering, Ser (S) at position 229 according to EU numbering, Cys (C) at position 351 according to EU numbering, and Glu (E) at position 439 according to EU numbering; and (6) the first polypeptide has Ser (S) at position 226 according to EU numbering, Pro (P) at position 228 according to EU numbering, Ser (S) at position 229 according to EU numbering, Cys (C) at position 407 according to EU numbering, and Lys (K) at position 356 according to EU numbering, and the second polypeptide has Ser (S) at position 226 according to EU numbering, Pro (P) at position 228 according to EU numbering, Ser (S) at position 229 according to EU numbering, Cys (C) at position 407 according to EU numbering, and Glu (E) at position 439 according to EU numbering.

In an alternative aspect, the present invention provides a bispecific antibody comprising first, second, third, and fourth polypeptides as constituents in which the first polypeptide which is an antibody heavy chain and the third polypeptide which is an antibody light chain form a dimer, and the second polypeptide which is an antibody heavy chain and the fourth polypeptide which is an antibody light chain form a dimer, wherein an amino acid residue at a predetermined position in a CH3 region contained in the heavy chain constant region of the first and/or the second polypeptide is cysteine.

Specifically, the present invention provides a bispecific antibody wherein in a CH3 region contained in the heavy chain constant region of the first and/or the second polypeptide, at least one amino acid residue selected from amino acid residues at positions 349, 351, 354, 356, 394, and 407 according to EU numbering is cysteine.

More specifically, the present invention provides a bispecific antibody wherein a set in which amino acid residues in the first and second polypeptides are each cysteine is any one of the following sets (1) to (5):

(1) amino acid residues at positions 349 and 356 according to EU numbering, (2) amino acid residues at positions 394 and 394 according to EU numbering, (3) amino acid residues at positions 351 and 351 according to EU numbering, (4) amino acid residues at positions 407 and 407 according to EU numbering, and (5) amino acid residues at positions 349 and 354 according to EU numbering.

Still more specifically, the present invention provides a bispecific antibody wherein the heavy chain constant regions of the first and second polypeptides each have amino acid residues shown in any of the following (1) to (5):

(1) the first polypeptide has an amino acid residue other than Cys (C) at position 226 according to EU numbering, an amino acid residue other than Cys (C) at position 229 according to EU numbering, and Cys (C) at position 349 according to EU numbering, and the second polypeptide has an amino acid residue other than Cys (C) at position 226 according to EU numbering, an amino acid residue other than Cys (C) at position 229 according to EU numbering, and Cys (C) at position 356 according to EU numbering;

(2) the first and second polypeptides have an amino acid residue other than Cys (C) at position 226 according to EU numbering, an amino acid residue other than Cys (C) at position 229 according to EU numbering, and Cys (C) at position 394 according to EU numbering;

(3) the first and second polypeptides have an amino acid residue other than Cys (C) at position 226 according to EU numbering, an amino acid residue other than Cys (C) at position 229 according to EU numbering, and Cys (C) at position 351 according to EU numbering;

(4) the first and second polypeptides have an amino acid residue other than Cys (C) at position 226 according to EU numbering, an amino acid residue other than Cys (C) at position 229 according to EU numbering, and Cys (C) at position 407 according to EU numbering; and (5) the first polypeptide has an amino acid residue other than Cys (C) at position 226 according to EU numbering, an amino acid residue other than Cys (C) at position 229 according to EU numbering, and Cys (C) at position 349 according to EU numbering, and the second polypeptide has an amino acid residue other than Cys (C) at position 226 according to EU numbering, an amino acid residue other than Cys (C) at position 229 according to EU numbering, and Cys (C) at position 354 according to EU numbering.

The present invention also provides a bispecific antibody wherein the heavy chain constant regions of the first and second polypeptides each have amino acid residues shown in any of the following (1) to (5):
(1) the first polypeptide has Ser (S) at position 226 according to EU numbering, Ser (S) at position 229 according to EU numbering, and Cys (C) at position 349 according to EU numbering, and the second polypeptide has Ser (S) at position 226 according to EU numbering, Ser (S) at position 229 according to EU numbering, and Cys (C) at position 356 according to EU numbering;
(2) the first and second polypeptides have Ser (S) at position 226 according to EU numbering, Ser (S) at position 229 according to EU numbering, and Cys (C) at position 394 according to EU numbering;
(3) the first and second polypeptides have Ser (S) at position 226 according to EU numbering, Ser (S) at position 229 according to EU numbering, and Cys (C) at position 351 according to EU numbering;
(4) the first and second polypeptides have Ser (S) at position 226 according to EU numbering, Ser (S) at position 229 according to EU numbering, and Cys (C) at position 407 according to EU numbering; and
(5) the first polypeptide has Ser (S) at position 226 according to EU numbering, Ser (S) at position 229 according to EU numbering, and Cys (C) at position 349 according to EU numbering, and the second polypeptide has Ser (S) at position 226 according to EU numbering, Ser (S) at position 229 according to EU numbering, and Cys (C) at position 354 according to EU numbering.

The present invention also provides a bispecific antibody wherein the heavy chain constant regions of the first and second polypeptides each have amino acid residues shown in any of the following (1) to (5):
(1) the first polypeptide has an amino acid residue other than Cys (C) at position 226 according to EU numbering, Pro (P) at position 228 according to EU numbering, an amino acid residue other than Cys (C) at position 229 according to EU numbering, and Cys (C) at position 349 according to EU numbering, and the second polypeptide has an amino acid residue other than Cys (C) at position 226 according to EU numbering, Pro (P) at position 228 according to EU numbering, an amino acid residue other than Cys (C) at position 229 according to EU numbering, and Cys (C) at position 356 according to EU numbering;
(2) the first and second polypeptides have an amino acid residue other than Cys (C) at position 226 according to EU numbering, Pro (P) at position 228 according to EU numbering, an amino acid residue other than Cys (C) at position 229 according to EU numbering, and Cys (C) at position 394 according to EU numbering;
(3) the first and second polypeptides have an amino acid residue other than Cys (C) at position 226 according to EU numbering, Pro (P) at position 228 according to EU numbering, an amino acid residue other than Cys (C) at position 229 according to EU numbering, and Cys (C) at position 351 according to EU numbering;
(4) the first and second polypeptides have an amino acid residue other than Cys (C) at position 226 according to EU numbering, Pro (P) at position 228 according to EU numbering, an amino acid residue other than Cys (C) at position 229 according to EU numbering, and Cys (C) at position 407 according to EU numbering; and
(5) the first polypeptide has an amino acid residue other than Cys (C) at position 226 according to EU numbering, Pro (P) at position 228 according to EU numbering, an amino acid residue other than Cys (C) at position 229 according to EU numbering, and Cys (C) at position 349 according to EU numbering, and the second polypeptide has an amino acid residue other than Cys (C) at position 226 according to EU numbering, Pro (P) at position 228 according to EU numbering, an amino acid residue other than Cys (C) at position 229 according to EU numbering, and Cys (C) at position 354 according to EU numbering.

The present invention also provides a bispecific antibody wherein the heavy chain constant regions of the first and second polypeptides each have amino acid residues shown in any of the following (1) to (5):
(1) the first polypeptide has Ser (S) at position 226 according to EU numbering, Pro (P) at position 228 according to EU numbering, Ser (S) at position 229 according to EU numbering, and Cys (C) at position 349 according to EU numbering, and the second polypeptide has Ser (S) at position 226 according to EU numbering, Pro (P) at position 228 according to EU numbering, Ser (S) at position 229 according to EU numbering, and Cys (C) at position 356 according to EU numbering;
(2) the first and second polypeptides have Ser (S) at position 226 according to EU numbering, Pro (P) at position 228 according to EU numbering, Ser (S) at position 229 according to EU numbering, and Cys (C) at position 394 according to EU numbering;
(3) the first and second polypeptides have Ser (S) at position 226 according to EU numbering, Pro (P) at position 228 according to EU numbering, Ser (S) at position 229 according to EU numbering, and Cys (C) at position 351 according to EU numbering;
(4) the first and second polypeptides have Ser (S) at position 226 according to EU numbering, Pro (P) at position 228 according to EU numbering, Ser (S) at position 229 according to EU numbering, and Cys (C) at position 407 according to EU numbering; and
(5) the first polypeptide has Ser (S) at position 226 according to EU numbering, Pro (P) at position 228 according to EU numbering, Ser (S) at position 229 according to EU numbering, and Cys (C) at position 349 according to EU numbering, and the second polypeptide has Ser (S) at position 226 according to EU numbering, Pro (P) at position 228 according to EU numbering, Ser (S) at position 229 according to EU numbering, and Cys (C) at position 354 according to EU numbering.

Still more specifically, the present invention provides a bispecific antibody wherein the heavy chain constant regions of the first and second polypeptides each have amino acid residues shown in any of the following (1) to (6):
(1) the first polypeptide has an amino acid residue other than Cys (C) at position 226 according to EU numbering, an amino acid residue other than Cys (C) at position 229 according to EU numbering, Cys (C) at position 349 according to EU numbering and any of Lys (K), Arg (R), and His (H) at position 356 according to EU numbering, and the second polypeptide has an amino acid residue other than Cys (C) at position 226 according to EU numbering, an amino acid residue other than Cys (C) at position 229 according to EU numbering, Cys (C) at position 356 according to EU numbering, and Glu (E) or Asp (D) at position 439 according to EU numbering;
(2) the first polypeptide has an amino acid residue other than Cys (C) at position 226 according to EU numbering, an amino acid residue other than Cys (C) at position 229 according to EU numbering, Cys (C) at position 349 according to EU numbering, Tyr (Y) at position 397 according to EU numbering, and any of Lys (K), Arg (R), and His (H) at position 356 according to EU numbering, and the second polypeptide has an amino acid residue other than Cys (C) at position 226 according to EU numbering, an amino acid residue other than Cys (C) at position 229 according to EU numbering, Cys (C) at position 356 according to EU numbering, Tyr (Y) at position 397 according to EU numbering, and Glu (E) or Asp (D) at position 439 according to EU numbering;

(3) the first and second polypeptides have an amino acid residue other than Cys (C) at position 226 according to EU numbering, an amino acid residue other than Cys (C) at position 229 according to EU numbering, and Cys (C) at position 394 according to EU numbering, one of the polypeptides has any of Lys (K), Arg (R), and His (H) at position 356 according to EU numbering, and the other polypeptide has Glu (E) or Asp (D) at position 439 according to EU numbering;

(4) the first polypeptide has an amino acid residue other than Cys (C) at position 226 according to EU numbering, an amino acid residue other than Cys (C) at position 229 according to EU numbering, and Cys (C) at position 349 according to EU numbering, the second polypeptide has an amino acid residue other than Cys (C) at position 226 according to EU numbering, an amino acid residue other than Cys (C) at position 229 according to EU numbering, and Cys (C) at position 354 according to EU numbering, one of the polypeptides has any of Lys (K), Arg (R), and His (H) at position 356 according to EU numbering, and the other polypeptide has Glu (E) or Asp (D) at position 439 according to EU numbering;

(5) the first and second polypeptides have an amino acid residue other than Cys (C) at position 226 according to EU numbering, an amino acid residue other than Cys (C) at position 229 according to EU numbering, and Cys (C) at position 351 according to EU numbering, one of the polypeptides has any of Lys (K), Arg (R), and His (H) at position 356 according to EU numbering, and the other polypeptide has Glu (E) or Asp (D) at position 439 according to EU numbering; and (6) the first and second polypeptides have an amino acid residue other than Cys (C) at position 226 according to EU numbering, an amino acid residue other than Cys (C) at position 229 according to EU numbering, and Cys (C) at position 407 according to EU numbering, one of the polypeptides has any of Lys (K), Arg (R), and His (H) at position 356 according to EU numbering, and the other polypeptide has Glu (E) or Asp (D) at position 439 according to EU numbering.

More specifically, the present invention also provides a bispecific antibody wherein the heavy chain constant regions of the first and second polypeptides each have amino acid residues shown in any of the following (1) to (6):

(1) the first polypeptide has Ser (S) at position 226 according to EU numbering, Ser (S) at position 229 according to EU numbering, Cys (C) at position 349 according to EU numbering, and any of Lys (K), Arg (R), and His (H) at position 356 according to EU numbering, and the second polypeptide has Ser (S) at position 226 according to EU numbering, Ser (S) at position 229 according to EU numbering, Cys (C) at position 356 according to EU numbering, and Glu (E) or Asp (D) at position 439 according to EU numbering;

(2) the first polypeptide has Ser (S) at position 226 according to EU numbering, Ser (S) at position 229 according to EU numbering, Cys (C) at position 349 according to EU numbering, Tyr (Y) at position 397 according to EU numbering, and any of Lys (K), Arg (R), and His (H) at position 356 according to EU numbering, and the second polypeptide has Ser (S) at position 226 according to EU numbering, Ser (S) at position 229 according to EU numbering, Cys (C) at position 356 according to EU numbering, Tyr (Y) at position 397 according to EU numbering, and Glu (E) or Asp (D) at position 439 according to EU numbering;

(3) the first and second polypeptides have Ser (S) at position 226 according to EU numbering, Ser (S) at position 229 according to EU numbering, and Cys (C) at position 394 according to EU numbering, one of the polypeptides has any of Lys (K), Arg (R), and His (H) at position 356 according to EU numbering, and the other polypeptide has Glu (E) or Asp (D) at position 439 according to EU numbering;

(4) the first polypeptide has Ser (S) at position 226 according to EU numbering, Ser (S) at position 229 according to EU numbering, and Cys (C) at position 349 according to EU numbering, the second polypeptide has Ser (S) at position 226 according to EU numbering, Ser (S) at position 229 according to EU numbering, and Cys (C) at position 354 according to EU numbering, one of the polypeptides has any of Lys (K), Arg (R), and His (H) at position 356 according to EU numbering, and the other polypeptide has Glu (E) or Asp (D) at position 439 according to EU numbering;

(5) the first and second polypeptides have Ser (S) at position 226 according to EU numbering, Ser (S) at position 229 according to EU numbering, and Cys (C) at position 351 according to EU numbering, one of the polypeptides has any of Lys (K), Arg (R), and His (H) at position 356 according to EU numbering, and the other polypeptide has Glu (E) or Asp (D) at position 439 according to EU numbering; and (6) the first and second polypeptides have Ser (S) at position 226 according to EU numbering, Ser (S) at position 229 according to EU numbering, and Cys (C) at position 407 according to EU numbering, one of the polypeptides has any of Lys (K), Arg (R), and His (H) at position 356 according to EU numbering, and the other polypeptide has Glu (E) or Asp (D) at position 439 according to EU numbering.

The present invention also provides a bispecific antibody wherein the heavy chain constant regions of the first and second polypeptides each have amino acid residues shown in any of the following (1) to (6):

(1) the first polypeptide has an amino acid residue other than Cys (C) at position 226 according to EU numbering, Pro (P) at position 228 according to EU numbering, an amino acid residue other than Cys (C) at position 229 according to EU numbering, Cys (C) at position 349 according to EU numbering, and any of Lys (K), Arg (R), and His (H) at position 356 according to EU numbering, and the second polypeptide has an amino acid residue other than Cys (C) at position 226 according to EU numbering, Pro (P) at position 228 according to EU numbering, an amino acid residue other than Cys (C) at position 229 according to EU numbering, Cys (C) at position 356 according to EU numbering, and Glu (E) or Asp (D) at position 439 according to EU numbering;

(2) the first polypeptide has an amino acid residue other than Cys (C) at position 226 according to EU numbering, Pro (P) at position 228 according to EU numbering, an amino acid residue other than Cys (C) at position 229 according to EU numbering, Cys (C) at position 349 according to EU numbering, Tyr (Y) at position 397 according to EU numbering, and any of Lys (K), Arg (R), and His (H) at position 356 according to EU numbering, and the second polypeptide has an amino acid residue other than Cys (C) at position 226 according to EU numbering, Pro (P) at position 228 according to EU numbering, an amino acid residue other than Cys (C) at position 229 according to EU numbering, Cys (C) at position 356 according to EU numbering, Tyr (Y) at position 397 according to EU numbering, and Glu (E) or Asp (D) at position 439 according to EU numbering;
(3) the first and second polypeptides have an amino acid residue other than Cys (C) at position 226 according to EU numbering, Pro (P) at position 228 according to EU numbering, an amino acid residue other than Cys (C) at position 229 according to EU numbering, and Cys (C) at position 394 according to EU numbering, one of the polypeptides has any of Lys (K), Arg (R), and His (H) at position 356 according to EU numbering, and the other polypeptide has Glu (E) or Asp (D) at position 439 according to EU numbering;
(4) the first polypeptide has an amino acid residue other than Cys (C) at position 226 according to EU numbering, Pro (P) at position 228 according to EU numbering, an amino acid residue other than Cys (C) at position 229 according to EU numbering, and Cys (C) at position 349 according to EU numbering, the second polypeptide has an amino acid residue other than Cys (C) at position 226 according to EU numbering, Pro (P) at position 228 according to EU numbering, an amino acid residue other than Cys (C) at position 229 according to EU numbering, and Cys (C) at position 354 according to EU numbering, one of the polypeptides has any of Lys (K), Arg (R), and His (H) at position 356 according to EU numbering, and the other polypeptide has Glu (E) or Asp (D) at position 439 according to EU numbering;
(5) the first and second polypeptides have an amino acid residue other than Cys (C) at position 226 according to EU numbering, Pro (P) at position 228 according to EU numbering, an amino acid residue other than Cys (C) at position 229 according to EU numbering, and Cys (C) at position 351 according to EU numbering, one of the polypeptides has any of Lys (K), Arg (R), and His (H) at position 356 according to EU numbering, and the other polypeptide has Glu (E) or Asp (D) at position 439 according to EU numbering; and
(6) the first and second polypeptides have an amino acid residue other than Cys (C) at position 226 according to EU numbering, Pro (P) at position 228 according to EU numbering, an amino acid residue other than Cys (C) at position 229 according to EU numbering, and Cys (C) at position 407 according to EU numbering, one of the polypeptides has any of Lys (K), Arg (R), and His (H) at position 356 according to EU numbering, and the other polypeptide has Glu (E) or Asp (D) at position 439 according to EU numbering.

The present invention also provides a bispecific antibody wherein the heavy chain constant regions of the first and second polypeptides each have amino acid residues shown in any of the following (1) to (6):
(1) the first polypeptide has Ser (S) at position 226 according to EU numbering, Pro (P) at position 228 according to EU numbering, Ser (S) at position 229 according to EU numbering, Cys (C) at position 349 according to EU numbering, and any of Lys (K), Arg (R), and His (H) at position 356 according to EU numbering, and the second polypeptide has Ser (S) at position 226 according to EU numbering, Pro (P) at position 228 according to EU numbering, Ser (S) at position 229 according to EU numbering, Cys (C) at position 356 according to EU numbering, and Glu (E) or Asp (D) at position 439 according to EU numbering;
(2) the first polypeptide has Ser (S) at position 226 according to EU numbering, Pro (P) at position 228 according to EU numbering, Ser (S) at position 229 according to EU numbering, Cys (C) at position 349 according to EU numbering, Tyr (Y) at position 397 according to EU numbering, and any of Lys (K), Arg (R), and His (H) at position 356 according to EU numbering, and the second polypeptide has Ser (S) at position 226 according to EU numbering, Pro (P) at position 228 according to EU numbering, Ser (S) at position 229 according to EU numbering, Cys (C) at position 356 according to EU numbering, Tyr (Y) at position 397 according to EU numbering, and Glu (E) or Asp (D) at position 439 according to EU numbering;
(3) the first and second polypeptides have Ser (S) at position 226 according to EU numbering, Pro (P) at position 228 according to EU numbering, Ser (S) at position 229 according to EU numbering, and Cys (C) at position 394 according to EU numbering, one of the polypeptides has any of Lys (K), Arg (R), and His (H) at position 356 according to EU numbering, and the other polypeptide has Glu (E) or Asp (D) at position 439 according to EU numbering;
(4) the first polypeptide has Ser (S) at position 226 according to EU numbering, Pro (P) at position 228 according to EU numbering, Ser (S) at EU numbering position 229 according to EU numbering, and Cys (C) at position 349 according to EU numbering, the second polypeptide has Ser (S) at position 226 according to EU numbering, Pro (P) at position 228 according to EU numbering, Ser (S) at position 229 according to EU numbering, and Cys (C) at position 354 according to EU numbering, one of the polypeptides has any of Lys (K), Arg (R), and His (H) at position 356 according to EU numbering, and the other polypeptide has Glu (E) or Asp (D) at position 439 according to EU numbering;
(5) the first and second polypeptides have Ser (S) at position 226 according to EU numbering, Pro (P) at position 228 according to EU numbering, Ser (S) at position 229 according to EU numbering, and Cys (C) at position 351 according to EU numbering, one of the polypeptides has any of Lys (K), Arg (R), and His (H) at position 356 according to EU numbering, and the other polypeptide has Glu (E) or Asp (D) at position 439 according to EU numbering; and
(6) the first and second polypeptides have Ser (S) at position 226 according to EU numbering, Pro (P) at position 228 according to EU numbering, Ser (S) at position 229 according to EU numbering, and Cys (C) at position 407 according to EU numbering, one of the polypeptides has any of Lys (K), Arg (R), and His (H) at position 356 according to EU numbering, and the other polypeptide has Glu (E) or Asp (D) at position 439 according to EU numbering.

Still more specifically, the present invention provides a bispecific antibody wherein the heavy chain constant regions of the first and second polypeptides each have amino acid residues shown in any of the following (1) to (6):
(1) the first polypeptide has an amino acid residue other than Cys (C) at position 226 according to EU numbering, an amino acid residue other than Cys (C) at position 229 according to EU numbering, Cys (C) at position 349 according to EU numbering, and Lys (K) at position 356 according to EU numbering, and the second polypeptide has an amino acid residue other than Cys (C) at position 226 according to EU numbering, an amino acid residue other than Cys (C) at position 229 according to EU numbering, Cys (C) at position 356 according to EU numbering, and Glu (E) at position 439 according to EU numbering;
(2) the first polypeptide has an amino acid residue other than Cys (C) at position 226 according to EU numbering, an amino acid residue other than Cys (C) at position 229 according to EU numbering, Cys (C) at position 349 according to EU numbering, Lys (K) at position 356 according to EU numbering, and Tyr (Y) at position 397 according to EU numbering, and the second polypeptide has an amino acid residue other than Cys (C) at position 226 according to EU numbering, an amino acid residue other than Cys (C) at position 229 according to EU numbering, Cys (C) at position 356 according to EU numbering, Tyr (Y) at position 397 according to EU numbering, and Glu (E) at position 439 according to EU numbering;
(3) the first polypeptide has an amino acid residue other than Cys (C) at position 226 according to EU numbering, an amino acid residue other than Cys (C) at position 229 according to EU numbering, Cys (C) at position 394 according to EU numbering, and Lys (K) at position 356 according to EU numbering, and the second polypeptide has an amino acid residue other than Cys (C) at position 226 according to EU numbering, an amino acid residue other than Cys (C) at position 229 according to EU numbering, Cys (C) at position 394 according to EU numbering, and Glu (E) at position 439 according to EU numbering;
(4) the first polypeptide has an amino acid residue other than Cys (C) at position 226 according to EU numbering, an amino acid residue other than Cys (C) at position 229 according to EU numbering, Cys (C) at position 349 according to EU numbering, and Lys (K) at position 356 according to EU numbering, and the second polypeptide has an amino acid residue other than Cys (C) at position 226 according to EU numbering, an amino acid residue other than Cys (C) at position 229 according to EU numbering, Cys (C) at position 354 according to EU numbering, and Glu (E) at position 439 according to EU numbering;
(5) the first polypeptide has an amino acid residue other than Cys (C) at position 226 according to EU numbering, an amino acid residue other than Cys (C) at position 229 according to EU numbering, Cys (C) at position 351 according to EU numbering, and Lys (K) at position 356 according to EU numbering, and the second polypeptide has an amino acid residue other than Cys (C) at position 226 according to EU numbering, an amino acid residue other than Cys (C) at position 229 according to EU numbering, Cys (C) at position 351 according to EU numbering, and Glu (E) at position 439 according to EU numbering; and
(6) the first polypeptide has an amino acid residue other than Cys (C) at position 226 according to EU numbering, an amino acid residue other than Cys (C) at position 229 according to EU numbering, Cys (C) at position 407 according to EU numbering, and Lys (K) at position 356 according to EU numbering, and the second polypeptide has an amino acid residue other than Cys (C) at position 226 according to EU numbering, an amino acid residue other than Cys (C) at position 229 according to EU numbering, Cys (C) at position 407 according to EU numbering, and Glu (E) at position 439 according to EU numbering.

More specifically, the present invention also provides a bispecific antibody wherein the heavy chain constant regions of the first and second polypeptides each have amino acid residues shown in any of the following (1) to (6):
(1) the first polypeptide has Ser (S) at position 226 according to EU numbering, Ser (S) at position 229 according to EU numbering, Cys (C) at position 349 according to EU numbering, and Lys (K) at position 356 according to EU numbering, and the second polypeptide has Ser (S) at position 226 according to EU numbering, Ser (S) at position 229 according to EU numbering, Cys (C) at EU numbering position 356 according to EU numbering, and Glu (E) at position 439 according to EU numbering;
(2) the first polypeptide has Ser (S) at position 226 according to EU numbering, Ser (S) at position 229 according to EU numbering, Cys (C) at position 349 according to EU numbering, Lys (K) at position 356 according to EU numbering, and Tyr (Y) at position 397 according to EU numbering, and the second polypeptide has Ser (S) at position 226 according to EU numbering, Ser (S) at position 229 according to EU numbering, Cys (C) at position 356 according to EU numbering, Tyr (Y) at position 397 according to EU numbering, and Glu (E) at position 439 according to EU numbering;
(3) the first polypeptide has Ser (S) at position 226 according to EU numbering, Ser (S) at position 229 according to EU numbering, Cys (C) at position 394 according to EU numbering, and Lys (K) at position 356 according to EU numbering, and the second polypeptide has Ser (S) at position 226 according to EU numbering, Ser (S) at position 229 according to EU numbering, Cys (C) at position 394 according to EU numbering, and Glu (E) at position 439 according to EU numbering;
(4) in the first polypeptide has Ser (S) at position 226 according to EU numbering, Ser (S) at position 229 according to EU numbering, Cys (C) at position 349 according to EU numbering, and Lys (K) at position 356 according to EU numbering, and the second polypeptide has Ser (S) at position 226 according to EU numbering, Ser (S) at position 229 according to EU numbering, Cys (C) at position 354 according to EU numbering, and Glu (E) at position 439 according to EU numbering;
(5) the first polypeptide has Ser (S) at position 226 according to EU numbering, Ser (S) at position 229 according to EU numbering, Cys (C) at position 351 according to EU numbering, and Lys (K) at position 356 according to EU numbering, and the second polypeptide has Ser (S) at position 226 according to EU numbering, Ser (S) at position 229 according to EU numbering, Cys (C) at position 351 according to EU numbering, and Glu (E) at position 439 according to EU numbering; and
(6) the first polypeptide has Ser (S) at position 226 according to EU numbering, Ser (S) at position 229 according to EU numbering, Cys (C) at position 407 according to EU numbering, and Lys (K) at position 356 according to EU numbering, and the second polypeptide has Ser (S) at position 226 according to EU numbering, Ser (S) at position 229 according to EU numbering, Cys (C) at position 407 according to EU numbering, and Glu (E) at position 439 according to EU numbering.

The present invention also provides a bispecific antibody wherein the heavy chain constant regions of the first and second polypeptides each have amino acid residues shown in any of the following (1) to (6):
(1) the first polypeptide has an amino acid residue other than Cys (C) at position 226 according to EU numbering, Pro (P) at position 228 according to EU numbering, an amino acid residue other than Cys (C) at position 229 according to EU numbering, Cys (C) at position 349 according to EU numbering, and Lys (K) at position 356 according to EU numbering, and the second polypeptide has an amino acid residue other than Cys (C) at position 226 according to EU numbering, Pro (P) at position 228 according to EU numbering, an amino acid residue other than Cys (C) at position 229 according to EU numbering, Cys (C) at position 356 according to EU numbering, and Glu (E) at position 439 according to EU numbering;
(2) the first polypeptide has an amino acid residue other than Cys (C) at position 226 according to EU numbering, Pro (P) at position 228 according to EU numbering, an amino acid residue other than Cys (C) at position 229 according to EU numbering, Cys (C) at position 349 according to EU numbering, Lys (K) at position 356 according to EU numbering, and Tyr (Y) at position 397 according to EU numbering, and the second polypeptide has an amino acid residue other than Cys (C) at position 226 according to EU numbering, Pro (P) at position 228 according to EU numbering, an amino acid residue other than Cys (C) at position 229 according to EU numbering, Cys (C) at position 356 according to EU numbering, Tyr (Y) at position 397 according to EU numbering, and Glu (E) at position 439 according to EU numbering;
(3) the first polypeptide has an amino acid residue other than Cys (C) at position 226 according to EU numbering, Pro (P) at position 228 according to EU numbering, an amino acid residue other than Cys (C) at position 229 according to EU numbering, Cys (C) at position 394 according to EU numbering, and Lys (K) at position 356 according to EU numbering, and the second polypeptide has an amino acid residue other than Cys (C) at position 226 according to EU numbering, Pro (P) at position 228 according to EU numbering, an amino acid residue other than Cys (C) at position 229 according to EU numbering, Cys (C) at position 394 according to EU numbering, and Glu (E) at position 439 according to EU numbering;
(4) the first polypeptide has an amino acid residue other than Cys (C) at position 226 according to EU numbering, Pro (P) at position 228 according to EU numbering, an amino acid residue other than Cys (C) at position 229 according to EU numbering, Cys (C) at position 349 according to EU numbering, and Lys (K) at position 356 according to EU numbering, and the second polypeptide has an amino acid residue other than Cys (C) at position 226 according to EU numbering, Pro (P) at position 228 according to EU numbering, an amino acid residue other than Cys (C) at position 229 according to EU numbering, Cys (C) at position 354 according to EU numbering, and Glu (E) at position 439 according to EU numbering;
(5) the first polypeptide has an amino acid residue other than Cys (C) at position 226 according to EU numbering, Pro (P) at position 228 according to EU numbering, an amino acid residue other than Cys (C) at position 229 according to EU numbering, Cys (C) at position 351 according to EU numbering, and Lys (K) at position 356 according to EU numbering, and the second polypeptide has an amino acid residue other than Cys (C) at position 226 according to EU numbering, Pro (P) at position 228 according to EU numbering, an amino acid residue other than Cys (C) at position 229 according to EU numbering, Cys (C) at position 351 according to EU numbering, and Glu (E) at position 439 according to EU numbering; and
(6) the first polypeptide has an amino acid residue other than Cys (C) at position 226 according to EU numbering, Pro (P) at position 228 according to EU numbering, an amino acid residue other than Cys (C) at position 229 according to EU numbering, Cys (C) at position 407 according to EU numbering, and Lys (K) at position 356 according to EU numbering, and the second polypeptide has an amino acid residue other than Cys (C) at position 226 according to EU numbering, Pro (P) at position 228 according to EU numbering, an amino acid residue other than Cys (C) at position 229 according to EU numbering, Cys (C) at position 407 according to EU numbering, and Glu (E) at position 439 according to EU numbering.

The present invention also provides a bispecific antibody wherein the heavy chain constant regions of the first and second polypeptides each have amino acid residues shown in any of the following (1) to (6):
(1) the first polypeptide has Ser (S) at position 226 according to EU numbering, Pro (P) at position 228 according to EU numbering, Ser (S) at position 229 according to EU numbering, Cys (C) at position 349 according to EU numbering, and Lys (K) at position 356 according to EU numbering, and the second polypeptide has Ser (S) at position 226 according to EU numbering, Pro (P) at position 228 according to EU numbering, Ser (S) at position 229 according to EU numbering, Cys (C) at position 356 according to EU numbering, and Glu (E) at position 439 according to EU numbering;
(2) the first polypeptide has Ser (S) at position 226 according to EU numbering, Pro (P) at position 228 according to EU numbering, Ser (S) at position 229 according to EU numbering, Cys (C) at position 349 according to EU numbering, Lys (K) at position 356 according to EU numbering, and Tyr (Y) at position 397 according to EU numbering, and the second polypeptide has Ser (S) at position 226 according to EU numbering, Pro (P) at position 228 according to EU numbering, Ser (S) at position 229 according to EU numbering, Cys (C) at position 356 according to EU numbering, Tyr (Y) at position 397 according to EU numbering, and Glu (E) at position 439 according to EU numbering;
(3) the first polypeptide has Ser (S) at position 226 according to EU numbering, Pro (P) at position 228 according to EU numbering, Ser (S) at position 229 according to EU numbering, Cys (C) at position 394 according to EU numbering, and Lys (K) at position 356 according to EU numbering, and the second polypeptide has Ser (S) at position 226 according to EU numbering, Pro (P) at position 228 according to EU numbering, Ser (S) at position 229 according to EU numbering, Cys (C) at position 394 according to EU numbering, and Glu (E) at position 439 according to EU numbering;
(4) the first polypeptide has Ser (S) at position 226 according to EU numbering, Pro (P) at position 228 according to EU numbering, Ser (S) at position 229 according to EU numbering, Cys (C) at position 349 according to EU numbering, and Lys (K) at position 356 according to EU numbering, and the second polypeptide has Ser (S) at position 226 according to EU numbering, Pro (P) at position 228 according to EU numbering, Ser (S) at position 229 according to EU numbering, Cys (C) at position 354 according to EU numbering, and Glu (E) at position 439 according to EU numbering;
(5) the first polypeptide has Ser (S) at position 226 according to EU numbering, Pro (P) at position 228 according to EU numbering, Ser (S) at position 229 according to EU numbering, Cys (C) at position 351 according to EU numbering, and Lys (K) at position 356 according to EU numbering, and the second polypeptide has Ser (S) at position 226 according to EU numbering, Pro (P) at position 228 according to EU numbering, Ser (S) at position 229 according to EU numbering, Cys (C) at position 351 according to EU numbering, and Glu (E) at position 439 according to EU numbering; and
(6) the first polypeptide has Ser (S) at position 226 according to EU numbering, Pro (P) at position 228 according to EU numbering, Ser (S) at position 229 according to EU numbering, Cys (C) at position 407 according to EU numbering, and Lys (K) at position 356 according to EU numbering, and the second polypeptide has Ser (S) at position 226 according to EU numbering, Pro (P) at position 228 according to EU numbering, Ser (S) at position 229 according to EU numbering, Cys (C) at position 407 according to EU numbering, and Glu (E) at position 439 according to EU numbering.

Disulfide Bond Reformation Between L Chains by Fab Arm Exchange Reaction (L-FAE)

In an alternative aspect, the present invention provides a method for producing a heteromultimer using the isomerization of a disulfide bond between cysteines in antibody light chain constant regions (inter-L chain disulfide bond). Each cysteine used in this method is not particularly limited as long as the cysteine is present in an antibody light chain constant region. Examples thereof include cysteine at the C terminus (position 214) of an L chain. In order to use the disulfide bond isomerization between cysteines in the light chain constant regions of, for example, IgG4 antibodies, cysteine at position 131 according to EU numbering of the heavy chain constant region of each antibody is modified to another amino acid, for example, Ser (S), although the modification according to the present invention is not particularly limited thereto. For IgG1 antibodies, cysteine at position 220 according to EU numbering of the heavy chain constant region of each antibody is modified to another amino acid, for example, Ser (S), although the modification according to the present invention is not particularly limited thereto. Alternatively, a polypeptide comprising an IgG4 antibody heavy chain constant region having an amino acid other than cysteine at position 131 according to EU numbering, or a polypeptide comprising an IgG1 antibody heavy chain constant region having an amino acid other than cysteine at position 220 according to EU numbering may be used.

The core hinge regions are preferably free from cysteine. For example, cysteine at position 226 and/or 229 according to EU numbering may be modified to another amino acid, and amino acid residues at positions 226 to 229 according to EU numbering may be SPPS or SPSS, though the core hinge region of the present invention is not particularly limited thereto. Alternatively, cysteine at position 226 and/or 229 according to EU numbering may be deleted.

Other amino acid residues contained in each hinge region may be modified and/or deleted, or other amino acids may be inserted thereto. For example, in IgG1, an amino acid residue at position 220 (EU numbering) may be substituted by serine, or amino acid residues at positions 220 to 225 (EU numbering) may be substituted by the sequence of IgG4, though the method of the present invention is not particularly limited thereto. In IgG1 or IgG4, amino acid residues at positions 219 to 229 (EU numbering) may be deleted, though the method of the present invention is not particularly limited thereto.

A portion or the whole of each hinge region may be deleted. For example, in IgG1 or IgG4, amino acid residues at positions 216 to 230 (EU numbering) may be deleted.

Specifically, the present invention provides a method for producing a heteromultimer comprising first and second polypeptides, wherein the heavy chain constant regions of the first and second polypeptides each have amino acid residues shown in any of the following (1) and (2):
(1) the first and second polypeptides have an amino acid residue other than Cys (C) at position 131 according to EU numbering; and
(2) the first and second polypeptides have an amino acid residue other than Cys (C) at position 220 according to EU numbering.

Preferably, the heavy chain constant regions having the manner (1) are derived from IgG4, and the heavy chain constant regions having the manner (2) are derived from IgG1.

The present invention also provides a method for producing a heteromultimer comprising first and second polypeptides, wherein the heavy chain constant regions of the first and second polypeptides each have amino acid residues shown in any of the following (1) and (2):
(1) the first and second polypeptides have Ser (S) at position 131 according to EU numbering; and
(2) the first and second polypeptides have Ser (S) or Tyr (Y) at position 220 according to EU numbering.

Preferably, the heavy chain constant regions having the manner (1) are derived from IgG4, and the heavy chain constant regions having the manner (2) are derived from IgG1.

Further specifically, the present invention provides a method for producing a heteromultimer comprising first and second polypeptides, wherein the heavy chain constant regions of the first and second polypeptides each have amino acid residues shown in any of the following (1) to (6):
(1) the first and second polypeptides have an amino acid residue other than Cys (C) at position 131 according to EU numbering, an amino acid residue other than Cys (C) at position 226 according to EU numbering, and an amino acid residue other than Cys (C) at position 229 according to EU numbering;
(2) the first and second polypeptides have an amino acid residue other than Cys (C) at position 131 according to EU numbering, an amino acid residue other than Cys (C) at position 226 according to EU numbering, Pro (P) at position 228 according to EU numbering, and an amino acid residue other than Cys (C) at position 229 according to EU numbering;
(3) the first and second polypeptides have an amino acid residue other than Cys (C) at position 220 according to EU numbering, an amino acid residue other than Cys (C) at position 226 according to EU numbering, and an amino acid residue other than Cys (C) at position 229 according to EU numbering;
(4) the first and second polypeptides have an amino acid residue other than Cys (C) at position 131 according to EU numbering, and deletion at positions 219 to 229 according to EU numbering;
(5) the first and second polypeptides have deletion at positions 219 to 229 according to EU numbering; and
(6) the first and second polypeptides have an amino acid residue other than Cys (C) at position 226 according to EU numbering, an amino acid residue other than Cys (C) at position 229 according to EU numbering, and Tyr (Y)-Gly (G)-Pro (P)-Pro (P) at positions 220 to 225 according to EU numbering.

Preferably, the heavy chain constant regions having the manner (1), (2), or (4) are derived from IgG4, and the heavy chain constant regions having the manner (3), (5), or (6) are derived from IgG1.

The present invention also provides a method for producing a heteromultimer comprising first and second polypeptides, wherein the heavy chain constant regions of the first and second polypeptides each have amino acid residues shown in any of the following (1) to (6):
(1) the first and second polypeptides have Ser (S) at position 131 according to EU numbering, Ser (S) at position 226 according to EU numbering, and Ser (S) at position 229 according to EU numbering;
(2) the first and second polypeptides have Ser (S) at position 131 according to EU numbering, Ser (S) at position 226 according to EU numbering, Pro (P) at position 228 according to EU numbering, and Ser (S) at position 229 according to EU numbering;
(3) the first and second polypeptides have Ser (S) or Tyr (Y) at position 220 according to EU numbering, Ser (S) at position 226 according to EU numbering, and Ser (S) at position 229 according to EU numbering;
(4) the first and second polypeptides have Ser (S) at position 131 according to EU numbering, and deletion at positions 219 to 229 according to EU numbering;
(5) the first and second polypeptides have deletion at positions 219 to 229 according to EU numbering; and
(6) the first and second polypeptides have Ser (S) at position 226 according to EU numbering, Ser (S) at position 229 according to EU numbering, and Tyr (Y)-Gly (G)-Pro (P)-Pro (P) at positions 220 to 225 according to EU numbering.

Preferably, the heavy chain constant regions having the manner (1), (2), or (4) are derived from IgG4, and the heavy chain constant regions having the manner (3), (5), or (6) are derived from IgG1.

Further specifically, the present invention provides a method for producing a heteromultimer comprising first and second polypeptides, wherein the heavy chain constant regions of the first and second polypeptides each have amino acid residues shown in any of the following (1) to (6):
(1) the first and second polypeptides have an amino acid residue other than Cys (C) at position 131 according to EU numbering, an amino acid residue other than Cys (C) at position 226 according to EU numbering, and an amino acid residue other than Cys (C) at position 229 according to EU numbering;
(2) the first and second polypeptides have an amino acid residue other than Cys (C) at position 131 according to EU numbering, an amino acid residue other than Cys (C) at position 226 according to EU numbering, Pro (P) at position 228 according to EU numbering, and an amino acid residue other than Cys (C) at position 229 according to EU numbering;
(3) the first and second polypeptides have an amino acid residue other than Cys (C) at position 220 according to EU numbering, an amino acid residue other than Cys (C) at position 226 according to EU numbering, an amino acid residue other than Cys (C) at position 229 according to EU numbering, and Arg (R) at position 409 according to EU numbering;
(4) the first and second polypeptides have an amino acid residue other than Cys (C) at position 131 according to EU numbering, and deletion at positions 219 to 229 according to EU numbering;
(5) the first and second polypeptides have deletion at positions 219 to 229 according to EU numbering, and Arg (R) at position 409 according to EU numbering; and
(6) the first and second polypeptides have an amino acid residue other than Cys (C) at position 226 according to EU numbering, an amino acid residue other than Cys (C) at position 229 according to EU numbering, Tyr (Y)-Gly (G)-Pro (P)-Pro (P) at positions 220 to 225 according to EU numbering, and Arg (R) at position 409 according to EU numbering.

Preferably, the heavy chain constant regions having the manner (1), (2), or (4) are derived from IgG4, and the heavy chain constant regions having the manner (3), (5), or (6) are derived from IgG1.

The present invention also provides a method for producing a heteromultimer comprising first and second polypeptides, wherein the heavy chain constant regions of the first and second polypeptides each have amino acid residues shown in any of the following (1) to (6):
(1) the first and second polypeptides have Ser (S) at position 131 according to EU numbering, Ser (S) at position 226 according to EU numbering, and Ser (S) at position 229 according to EU numbering;
(2) the first and second polypeptides have Ser (S) at position 131 according to EU numbering, Ser (S) at position 226 according to EU numbering, Pro (P) at position 228 according to EU numbering, and Ser (S) at position 229 according to EU numbering;
(3) the first and second polypeptides have Ser (S) or Tyr (Y) at position 220 according to EU numbering, Ser (S) at position 226 according to EU numbering, Ser (S) at position 229 according to EU numbering, and Arg (R) at position 409 according to EU numbering;
(4) the first and second polypeptides have Ser (S) at position 131 according to EU numbering, and deletion at positions 219 to 229 according to EU numbering;
(5) the first and second polypeptides have deletion at positions 219 to 229 according to EU numbering, and Arg (R) at position 409 according to EU numbering; and
(6) the first and second polypeptides have Ser (S) at position 226 according to EU numbering, Ser (S) at position 229 according to EU numbering, Tyr (Y)-Gly (G)-Pro (P)-Pro (P) at positions 220 to 225 according to EU numbering, and Arg (R) at position 409 according to EU numbering.

Preferably, the heavy chain constant regions having the manner (1), (2), or (4) are derived from IgG4, and the heavy chain constant regions having the manner (3), (5), or (6) are derived from IgG1.

Further specifically, the present invention provides a method for producing a heteromultimer comprising first and second polypeptides, wherein the heavy chain constant regions of the first and second polypeptides each have amino acid residues shown in any of the following (1) to (6):
(1) the first polypeptide has an amino acid residue other than Cys (C) at position 131 according to EU numbering, an amino acid residue other than Cys (C) at position 226 according to EU numbering, an amino acid residue other than Cys (C) at position 229 according to EU numbering, and any of Lys (K), Arg (R), and His (H) at position 356 according to EU numbering, and the second polypeptide has an amino acid residue other than Cys (C) at position 131 according to EU numbering, an amino acid residue other than Cys (C) at position 226 according to EU numbering, an amino acid residue other than Cys (C) at position 229 according to EU numbering, and Glu (E) or Asp (D) at position 439 according to EU numbering;
(2) the first polypeptide has an amino acid residue other than Cys (C) at position 131 according to EU numbering, an amino acid residue other than Cys (C) at position 226 according to EU numbering, Pro (P) at position 228 according to EU numbering, an amino acid residue other than Cys (C) at position 229 according to EU numbering, and any of Lys (K), Arg (R), and His (H) at position 356 according to EU numbering, and the second polypeptide has an amino acid residue other than Cys (C) at position 131 according to EU numbering, an amino acid residue other than Cys (C) at position 226 according to EU numbering, Pro (P) at position 228 according to EU numbering, an amino acid residue other than Cys (C) at position 229 according to EU numbering, and Glu (E) or Asp (D) at position 439 according to EU numbering;
(3) the first polypeptide has an amino acid residue other than Cys (C) at position 220 according to EU numbering, an amino acid residue other than Cys (C) at position 226 according to EU numbering, an amino acid residue other than Cys (C) at position 229 according to EU numbering, and any of Lys (K), Arg (R), and His (H) at position 356 according to EU numbering, and the second polypeptide has an amino acid residue other than Cys (C) at position 220 according to EU numbering, an amino acid residue other than Cys (C) at position 226 according to EU numbering, an amino acid residue other than Cys (C) at position 229 according to EU numbering, and Glu (E) or Asp (D) at position 439 according to EU numbering;
(4) the first polypeptide has an amino acid residue other than Cys (C) at position 131 according to EU numbering, deletion at positions 219 to 229 according to EU numbering, and any of Lys (K), Arg (R), and His (H) at position 356 according to EU numbering, and the second polypeptide has an amino acid residue other than Cys (C) at position 131 according to EU numbering, deletion at positions 219 to 229 according to EU numbering, and Glu (E) or Asp (D) at position 439 according to EU numbering;
(5) the first polypeptide has deletion at positions 219 to 229 according to EU numbering, and any of Lys (K), Arg (R), and His (H) at position 356 according to EU numbering, and the second polypeptide has deletion at positions 219 to 229 according to EU numbering, and Glu (E) or Asp (D) at position 439 according to EU numbering; and
(6) the first polypeptide has an amino acid residue other than Cys (C) at position 226 according to EU numbering, an amino acid residue other than Cys (C) at position 229 according to EU numbering, Tyr (Y)-Gly (G)-Pro (P)-Pro (P) at positions 220 to 225 according to EU numbering, and any of Lys (K), Arg (R), and His (H) at position 356 according to EU numbering, and the second polypeptide has an amino acid residue other than Cys (C) at position 226 according to EU numbering, an amino acid residue other than Cys (C) at position 229 according to EU numbering, Tyr (Y)-Gly (G)-Pro (P)-Pro (P) at positions 220 to 225 according to EU numbering, and Glu (E) or Asp (D) at position 439 according to EU numbering.

Preferably, the heavy chain constant regions having the manner (1), (2), or (4) are derived from IgG4, and the heavy chain constant regions having the manner (3), (5), or (6) are derived from IgG1.

Further specifically, the present invention provides a method for producing a heteromultimer comprising first and second polypeptides, wherein the heavy chain constant regions of the first and second polypeptides each have amino acid residues shown in any of the following (1) to (6):
(1) the first polypeptide has an amino acid residue other than Cys (C) at position 131 according to EU numbering, an amino acid residue other than Cys (C) at position 226 according to EU numbering, an amino acid residue other than Cys (C) at position 229 according to EU numbering, and any of Lys (K), Arg (R), and His (H) at position 356 according to EU numbering, and the second polypeptide has an amino acid residue other than Cys (C) at position 131 according to EU numbering, an amino acid residue other than Cys (C) at position 226 according to EU numbering, an amino acid residue other than Cys (C) at position 229 according to EU numbering, and Glu (E) or Asp (D) at position 439 according to EU numbering;
(2) the first polypeptide has an amino acid residue other than Cys (C) at position 131 according to EU numbering, an amino acid residue other than Cys (C) at position 226 according to EU numbering, Pro (P) at position 228 according to EU numbering, an amino acid residue other than Cys (C) at position 229 according to EU numbering, and any of Lys (K), Arg (R), and His (H) at position 356 according to EU numbering, and the second polypeptide has an amino acid residue other than Cys (C) at position 131 according to EU numbering, an amino acid residue other than Cys (C) at position 226 according to EU numbering, Pro (P) at position 228 according to EU numbering, an amino acid residue other than Cys (C) at position 229 according to EU numbering, and Glu (E) or Asp (D) at position 439 according to EU numbering;
(3) the first polypeptide has an amino acid residue other than Cys (C) at position 220 according to EU numbering, an amino acid residue other than Cys (C) at position 226 according to EU numbering, an amino acid residue other than Cys (C) at position 229 according to EU numbering, Arg (R) at position 409 according to EU numbering, and any of Lys (K), Arg (R), and His (H) at position 356 according to EU numbering, and the second polypeptide has an amino acid residue other than Cys (C) at position 220 according to EU numbering, an amino acid residue other than Cys (C) at position 226 according to EU numbering, an amino acid residue other than Cys (C) at position 229 according to EU numbering, Arg (R) at position 409 according to EU numbering, and Glu (E) or Asp (D) at position 439 according to EU numbering;
(4) the first polypeptide has an amino acid residue other than Cys (C) at position 131 according to EU numbering, deletion at positions 219 to 229 according to EU numbering, and any of Lys (K), Arg (R), and His (H) at position 356 according to EU numbering, and the second polypeptide has an amino acid residue other than Cys (C) at position 131 according to EU numbering, deletion at positions 219 to 229 according to EU numbering, and Glu (E) or Asp (D) at position 439 according to EU numbering;
(5) the first polypeptide has deletion at positions 219 to 229 according to EU numbering, Arg (R) at position 409 according to EU numbering, and any of Lys (K), Arg (R), and His (H) at position 356 according to EU numbering, and the second polypeptide has deletion at positions 219 to 229 according to EU numbering, Arg (R) at position 409 according to EU numbering, and Glu (E) or Asp (D) at position 439 according to EU numbering; and
(6) the first polypeptide has an amino acid residue other than Cys (C) at position 226 according to EU numbering, an amino acid residue other than Cys (C) at position 229 according to EU numbering, Tyr (Y)-Gly (G)-Pro (P)-Pro (P) at positions 220 to 225 according to EU numbering, Arg (R) at position 409 according to EU numbering, and any of Lys (K), Arg (R), and His (H) at position 356 according to EU numbering, and the second polypeptide has an amino acid residue other than Cys (C) at position 226 according to EU numbering, an amino acid residue other than Cys (C) at position 229 according to EU numbering, Tyr (Y)-Gly (G)-Pro (P)-Pro (P) at positions 220 to 225 according to EU numbering, Arg (R) at position 409 according to EU numbering, and Glu (E) or Asp (D) at position 439 according to EU numbering.

Preferably, the heavy chain constant regions having the manner (1), (2), or (4) are derived from IgG4, and the heavy chain constant regions having the manner (3), (5), or (6) are derived from IgG1.

The present invention also provides a method for producing a heteromultimer comprising first and second polypeptides, wherein the heavy chain constant regions of the first and second polypeptides each have amino acid residues shown in any of the following (1) to (6):
(1) the first polypeptide has Ser (S) at position 131 according to EU numbering, Ser (S) at position 226 according to EU numbering, Ser (S) at position 229 according to EU numbering, and any of Lys (K), Arg (R), and His (H) at position 356 according to EU numbering, and the second polypeptide has Ser (S) at position 131 according to EU numbering, Ser (S) at position 226 according to EU numbering, Ser (S) at position 229 according to EU numbering, and Glu (E) or Asp (D) at position 439 according to EU numbering;
(2) the first polypeptide has Ser (S) at position 131 according to EU numbering, Ser (S) at position 226 according to EU numbering, Pro (P) at position 228 according to EU numbering, Ser (S) at position 229 according to EU numbering, and any of Lys (K), Arg (R), and His (H) at position 356 according to EU numbering, and the second polypeptide has Ser (S) at position 131 according to EU numbering, Ser (S) at position 226 according to EU numbering, Pro (P) at position 228 according to EU numbering, Ser (S) at position 229 according to EU numbering, and Glu (E) or Asp (D) at position 439 according to EU numbering;
(3) the first polypeptide has Ser (S) or Tyr (Y) at position 220 according to EU numbering, Ser (S) at position 226 according to EU numbering, Ser (S) at position 229 according to EU numbering, and any of Lys (K), Arg (R), and His (H) at position 356 according to EU numbering, and the second polypeptide has Ser (S) or Tyr (Y) at position 220 according to EU numbering, Ser (S) at position 226 according to EU numbering, Ser (S) at position 229 according to EU numbering, and Glu (E) or Asp (D) at position 439 according to EU numbering;
(4) the first polypeptide has Ser (S) at position 131 according to EU numbering, deletion at positions 219 to 229 according to EU numbering, and any of Lys (K), Arg (R), and His (H) at position 356 according to EU numbering, and the second polypeptide has Ser (S) at position 131 according to EU numbering, deletion at positions 219 to 229 according to EU numbering, and Glu (E) or Asp (D) at position 439 according to EU numbering;
(5) the first polypeptide has deletion at positions 219 to 229 according to EU numbering, and any of Lys (K), Arg (R), and His (H) at position 356 according to EU numbering, and the second polypeptide has deletion at positions 219 to 229 according to EU numbering, and Glu (E) or Asp (D) at position 439 according to EU numbering; and
(6) the first polypeptide has Ser (S) at position 226 according to EU numbering, Ser (S) at position 229 according to EU numbering, Tyr (Y)-Gly (G)-Pro (P)-Pro (P) at positions 220 to 225 according to EU numbering, and any of Lys (K), Arg (R), and His (H) at position 356 according to EU numbering, and the second polypeptide has Ser (S) at position 226 according to EU numbering, Ser (S) at position 229 according to EU numbering, Tyr (Y)-Gly (G)-Pro (P)-Pro (P) at positions 220 to 225 according to EU numbering, and Glu (E) or Asp (D) at position 439 according to EU numbering.

Preferably, the heavy chain constant regions having the manner (1), (2), or (4) are derived from IgG4, and the heavy chain constant regions having the manner (3), (5), or (6) are derived from IgG1.

The present invention also provides a method for producing a heteromultimer comprising first and second polypeptides, wherein the heavy chain constant regions of the first and second polypeptides each have amino acid residues shown in any of the following (1) to (6):
(1) the first polypeptide has Ser (S) at position 131 according to EU numbering, Ser (S) at position 226 according to EU numbering, Ser (S) at position 229 according to EU numbering, and any of Lys (K), Arg (R), and His (H) at position 356 according to EU numbering, and the second polypeptide has Ser (S) at position 131 according to EU numbering, Ser (S) at position 226 according to EU numbering, Ser (S) at position 229 according to EU numbering, and Glu (E) or Asp (D) at position 439 according to EU numbering;
(2) the first polypeptide has Ser (S) at position 131 according to EU numbering, Ser (S) at position 226 according to EU numbering, Pro (P) at position 228 according to EU numbering, Ser (S) at position 229 according to EU numbering, and any of Lys (K), Arg (R), and His (H) at position 356 according to EU numbering, and the second polypeptide has Ser (S) at position 131 according to EU numbering, Ser (S) at position 226 according to EU numbering, Pro (P) at position 228 according to EU numbering, Ser (S) at position 229 according to EU numbering, and Glu (E) or Asp (D) at position 439 according to EU numbering;
(3) the first polypeptide has Ser (S) or Tyr (Y) at position 220 according to EU numbering, Ser (S) at position 226 according to EU numbering, Ser (S) at position 229 according to EU numbering, Arg (R) at position 409 according to EU numbering, and any of Lys (K), Arg (R), and His (H) at position 356 according to EU numbering, and the second polypeptide has Ser (S) or Tyr (Y) at position 220 according to EU numbering, Ser (S) at position 226 according to EU numbering, Ser (S) at position 229 according to EU numbering, and Arg (R) at position 409 according to EU numbering, and Glu (E) or Asp (D) at position 439 according to EU numbering;
(4) the first polypeptide has Ser (S) at position 131 according to EU numbering, deletion at positions 219 to 229 according to EU numbering, and any of Lys (K), Arg (R), and His (H) at position 356 according to EU numbering, and the second polypeptide has Ser (S) at position 131 according to EU numbering, deletion at positions 219 to 229 according to EU numbering, and Glu (E) or Asp (D) at position 439 according to EU numbering;
(5) the first polypeptide has deletion at positions 219 to 229 according to EU numbering, Arg (R) at position 409 according to EU numbering, and any of Lys (K), Arg (R), and His (H) at position 356 according to EU numbering, and the second polypeptide has deletion at positions 219 to 229 according to EU numbering, Arg (R) at position 409 according to EU numbering, and Glu (E) or Asp (D) at position 439 according to EU numbering; and
(6) the first polypeptide has Ser (S) at position 226 according to EU numbering, Ser (S) at position 229 according to EU numbering, Tyr (Y)-Gly (G)-Pro (P)-Pro (P) at positions 220 to 225 according to EU numbering, Arg (R) at position 409 according to EU numbering, and any of Lys (K), Arg (R), and His (H) at position 356 according to EU numbering, and the second polypeptide has Ser (S) at position 226 according to EU numbering, Ser (S) at position 229 according to EU numbering, Tyr (Y)-Gly (G)-Pro (P)-Pro (P) at positions 220 to 225 according to EU numbering, Arg (R) at position 409 according to EU numbering, and Glu (E) or Asp (D) at position 439 according to EU numbering.

Preferably, the heavy chain constant regions having the manner (1), (2), or (4) are derived from IgG4, and the heavy chain constant regions having the manner (3), (5), or (6) are derived from IgG1.

Further specifically, the present invention provides a method for producing a heteromultimer comprising first and second polypeptides, wherein the heavy chain constant regions of the first and second polypeptides each have amino acid residues shown in any of the following (1) to (6):
(1) the first polypeptide has an amino acid residue other than Cys (C) at position 131 according to EU numbering, an amino acid residue other than Cys (C) at position 226 according to EU numbering, an amino acid residue other than Cys (C) at position 229 according to EU numbering, and Lys (K) at position 356 according to EU numbering, and the second polypeptide has an amino acid residue other than Cys (C) at position 131 according to EU numbering, an amino acid residue other than Cys (C) at position 226 according to EU numbering, an amino acid residue other than Cys (C) at position 229 according to EU numbering, and Glu (E) at position 439 according to EU numbering;
(2) the first polypeptide has an amino acid residue other than Cys (C) at position 131 according to EU numbering, an amino acid residue other than Cys (C) at position 226 according to EU numbering, Pro (P) at position 228 according to EU numbering, an amino acid residue other than Cys (C) at position 229 according to EU numbering, and Lys (K) at position 356 according to EU numbering, and the second polypeptide has an amino acid residue other than Cys (C) at position 131 according to EU numbering, an amino acid residue other than Cys (C) at position 226 according to EU numbering, Pro (P) at position 228 according to EU numbering, an amino acid residue other than Cys (C) at position 229 according to EU numbering, and Glu (E) at position 439 according to EU numbering;
(3) the first polypeptide has an amino acid residue other than Cys (C) at position 220 according to EU numbering, an amino acid residue other than Cys (C) at position 226 according to EU numbering, an amino acid residue other than Cys (C) at position 229 according to EU numbering, and Lys (K) at position 356 according to EU numbering, and the second polypeptide has an amino acid residue other than Cys (C), or Tyr (Y) at position 220 according to EU numbering, an amino acid residue other than Cys (C) at position 226 according to EU numbering, an amino acid residue other than Cys (C) at position 229 according to EU numbering, and Glu (E) at position 439 according to EU numbering;
(4) the first polypeptide has an amino acid residue other than Cys (C) at position 131 according to EU numbering, deletion at position 219 to 229 according to EU numbering, and Lys (K) at position 356 according to EU numbering, and the second polypeptide has an amino acid residue other than Cys (C) at position 131 according to EU numbering, deletion at positions 219 to 229 according to EU numbering, and Glu (E) at position 439 according to EU numbering;
(5) the first polypeptide has deletion at positions 219 to 229 according to EU numbering, and Lys (K) at position 356 according to EU numbering, and the second polypeptide has deletion at positions 219 to 229 according to EU numbering, and Glu (E) at position 439 according to EU numbering; and
(6) the first polypeptide has an amino acid residue other than Cys (C) at position 226 according to EU numbering, an amino acid residue other than Cys (C) at position 229 according to EU numbering, Tyr (Y)-Gly (G)-Pro (P)-Pro (P) at positions 220 to 225 according to EU numbering, and Lys (K) at position 356 according to EU numbering, and the second polypeptide has an amino acid residue other than Cys (C) at position 226 according to EU numbering, Ser (S) at position 229 according to EU numbering, Tyr (Y)-Gly (G)-Pro (P)-Pro (P) at positions 220 to 225 according to EU numbering, and Glu (E) at position 439 according to EU numbering.

Preferably, the heavy chain constant regions having the manner (1), (2), or (4) are derived from IgG4, and the heavy chain constant regions having the manner (3), (5), or (6) are derived from IgG1.

Further specifically, the present invention provides a method for producing a heteromultimer comprising first and second polypeptides, wherein the heavy chain constant regions of the first and second polypeptides each have amino acid residues shown in any of the following (1) to (6):
(1) the first polypeptide has an amino acid residue other than Cys (C) at position 131 according to EU numbering, an amino acid residue other than Cys (C) at position 226 according to EU numbering, an amino acid residue other than Cys (C) at position 229 according to EU numbering, and Lys (K) at position 356 according to EU numbering, and the second polypeptide has an amino acid residue other than Cys (C) at position 131 according to EU numbering, an amino acid residue other than Cys (C) at position 226 according to EU numbering, an amino acid residue other than Cys (C) at position 229 according to EU numbering, and Glu (E) at position 439 according to EU numbering;
(2) the first polypeptide has an amino acid residue other than Cys (C) at position 131 according to EU numbering, an amino acid residue other than Cys (C) at position 226 according to EU numbering, Pro (P) at position 228 according to EU numbering, an amino acid residue other than Cys (C) at position 229 according to EU numbering, and Lys (K) at position 356 according to EU numbering, and the second polypeptide has an amino acid residue other than Cys (C) at position 131 according to EU numbering, an amino acid residue other than Cys (C) at position 226 according to EU numbering, Pro (P) at position 228 according to EU numbering, an amino acid residue other than Cys (C) at position 229 according to EU numbering, and Glu (E) at position 439 according to EU numbering;
(3) the first polypeptide has an amino acid residue other than Cys (C) at position 220 according to EU numbering, an amino acid residue other than Cys (C) at position 226 according to EU numbering, an amino acid residue other than Cys (C) at position 229 according to EU numbering, Arg (R) at position 409 according to EU numbering, and Lys (K) at position 356 according to EU numbering, and the second polypeptide has an amino acid residue other than Cys (C), or Tyr (Y) at position 220 according to EU numbering, an amino acid residue other than Cys (C) at position 226 according to EU numbering, an amino acid residue other than Cys (C) at position 229 according to EU numbering, Arg (R) at position 409 according to EU numbering, and Glu (E) at position 439 according to EU numbering;
(4) the first polypeptide has an amino acid residue other than Cys (C) at position 131 according to EU numbering, deletion at positions 219 to 229 according to EU numbering, and Lys (K) at position 356 according to EU numbering, and the second polypeptide has an amino acid residue other than Cys (C) at position 131 according to EU numbering, deletion at positions 219 to 229 according to EU numbering, and Glu (E) at position 439 according to EU numbering;
(5) the first polypeptide has deletion at positions 219 to 229 according to EU numbering, Arg (R) at position 409 according to EU numbering, and Lys (K) at position 356 according to EU numbering, and the second polypeptide has deletion at positions 219 to 229 according to EU numbering, Arg (R) at position 409 according to EU numbering, and Glu (E) at position 439 according to EU numbering; and
(6) the first polypeptide has an amino acid residue other than Cys (C) at position 226 according to EU numbering, an amino acid residue other than Cys (C) at position 229 according to EU numbering, Tyr (Y)-Gly (G)-Pro (P)-Pro (P) at positions 220 to 225 according to EU numbering, Arg (R) at position 409 according to EU numbering, and Lys (K) at position 356 according to EU numbering, and the second polypeptide has an amino acid residue other than Cys (C) at position 226 according to EU numbering, Ser (S) at position 229 according to EU numbering, Tyr (Y)-Gly (G)-Pro (P)-Pro (P) at positions 220 to 225 according to EU numbering, Arg (R) at position 409 according to EU numbering, and Glu (E) at position 439 according to EU numbering.

Preferably, the heavy chain constant regions having the manner (1), (2), or (4) are derived from IgG4, and the heavy chain constant regions having the manner (3), (5), or (6) are derived from IgG1.

The present invention also provides a method for producing a heteromultimer comprising first and second polypeptides, wherein the heavy chain constant regions of the first and second polypeptides each have amino acid residues shown in any of the following (1) to (6):
(1) the first polypeptide has Ser (S) at position 131 according to EU numbering, Ser (S) at position 226 according to EU numbering, Ser (S) at position 229 according to EU numbering, and Lys (K) at position 356 according to EU numbering, and the second polypeptide has Ser (S) at position 131 according to EU numbering, Ser (S) at position 226 according to EU numbering, Ser (S) at position 229 according to EU numbering, and Glu (E) at position 439 according to EU numbering;

(2) the first polypeptide has Ser (S) at position 131 according to EU numbering, Ser (S) at position 226 according to EU numbering, Pro (P) at position 228 according to EU numbering, Ser (S) at position 229 according to EU numbering, and Lys (K) at position 356 according to EU numbering, and the second polypeptide has Ser (S) at position 131 according to EU numbering, Ser (S) at position 226 according to EU numbering, Pro (P) at position 228 according to EU numbering, Ser (S) at position 229 according to EU numbering, and Glu (E) at position 439 according to EU numbering;

(3) the first polypeptide has Ser (S) or Tyr (Y) at position 220 according to EU numbering, Ser (S) at position 226 according to EU numbering, Ser (S) at position 229 according to EU numbering, and Lys (K) at position 356 according to EU numbering, and the second polypeptide has Ser (S) or Tyr (Y) at position 220 according to EU numbering, Ser (S) at position 226 according to EU numbering, Ser (S) at position 229 according to EU numbering, and Glu (E) at position 439 according to EU numbering;

(4) the first polypeptide has Ser (S) at position 131 according to EU numbering, deletion at positions 219 to 229 according to EU numbering, and Lys (K) at position 356 according to EU numbering, and the second polypeptide has Ser (S) at position 131 according to EU numbering, deletion at positions 219 to 229 according to EU numbering, and Glu (E) at position 439 according to EU numbering;

(5) the first polypeptide has deletion at positions 219 to 229 according to EU numbering, and Lys (K) at position 356 according to EU numbering, and the second polypeptide has deletion at positions 219 to 229 according to EU numbering, and Glu (E) at position 439 according to EU numbering; and (6) the first polypeptide has Ser (S) at position 226 according to EU numbering, Ser (S) at position 229 according to EU numbering, Tyr (Y)-Gly (G)-Pro (P)-Pro (P) at positions 220 to 225 according to EU numbering, and Lys (K) at position 356 according to EU numbering, and the second polypeptide has Ser (S) at position 226 according to EU numbering, Ser (S) at position 229 according to EU numbering, Tyr (Y)-Gly (G)-Pro (P)-Pro (P) at positions 220 to 225 according to EU numbering, and Glu (E) at position 439 according to EU numbering.

Preferably, the heavy chain constant regions having the manner (1), (2), or (4) are derived from IgG4, and the heavy chain constant regions having the manner (3), (5), or (6) are derived from IgG1.

The present invention also provides a method for producing a heteromultimer comprising first and second polypeptides, wherein the heavy chain constant regions of the first and second polypeptides each have amino acid residues shown in any of the following (1) to (6):

(1) the first polypeptide has Ser (S) at position 131 according to EU numbering, Ser (S) at position 226 according to EU numbering, Ser (S) at position 229 according to EU numbering, and Lys (K) at position 356 according to EU numbering, and the second polypeptide has Ser (S) at position 131 according to EU numbering, Ser (S) at position 226 according to EU numbering, Ser (S) at position 229 according to EU numbering, and Glu (E) at position 439 according to EU numbering;

(2) the first polypeptide has Ser (S) at position 131 according to EU numbering, Ser (S) at position 226 according to EU numbering, Pro (P) at position 228 according to EU numbering, Ser (S) at position 229 according to EU numbering, and Lys (K) at position 356 according to EU numbering, and the second polypeptide has Ser (S) at position 131 according to EU numbering, Ser (S) at position 226 according to EU numbering, Pro (P) at position 228 according to EU numbering, Ser (S) at position 229 according to EU numbering, and Glu (E) at position 439 according to EU numbering;

(3) the first polypeptide has Ser (S) or Tyr (Y) at position 220 according to EU numbering, Ser (S) at position 226 according to EU numbering, Ser (S) at position 229 according to EU numbering, Arg (R) at position 409 according to EU numbering, and Lys (K) at position 356 according to EU numbering, and the second polypeptide has Ser (S) or Tyr (Y) at position 220 according to EU numbering, Ser (S) at position 226 according to EU numbering, Ser (S) at position 229 according to EU numbering, Arg (R) at position 409 according to EU numbering, and Glu (E) at position 439 according to EU numbering;

(4) the first polypeptide has Ser (S) at position 131 according to EU numbering, deletion at positions 219 to 229 according to EU numbering, and Lys (K) at position 356 according to EU numbering, and the second polypeptide has Ser (S) at position 131 according to EU numbering, deletion at positions 219 to 229 according to EU numbering, and Glu (E) at position 439 according to EU numbering;

(5) the first polypeptide has deletion at positions 219 to 229 according to EU numbering, Arg (R) at position 409 according to EU numbering, and Lys (K) at position 356 according to EU numbering, and the second polypeptide has deletion at positions 219 to 229 according to EU numbering, Arg (R) at position 409 according to EU numbering, and Glu (E) at position 439 according to EU numbering; and (6) the first polypeptide has Ser (S) at position 226 according to EU numbering, Ser (S) at position 229 according to EU numbering, Tyr (Y)-Gly (G)-Pro (P)-Pro (P) at positions 220 to 225 according to EU numbering, Arg (R) at position 409 according to EU numbering, and Lys (K) at position 356 according to EU numbering, and the second polypeptide has Ser (S) at position 226 according to EU numbering, Ser (S) at position 229 according to EU numbering, Tyr (Y)-Gly (G)-Pro (P)-Pro (P) at positions 220 to 225 according to EU numbering, Arg (R) at position 409 according to EU numbering, and Glu (E) at position 439 according to EU numbering.

Preferably, the heavy chain constant regions having the manner (1), (2), or (4) are derived from IgG4, and the heavy chain constant regions having the manner (3), (5), or (6) are derived from IgG1.

In an alternative aspect, the present invention provides a bispecific antibody comprising first and second polypeptides, wherein the bispecific antibody comprises first, second, third, and fourth polypeptides as constituents in which the first polypeptide which is an antibody heavy chain and the third polypeptide which is an antibody light chain form a dimer, and the second polypeptide which is an antibody heavy chain and the fourth polypeptide which is an antibody light chain form a dimer, wherein the first and/or second polypeptide have amino acid residues given below.

Specifically, the present invention provides a bispecific antibody comprising first and second polypeptides, wherein the heavy chain constant regions of the first and second polypeptides each have amino acid residues shown in any of the following (1) and (2):

(1) the first and second polypeptides have an amino acid residue other than Cys (C) at position 131 according to EU numbering; and (2) the first and second polypeptides have an amino acid residue other than Cys (C) at position 220 according to EU numbering.

Preferably, the heavy chain constant regions having the manner (1) are derived from IgG4, and the heavy chain constant regions having the manner (2) are derived from IgG1.

The present invention also provides a bispecific antibody comprising first and second polypeptides, wherein the heavy chain constant regions of the first and second polypeptides each have amino acid residues shown in any of the following (1) and (2):
(1) the first and second polypeptides have Ser (S) at position 131 according to EU numbering; and
(2) the first and second polypeptides have Ser (S) or Tyr (Y) at position 220 according to EU numbering.

Preferably, the heavy chain constant regions having the manner (1) are derived from IgG4, and the heavy chain constant regions having the manner (2) are derived from IgG1.

Further specifically, the present invention provides a bispecific antibody comprising first and second polypeptides, wherein the heavy chain constant regions of the first and second polypeptides each have amino acid residues shown in any of the following (1) to (6):
(1) the first and second polypeptides have an amino acid residue other than Cys (C) at position 131 according to EU numbering, an amino acid residue other than Cys (C) at position 226 according to EU numbering, and an amino acid residue other than Cys (C) at position 229 according to EU numbering;
(2) the first and second polypeptides have an amino acid residue other than Cys (C) at position 131 according to EU numbering, an amino acid residue other than Cys (C) at position 226 according to EU numbering, Pro (P) at position 228 according to EU numbering, and an amino acid residue other than Cys (C) at position 229 according to EU numbering;
(3) the first and second polypeptides have an amino acid residue other than Cys (C) at position 220 according to EU numbering, an amino acid residue other than Cys (C) at position 226 according to EU numbering, and an amino acid residue other than Cys (C) at position 229 according to EU numbering;
(4) the first and second polypeptides have an amino acid residue other than Cys (C) at position 131 according to EU numbering, and deletion at positions 219 to 229 according to EU numbering;
(5) the first and second polypeptides have deletion at positions 219 to 229 according to EU numbering; and
(6) the first and second polypeptides have an amino acid residue other than Cys (C) at position 226 according to EU numbering, an amino acid residue other than Cys (C) at position 229 according to EU numbering, and Tyr (Y)-Gly (G)-Pro (P)-Pro (P) at positions 220 to 225 according to EU numbering.

Preferably, the heavy chain constant regions having the manner (1), (2), or (4) are derived from IgG4, and the heavy chain constant regions having the manner (3), (5), or (6) are derived from IgG1.

The present invention also provides a bispecific antibody comprising first and second polypeptides, wherein the heavy chain constant regions of the first and second polypeptides each have amino acid residues shown in any of the following (1) to (6):
(1) the first and second polypeptides have Ser (S) at position 131 according to EU numbering, Ser (S) at position 226 according to EU numbering, and Ser (S) at position 229 according to EU numbering;
(2) the first and second polypeptides have Ser (S) at position 131 according to EU numbering, Ser (S) at position 226 according to EU numbering, Pro (P) at position 228 according to EU numbering, and Ser (S) at position 229 according to EU numbering;
(3) the first and second polypeptides have Ser (S) or Tyr (Y) at position 220 according to EU numbering, Ser (S) at position 226 according to EU numbering, and Ser (S) at position 229 according to EU numbering;
(4) the first and second polypeptides have Ser (S) at position 131 according to EU numbering, and deletion at positions 219 to 229 according to EU numbering;
(5) the first and second polypeptides have deletion at positions 219 to 229 according to EU numbering; and
(6) the first and second polypeptides have Ser (S) at position 226 according to EU numbering, Ser (S) at position 229 according to EU numbering, and Tyr (Y)-Gly (G)-Pro (P)-Pro (P) at positions 220 to 225 according to EU numbering.

Preferably, the heavy chain constant regions having the manner (1), (2), or (4) are derived from IgG4, and the heavy chain constant regions having the manner (3), (5), or (6) are derived from IgG1.

Further specifically, the present invention provides a bispecific antibody comprising first and second polypeptides, wherein the heavy chain constant regions of the first and second polypeptides each have amino acid residues shown in any of the following (1) to (6):
(1) the first and second polypeptides have an amino acid residue other than Cys (C) at position 131 according to EU numbering, an amino acid residue other than Cys (C) at position 226 according to EU numbering, and an amino acid residue other than Cys (C) at position 229 according to EU numbering;
(2) the first and second polypeptides have an amino acid residue other than Cys (C) at position 131 according to EU numbering, an amino acid residue other than Cys (C) at position 226 according to EU numbering, Pro (P) at position 228 according to EU numbering, and an amino acid residue other than Cys (C) at position 229 according to EU numbering;
(3) the first and second polypeptides have an amino acid residue other than Cys (C) at position 220 according to EU numbering, an amino acid residue other than Cys (C) at position 226 according to EU numbering, an amino acid residue other than Cys (C) at position 229 according to EU numbering, and Arg (R) at position 409 according to EU numbering;
(4) the first and second polypeptides have an amino acid residue other than Cys (C) at position 131 according to EU numbering, and deletion at positions 219 to 229 according to EU numbering;
(5) the first and second polypeptides have deletion at positions 219 to 229 according to EU numbering, and Arg (R) at position 409 according to EU numbering; and
(6) the first and second polypeptides have an amino acid residue other than Cys (C) at position 226 according to EU numbering, an amino acid residue other than Cys (C) at position 229 according to EU numbering, Tyr (Y)-Gly (G)-Pro (P)-Pro (P) at positions 220 to 225 according to EU numbering, and Arg (R) at position 409 according to EU numbering.

Preferably, the heavy chain constant regions having the manner (1), (2), or (4) are derived from IgG4, and the heavy chain constant regions having the manner (3), (5), or (6) are derived from IgG1.

The present invention also provides a bispecific antibody comprising first and second polypeptides, wherein the heavy chain constant regions of the first and second polypeptides each have amino acid residues shown in any of the following (1) to (6):
(1) the first and second polypeptides have Ser (S) at position 131 according to EU numbering, Ser (S) at position 226 according to EU numbering, and Ser (S) at position 229 according to EU numbering;
(2) the first and second polypeptides have Ser (S) at position 131 according to EU numbering, Ser (S) at position 226 according to EU numbering, Pro (P) at position 228 according to EU numbering, and Ser (S) at position 229 according to EU numbering;
(3) the first and second polypeptides have Ser (S) or Tyr (Y) at position 220 according to EU numbering, Ser (S) at position 226 according to EU numbering, Ser (S) at position 229 according to EU numbering, and Arg (R) at position 409 according to EU numbering;
(4) the first and second polypeptides have Ser (S) at position 131 according to EU numbering, and deletion at positions 219 to 229 according to EU numbering;
(5) the first and second polypeptides have deletion at positions 219 to 229 according to EU numbering, and Arg (R) at position 409 according to EU numbering; and
(6) the first and second polypeptides have Ser (S) at position 226 according to EU numbering, Ser (S) at position 229 according to EU numbering, Tyr (Y)-Gly (G)-Pro (P)-Pro (P) at positions 220 to 225 according to EU numbering, and Arg (R) at position 409 according to EU numbering.

Preferably, the heavy chain constant regions having the manner (1), (2), or (4) are derived from IgG4, and the heavy chain constant regions having the manner (3), (5), or (6) are derived from IgG1.

Further specifically, the present invention provides a bispecific antibody comprising first and second polypeptides, wherein the heavy chain constant regions of the first and second polypeptides each have amino acid residues shown in any of the following (1) to (6): (1) the first polypeptide has an amino acid residue other than Cys (C) at position 131 according to EU numbering, an amino acid residue other than Cys (C) at position 226 according to EU numbering, an amino acid residue other than Cys (C) at position 229 according to EU numbering, and any of Lys (K), Arg (R), and His (H) at position 356 according to EU numbering, and the second polypeptide has an amino acid residue other than Cys (C) at position 131 according to EU numbering, an amino acid residue other than Cys (C) at position 226 according to EU numbering, an amino acid residue other than Cys (C) at position 229 according to EU numbering, and Glu (E) or Asp (D) at position 439 according to EU numbering;
(2) the first polypeptide has an amino acid residue other than Cys (C) at position 131 according to EU numbering, an amino acid residue other than Cys (C) at position 226 according to EU numbering, Pro (P) at position 228 according to EU numbering, an amino acid residue other than Cys (C) at position 229 according to EU numbering, and any of Lys (K), Arg (R), and His (H) at position 356 according to EU numbering, and the second polypeptide has an amino acid residue other than Cys (C) at position 131 according to EU numbering, an amino acid residue other than Cys (C) at position 226 according to EU numbering, Pro (P) at position 228 according to EU numbering, an amino acid residue other than Cys (C) at position 229 according to EU numbering, and Glu (E) or Asp (D) at position 439 according to EU numbering;
(3) the first polypeptide has an amino acid residue other than Cys (C) at position 220 according to EU numbering, an amino acid residue other than Cys (C) at position 226 according to EU numbering, an amino acid residue other than Cys (C) at position 229 according to EU numbering, and any of Lys (K), Arg (R), and His (H) at position 356 according to EU numbering, and the second polypeptide has an amino acid residue other than Cys (C) at position 220 according to EU numbering, an amino acid residue other than Cys (C) at position 226 according to EU numbering, an amino acid residue other than Cys (C) at position 229 according to EU numbering, and Glu (E) or Asp (D) at position 439 according to EU numbering;
(4) the first polypeptide has an amino acid residue other than Cys (C) at position 131 according to EU numbering, deletion at positions 219 to 229 according to EU numbering, and any of Lys (K), Arg (R), and His (H) at position 356 according to EU numbering, and the second polypeptide has an amino acid residue other than Cys (C) at position 131 according to EU numbering, deletion at positions 219 to 229 according to EU numbering, and Glu (E) or Asp (D) at position 439 according to EU numbering;
(5) the first polypeptide has deletion at positions 219 to 229 according to EU numbering, and any of Lys (K), Arg (R), and His (H) at position 356 according to EU numbering, and the second polypeptide has deletion at positions 219 to 229 according to EU numbering, and Glu (E) or Asp (D) at position 439 according to EU numbering; and
(6) the first polypeptide has an amino acid residue other than Cys (C) at position 226 according to EU numbering, an amino acid residue other than Cys (C) at position 229 according to EU numbering, Tyr (Y)-Gly (G)-Pro (P)-Pro (P) at positions 220 to 225 according to EU numbering, and any of Lys (K), Arg (R), and His (H) at position 356 according to EU numbering, and the second polypeptide has an amino acid residue other than Cys (C) at position 226 according to EU numbering, an amino acid residue other than Cys (C) at position 229 according to EU numbering, Tyr (Y)-Gly (G)-Pro (P)-Pro (P) at positions 220 to 225 according to EU numbering, and Glu (E) or Asp (D) at position 439 according to EU numbering.

Preferably, the heavy chain constant regions having the manner (1), (2), or (4) are derived from IgG4, and the heavy chain constant regions having the manner (3), (5), or (6) are derived from IgG1.

Further specifically, the present invention provides a bispecific antibody comprising first and second polypeptides, wherein the heavy chain constant regions of the first and second polypeptides each have amino acid residues shown in any of the following (1) to (6):
(1) the first polypeptide has an amino acid residue other than Cys (C) at position 131 according to EU numbering, an amino acid residue other than Cys (C) at position 226 according to EU numbering, an amino acid residue other than Cys (C) at position 229 according to EU numbering, and any of Lys (K), Arg (R), and His (H) at position 356 according to EU numbering, and the second polypeptide has an amino acid residue other than Cys (C) at position 131 according to EU numbering, an amino acid residue other than Cys (C) at position 226 according to EU numbering, an amino acid residue other than Cys (C) at position 229 according to EU numbering, and Glu (E) or Asp (D) at position 439 according to EU numbering;

(2) the first polypeptide has an amino acid residue other than Cys (C) at position 131 according to EU numbering, an amino acid residue other than Cys (C) at position 226 according to EU numbering, Pro (P) at position 228 according to EU numbering, an amino acid residue other than Cys (C) at position 229 according to EU numbering, and any of Lys (K), Arg (R), and His (H) at position 356 according to EU numbering, and the second polypeptide has an amino acid residue other than Cys (C) at position 131 according to EU numbering, an amino acid residue other than Cys (C) at position 226 according to EU numbering, Pro (P) at position 228 according to EU numbering, an amino acid residue other than Cys (C) at position 229 according to EU numbering, and Glu (E) or Asp (D) at position 439 according to EU numbering;
(3) the first polypeptide has an amino acid residue other than Cys (C) at position 220 according to EU numbering, an amino acid residue other than Cys (C) at position 226 according to EU numbering, an amino acid residue other than Cys (C) at position 229 according to EU numbering, Arg (R) at position 409 according to EU numbering, and any of Lys (K), Arg (R), and His (H) at position 356 according to EU numbering, and the second polypeptide has an amino acid residue other than Cys (C) at position 220 according to EU numbering, an amino acid residue other than Cys (C) at position 226 according to EU numbering, an amino acid residue other than Cys (C) at position 229 according to EU numbering, Arg (R) at position 409 according to EU numbering, and Glu (E) or Asp (D) at position 439 according to EU numbering;
(4) the first polypeptide has an amino acid residue other than Cys (C) at position 131 according to EU numbering, deletion at positions 219 to 229 according to EU numbering, and any of Lys (K), Arg (R), and His (H) at position 356 according to EU numbering, and the second polypeptide has an amino acid residue other than Cys (C) at position 131 according to EU numbering, deletion at positions 219 to 229 according to EU numbering, and Glu (E) or Asp (D) at position 439 according to EU numbering;
(5) the first polypeptide has deletion at positions 219 to 229 according to EU numbering, Arg (R) at position 409 according to EU numbering, and any of Lys (K), Arg (R), and His (H) at position 356 according to EU numbering, and the second polypeptide has deletion at positions 219 to 229 according to EU numbering, Arg (R) at position 409 according to EU numbering, and Glu (E) or Asp (D) at position 439 according to EU numbering; and
(6) the first polypeptide has an amino acid residue other than Cys (C) at position 226 according to EU numbering, an amino acid residue other than Cys (C) at position 229 according to EU numbering, Tyr (Y)-Gly (G)-Pro (P)-Pro (P) at positions 220 to 225 according to EU numbering, Arg (R) at position 409 according to EU numbering, and any of Lys (K), Arg (R), and His (H) at position 356 according to EU numbering, and the second polypeptide has an amino acid residue other than Cys (C) at position 226 according to EU numbering, an amino acid residue other than Cys (C) at position 229 according to EU numbering, Tyr (Y)-Gly (G)-Pro (P)-Pro (P) at positions 220 to 225 according to EU numbering, Arg (R) at position 409 according to EU numbering, and Glu (E) or Asp (D) at position 439 according to EU numbering.

Preferably, the heavy chain constant regions having the manner (1), (2), or (4) are derived from IgG4, and the heavy chain constant regions having the manner (3), (5), or (6) are derived from IgG1.

The present invention also provides a bispecific antibody comprising first and second polypeptides, wherein the heavy chain constant regions of the first and second polypeptides each have amino acid residues shown in any of the following (1) to (6):
(1) the first polypeptide has Ser (S) at position 131 according to EU numbering, Ser (S) at position 226 according to EU numbering, Ser (S) at position 229 according to EU numbering, and any of Lys (K), Arg (R), and His (H) at position 356 according to EU numbering, and the second polypeptide has Ser (S) at position 131 according to EU numbering, Ser (S) at position 226 according to EU numbering, Ser (S) at position 229 according to EU numbering, and Glu (E) or Asp (D) at position 439 according to EU numbering;
(2) the first polypeptide has Ser (S) at position 131 according to EU numbering, Ser (S) at position 226 according to EU numbering, Pro (P) at position 228 according to EU numbering, Ser (S) at position 229 according to EU numbering, and any of Lys (K), Arg (R), and His (H) at position 356 according to EU numbering, and the second polypeptide has Ser (S) at position 131 according to EU numbering, Ser (S) at position 226 according to EU numbering, Pro (P) at position 228 according to EU numbering, Ser (S) at position 229 according to EU numbering, and Glu (E) or Asp (D) at position 439 according to EU numbering;
(3) the first polypeptide has Ser (S) or Tyr (Y) at position 220 according to EU numbering, Ser (S) at position 226 according to EU numbering, Ser (S) at position 229 according to EU numbering, and any of Lys (K), Arg (R), and His (H) at position 356 according to EU numbering, and the second polypeptide has Ser (S) or Tyr (Y) at position 220 according to EU numbering, Ser (S) at position 226 according to EU numbering, Ser (S) at position 229 according to EU numbering, and Glu (E) or Asp (D) at position 439 according to EU numbering;
(4) the first polypeptide has Ser (S) at position 131 according to EU numbering, deletion at positions 219 to 229 according to EU numbering, and any of Lys (K), Arg (R), and His (H) at position 356 according to EU numbering, and the second polypeptide has Ser (S) at position 131 according to EU numbering, deletion at positions 219 to 229 according to EU numbering, and Glu (E) or Asp (D) at position 439 according to EU numbering;
(5) the first polypeptide has deletion at positions 219 to 229 according to EU numbering, and any of Lys (K), Arg (R), and His (H) at position 356 according to EU numbering, and the second polypeptide has deletion at positions 219 to 229 according to EU numbering, and Glu (E) or Asp (D) at position 439 according to EU numbering; and
(6) the first polypeptide has Ser (S) at position 226 according to EU numbering, Ser (S) at position 229 according to EU numbering, Tyr (Y)-Gly (G)-Pro (P)-Pro (P) at positions 220 to 225 according to EU numbering, and any of Lys (K), Arg (R), and His (H) at position 356 according to EU numbering, and the second polypeptide has Ser (S) at position 226 according to EU numbering, Ser (S) at position 229 according to EU numbering, Tyr (Y)-Gly (G)-Pro (P)-Pro (P) at positions 220 to 225 according to EU numbering, and Glu (E) or Asp (D) at position 439 according to EU numbering.

Preferably, the heavy chain constant regions having the manner (1), (2), or (4) are derived from IgG4, and the heavy chain constant regions having the manner (3), (5), or (6) are derived from IgG1.

The present invention also provides a bispecific antibody comprising first and second polypeptides, wherein the heavy chain constant regions of the first and second polypeptides each have amino acid residues shown in any of the following (1) to (6):

(1) the first polypeptide has Ser (S) at position 131 according to EU numbering, Ser (S) at position 226 according to EU numbering, Ser (S) at position 229 according to EU numbering, and any of Lys (K), Arg (R), and His (H) at position 356 according to EU numbering, and the second polypeptide has Ser (S) at position 131 according to EU numbering, Ser (S) at position 226 according to EU numbering, Ser (S) at position 229 according to EU numbering, and Glu (E) or Asp (D) at position 439 according to EU numbering;

(2) the first polypeptide has Ser (S) at position 131 according to EU numbering, Ser (S) at position 226 according to EU numbering, Pro (P) at position 228 according to EU numbering, Ser (S) at position 229 according to EU numbering, and any of Lys (K), Arg (R), and His (H) at position 356 according to EU numbering, and the second polypeptide has Ser (S) at position 131 according to EU numbering, Ser (S) at position 226 according to EU numbering, Pro (P) at position 228 according to EU numbering, Ser (S) at position 229 according to EU numbering, and Glu (E) or Asp (D) at position 439 according to EU numbering;

(3) the first polypeptide has Ser (S) or Tyr (Y) at position 220 according to EU numbering, Ser (S) at position 226 according to EU numbering, Ser (S) at position 229 according to EU numbering, Arg (R) at position 409 according to EU numbering, and any of Lys (K), Arg (R), and His (H) at position 356 according to EU numbering, and the second polypeptide has Ser (S) or Tyr (Y) at position 220 according to EU numbering, Ser (S) at position 226 according to EU numbering, Ser (S) at position 229 according to EU numbering, and Arg (R) at position 409 according to EU numbering, and Glu (E) or Asp (D) at position 439 according to EU numbering;

(4) the first polypeptide has Ser (S) at position 131 according to EU numbering, deletion at positions 219 to 229 according to EU numbering, and any of Lys (K), Arg (R), and His (H) at position 356 according to EU numbering, and the second polypeptide has Ser (S) at position 131 according to EU numbering, deletion at positions 219 to 229 according to EU numbering, and Glu (E) or Asp (D) at position 439 according to EU numbering;

(5) the first polypeptide has deletion at positions 219 to 229 according to EU numbering, Arg (R) at position 409 according to EU numbering, and any of Lys (K), Arg (R), and His (H) at position 356 according to EU numbering, and the second polypeptide has deletion at positions 219 to 229 according to EU numbering, Arg (R) at position 409 according to EU numbering, and Glu (E) or Asp (D) at position 439 according to EU numbering; and (6) the first polypeptide has Ser (S) at position 226 according to EU numbering, Ser (S) at position 229 according to EU numbering, Tyr (Y)-Gly (G)-Pro (P)-Pro (P) at positions 220 to 225 according to EU numbering, Arg (R) at position 409 according to EU numbering, and any of Lys (K), Arg (R), and His (H) at position 356 according to EU numbering, and the second polypeptide has Ser (S) at position 226 according to EU numbering, Ser (S) at position 229 according to EU numbering, Tyr (Y)-Gly (G)-Pro (P)-Pro (P) at positions 220 to 225 according to EU numbering, Arg (R) at position 409 according to EU numbering, and Glu (E) or Asp (D) at position 439 according to EU numbering.

Preferably, the heavy chain constant regions having the manner (1), (2), or (4) are derived from IgG4, and the heavy chain constant regions having the manner (3), (5), or (6) are derived from IgG1.

Further specifically, the present invention provides a bispecific antibody comprising first and second polypeptides, wherein the heavy chain constant regions of the first and second polypeptides each have amino acid residues shown in any of the following (1) to (6): (1) the first polypeptide has an amino acid residue other than Cys (C) at position 131 according to EU numbering, an amino acid residue other than Cys (C) at position 226 according to EU numbering, an amino acid residue other than Cys (C) at position 229 according to EU numbering, and Lys (K) at position 356 according to EU numbering, and the second polypeptide has an amino acid residue other than Cys (C) at position 131 according to EU numbering, an amino acid residue other than Cys (C) at position 226 according to EU numbering, an amino acid residue other than Cys (C) at position 229 according to EU numbering, and Glu (E) at position 439 according to EU numbering;

(2) the first polypeptide has an amino acid residue other than Cys (C) at position 131 according to EU numbering, an amino acid residue other than Cys (C) at position 226 according to EU numbering, Pro (P) at position 228 according to EU numbering, an amino acid residue other than Cys (C) at position 229 according to EU numbering, and Lys (K) at position 356 according to EU numbering, and the second polypeptide has an amino acid residue other than Cys (C) at position 131 according to EU numbering, an amino acid residue other than Cys (C) at position 226 according to EU numbering, Pro (P) at position 228 according to EU numbering, an amino acid residue other than Cys (C) at position 229 according to EU numbering, and Glu (E) at position 439 according to EU numbering;

(3) the first polypeptide has an amino acid residue other than Cys (C) at position 220 according to EU numbering, an amino acid residue other than Cys (C) at position 226 according to EU numbering, an amino acid residue other than Cys (C) at position 229 according to EU numbering, and Lys (K) at position 356 according to EU numbering, and the second polypeptide has an amino acid residue other than Cys (C), or Tyr (Y) at position 220 according to EU numbering, an amino acid residue other than Cys (C) at position 226 according to EU numbering, an amino acid residue other than Cys (C) at position 229 according to EU numbering, and Glu (E) at position 439 according to EU numbering;

(4) the first polypeptide has an amino acid residue other than Cys (C) at position 131 according to EU numbering, deletion at position 219 to 229 according to EU numbering, and Lys (K) at position 356 according to EU numbering, and the second polypeptide has an amino acid residue other than Cys (C) at position 131 according to EU numbering, deletion at positions 219 to 229 according to EU numbering, and Glu (E) at position 439 according to EU numbering;

(5) the first polypeptide has deletion at positions 219 to 229 according to EU numbering, and Lys (K) at position 356 according to EU numbering, and the second polypeptide has deletion at positions 219 to 229 according to EU numbering, and Glu (E) at position 439 according to EU numbering; and (6) the first polypeptide has an amino acid residue other than Cys (C) at position 226 according to EU numbering, an amino acid residue other than Cys (C) at position 229 according to EU numbering, Tyr (Y)-Gly (G)-Pro (P)-Pro (P) at positions 220 to 225 according to EU numbering, and Lys (K) at position 356 according to EU numbering, and the second polypeptide has an amino acid residue other than Cys (C) at position 226 according to EU numbering, Ser (S) at position 229 according to EU numbering, Tyr (Y)-Gly (G)-Pro (P)-Pro (P) at positions 220 to 225 according to EU numbering, and Glu (E) at position 439 according to EU numbering.

Preferably, the heavy chain constant regions having the manner (1), (2), or (4) are derived from IgG4, and the heavy chain constant regions having the manner (3), (5), or (6) are derived from IgG1.

Further specifically, the present invention provides a bispecific antibody comprising first and second polypeptides, wherein the heavy chain constant regions of the first and second polypeptides each have amino acid residues shown in any of the following (1) to (6):
(1) the first polypeptide has an amino acid residue other than Cys (C) at position 131 according to EU numbering, an amino acid residue other than Cys (C) at position 226 according to EU numbering, an amino acid residue other than Cys (C) at position 229 according to EU numbering, and Lys (K) at position 356 according to EU numbering, and the second polypeptide has an amino acid residue other than Cys (C) at position 131 according to EU numbering, an amino acid residue other than Cys (C) at position 226 according to EU numbering, an amino acid residue other than Cys (C) at position 229 according to EU numbering, and Glu (E) at position 439 according to EU numbering;
(2) the first polypeptide has an amino acid residue other than Cys (C) at position 131 according to EU numbering, an amino acid residue other than Cys (C) at position 226 according to EU numbering, Pro (P) at position 228 according to EU numbering, an amino acid residue other than Cys (C) at position 229 according to EU numbering, and Lys (K) at position 356 according to EU numbering, and the second polypeptide has an amino acid residue other than Cys (C) at position 131 according to EU numbering, an amino acid residue other than Cys (C) at position 226 according to EU numbering, Pro (P) at position 228 according to EU numbering, an amino acid residue other than Cys (C) at position 229 according to EU numbering, and Glu (E) at position 439 according to EU numbering;
(3) the first polypeptide has an amino acid residue other than Cys (C) at position 220 according to EU numbering, an amino acid residue other than Cys (C) at position 226 according to EU numbering, an amino acid residue other than Cys (C) at position 229 according to EU numbering, Arg (R) at position 409 according to EU numbering, and Lys (K) at position 356 according to EU numbering, and the second polypeptide has an amino acid residue other than Cys (C), or Tyr (Y) at position 220 according to EU numbering, an amino acid residue other than Cys (C) at position 226 according to EU numbering, an amino acid residue other than Cys (C) at position 229 according to EU numbering, Arg (R) at position 409 according to EU numbering, and Glu (E) at position 439 according to EU numbering;
(4) the first polypeptide has an amino acid residue other than Cys (C) at position 131 according to EU numbering, deletion at positions 219 to 229 according to EU numbering, and Lys (K) at position 356 according to EU numbering, and the second polypeptide has an amino acid residue other than Cys (C) at position 131 according to EU numbering, deletion at positions 219 to 229 according to EU numbering, and Glu (E) at position 439 according to EU numbering;
(5) the first polypeptide has deletion at positions 219 to 229 according to EU numbering, Arg (R) at position 409 according to EU numbering, and Lys (K) at position 356 according to EU numbering, and the second polypeptide has deletion at positions 219 to 229 according to EU numbering, Arg (R) at position 409 according to EU numbering, and Glu (E) at position 439 according to EU numbering; and
(6) the first polypeptide has an amino acid residue other than Cys (C) at position 226 according to EU numbering, an amino acid residue other than Cys (C) at position 229 according to EU numbering, Tyr (Y)-Gly (G)-Pro (P)-Pro (P) at positions 220 to 225 according to EU numbering, Arg (R) at position 409 according to EU numbering, and Lys (K) at position 356 according to EU numbering, and the second polypeptide has an amino acid residue other than Cys (C) at position 226 according to EU numbering, Ser (S) at position 229 according to EU numbering, Tyr (Y)-Gly (G)-Pro (P)-Pro (P) at positions 220 to 225 according to EU numbering, Arg (R) at position 409 according to EU numbering, and Glu (E) at position 439 according to EU numbering.

Preferably, the heavy chain constant regions having the manner (1), (2), or (4) are derived from IgG4, and the heavy chain constant regions having the manner (3), (5), or (6) are derived from IgG1.

The present invention also provides a bispecific antibody comprising first and second polypeptides, wherein the heavy chain constant regions of the first and second polypeptides each have amino acid residues shown in any of the following (1) to (6):
(1) the first polypeptide has Ser (S) at position 131 according to EU numbering, Ser (S) at position 226 according to EU numbering, Ser (S) at position 229 according to EU numbering, and Lys (K) at position 356 according to EU numbering, and the second polypeptide has Ser (S) at position 131 according to EU numbering, Ser (S) at position 226 according to EU numbering, Ser (S) at position 229 according to EU numbering, and Glu (E) at position 439 according to EU numbering;
(2) the first polypeptide has Ser (S) at position 131 according to EU numbering, Ser (S) at position 226 according to EU numbering, Pro (P) at position 228 according to EU numbering, Ser (S) at position 229 according to EU numbering, and Lys (K) at position 356 according to EU numbering, and the second polypeptide has Ser (S) at position 131 according to EU numbering, Ser (S) at position 226 according to EU numbering, Pro (P) at position 228 according to EU numbering, Ser (S) at position 229 according to EU numbering, and Glu (E) at position 439 according to EU numbering;
(3) the first polypeptide has Ser (S) or Tyr (Y) at position 220 according to EU numbering, Ser (S) at position 226 according to EU numbering, Ser (S) at position 229 according to EU numbering, and Lys (K) at position 356 according to EU numbering, and the second polypeptide has Ser (S) or Tyr (Y) at position 220 according to EU numbering, Ser (S) at position 226 according to EU numbering, Ser (S) at position 229 according to EU numbering, and Glu (E) at position 439 according to EU numbering;
(4) the first polypeptide has Ser (S) at position 131 according to EU numbering, deletion at positions 219 to 229 according to EU numbering, and Lys (K) at position 356 according to EU numbering, and the second polypeptide has Ser (S) at position 131 according to EU numbering, deletion at positions 219 to 229 according to EU numbering, and Glu (E) at position 439 according to EU numbering;
(5) the first polypeptide has deletion at positions 219 to 229 according to EU numbering, and Lys (K) at position 356 according to EU numbering, and the second polypeptide has deletion at positions 219 to 229 according to EU numbering, and Glu (E) at position 439 according to EU numbering; and
(6) the first polypeptide has Ser (S) at position 226 according to EU numbering, Ser (S) at position 229 according to EU numbering, Tyr (Y)-Gly (G)-Pro (P)-Pro (P) at positions 220 to 225 according to EU numbering, and Lys (K) at position 356 according to EU numbering, and the second polypeptide has Ser (S) at position 226 according to EU numbering, Ser (S) at position 229 according to EU numbering, Tyr (Y)-Gly (G)-Pro (P)-Pro (P) at positions 220 to 225 according to EU numbering, and Glu (E) at position 439 according to EU numbering.

Preferably, the heavy chain constant regions having the manner (1), (2), or (4) are derived from IgG4, and the heavy chain constant regions having the manner (3), (5), or (6) are derived from IgG1.

The present invention also provides a bispecific antibody comprising first and second polypeptides, wherein the heavy chain constant regions of the first and second polypeptides each have amino acid residues shown in any of the following (1) to (6):
(1) the first polypeptide has Ser (S) at position 131 according to EU numbering, Ser (S) at position 226 according to EU numbering, Ser (S) at position 229 according to EU numbering, and Lys (K) at position 356 according to EU numbering, and the second polypeptide has Ser (S) at position 131 according to EU numbering, Ser (S) at position 226 according to EU numbering, Ser (S) at position 229 according to EU numbering, and Glu (E) at position 439 according to EU numbering;
(2) the first polypeptide has Ser (S) at position 131 according to EU numbering, Ser (S) at position 226 according to EU numbering, Pro (P) at position 228 according to EU numbering, Ser (S) at position 229 according to EU numbering, and Lys (K) at position 356 according to EU numbering, and the second polypeptide has Ser (S) at position 131 according to EU numbering, Ser (S) at position 226 according to EU numbering, Pro (P) at position 228 according to EU numbering, Ser (S) at position 229 according to EU numbering, and Glu (E) at position 439 according to EU numbering;
(3) the first polypeptide has Ser (S) or Tyr (Y) at position 220 according to EU numbering, Ser (S) at position 226 according to EU numbering, Ser (S) at position 229 according to EU numbering, Arg (R) at position 409 according to EU numbering, and Lys (K) at position 356 according to EU numbering, and the second polypeptide has Ser (S) or Tyr (Y) at position 220 according to EU numbering, Ser (S) at position 226 according to EU numbering, Ser (S) at position 229 according to EU numbering, Arg (R) at position 409 according to EU numbering, and Glu (E) at position 439 according to EU numbering;
(4) the first polypeptide has Ser (S) at position 131 according to EU numbering, deletion at positions 219 to 229 according to EU numbering, and Lys (K) at position 356 according to EU numbering, and the second polypeptide has Ser (S) at position 131 according to EU numbering, deletion at positions 219 to 229 according to EU numbering, and Glu (E) at position 439 according to EU numbering;
(5) the first polypeptide has deletion at positions 219 to 229 according to EU numbering, Arg (R) at position 409 according to EU numbering, and Lys (K) at position 356 according to EU numbering, and the second polypeptide has deletion at positions 219 to 229 according to EU numbering, Arg (R) at position 409 according to EU numbering, and Glu (E) at position 439 according to EU numbering; and
(6) the first polypeptide has Ser (S) at position 226 according to EU numbering, Ser (S) at position 229 according to EU numbering, Tyr (Y)-Gly (G)-Pro (P)-Pro (P) at positions 220 to 225 according to EU numbering, Arg (R) at position 409 according to EU numbering, and Lys (K) at position 356 according to EU numbering, and the second polypeptide has Ser (S) at position 226 according to EU numbering, Ser (S) at position 229 according to EU numbering, Tyr (Y)-Gly (G)-Pro (P)-Pro (P) at positions 220 to 225 according to EU numbering, Arg (R) at position 409 according to EU numbering, and Glu (E) at position 439 according to EU numbering.

Preferably, the heavy chain constant regions having the manner (1), (2), or (4) are derived from IgG4, and the heavy chain constant regions having the manner (3), (5), or (6) are derived from IgG1.

Modification Using Charge Repulsion of Amino Acid Residues

The production method of the present invention may additionally comprise the step of modifying amino acid residues that form the interface between polypeptides in order to promote the dissociation of the homologous forms of the first and second polypeptides and to control association between the polypeptides constituting one or more types of multimers.

The polypeptide having a first antigen-binding activity and the polypeptide having a second antigen-binding activity according to the present invention can each comprise the amino acid sequence of an antibody heavy chain constant region or the amino acid sequence of an antibody Fc region. Examples of the amino acid sequence of the antibody Fc region or the antibody heavy chain constant region include, but are not limited to, the amino acid sequences of human IgG-type constant regions or Fc regions. The IgG-type constant regions or Fc regions can be any of naturally occurring isotypes IgG1, IgG2, IgG3, and IgG4. Alternatively, their variants may be used. Lysine at position 447 according to EU numbering and glycine at position 446 according to EU numbering in the Fc region may be removed by the recombinant gene manipulation of nucleic acids encoding these amino acids.

The polypeptide having a third antigen-binding activity and the polypeptide having a fourth antigen-binding activity according to the present invention can each comprise the amino acid sequence of an antibody light chain constant region. Examples of the amino acid sequence of the antibody light chain constant region can include, but are not limited to, the amino acid sequences of human kappa- and human lambda-type constant regions. Alternatively, their variants may be used.

The polypeptide having an antigen-binding activity according to the present invention can comprise the amino acid sequence of an antibody variable region (e.g., the amino acid sequences of CDR1, CDR2, CDR3, FR1, FR2, FR3, and FR4).

In a preferred embodiment, examples of the step include the step of introducing charge repulsion to the interface between the constant regions of heavy chains in order to suppress the association between the heavy chains. Examples of the combination of the amino acid residues coming in contact with each other at the interface between the heavy chain constant regions can include pairs at positions 356 and 439, at positions 357 and 370, and at positions 399 and 409 in CH3 regions. The sites in the heavy chain constant regions are represented by the EU numbering system.

As shown in Examples, the step is added to control dissociation and/or association between heavy chains. As a result, the desired heteromultimer can be more preferentially produced. In a preferred aspect, the present invention provides a polypeptide which is an antibody or an Fc region-containing protein (e.g., an IgG-type antibody, minibody (Alt M et al., FEBS Letters 1999; 454: 90-94), and immunoadhesin (Non-patent Document 2)) comprising two or more types of heavy chain variable regions, wherein 1 to 3 sets of amino acid residues selected from the following sets of amino acid residues (1) to (3) in a first heavy chain constant region have the same type of charge:
(1) amino acid residues at positions 356 and 439 according to EU numbering,
(2) amino acid residues at positions 357 and 370 according to EU numbering, and
(3) amino acid residues at positions 399 and 409 according to EU numbering.

The present invention further provides a polypeptide wherein 1 to 3 sets of amino acid residues selected from the sets of amino acid residues (1) to (3) in a second heavy chain constant region different from the first heavy chain constant region have a charge opposite to that of the counterpart amino acid residues having the same type of charge as each other in the corresponding set(s) among the sets of amino acid residues (1) to (3) in the first heavy chain constant region.

In the polypeptide, the "amino acid residues having a charge" are preferably selected from, for example, amino acid residues included in any of the following groups (a) and (b):
(a) glutamic acid (E) and aspartic acid (D); and
(b) lysine (K), arginine (R), and histidine (H).

In the polypeptide, the phrase "having the same type of charge" means that, for example, all of two or more amino acid residues are amino acid residues included in any one of the groups (a) and (b). The phrase "having a charge opposite" means that, for example, when at least one amino acid residue among two or more amino acid residues is an amino acid residue included in any one of the groups (a) and (b), the remaining amino acid residue(s) is an amino acid residue included in the other group.

In a preferred embodiment, the polypeptide may have the cross-link between the first heavy chain CH3 region and the second heavy chain CH3 region through a disulfide bond.

In the present invention, examples of the "association interface-controlling modification" include the following modifications:
(1) the modification of Asp (D) at position 356 according to EU numbering in the first heavy chain constant region to Lys (K), Arg (R), or His (H), and the modification of Lys (K) at position 439 according to EU numbering in the second heavy chain constant region to Glu (E) or Asp (D);
(2) the modification of Glu (E) at position 357 according to EU numbering in the first heavy chain constant region to Lys (K), Arg (R), or His (H), and the modification of Lys (K) at position 370 according to EU numbering in the second heavy chain constant region to Glu (E) or Asp (D); and
(3) the modification of Asp (D) at position 399 according to EU numbering in the first heavy chain constant region to Lys (K), Arg (R), or His (H), and the modification of Lys (K) at position 409 according to EU numbering in the second heavy chain constant region to Glu (E) or Asp (D).

In a non-limiting embodiment, the method for producing a mouse heteromultimer according to the present invention may additionally comprise the step of modifying amino acid residues that form the interface between polypeptides in order to promote the dissociation of the homologous forms of the first and second polypeptides and to control association between the polypeptides constituting one or more types of multimers. Examples of the combination of the amino acid residues coming in contact with each other at the interface between the heavy chain constant regions can include pairs at positions 356 and 439, at positions 360 and 371, and at positions 399 and 409 in CH3 regions. The sites in the heavy chain constant regions are represented by the EU numbering system.

The step of modifying the amino acid residues in the mouse-derived CH3 regions is added to control dissociation and/or association between heavy chains. As a result, the desired heteromultimer can be more preferentially produced. In a preferred aspect, the present invention provides a polypeptide which is an antibody or an Fc region-containing protein (e.g., an IgG-type antibody, minibody (Alt M et al., FEBS Letters 199, 9; 454: 90-94), and immunoadhesin (Non-patent Document 2)) comprising two or more types of heavy chain constant regions, wherein 1 to 3 sets of amino acid residues selected from the following sets of amino acid residues (1) to (3) in a first heavy chain constant region have the same type of charge:
(1) amino acid residues at positions 356 and 439 according to EU numbering,
(2) amino acid residues at positions 360 and 371 according to EU numbering, and
(3) amino acid residues at positions 399 and 409 according to EU numbering.

The present invention further provides a polypeptide wherein 1 to 3 sets of amino acid residues selected from the sets of amino acid residues (1) to (3) in a second heavy chain constant region different from the first heavy chain constant region have a charge opposite to that of the counterpart amino acid residues having the same type of charge as each other in the corresponding set(s) among the sets of amino acid residues (1) to (3) in the first heavy chain constant region.

In the polypeptide, the "amino acid residues having a charge" are preferably selected from, for example, amino acid residues included in any of the following groups (a) and (b):
(a) glutamic acid (E) and aspartic acid (D); and
(b) lysine (K), arginine (R), and histidine (H).

In the polypeptide, the phrase "having the same type of charge" means that, for example, all of two or more amino acid residues are amino acid residues included in any one of the groups (a) and (b). The phrase "having a charge opposite" means that, for example, when at least one amino acid residue among two or more amino acid residues is an amino acid residue included in any one of the groups (a) and (b), the remaining amino acid residue(s) is an amino acid residue included in the other group.

In a preferred embodiment, the polypeptide may have the cross-link between the first heavy chain CH3 region and the second heavy chain CH3 region through a disulfide bond.

In the present invention, examples of the "association interface-controlling modification" include the following modifications:
(1) the modification of Asp (D) at position 356 according to EU numbering in the first heavy chain constant region to Lys (K), Arg (R), or His (H), and the modification of Lys (K) at position 439 according to EU numbering in the second heavy chain constant region to Glu (E) or Asp (D);
(2) the modification of Glu (E) at position 360 according to EU numbering in the first heavy chain constant region to Lys (K), Arg (R), or His (H), and the modification of Lys (K) at position 371 according to EU numbering in the second heavy chain constant region to Glu (E) or Asp (D); and
(3) the modification of Asp (D) at position 399 according to EU numbering in the first heavy chain constant region to Lys (K), Arg (R), or His (H), and the modification of Lys (K) at position 409 according to EU numbering in the second heavy chain constant region to Glu (E) or Asp (D).

The amino acid residues to be "modified" according to the present invention are not limited to the amino acid residues in the polypeptide constant regions. Those skilled in the art can find amino acid residues that form the interface in a polypeptide variant or a heteromultimer by homology modeling or the like using commercially available software, and can modify amino acid residues at the sites so as to control association.

The "modification" of amino acid residues in the method of the present invention specifically refers to, for example, the substitution of the original amino acid residues by other amino acid residues, the deletion of the original amino acid residues, or the addition of a new amino acid residue and preferably refers to the substitution of the original amino acid residues by other amino acid residues.

Method for Producing Heteromultimer by Amino Acid Modification so as to Destabilize the Stability of Heavy Chain CH3 Region The production method of the present invention may additionally comprise the step of introducing a mutation of an amino acid residue to a heavy chain constant region so as to destabilize the stability of the heavy chain CH3 region.

In the present invention, the "destabilization of the stability of the CH3 region" means that a polypeptide homo variant with at least one or more amino acid residues modified in the Fc region becomes more susceptible to separate into the single polypeptides than the unmodified polypeptide homo variant.

In the present invention, the "destabilization of the stability of the CH3 region" preferably means a condition where modification is introduced to the amino acid residues of the CH3 region so that the intermediate temperature of thermal denaturation (Tm) of the heavy chain CH3 region at pH 7.4 is 72.5° C. or lower, 72.0° C. or lower, 71.5° C. or lower, 71.0° C. or lower, or 70.5° C. or lower, more preferably 70.4° C. or lower, 70.3° C. or lower, 70.2° C. or lower, 70.1° C. or lower, 70.0° C. or lower, 69.9° C. or lower, 69.8° C. or lower, 69.7° C. or lower, 69.6° C. or lower, 69.5° C. or lower, 69.0° C. or lower, 68.5° C. or lower, 68.0° C. or lower, or 67.5° C. or lower.

The Tm of the heavy chain CH3 region can be measured by, for example, a method described in Reference Example 6 in the present specification. A buffer solution or the like for use in this measurement can be appropriately selected.

The step of introducing a mutation of an amino acid residue to a heavy chain constant region so as to destabilize the stability of the heavy chain CH3 region is a step comprising introducing a mutation to an amino acid residue at position 397 and/or 392 (EU numbering) in a heavy chain CH3 region. This step may be further combined with the optional step of introducing the aforementioned amino acid modification related to interface control using charge repulsion or the like.

In a non-limiting embodiment of the present invention, a mutation can also be introduced to an amino acid residue at position 397 and/or 392 (EU numbering) in a heavy chain CH3 region in the step of introducing a mutation of an amino acid residue to a heavy chain constant region so as to destabilize the stability of a mouse-derived heavy chain CH3 region. This step may be further combined with the optional step of introducing the aforementioned amino acid modification related to interface control using charge repulsion or the like.

The amino acid residue for the introduction of a mutation at position 397 is preferably modified to an amino acid having a bulky side chain or an amino acid having a branched side chain.

The amino acid residue for the introduction of a mutation at position 392 is preferably modified to an amino acid having a negative charge, an amino acid having a bulky side chain, or an amino acid having a branched side chain.

In the present invention, examples of the "amino acid having a bulky side chain" include Met (M), Phe (F), Tyr (Y), Val (V), Leu (L), Ile (I), Trp (W), Arg (R), His (H), Glu (E), Lys (K), Gln (Q), Asp (D), Asn (N), Cys (C), and Thr (T) and preferably include Met (M), Phe (F), Thr (T), and Tyr (Y).

In the present invention, examples of the "amino acid having a branched side chain" include Val (V), Ile (I), and Leu (L) and preferably include Val (V) and Ile (I).

In the present invention, examples of the "amino acid having a negative charge" include Asp (D) and Glu (E).

In an alternative embodiment, in the step of introducing a mutation of an amino acid residue to a heavy chain constant region so as to destabilize the stability of the heavy chain CH3 region, one or more of amino acids at positions 355, 356, 409, 419, and 445 according to EU numbering may be modified when the antibody heavy chain constant region is, for example, IgG1 type. For example, the amino acids may be modified to Gln (Q) at position 355 according to EU numbering, Glu (E) at position 356 according to EU numbering, Arg (R) at position 409 according to EU numbering, Glu (E) at position 419 according to EU numbering, and/or Leu (L) at position 445 according to EU numbering.

In the present invention, preferred examples of the "heteromultimer" can include multispecific antibodies and hetero-fusion proteins.

In a non-limiting aspect, the present invention provides the amino acid modification of a heteromultimer to enhance binding to FcγR. Preferred examples of the amino acid modification site include, but are not limited to, an amino acid at position 397 (EU numbering). The amino acid residue for the introduction of a mutation at position 397 is preferably modified to an amino acid having a bulky side chain or an amino acid having a branched side chain.

In the present invention, more preferred examples of the multispecific antibody include IgG type, scFv-IgG, Tandem scFv-Fc, DVD-Ig, Diabody-Fc, Single chain Diabody-Fc, IgG-scFv, sVD-IgG, Tandemab, scFv light chain C-terminal fusion, Tri-specific C-terminal fusion, Tri-specific N-terminal fusion, and IgG-Fab (Bispecific Antibodies, Roland E. Kontermann, 2011, WO2010034441, and WO2010145792).

In the present invention, the term "antibody" is used in the broadest sense and includes monoclonal antibodies, polyclonal antibodies, and antibody variants (chimeric antibodies, humanized antibodies, low-molecular antibodies (also including antibody fragments), multispecific antibodies, etc.) as long as the antibody exhibits a desired biological activity. In the present invention, the "antibody" may be a polypeptide or may be a heteromultimer. The antibody is preferably a monoclonal antibody, a chimeric antibody, a humanized antibody, or a low-molecular antibody such as an antibody fragment. In the present invention, the method for controlling dissociation and/or association according to the present invention can be preferably used for obtaining (preparing) these antibodies.

Preferred examples of the polypeptide or the heteromultimer subjected to the method of the present invention can include a polypeptide or a heteromultimer having an antibody heavy chain variable region and light chain variable region. In a more preferred aspect, the present invention provides a method for controlling the dissociation and/or association of the polypeptide or the heteromultimer of the present invention comprising two or more types of heavy chain variable regions and two or more types of light chain variable regions.

The polypeptide having an antigen-binding activity according to the present invention can comprise the amino acid sequence of an antibody heavy chain or the amino acid sequence of an antibody light chain. More specifically, the polypeptide having a first antigen-binding activity and the polypeptide having a second antigen-binding activity can each comprise the amino acid sequence of an antibody heavy chain. The polypeptide having a third antigen-binding activity and the polypeptide having a fourth antigen-binding activity can each comprise the amino acid sequence of an antibody light chain.

When the polypeptide multimer of interest is a tetramer which is a tetramer wherein the first polypeptide and the third polypeptide form a dimer and the second polypeptide and the fourth polypeptide form a dimer, and wherein these dimers form a multimer, for example, a polypeptide multimer in which the polypeptides having the first and second antigen-binding activities are polypeptides each comprising the amino acid sequence of an antibody heavy chain while the polypeptides having the third and fourth antigen-binding activities are polypeptides each comprising the amino acid sequence of an antibody light chain can also be used as the polypeptide multimer of the present invention.

Further preferred examples of the multispecific antibody of the present invention can include bispecific antibodies.

In a preferred aspect of the present invention, the present invention relates to, for example, a method for controlling dissociation and/or association as to a bispecific antibody comprising two types of heavy chains (the first polypeptide and the second polypeptide in the polypeptide multimer according to the present invention) and two types of light chains (the third polypeptide and the fourth polypeptide in the polypeptide multimer according to the present invention).

The "bispecific antibody" according to a preferred aspect of the present invention will be described in more detail. The "first polypeptide and the second polypeptide" refer to one (first H chain) of two heavy chains (H chains) constituting the antibody and the other H chain (second H chain) different from the first H chain. In short, any one of the two H chains can be arbitrarily selected as the first H chain, and the other H chain can be set to the second H chain. Likewise, the "third polypeptide and the fourth polypeptide" refer to one (first L chain) of two light chains (L chains) constituting the bispecific antibody and the other L chain (second L chain) different from the first L chain. Any one of the two L chains can be arbitrarily selected as the first L chain, and the other H chain can be set to the second L chain. Usually, the first L chain and the first H chain are derived from the same antibody that recognizes a certain antigen (or epitope). The second L chain and the second H chain are also derived from the same antibody that recognizes a certain antigen (or epitope). In this context, an L-H chain pair formed by the first H chain and L chain is referred to as a first pair (or first HL molecule). An L-H chain pair formed by the second H chain and L chain is referred to as a second pair (or second HL molecule). The first pair and the second pair may recognize the same antigen and preferably recognize different epitopes. In this case, the H chains or the L chains in the first pair and the second pair preferably have amino acid sequences different from each other. When the first pair and the second pair recognize different epitopes, the first pair may recognize an antigen totally different from that of the second pair, or the first pair and the second pair may recognize different sites (different epitopes) on the same antigen (e.g., when the antigen is a heteromeric receptor, the multispecific antibody recognizes different domains constituting the heteromeric receptor; or when the antigen is a monomer, the multispecific antibody recognizes a plural sites in the monomer antigen). Such a molecule usually binds to two antigens, but may have specificities for two or more (e.g., 3 types of) antigens. Alternatively, one of the pairs may recognize an antigen such as a protein, a peptide, a gene, or a sugar, and the other pair may recognize, for example, a cytotoxic substance such as a radioactive substance, a chemotherapeutic agent, or a cell-derived toxin. In the case of preparing a desired antibody having pairs formed by particular H chains and L chains in combination, the particular H chains and L chains can be arbitrarily determined as the first pair and the second pair.

In the present invention, the "fusion protein" refers to a protein in which two or more identical or substantially analogous protein molecules are joined via an Ig hinge region amino acid sequence linker. The prefix "hetero-" is used for describing a fusion protein containing more than one type of proteins. The "hetero-fusion protein" contains, for example, two or more proteins which are one or more residual proteins and one or more different proteins joined together.

The "antibody" according to the present invention includes those obtained by further modifying the amino acid sequence of the aforementioned antibody by amino acid substitution, deletion, addition and/or insertion, or chimerization, humanization, etc. The modification of an amino acid sequence by amino acid substitution, deletion, addition and/or insertion, or humanization, chimerization, etc., can be practiced by a method generally known to those skilled in the art. Likewise, the amino acid sequences of antibody variable regions and constant regions for use in preparing the antibody according to the present invention as a recombinant antibody may be modified by amino acid substitution, deletion, addition and/or insertion, or chimerization, humanization, etc.

The antibody according to the present invention may be an antibody derived from any animal, such as a mouse antibody, a human antibody, a rat antibody, a rabbit antibody, a goat antibody, or a camel antibody. The antibody according to the present invention may be a modified antibody prepared by the substitution of the amino acid sequence of, for example, a chimeric antibody, particularly, a humanized antibody. Alternatively, any antibody such as a modified antibody conjugated with various molecules, an antibody fragment, or a low-molecular antibody can be used.

The "chimeric antibody" is an antibody prepared from a combination of sequences derived from different animals. Examples thereof can include an antibody composed of heavy chain and light chain variable (V) regions of a mouse antibody and heavy chain and light chain constant (C) regions of a human antibody. The preparation of the chimeric antibody is known in the art. The chimeric antibody can be obtained, for example, by: ligating DNAs encoding the antibody V regions with DNAs encoding the human antibody C regions; incorporating the resulting ligation products into expression vectors; and transfecting the vectors into hosts for antibody production.

The "humanized antibody", also called reshaped human antibody, is obtained by grafting complementarity-determining regions (CDRs) of an antibody derived from a non-human mammal, for example, a mouse antibody, to CDRs of a human antibody. A method for identifying CDRs is known in the art (Kabat et al., Sequence of Proteins of Immunological Interest (1987), National Institute of Health, Bethesda, Md.; and Chothia et al., Nature (1989) 342: 877). A general gene recombination approach therefor is also known in the art (see European Patent Application Publication No. EP 125023 and WO 96/02576). Accordingly, for example, mouse antibody CDRs are determined by a method known in the art. A DNA encoding an antibody having these CDRs linked to human antibody framework regions (FRs) is obtained. The humanized antibody can be produced in a system using usual expression vectors. Such a DNA can be synthesized by PCR using several oligonucleotide primers prepared so as to have a portion overlapping the terminal regions of both CDR and FR (see a method described in WO98/13388). The human antibody FRs connected via the CDRs are selected such that the CDRs form a favorable antigen-binding site. If necessary, amino acids in the FRs of antibody variable regions may be modified such that the CDRs of the resulting reshaped human antibody form an appropriate antigen-binding site (Sato et al., Cancer Res. (1993) 53: 851-6). The amino acid residues in the FRs that can be modified include moieties binding directly to an antigen through a noncovalent bond (Amit et al., Science (1986) 233: 747-53), moieties influencing or acting on CDR structures (Chothia et al., J. Mol. Biol. (1987) 196: 901-17), and moieties related to VH-VL interaction (EP239400).

When the antibody according to the present invention is a chimeric antibody or a humanized antibody, human antibody-derived constant regions are preferably used as the C regions of the antibody. For example, Cγ1, Cγ2, Cγ3, or Cγ4 can be used for an H chain, and Cκ or Cλ can be used for an L chain. Also, the human antibody C regions may be modified, if necessary, in order to improve the antibody or the stability of its production. The chimeric antibody according to the present invention preferably comprises variable regions of a non-human mammal-derived antibody and constant regions derived from a human antibody. On the other hand, the humanized antibody preferably comprises CDRs of a non-human mammal-derived antibody and FRs and C regions derived from a human antibody. The constant regions derived from a human antibody have amino acid sequences specific for each isotype such as IgG (IgG1, IgG2, IgG3, or IgG4), IgM, IgA, IgD, or IgE. The constant regions used in the humanized antibody according to the present invention may be constant regions of an antibody belonging to any isotype. Preferably, human IgG constant regions are used, though the constant regions according to the present invention are not limited thereto. The FRs derived from a human antibody used in the humanized antibody are not particularly limited and may be derived from an antibody belonging to any isotype.

The variable regions and the constant regions of the chimeric antibody or the humanized antibody according to the present invention may be modified by deletion, substitution, insertion and/or addition, etc., as long as the resulting antibody exhibits the binding specificity of the original antibody.

The chimeric antibody or the humanized antibody containing a human-derived sequence exhibits reduced antigenicity in a human body and is therefore considered to be useful when administered to humans for a therapeutic purpose or the like.

Combination with Isoelectric Point Modification Technique, Etc.

In a further preferred embodiment of the present invention, an amino acid mutation that modifies the isoelectric point (pI value) of a polypeptide can be introduced to the polypeptide of the present invention to thereby purify or produce the polypeptide multimer having the first to fourth polypeptides of interest with higher purity and higher efficiency (WO2007114325 and US20130171095). For example, a method for hetero-associating polypeptides comprising two types of heavy chain constant regions by modifying the CH3 domains of the heavy chain constant regions (which is described in, e.g., Protein Eng. 1996 July; 9 (7): 617-21; Protein Eng Des Sel. 2010 April; 23 (4): 195-202; J Biol Chem. 2010 Jun. 18; 285 (25): 19637-46; WO2009080254; and US20130195849) and a method for promoting the association of a heavy chain and a light chain in a particular combination (which is described in, e.g., WO2009080251, WO2009080252, and WO2009080253) may be used for the amino acid mutation that is introduced for promoting association between polypeptides.

Combination with Technique Related to Target Tissue-Specific Antigen-Binding Molecule In a non-limiting embodiment of the present invention, the method of the present invention can be combined with an antibody technique for dissociation from or binding to an antigen existed specifically in a target tissue in a concentration-dependent manner (WO2013/180200).

Combination with Other Constant Region and/or Variable Region Modification Techniques In a non-limiting embodiment of the present invention, the method of the present invention can be combined with a technique of modifying constant regions with the aim of enhancing binding to FcγR (WO2013047752).

In an alternative embodiment, examples of the combination of the method of the present invention with other constant region modification techniques include its combination with a technique of controlling binding to a complement. Any complement component can be used as the complement as long as the complement is a polypeptide that forms a complement cascade. Preferred examples of the complement include complement components C1q, C1r, and C1s involved in the binding of opsonin. An Fc region having a higher binding activity against a complement than that of a naturally occurring Fc region against the complement can be prepared by the amino acid modification of the naturally occurring Fc region. In this context, the naturally occurring Fc region refers to a human IgG1, IgG2, IgG3, or IgG4 Fc region. Whether or not the Fc region has a higher binding activity against a complement than that of a naturally occurring Fc region against the complement can be appropriately confirmed by use of an immunological method known in the art such as FACS or ELISA. The term "modification of amino acid(s)" or "amino acid modification" of the Fc region includes the modification of the amino acid sequence of a starting Fc region to a different amino acid sequence. Any Fc region can be used as the starting domain as long as the resulting modified or variant of the starting Fc region can bind to the complement in a neutral pH region. An Fc region prepared by further modifying an already modified Fc region as a starting Fc region can also be preferably used as the Fc region of the present invention. The starting Fc region can mean the polypeptide itself, a composition containing the starting Fc region, or an amino acid sequence encoding the starting Fc region. The starting Fc region may include an IgG antibody Fc region known in the art, which is produced by the recombination summarized in the section about the antibody. The origin of the starting Fc region is not limited, and the starting Fc region can be obtained from an arbitrary organism of a non-human animal or a human. Preferred examples of the arbitrary organism include organisms selected from mice, rats, guinea pigs, hamsters, gerbils, cats, rabbits, dogs, goats, sheep, cattle, horses, camels, and non-human primates. In another embodiment, the starting Fc region may be obtained from a cynomolgus monkey, a marmoset, a rhesus monkey, a chimpanzee, or a human. Preferably, the starting Fc region can be obtained from human IgG1, but is not limited by the particular class of IgG. This means that a human IgG1, IgG2, IgG3, or IgG4 Fc region can be appropriately used as the starting Fc region. This also means that an Fc region of any IgG class or subclass from the arbitrary organism can be preferably used as the starting Fc region in the present specification. Examples of variants or engineered models of naturally occurring IgG are described in publicly known literatures (Curr. Opin. Biotechnol. (2009) 20 (6), 685-91; Curr. Opin. Immunol. (2008) 20 (4), 460-470; Protein Eng. Des. Sel. (2010) 23 (4), 195-202; and WO2009086320, WO2008092117, WO2007041635, and WO2006105338), though the Fc region according to the present invention is not limited thereto.

An amino acid at any position can be modified as long as the amino acid modification can confer the binding activity against the complement or can enhance binding activity for binding to the complement. The antigen-binding molecule comprising a human IgG1 Fc region as a human Fc region preferably contains the modification to bring about the effect of enhancing its binding activity against the complement over the binding activity of the starting Fc region of human IgG1. Examples of the amino acid for modifying the binding activity against the complement include amino acids in Fc region with modified binding activity against C1q reported in, for example, Duncan et al. (Nature (1988) 332, 738-740), Tao et al. (J. Exp. Med. (1993) 178, 661-667), Brekke et al. (Eur. J. Immunol. (1994) 24, 2542-2547), Xu et al. (Immunol. (1993) 150, 152A), WO1994029351, WO2000042072, and WO2011091078.

Examples of such an amino acid that permits the modification to enhance the binding activity against C1q include at least one or more amino acids selected from positions 231 to 238 and positions 318 to 337 according to EU numbering. One non-limiting example of the amino acid includes at least one or more amino acids selected from the group consisting of positions 235, 237, 267, 268, 276, 318, 320, 322, 324, 327, 331, and 333. The modification of these amino acids enhances the binding of an IgG-type immunoglobulin Fc region to the complement.

Particularly preferred examples of the modification include the modification of an amino acid at position 267 according to EU numbering to Glu, an amino acid at position 268 according to EU numbering to any of Phe and Tyr, an amino acid at position 276 according to EU numbering to Arg, an amino acid at position 324 according to EU numbering to Thr, an amino acid at position 327 according to EU numbering to Gly, an amino acid at position 331 according to EU numbering to Pro, or an amino acid at position 333 according to EU numbering to any of Ala, Asp, Gly, Ser, and Val in the Fc region.

The number of amino acids to be modified is not particularly limited. An amino acid at only one site may be modified, or amino acids at two or more sites in arbitrary combination selected from those described above may be modified.

In an alternative embodiment, examples of the combination of the method of the present invention with other constant region modification techniques include its combination with antibody modification techniques such as an Fc modification technique of enhancing binding to FcRn at acidic pH (WO2002060919, WO2004035752, and WO2000042072), an Fc modification technique of enhancing binding to FcRn at neutral pH (WO2011122011 and WO2012133782), a technique of enhancing selective binding to inhibitory Fcγ receptors (WO2012115241 and WO2013125667), a technique of enhancing selective binding to active Fcγ receptors (ADCC activity enhancement technique) (WO2013002362), and a technique of reducing binding activity against rheumatoid factors (WO2013046704).

In a non-limiting embodiment, examples of the combination of the method of the present invention with a variable region modification technique include its combination with modification techniques such as a pH-dependent antibody (WO2009125825) and a calcium-dependent antibody (WO2012073992).

Antibody library, immunization, and hybridoma preparation

A known sequence may be used as a gene encoding the H chain or the L chain of the antibody before the introduction of a mutation (in the present specification, also simply referred to as the "antibody of the present invention") in the method of the present invention. Alternatively, the gene may be obtained by a method generally known to those skilled in the art. For example, the gene may be obtained from an antibody library or may be obtained by the cloning of an antibody-encoding gene from monoclonal antibody-producing hybridomas.

Many antibody libraries have already been known in the art as such an antibody library. Also, methods for preparing the antibody library are known in the art. Thus, those skilled in the art can appropriately obtain the antibody library. For an antibody phage library, for example, see literatures such as Clackson et al., Nature 1991, 352: 624-8, Marks et al., J. Mol. Biol. 1991, 222: 581-97, Waterhouses et al., Nucleic Acids Res. 1993, 21: 2265-6, Griffiths et al., EMBO J. 1994, 13: 3245-60, Vaughan et al., Nature Biotechnology 1996, 14: 309-14, and National Publication of International Patent Application No. 2008-504970. In addition, a method known in the art such as a method for preparing a library using eukaryotic cells (WO95/15393) or a ribosome display method may be used. In addition, a technique of obtaining a human antibody by panning using a human antibody library is also known. For example, human antibody variable regions are expressed as a single-chain antibody (scFv) on the surface of phages by a phage display method and a phage binding to the antigen can be selected. The gene of the selected phage can be analyzed to determine DNA sequences encoding the variable regions of the human antibody binding to the antigen. If the DNA sequence of the scFv binding to the antigen can be determined, appropriate expression vectors can be prepared on the basis of this sequence and used to obtain the human antibody. These methods have already been well known. See WO92/01047, WO92/20791, WO93/06213, WO93/11236, WO93/19172, WO95/01438, and WO95/15388.

Basically, a technique known in the art is used in a method for obtaining the antibody-encoding gene from hybridomas. A desired antigen or cells expressing the desired antigen are used as a sensitizing antigen. Animals are immunized with this sensitizing antigen according to a usual immunization method. Immunocytes thus obtained are fused with parental cells known in the art by a usual cell fusion method. Monoclonal antibody-producing cells (hybridomas) are screened for by a usual screening method. From mRNAs of the obtained hybridomas, cDNAs of antibody variable regions (V regions) can be synthesized using reverse transcriptase and ligated with DNAs encoding desired antibody constant regions (C regions) to obtain the antibody-encoding gene.

More specifically, although the present invention is not limited by examples below, the sensitizing antigen for obtaining the genes encoding the antibody H chain and L chain includes both of a complete antigen having immunogenicity and an incomplete antigen (including hapten, etc.) that exhibits no immunogenicity. For example, a full-length protein or a partial peptide of the protein of interest can be used. In addition, a substance constituted by a polysaccharide, a nucleic acid, a lipid, or the like is known to serve as an antigen. The antigen for the antibody of the present invention is not particularly limited. The antigen can be prepared by a method generally known to those skilled in the art and can be obtained according to, for example, a method using baculovirus (e.g., WO98/46777). The hybridomas can be prepared according to, for example, the method of Milstein et al. (G. Kohler and C. Milstein, Methods Enzymol. 1981, 73: 3-46). When the antigen has low immunogenicity, this antigen can be bound to an immunogenic macromolecule such as albumin for immunization. If necessary, the antigen may be bound to another molecule to form a soluble antigen. In the case of using a transmembrane molecule such as a receptor as the antigen, a portion of the extracellular region of the receptor may be used as a fragment, or cells expressing the transmembrane molecule on their surface may be used as the immunogen.

The antibody-producing cells can be obtained by the immunization of animals with any of the appropriate sensitizing antigens mentioned above. Alternatively, lymphocytes capable of producing antibodies may be immunized in vitro and used as the antibody-producing cells. Various mammals can be used as the animals to be immunized. An animal of the order Rodentia, Lagomorpha, or Primates is generally used. Examples thereof can include: Rodentia animals such as mice, rats, and hamsters; Lagomorpha animals such as rabbits; and Primates animals such as monkeys including cynomolgus monkeys, rhesus monkeys, hamadryas baboons, and chimpanzees. In addition, transgenic animals having repertoires of human antibody genes are also known, and such animals can also be used to obtain the human antibody (see WO96/34096; and Mendez et al., Nat. Genet. 1997, 15: 146-56). Instead of using such transgenic animals, for example, human lymphocytes are sensitized in vitro with the desired antigen or cells expressing the desired antigen, and the sensitized lymphocytes can be fused with human myeloma cells, for example, U266, to obtain the desired human antibody having binding activity against the antigen (see Japanese Patent Publication No. 1-59878). Furthermore, transgenic animals having all repertoires of human antibody genes can be immunized with the desired antigen to obtain the desired human antibody (see WO93/12227, WO92/03918, WO94/02602, WO96/34096, and WO96/33735).

For the immunization of these animals, for example, the sensitizing antigen is appropriately diluted with or suspended in phosphate-buffered saline (PBS), saline, or the like, mixed with an adjuvant, if necessary, and emulsified. Then, the resulting sensitizing antigen is intraperitoneally or subcutaneously injected to the animals. Then, the sensitizing antigen, preferably, mixed with a Freund's incomplete adjuvant, is administered to the animals several times at 4- to 21-day intervals. The antibody production can be confirmed by measuring the antibody titer of interest in the serum of the animals by a method routinely used.

The hybridomas can be prepared by fusing the antibody-producing cells obtained from the animals or the lymphocytes immunized with the desired antigen with myeloma cells using a fusion agent (e.g., polyethylene glycol) routinely used (Goding, Monoclonal Antibodies: Principles and Practice, Academic Press, 1986, 59-103). If necessary, the hybridoma cells are cultured for growth, and the binding specificity of antibodies produced by the hybridomas is measured by an analysis method known in the art such as immunoprecipitation, radioimmunoassay (RIA), or enzyme-linked immunosorbent assay (ELISA). Then, the hybridoma producing the antibody confirmed by the measurement to have the specificity, affinity, or activity of interest can also be subcloned, if necessary, by an approach such as a limiting dilution method.

Subsequently, a gene encoding the selected antibody can be cloned from the hybridoma or the antibody-producing cells (sensitized lymphocytes, etc.) using a probe (e.g., an oligonucleotide complementary to a sequence encoding an antibody constant region) capable of specifically binding to the antibody gene. The gene can also be cloned from mRNA by RT-PCR. Immunoglobulins are classified into five different classes: IgA, IgD, IgE, IgG, and IgM. These classes are further divided into some subclasses (isotypes) (e.g., IgG-1, IgG-2, IgG-3, and IgG-4; and IgA-1 and IgA-2). In the present invention, the H chain and the L chain used in the antibody production can be derived from an antibody belonging to any of these classes and subclasses. Such an antibody is not particularly limited and is particularly preferably IgG.

In this context, the genes encoding the H chain and the L chain may be modified by a genetic engineering approach. For example, a generically recombinant antibody, for example, a chimeric antibody or a humanized antibody, can be appropriately prepared by artificially modifying an antibody such as a mouse antibody, a rat antibody, a rabbit antibody, a hamster antibody, a sheep antibody, or a camel antibody for the purpose of, for example, reducing heteroantigenicity in humans. The chimeric antibody is an antibody composed of H chain and L chain variable regions of a non-human mammal antibody, for example, a mouse antibody, and H chain and L chain constant regions of a human antibody. The chimeric antibody can be obtained by: ligating DNAs encoding the mouse antibody variable regions with DNAs encoding the human antibody constant regions; incorporating the resulting ligation products into expression vectors; and transfecting the vectors into hosts for antibody production. The humanized antibody is also called reshaped human antibody. DNA sequences designed to connect complementarity-determining regions (CDRs) of a non-human mammal antibody, for example, a mouse antibody, are synthesized by PCR from several prepared oligonucleotides having overlapping terminal portions. The obtained DNAs are ligated with DNAs encoding human antibody constant regions, and the resulting ligation products are subsequently incorporated to expression vectors, which are then transfected to hosts for antibody production (see EP239400; and WO96/02576). The human antibody FRs connected via the CDRs are selected such that the complementarity-determining regions form a favorable antigen-binding site. If necessary, amino acids in the framework regions of antibody variable regions may be substituted such that the complementarity-determining regions of the resulting reshaped human antibody form an appropriate antigen-binding site (K. Sato et al., Cancer Res. 1993, 53: 851-856).

In addition to the aforementioned humanization, for example, modification is also possible for improving the biological properties of the antibody such as binding activity against the antigen. Such modification can be carried out by a method such as site-directed mutagenesis (see e.g., Kunkel (1985) Proc. Natl. Acad. Sci. USA 82: 488), PCR mutagenesis, or cassette mutagenesis. In general, such an antibody variant having the improved biological properties has 70% or higher, more preferably 80% or higher, further preferably 90% or higher (e.g., 95% or higher, 97%, 98%, or 99%) amino acid sequence homology and/or similarity to the variable region amino acid sequences of the original antibody. In the present specification, the sequence homology and/or similarity is defined as the percentage of amino acid residues homologous (identical amino acid residues) or similar (amino acid residues classified into the same group on the basis of the side chain properties of general amino acids) to the original antibody residues after sequence alignment and gap introduction as needed so as to attain the largest value of sequence homology. Typically, natural amino acid residues are classified on the basis of the properties of their side chains into (1) hydrophobic group: alanine, isoleucine, norleucine, valine, methionine, and leucine; (2) neutral hydrophilic group: asparagine, glutamine, cysteine, threonine, and serine; (3) acidic group: aspartic acid and glutamic acid; (4) basic group: arginine, histidine, and lysine; (5) group of residues influencing chain orientation: glycine and proline; and (6) aromatic group: tyrosine, tryptophan, and phenylalanine.

A total of six complementarity determining regions (hypervariable domains; CDRs) present in H chain and L chain variable regions usually interact with each other to form an antigen-binding site in the antibody. Even one of these variable regions is known to have the ability to recognize and bind to the antigen, albeit with lower affinity than that of a molecule containing the whole binding site. Thus, the genes encoding the H chain and the L chain of the antibody of the present invention can encode fragments or moieties containing the respective antigen-binding sites of the H chain and the L chain as long as the polypeptides encoded by the genes should maintain the binding activity against the desired antigen.

Activity of Polypeptide and Examples of Antigen

For example, an antibody or a polypeptide having an activity can be efficiently prepared by use of the method for controlling dissociation and/or association according to the present invention. Examples of the activity can include binding activity, neutralizing activity, cytotoxic activity, agonistic activity, antagonistic activity, and enzymatic activity. The agonistic activity is an activity of intracellularly transducing signals, for example, through the binding of an antibody to an antigen such as a receptor to induce change in some physiological activity. Examples of the physiological activity can include, but are not limited to, proliferative activity, survival activity, differentiation activity, transcriptional activity, membrane transport activity, binding activity, proteolytic activity, phosphorylating/dephosphorylating activity, redox activity, transfer activity, nucleolytic activity, dehydration activity, cell death-inducing activity, and apoptosis-inducing activity.

Also, an antibody or a polypeptide that recognizes a desired antigen or binds to a desired receptor can be efficiently prepared by the method of the present invention.

In the present specification, the antigen is not particularly limited, and any antigen can be used. Preferred examples of the antigen include ligands (cytokines, chemokines, etc.), receptors, cancer antigens, MHC antigens, differentiation antigens, immunoglobulins, and immunocomplexes partially containing an immunoglobulin.

Examples of the cytokines can include interleukins 1 to 18, colony-stimulating factors (G-CSF, M-CSF, GM-CSF, etc.), interferons (IFN-α, IFN-β, IFN-γ, etc.), growth factors (EGF, FGF, IGF, NGF, PDGF, TGF, HGF, etc.), tumor necrosis factors (TNF-α and TNF-β), lymphotoxin, erythropoietin, leptin, SCF, TPO, MCAF, and BMP.

Examples of the chemokines can include CC chemokines such as CCL1 to CCL28, CXC chemokines such as CXCL1 to CXCL17, C chemokines such as XCL1 to XCL2, and CX3C chemokines such as CX3CL1.

Examples of the receptors can include receptors belonging to receptor families such as hematopoietic factor receptor family, cytokine receptor family, tyrosine kinase receptor family, serine/threonine kinase receptor family, TNF receptor family, G protein-coupled receptor family, GPI-anchored receptor family, tyrosine phosphatase receptor family, adhesion factor family, and hormone receptor family. The receptors belonging to these receptor families and features thereof are described in many literatures, for example, Cooke B A., King R J B., van der Molen H J. ed. New Comprehensive Biochemistry Vol. 18B "Hormones and their Actions Part II" pp. 1-46 (1988) Elsevier Science Publishers BV., Patthy (Cell (1990) 61 (1), 13-14), Ullrich et al. (Cell (1990) 61 (2), 203-212), Massague (e carries an acute accent) (Cell (1992) 69 (6), 1067-1070), Miyajima et al. (Annu. Rev. Immunol. (1992) 10, 295-331), Taga et al. (FASEB J. (1992) 6, 3387-3396), Fantl et al. (Annu. Rev. Biochem. (1993), 62, 453-481), Smith et al. (Cell (1994) 76 (6) 959-962), and Flower D R. (Biochim. Biophys. Acta (1999) 1422 (3) 207-234).

Preferred examples of specific receptors belonging to the receptor families include human or mouse erythropoietin (EPO) receptor (Blood (1990) 76 (1), 31-35; and Cell (1989) 57 (2), 277-285), human or mouse granulocyte colony-stimulating factor (G-CSF) receptor (Proc. Natl. Acad. Sci. USA. (1990) 87 (22), 8702-8706; mG-CSFR; and Cell (1990) 61 (2), 341-350), human or mouse thrombopoietin (TPO) receptor (Proc Natl Acad Sci USA. (1992) 89 (12), 5640-5644; and EMBO J. (1993) 12 (7), 2645-53), human or mouse insulin receptor (Nature (1985) 313 (6005), 756-761), human or mouse Flt-3 ligand receptor (Proc. Natl. Acad. Sci. USA. (1994) 91 (2), 459-463), human or mouse platelet-derived growth factor (PDGF) receptor (Proc. Natl. Acad. Sci. USA. (1988) 85 (10) 3435-3439), human or mouse interferon (IFN)-α/β receptor (Cell (1990) 60 (2), 225-234; and Cell (1994) 77 (3), 391-400), human or mouse leptin receptor, human or mouse growth hormone (GH) receptor, human or mouse interleukin (IL)-10 receptor, human or mouse insulin-like growth factor (IGF)-I receptor, human or mouse leukemia inhibitory factor (LIF) receptor, and human or mouse ciliary neurotrophic factor (CNTF) receptor.

The cancer antigens are antigens that are expressed with the malignant transformation of cells, and are also called tumor-specific antigens. Abnormal sugar chains that appear on cell surface or protein molecules when cells are cancerated are also included in the cancer antigens and are also called cancer carbohydrate antigens. Preferred examples of the cancer antigens include GPC3 that belongs to the GPI-anchored receptor family as the aforementioned receptors but is expressed in some cancers including liver cancer (Int J Cancer. (2003) 103 (4), 455-65), EpCAM that is expressed in a plurality of cancers including lung cancer (Proc Natl Acad Sci USA. (1989) 86 (1), 27-31), CA19-9, CA15-3, and sialyl SSEA-1 (SLX).

The MHC antigens are mainly classified into MHC class I antigens and MHC class II antigens. The MHC class I antigens include HLA-A, -B, -C, -E, -F, -G, and -H. The MHC class II antigens include HLA-DR, -DQ, and -DP.

The differentiation antigens can include CD1, CD2, CD4, CD5, CD6, CD7, CD8, CD10, CD11a, CD11b, CD11c, CD13, CD14, CD15s, CD16, CD18, CD19, CD20, CD21, CD23, CD25, CD28, CD29, CD30, CD32, CD33, CD34, CD35, CD38, CD40, CD41a, CD41b, CD42a, CD42b, CD43, CD44, CD45, CD45RO, CD48, CD49a, CD49b, CD49c, CD49d, CD49e, CD49f, CD51, CD54, CD55, CD56, CD57, CD58, CD61, CD62E, CD62L, CD62P, CD64, CD69, CD71, CD73, CD95, CD102, CD106, CD122, CD126, and CDw130.

The immunoglobulins include IgA, IgM, IgD, IgG, and IgE. The immunocomplexes contain at least any component of immunoglobulins.

Other examples of the antigen can include the following molecules: 17-IA, 4-1BB, 4Dc, 6-keto-PGF1a, 8-iso-PGF2a, 8-oxo-dG, A1 adenosine receptor, A33, ACE, ACE-2, activin, activin A, activin AB, activin B, activin C, activin RIA, activin RIA ALK-2, activin RIB ALK-4, activin RIIA, activin RIIB, ADAM, ADAM10, ADAM12, ADAM15, ADAM17/TACE, ADAM8, ADAM9, ADAMTS, ADAMTS4, ADAMTS5, addressin, aFGF, ALCAM, ALK, ALK-1, ALK-7, alpha-1-antitrypsin, alpha-V/beta-1 antagonist, ANG, Ang, APAF-1, APE, APJ, APP, APRIL, AR, ARC, ART, artemin, anti-Id, ASPARTIC, atrial natriuretic factor, av/b3 integrin, Ax1, b2M, B7-1, B7-2, B7-H, B-lymphocyte-stimulating factor (BlyS), BACE, BACE-1, Bad, BAFF, BAFF-R, Bag-1, BAK, Bax, BCA-1, BCAM, Bcl, BCMA, BDNF, b-ECGF, bFGF, BID, Bik, BIM, BLC, BL-CAM, BLK, BMP, BMP-2 BMP-2a, BMP-3 (osteogenin), BMP-4 BMP-2b, BMP-5, BMP-6 Vgr-1, BMP-7 (OP-1), BMP-8 (BMP-8a, OP-2), BMPR, BMPR-IA (ALK-3), BMPR-IB (ALK-6), BRK-2, RPK-1, BMPR-II (BRK-3), BMP, b-NGF, BOK, bombesin, bone-derived neurotrophic factor, BPDE, BPDE-DNA, BTC, complement factor 3 (C3), C3a, C4, C10, CA125, CAD-8, calcitonin, cAMP, carcinoembryonic antigen (CEA), cancer-associated antigen, cathepsin A, cathepsin B, cathepsin C/DPPI, cathepsin D, cathepsin E, cathepsin H, cathepsin L, cathepsin 0, cathepsin S, cathepsin V, cathepsin X/Z/P, CBL, CCI, CCK2, CCL, CCL1, CCL11, CCL12, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL4, CCL5, CCL6, CCL7, CCL8, CCL9/10, CCR, CCR1, CCR10, CCR10, CCR2, CCR3, CCR4, CCR5, CCR6, CCR7, CCR8, CCR9, CD1, CD2, CD3, CD3E, CD4, CD5, CD6, CD7, CD8, CD10, CD11a, CD11b, CD11c, CD13, CD14, CD15, CD16, CD18, CD19, CD20, CD21, CD22, CD23, CD25, CD27L, CD28, CD29, CD30, CD30L, CD32, CD33 (p67 protein), CD34, CD38, CD40, CD40L, CD44, CD45, CD46, CD49a, CD52, CD54, CD55, CD56, CD61, CD64, CD66e, CD74, CD80 (B7-1), CD89, CD95, CD123, CD137, CD138, CD140a, CD146, CD147, CD148, CD152, CD164, CEACAM5, CFTR, cGMP, CINC, *Clostridium botulinum* toxin, *Clostridium perfringens* toxin, CKb8-1, CLC, CMV, CMV UL, CNTF, CNTN-1, COX, C-Ret, CRG-2, CT-1, CTACK, CTGF, CTLA-4, CX3CL1, CX3CR1, CXCL, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCR, CXCR1, CXCR2, CXCR3, CXCR4, CXCR5, CXCR6, cytokeratin tumor-associated antigen, DAN, DCC, DcR3, DC-SIGN, decay accelerating factor, des (1-3)-IGF-I (brain IGF-1), Dhh, digoxin, DNAM-1, Dnase, Dpp, DPPIV/CD26, Dtk, ECAD, EDA, EDA-A1, EDA-A2, EDAR, EGF, EGFR (ErbB-1), EMA, EMMPRIN, ENA, endothelin receptor, enkephalinase, eNOS, Eot, eotaxin 1, EpCAM, ephrin B2/EphB4, EPO, ERCC, E-selectin, ET-1, factor IIa, factor VII, factor VIIIc, factor IX, fibroblast-activating protein (FAP), Fas, FcR1, FEN-1, ferritin, FGF, FGF-19, FGF-2, FGF3, FGF-8, FGFR, FGFR-3, fibrin, FL, FLIP, Flt-3, Flt-4, follicle-stimulating hormone, fractalkine, FZD1, FZD2, FZD3, FZD4, FZD5, FZD6, FZD7, FZD8, FZD9, FZD10, G250, Gas6, GCP-2, GCSF, GD2, GD3, GDF, GDF-1, GDF-3 (Vgr-2), GDF-5 (BMP-14, CDMP-1), GDF-6 (BMP-13, CDMP-2), GDF-7 (BMP-12, CDMP-3), GDF-8 (myostatin), GDF-9, GDF-15 (MIC-1), GDNF, GDNF, GFAP, GFRa-1, GFR-alpha 1, GFR-alpha 2, GFR-alpha 3, GITR, glucagon, Glut4, glycoprotein IIb/IIIa (GPIIb/IIIa), GM-CSF, gp130, gp72, GRO, growth hormone-releasing factor, hapten (NP-cap or NIP-cap), HB-EGF, HCC, HCMV gB envelope glycoprotein, HCMV gH envelope glycoprotein, HCMV UL, hematopoietic growth factor (HGF), Hep B gp120, heparanase, Her2, Her2/neu (ErbB-2), Her3 (ErbB-3), Her4 (ErbB-4), herpes simplex virus (HSV) gB glycoprotein, HSV gD glycoprotein, HGFA, high-molecular-weight melanoma-associated antigen (HMW-MAA), HIV gp120, HIV IIIB gp 120 V3 loop, HLA, HLA-DR, HM1.24, HMFG PEM, HRG, Hrk, human heart myosin, human cytomegalovirus (HCMV), human growth hormone (HGH), HVEM, 1-309, IAP, ICAM, ICAM-1, ICAM-3, ICE, ICOS, IFNg, Ig, IgA receptor, IgE, IGF, IGF-binding protein, IGF-1R, IGFBP, IGF-I, IGF-II, IL, IL-1, IL-1R, IL-2, IL-2R, IL-4, IL-4R, IL-5, IL-5R, IL-6, IL-6R, IL-8, IL-9, IL-10, IL-12, IL-13, IL-15, IL-18, IL-18R, IL-23, interferon (INF)-alpha, INF-beta, INF-gamma, inhibin, iNOS, insulin A chain, insulin B chain, insulin-like growth factor 1, integrin alpha 2, integrin alpha 3, integrin alpha 4, integrin alpha 4/beta 1, integrin alpha 4/beta 7, integrin alpha 5 (alpha V), integrin alpha 5/beta 1, integrin alpha 5/beta 3, integrin alpha 6, integrin beta 1, integrin beta 2, interferon gamma, IP-10, I-TAC, JE, kallikrein 2, kallikrein 5, kallikrein 6, kallikrein 11, kallikrein 12, kallikrein 14, kallikrein 15, kallikrein L1, kallikrein L2, kallikrein L3, kallikrein L4, KC, KDR, keratinocyte growth factor (KGF), laminin 5, LAMP, LAP, LAP (TGF-1), latent TGF-1, latent TGF-1 bpl, LBP, LDGF, LECT2, lefty, Lewis-Y antigen, Lewis-Y-related antigen, LFA-1, LFA-3, Lfo, LIF, LIGHT, lipoprotein, LIX, LKN, Lptn, L-selectin, LT-a, LT-b, LTB4, LTBP-1, lung surfactant, luteinizing hormone, lymphotoxin beta receptor, Mac-1, MAdCAM, MAG, MAP2, MARC, MCAM, MCAM, MCK-2, MCP, M-CSF, MDC, Mer, metalloprotease, MGDF receptor, MGMT, MHC (HLA-DR), MIF, MIG, MIP, MIP-1-alpha, MK, MMAC1, MMP, MMP-1, MMP-10, MMP-11, MMP-12, MMP-13, MMP-14, MMP-15, MMP-2, MMP-24, MMP-3, MMP-7, MMP-8, MMP-9, MPIF, Mpo, MSK, MSP, mucin (Mucl), MUC18, mullerian-inhibiting factor, Mug, MuSK, NAIP, NAP, NCAD, N-cadherin, NCA 90, NCAM, NCAM, neprilysin, neurotrophin-3, -4, or -6, neurturin, nerve growth factor (NGF), NGFR, NGF-beta, nNOS, NO, NOS, Npn, NRG-3, NT, NTN, OB, OGG1, OPG, OPN, OSM, OX40L, OX40R, p150, p95, PADPr, parathyroid hormone, PARC, PARP, PBR, PBSF, PCAD, P-cadherin, PCNA, PDGF, PDGF, PDK-1, PECAM, PEM, PF4, PGE, PGF, PGI2, PGJ2, PIN, PLA2, placental alkaline phosphatase (PLAP), P1GF, PLP, PP14, proinsulin, prorelaxin, protein C, PS, PSA, PSCA, prostate-specific membrane antigen (PSMA), PTEN, PTHrp, Ptk, PTN, R51, RANK, RANKL, RANTES, RANTES, relaxin A chain, relaxin B chain, renin, respiratory syncytial virus (RSV) F, RSV Fgp, Ret, rheumatoid factor, RLIP76, RPA2, RSK, 5100, SCF/KL, SDF-1, SERINE, serum albumin, sFRP-3, Shh, SIGIRR, SK-1, SLAM, SLPI, SMAC, SMDF, SMOH, SOD, SPARC, Stat, STEAP, STEAP-II, TACE, TACI, TAG-72 (tumor-associated glycoprotein-72), TARC, TCA-3, T cell receptor (e.g., T cell receptor alpha/beta), TdT, TECK, TEM1, TEM5, TEM7, TEM8, TERT, testicular PLAP-like alkaline phosphatase, TfR, TGF, TGF-alpha, TGF-beta, TGF-beta Pan Specific, TGF-beta RI (ALK-5), TGF-beta RII, TGF-beta RIIb, TGF-beta RIII, TGF-beta 1, TGF-beta 2, TGF-beta 3, TGF-beta 4, TGF-beta 5, thrombin, thymus Ck-1, thyroid stimulating hormone, Tie, TIMP, TIQ, tissue factor, TMEFF2, Tmpo, TMPRSS2, TNF, TNF-alpha, TNF-alpha/beta, TNF-beta 2, TNFc, TNF-RI, TNF-RII, TNFRSF10A (TRAIL R1 Apo-2, DR4), TNFRSF10B (TRAIL R2 DR5, KILLER, TRICK-2A, TRICK-B), TNFRSF10C (TRAIL R3 DcR1, LIT, TRID), TNFRSF10D (TRAIL R4 DcR2, TRUNDD), TNFRSF11A (RANK ODF R, TRANCE R), TNFRSF11B (OPG OCIF, TR1), TNFRSF12 (TWEAK R FN14), TNFRSF13B (TACI), TNFRSF13C (BAFF R), TNFRSF14 (HVEM ATAR, HveA, LIGHT R, TR2), TNFRSF16 (NGFR p75NTR), TNFRSF17 (BCMA), TNFRSF18 (GITR AITR), TNFRSF19 (TROY TAJ, TRADE), TNFRSF19L (RELT), TNFRSF1A (TNF RI CD120a, p55-60), TNFRSF1B (TNF RII CD120b, p75-80), TNFRSF26 (TNFRH3), TNFRSF3 (LTbR TNF RIII, TNFC R), TNFRSF4 (OX40 ACT35, TXGP1 R), TNFRSF5 (CD40 p50), TNFRSF6 (Fas Apo-1, APT1, CD95), TNFRSF6B (DcR3 M68, TR6), TNFRSF7 (CD27), TNFRSF8 (CD30), TNFRSF9 (4-1BB CD137, ILA), TNFRSF21 (DR6), TNFRSF22 (DcTRAIL R2 TNFRH2), TNFRST23 (Dc-TRAIL R1 TNFRH1), TNFRSF25 (DR3 Apo-3, LARD, TR-3, TRAMP, WSL-1), TNFSF10 (TRAIL Apo-2 ligand, TL2), TNFSF11 (TRANCE/RANK ligand ODF, OPG ligand), TNFSF12 (TWEAK Apo-3 ligand, DR3 ligand), TNFSF13 (APRIL TALL2), TNFSF13B (BAFF BLYS, TALL1, THANK, TNFSF20), TNFSF14 (LIGHT HVEM ligand, LTg), TNFSF15 (TL1A/VEGI), TNFSF18 (GITR ligand AITR ligand, TL6), TNFSF1A (TNF-α conectin, DIF, TNFSF2), TNFSF1B (TNF-b LTa, TNFSF1), TNFSF3 (LTb TNFC, p33), TNFSF4 (OX40 ligand gp34, TXGP1), TNFSF5 (CD40 ligand CD154, gp39, HIGM1, IMD3, TRAP), TNFSF6 (Fas ligand Apo-1 ligand, APT1 ligand), TNFSF7 (CD27 ligand CD70), TNFSF8 (CD30 ligand CD153), TNFSF9 (4-1BB ligand CD137 ligand), TP-1, t-PA, Tpo, TRAIL, TRAIL R, TRAIL-R1, TRAIL-R2, TRANCE, transferrin receptor, TRF, Trk, TROP-2, TSG, TSLP, tumor-associated antigen CA125, tumor-associated antigen exhibiting Lewis Y-related carbohydrate, TWEAK, TXB2, Ung, uPAR, uPAR-1, urokinase, VCAM, VCAM-1, VECAD, VE-cadherin, VE-cadherin-2, VEFGR-1 (flt-1), VEGF, VEGFR, VEGFR-3 (flt-4), VEGI, VIM, viral antigen, VLA, VLA-1, VLA-4, VNR integrin, von Willebrand factor, WIF-1, WNT1, WNT2, WNT2B/13, WNT3, WNT3A, WNT4, WNTSA, WNT5B, WNT6, WNT7A, WNT7B, WNT8A, WNT8B, WNT9A, WNT9A, WNT9B, WNT10A, WNT10B, WNT11, WNT16, XCL1, XCL2, XCR1, XCR1, XEDAR, XIAP, XPD, HMGB1, IgA, Aβ, CD81, CD97, CD98, DDR1, DKK1, EREG, Hsp90, IL-17/IL-17R, IL-20/IL-20R, oxidized LDL, PCSK9, prekallikrein, RON, TMEM16F, SOD1, Chromogranin A, Chromogranin B, tau, VAP1, high-molecular-weight kininogen, IL-31, IL-31R, Nav1.1, Nav1.2, Nav1.3, Nav1.4, Nav1.5, Nav1.6, Nav1.7, Nav1.8, Nav1.9, EPCR, C1, C1q, C1r, C1s, C2, C2a, C2b, C3, C3a, C3b, C4, C4a, C4b, C5, C5a, C5b, C6, C7, C8, C9, factor B, factor D, factor H, properdin, sclerostin, fibrinogen, fibrin, prothrombin, thrombin, tissue factor, factor V, factor Va, factor VII, factor VIIa, factor VIII, factor VIIIa, factor IX, factor IXa, factor X, factor Xa, factor XI, factor XIa, factor XII, factor XIIa, factor XIII, factor XIIIa, TFPI, antithrombin III, EPCR, thrombomodulin, TAPI, tPA, plasminogen, plasmin, PAI-1, PAI-2, GPC3, Syndecan-1, Syndecan-2, Syndecan-3, Syndecan-4, LPA, SIP, and receptors for hormones and growth factors.

In a non-limiting embodiment of the present invention, one specificity of the bispecific antibody can target a cancer antigen, and the other specificity can target an antigen expressed on CTL (cytotoxic T lymphocyte), for example, CD3 or TNFRSF (tumor necrosis factor receptor super family), though these specificities are not limited to this combination. Examples of the TNFRSF include TNFRSF9 (CD137), TNFRSF5 (CD40), and TNFRSF4 (OX40).

Modification of Nucleic Acid

In another aspect of the production method of the present invention, the present invention provides a method for producing a heteromultimer having the modification of amino acid residues capable of causing disulfide bond isomerization via cysteines outside of core hinge regions (e.g., the modification of amino acid residues at positions 131, 220, 349, 356, 394, 351, 354, and 407 according to EU numbering) so as to control dissociation and/or association between polypeptides, the production method comprising the steps of: (a) modifying nucleic acids encoding the amino acid residues capable of causing disulfide bond isomerization via cysteines outside of core hinge regions from their original nucleic acids so as to control dissociation and association between the polypeptides; (b) culturing a host cell having the nucleic acids to express the polypeptides; (c) recovering the polypeptides from the cultures of the host cell; and (d) incubating these polypeptides under a reducing condition to recover a heteromer of the desired polypeptides.

In the method of the present invention, the phrase "modifying nucleic acids" means to modify nucleic acids so as to correspond to the amino acid residues that are introduced by the "modification" according to the present invention. More specifically, the phrase "modifying nucleic acids" means to modify nucleic acids encoding the original amino acid residues (amino acid residues before the modification) to nucleic acids encoding the amino acid residues that are introduced by the modification. Usually, this phrase means to carry out gene manipulation or mutation treatment for the insertion, deletion, or substitution of at least one base in the original nucleic acids so as to become codons encoding the amino acid residues of interest. Specifically, the codons encoding the original amino acid residues are substituted by codons encoding the amino acid residues that are introduced by the modification. Such nucleic acid modification can be appropriately carried out using a technique generally known to those skilled in the art, for example, site-directed mutagenesis or PCR mutagenesis.

The nucleic acids according to the present invention are usually carried by (or inserted in) appropriate vectors and transfected to host cells. The vectors are not particularly limited as long as the vectors can stably retain the inserted nucleic acids. For example, when E. coli is used as the host, pBluescript vectors (manufactured by Stratagene Corp.) or the like are preferred as vectors for cloning. Various commercially available vectors can be used. In the case of using the vectors for the purpose of producing the polypeptide of the present invention, expression vectors are particularly useful. The expression vectors are not particularly limited as long as the vectors permit expression of the polypeptide in vitro, in E. coli, in cultured cells, or in organism individuals. The expression vectors are preferably, for example, pBEST vectors (manufactured by Promega K.K.) for in vitro expression, pET vectors (manufactured by Invitrogen Corp.) for E. coli, pME18S-FL3 vectors (GenBank Accession No. AB009864) for cultured cells, and pME18S vectors (Mol Cell Biol. 8: 466-472 (1988)) for organism individuals. The insertion of the DNAs of the present invention into the vectors can be carried out by a routine method, for example, ligase reaction using restriction sites (Current protocols in Molecular Biology edit. Ausubel et al. (1987) Publish. John Wiley & Sons. Section 11.4-11.11).

The host cells are not particularly limited, and various host cells are used according to the purpose. Examples of the cells for polypeptide expression can include bacterial cells (e.g., *Streptococcus, Staphylococcus, E. coli, Streptomyces*, and *Bacillus subtilis*), fungus cells (e.g., yeasts and *Aspergillus*), insect cells (e.g., *Drosophila* S2 and *Spodoptera* SF9), animal cells (e.g., CHO, COS, HeLa, C127, 3T3, BHK, HEK293, and Bowes melanoma cells), and plant cells. The transfection of the vectors to the host cells can be carried out by a method known in the art, for example, a calcium phosphate precipitation method, an electroporation method (Current protocols in Molecular Biology edit. Ausubel et al., (1987) Publish. John Wiley & Sons. Section 9.1-9.9), a Lipofectamine method (manufactured by GIBCO-BRL/Life Technologies, Inc.), or a microinjection method.

An appropriate secretory signal can be incorporated into the polypeptide of interest in order to secrete the polypeptide expressed in the host cells to the lumen of the endoplasmic reticulum, periplasmic space, or an extracellular environment. The signal may be endogenous to the polypeptide of interest or may be a foreign signal.

When the polypeptide of the present invention is secreted into a medium, the recovery of the polypeptide in the production method is carried out by the recovery of the medium. When the polypeptide of the present invention is produced into cells, the cells are first lysed and then the polypeptide is recovered.

A method known in the art including ammonium sulfate or ethanol precipitation, acid extraction, anion- or cation-exchange chromatography, phosphocellulose chromatography, hydrophobic interaction chromatography, affinity chromatography, hydroxyapatite chromatography, and lectin chromatography can be used for recovering and purifying the polypeptide of the present invention from the recombinant cell cultures.

In a non-limiting embodiment of the present invention, examples of the production method include: a method which involves separately culturing cell lines respectively producing the homologous forms of the first and second polypeptides, and purifying the culture supernatants, followed by FAE (Fab arm exchange) reaction using the purified antibodies; a method which involves separately culturing cell lines respectively producing the homologous forms of the first and second polypeptides, mixing the culture supernatants without purification, and causing FAE reaction in the mixed culture supernatant, followed by purification; a method which involves mixing a cell line producing the homologous form of the first polypeptides with a cell line producing the homologous form of the second polypeptides, culturing the mixture, and purifying the culture supernatant, followed by FAE reaction using the purified antibodies; and a method which involves mixing a cell line producing the homologous form of the first polypeptide with a cell line producing the homologous form of the second polypeptide, culturing the mixture, and causing FAE reaction in the culture supernatant, followed by purification.

In a non-limiting embodiment, the present invention provides a method for producing a heteromultimer, comprising the following steps a) to c):
a) culturing cell lines respectively producing the homologous forms of the first and second polypeptides;
b) mixing the respective culture supernatants of the cell lines, and incubating the homologous form of the first polypeptide and the homologous form of the second polypeptide together so as to allow an inter-heavy chain or inter-light chain disulfide bond-forming cysteines outside of core hinge regions to cause disulfide bond isomerization; and
c) obtaining a heteromultimer comprising the first and second polypeptides.

In a non-limiting embodiment, the present invention provides a method for producing a heteromultimer, comprising the following steps a) to c):
a) separately culturing cell lines respectively producing the homologous forms of the first and second polypeptides;
b) mixing the respective culture supernatants of the cell lines and incubating the homologous form of the first polypeptide and the homologous form of the second polypeptide together so as to allow cysteines outside of core hinge regions to cause disulfide bond isomerization; and
c) obtaining a heteromultimer comprising the first and second polypeptides.

Method for Selecting Desired Heteromultimer (Method for Screening for Heteromultimer)

The present invention further provides a method for selecting (screening for) a desired heteromultimer. In a preferred embodiment, the method is a method for selecting a heteromultimer having a desired property (activity), comprising the following steps:
a) providing a first polypeptide set and a second polypeptide set, wherein each polypeptide constituting the first set has target specificity different from that of each polypeptide constituting the second set, and each polypeptide constituting the first and second sets contains amino acid modification that allows an inter-heavy chain or inter-light chain disulfide bond-forming cysteines outside of core hinge regions to cause disulfide bond isomerization;
b) incubating each polypeptide constituting the first set together with each polypeptide constituting the second set under a reducing condition, thereby preparing a mixture of plural types of heteromultimers;
c) assaying the resulting mixture of plural types of heteromultimers for the predetermined desired property (activity); and
d) selecting a heteromultimer having the desired property (activity).

The present invention also provides a method for screening for a heteromultimer, comprising further performing, after the method for producing a heteromultimer according to the present invention, the steps of:
  measuring the activity of the heteromultimer; and
  selecting a heteromultimer having a desired activity.

Specifically, the screening method comprises the following steps:
a) providing a homologous form of a first polypeptide having a first antigen-binding activity and comprising a heavy chain constant region;
b) providing a homologous form of a second polypeptide having a second antigen-binding activity that is different from the first antigen-binding activity and comprising a heavy chain constant region;
c) incubating the homologous form of the first polypeptide and the homologous form of the second polypeptide together under a reducing condition that allows cysteines outside of core hinge regions to cause disulfide bond isomerization;
d) obtaining a heteromultimer comprising the first and second polypeptides;
e) measuring the activity of the heteromultimer obtained in step d); and
f) selecting a heteromultimer having a desired activity.

In the method of the present invention, examples of the desired property (activity) can include, but are not particularly limited to, binding activity, neutralizing activity, cytotoxic activity, agonistic activity, antagonistic activity, and enzymatic activity. The agonistic activity is an activity of intracellularly transducing signals, for example, through the binding of an antibody to an antigen such as a receptor to induce change in some physiological activity. Examples of the physiological activity can include, but are not limited to, proliferative activity, survival activity, differentiation activity, transcriptional activity, membrane transport activity, binding activity, proteolytic activity, phosphorylating/dephosphorylating activity, redox activity, transfer activity, nucleolytic activity, dehydration activity, cell death-inducing activity, and apoptosis-inducing activity.

The present invention further provides a method for producing a heteromultimer, comprising further performing, after the screening method of the present invention, the steps of:

obtaining the desired regions (e.g., CDRs, variable regions, or constant regions) of the first polypeptide, the second polypeptide, the third polypeptide, and the fourth polypeptide of the selected heteromultimer; and grafting the obtained regions to another heteromultimer.

Specifically, the production method comprises the following steps:
a) providing a homologous form of a first polypeptide having a first antigen-binding activity and comprising a heavy chain constant region;
b) providing a homologous form of a second polypeptide having a second antigen-binding activity that is different from the first antigen-binding activity and comprising a heavy chain constant region;
c) incubating the homologous form of the first polypeptide and the homologous form of the second polypeptide together under a reducing condition that allows cysteines outside of core hinge regions to cause disulfide bond isomerization;
d) obtaining a heteromultimer comprising the first and second polypeptides;
e) measuring the activity of the heteromultimer obtained in step d);
f) selecting a heteromultimer having a desired activity;
g) obtaining the desired regions (e.g., CDRs, variable regions, or constant regions) of the first polypeptide, the second polypeptide, the third polypeptide, and the fourth polypeptide of the heteromultimer selected in step 0; and
h) grafting the obtained regions to another heteromultimer.

Pharmaceutical Composition

The present invention also relates to a composition (drug) comprising the heteromultimer of the present invention and a pharmaceutically acceptable carrier.

In the present invention, the pharmaceutical composition usually refers to a drug for the treatment or prevention of a disease or for testing or diagnosis.

The pharmaceutical composition of the present invention can be formulated by a method generally known to those skilled in the art. For example, the pharmaceutical composition can be used in the form of a parenteral injection of an aseptic solution or suspension with water or any other pharmaceutically acceptable solution. For example, the pharmaceutical composition may be formulated with the heteromultimer mixed in a unit dosage form required for generally accepted pharmaceutical practice, in appropriate combination with pharmacologically acceptable carriers or media, specifically, sterilized water, physiological saline, plant oil, an emulsifier, a suspending agent, a surfactant, a stabilizer, a flavoring agent, an excipient, a vehicle, a preservative, a binder, etc. The amount of the active ingredient in these preparations is set so as to give an appropriate volume within a prescribed range.

An aseptic composition for injection can be formulated according to conventional pharmaceutical practice using a vehicle such as injectable distilled water.

Examples of aqueous solutions for injection include physiological saline, and isotonic solutions containing glucose and other adjuvants (e.g., D-sorbitol, D-mannose, D-mannitol, and sodium chloride). These solutions may be used in combination with an appropriate solubilizer, for example, an alcohol (ethanol, etc.) or a polyalcohol (propylene glycol, polyethylene glycol, etc.), or a nonionic surfactant (polysorbate 80(TM), HCO-50, etc.).

Examples of oily solutions include sesame oil and soybean oil. These solutions may be used in combination with benzyl benzoate and/or benzyl alcohol as a solubilizer. The solutions may be further mixed with a buffer (e.g., a phosphate buffer solution and a sodium acetate buffer solution), a soothing agent (e.g., procaine hydrochloride), a stabilizer (e.g., benzyl alcohol and phenol), and an antioxidant. The injection solutions thus prepared are usually charged into appropriate ampules.

The pharmaceutical composition of the present invention is preferably administered parenterally. The composition can be in the dosage form of, for example, an injection, a nasal administration agent, a transpulmonary administration agent, or a percutaneous administration agent. The pharmaceutical composition can be administered systemically or locally through, for example, intravenous injection, intramuscular injection, intraperitoneal injection, or subcutaneous injection.

The administration method can be appropriately selected depending on the age and symptoms of a patient. The dose of a pharmaceutical composition containing an antibody or a polynucleotide encoding the antibody can be set to within a range of, for example, 0.0001 to 1000 mg/kg of body weight per dose. Alternatively, the dose may be, for example, 0.001 to 100000 mg per patient, though the present invention is not necessarily limited by these numeric values. Although the dose and the administration method vary depending on the weight, age, symptoms, etc., of a patient, those skilled in the art can appropriately select an appropriate dose and administration method in consideration of their conditions.

In the present invention, the heteromultimer of the present invention is useful as an active ingredient for a therapeutic or preventive agent for a cancer. Examples of the cancer include, but are not limited to: lung cancer (including small-cell lung cancer, non-small-cell lung cancer, lung adenocarcinoma, and lung squamous cell carcinoma), large bowel cancer, rectal cancer, colon cancer, breast cancer, liver cancer, stomach cancer, pancreatic cancer, kidney cancer, prostate cancer, ovary cancer, thyroid gland cancer, bile duct cancer, peritoneal cancer, mesothelioma, squamous cell cancer, uterine cervix cancer, uterine body cancer, bladder cancer, esophagus cancer, head and neck cancer, nasopharyngeal cancer, salivary gland tumor, thymoma, skin cancer, basal cell tumor, malignant melanoma, anus cancer, penis cancer, testis cancer, Wilms's tumor, acute myeloid leukemia (including acute myeloleukemia, acute myeloblastic leukemia, acute promyelocytic leukemia, acute myelomonocytic leukemia, and acute monocytic leukemia), chronic myeloid leukemia, acute lymphoid leukemia, chronic lymphoid leukemia, Hodgkin's lymphoma, non-Hodgkin's lymphoma (Burkitt's lymphoma, chronic lymphocytic leukemia, mycosis fungoides, mantle cell lymphoma, follicular lymphoma, diffuse large-cell lymphoma, marginal zone lymphoma, hairy cell leukemia, plasmacytoma, peripheral T-cell lymphoma, and adult T-cell leukemia/lymphoma), Langerhans' cell histiocytosis, multiple myeloma, myelodysplastic syndrome, brain tumor (including glioma, astroglioma, glioblastoma, meningioma, and ependymoma), neuroblastoma, retinoblastoma, osteosarcoma, Kaposi's sarcoma, Ewing's sarcoma, angiosarcoma, and hemangiopericytoma.

If necessary, the polypeptide or the heteromultimer of the present invention can be made into preparations in combination with other pharmaceutical ingredients.

The present invention relates to a method for treating or preventing diseases such as immunological and inflammatory diseases (e.g., cancer), comprising administering the heteromultimer of the present invention, a heteromultimer produced by the production method of the present invention, or the pharmaceutical composition of the present invention. The present invention also provides a kit for use in the treatment method or the prevention method of the present invention, comprising at least the heteromultimer of the present invention, a heteromultimer produced by the production method of the present invention, or the pharmaceutical composition of the present invention. In the kit, for example, a pharmaceutically acceptable carrier, a vehicle, or an instruction stating the usage can also be additionally packaged. The present invention also relates to use of the heteromultimer of the present invention or a heteromultimer produced by the production method of the present invention for producing a drug (e.g., a therapeutic or preventive agent for immunological and inflammatory diseases). The present invention further relates to the heteromultimer of the present invention or a heteromultimer produced by the production method of the present invention for use in the treatment method or the prevention method of the present invention.

The three-letter codes of the amino acids used herein and their corresponding one-letter codes are as follows:
Alanine: Ala: A
Arginine: Arg: R
Asparagine: Asn: N
Aspartic acid: Asp: D
Cysteine: Cys: C
Glutamine: Gln: Q
Glutamic acid: Glu: E
Glycine: Gly: G
Histidine: His: H
Isoleucine: Ile: I
Leucine: Leu: L
Lysine: Lys: K
Methionine: Met: M
Phenylalanine: Phe: F
Proline: Pro: P
Serine: Ser: S
Threonine: Thr: T
Tryptophan: Trp: W
Tyrosine: Tyr: Y
Valine: Val: V All prior art documents cited herein are incorporated herein by reference.

EXAMPLES

[Example 1] Study on Improvement in Fab Arm Exchange Efficiency by Introduction of Association Interface-Controlling Modification to Antibody In Fab arm exchange, two types of homologous antibodies are mixed in the presence of a reducing agent, and the resulting four arms of the antibody molecules (referred to as half-molecules or HL molecules, each of which is a molecule composed of one heavy chain and one light chain) reassociate to yield bispecific antibodies. Since the reassociation of HL molecules occurs at random, the bispecific antibody of interest is theoretically obtained at only 50% of the total amount of antibodies present in the system. However, by introducing different charges in advance to two types of homologous antibodies, there is a possibility that heterodimerization can occur preferentially over homodimerization during the reassociation of the resulting HL molecules and a bispecific antibody may be prepared with high efficiency. Accordingly, the modification to control association interface between antibody CH3 regions (modification to hetero-associate two types of H chains through the use of the charge interaction and repulsion between their CH3 regions) as reported in WO2006/106905 was used to test whether or not the reaction efficiency of Fab arm exchange (rate of bispecific antibody formation) can be improved.

The antibody H chain variable regions used were heavy chain variable regions WT(H) (SEQ ID NO: 1; hereinafter, referred to as MRAH) and H54 (SEQ ID NO: 2) of the antibody against human interleukin 6 receptor disclosed in WO2009/125825. In connection to the above heavy chain variable regions, MRAH-G1d (SEQ ID NO: 3) and H54-G1d (SEQ ID NO: 4) having G1d prepared by removing C-terminal Gly and Lys from a human IgG1 heavy chain constant region and MRAH-wtG4d (SEQ ID NO: 5) and H54-wtG4d (SEQ ID NO: 6) having wtG4d prepared by removing C-terminal Gly and Lys from a human IgG4 heavy chain constant region were prepared as antibody heavy chain constant regions. Next, P228S and K409R modifications were introduced to MRAH-G1d and H54-G1d to prepare MRAH-G1dsr (SEQ ID NO: 7) and H54-G1dsr (SEQ ID NO: 8) having an IgG4-type hinge sequence and CH3 domain sequence. D356K was further introduced as association interface-controlling modification to MRAH-G1dsr to prepare MRAH-G1dsrP1 (SEQ ID NO: 9). K439E was further introduced as association interface-controlling modification to H54-G1dsr to prepare H54-G1dsrN1 (SEQ ID NO: 10). E356K was further introduced as association interface-controlling modification to MRAH-wtG4d to prepare MRAH-wtG4dP1 (SEQ ID NO: 11). K439E was further introduced as association interface-controlling modification to H54-wtG4d to prepare H54-wtG4dN1 (SEQ ID NO: 12). Antibody L chains MRAL-k0 (SEQ ID NO: 13) and L28-k0 (SEQ ID NO: 14) were used for the heavy chain variable regions MRAH and H54, respectively. MRAH-G1dsr/MRAL-k0, H54-G1dsr/L28-k0, MRAH-G1dsrP1/MRAL-k0, H54-G1dsrN1/L28-k0, MRAH-wtG4d/MRAL-k0, H54-wtG4d/L28-k0, MRAH-wtG4dP1/MRAL-k0, and H54-wtG4dN1/L28-k0 were expressed and purified according to the method of Reference Example 1.

Next, two types of homologous forms thus obtained were mixed in the combinations given below under the reaction condition given below, and the reaction products were evaluated according to the method of Reference Example 2.
(1) MRAH-wtG4d/MRAL-k0 and H54-wtG4d/L28-k0
(2) MRAH-wtG4dP1/MRAL-k0 and H54-wtG4dN1/L28-k0
(3) MRAH-G1dsr/MRAL-k0 and H54-G1dsr/L28-k0
(4) MRAH-G1dsrP1/MRAL-k0 and H54-G1dsrN1/L28-k0

Reaction conditions: in PBS (Sigma-Aldrich Corp., pH 7.4), [each mAb]=0.2 mg/ml, [GSH (Sigma-Aldrich Corp.)]=0.5 mM, 0.05% Tween 20 (Junsei Chemical Co., Ltd.), 37° C., 24 hours.

The two types of antibody variable regions MRAH/MRAL and H54/L28 used in this study differ largely in pI. Therefore, peaks corresponding to their respective homologous forms and the resulting bispecific antibodies can be easily separated by ion-exchange chromatography, and the reaction efficiency of Fab arm exchange can be evaluated. FIG. 1 shows the results of evaluating the reaction products by ion-exchange chromatography. The reaction product wtG4d of MRAH-wtG4d/MRAL-k0 and H54-wtG4d/L28-k0 and the reaction product G1dsr of MRAH-G1dsr/MRAL-k0 and H54-G1dsr/L28-k0 carrying no association interface-controlling modification had 50.5% and 52.7% rates, respectively, of bispecific antibody formation. By contrast, the reaction product wtG4dP1/N1 of MRAH-wtG4dP1/MRAL-k0 and H54-wtG4dN1/L28-k0 carrying the association interface-controlling modification had 99.0% rate of bispecific antibody formation, and the reaction product G1dsrP1/N1 of MRAH-G1dsrP1/MRAL-k0 and H54-G1dsrN1/L28-k0 carrying the association interface-controlling modification had 98.5% rate of bispecific antibody formation. Thus, the bispecific antibody was found to be formed with exceedingly high efficiency. These results demonstrated that the bispecific antibody can be prepared with exceedingly high efficiency by mixing two types of homologous forms carrying the association interface-controlling modification reported in WO2006/106905 in the presence of a reducing agent.

[Example 2] Fab Arm Exchange in Homologous Forms Having Hinge Sequence of Naturally Occurring Human IgG1

In Example 1, Fab arm exchange was conducted by the introduction of P228S modification to human IgG1 in order to obtain a hinge region having a sequence of naturally occurring human IgG4 type. However, naturally occurring IgG4 administered into a living body reportedly causes half-molecule exchange with endogenous IgG4. This is due to Ser at position 228 (EU numbering) in the hinge region. The substitution of this amino acid by IgG1-type Pro has been reported to improve stability and to prevent the in vivo exchange (Labrijn A F et al., Nat. Biotechnol. 2009, 27, 767-771). Thus, in consideration of administration into a living body, the hinge sequence of the prepared bispecific antibody is desirably 226C-227P-228P-229C. Accordingly, this study was conducted to test whether or not Fab arm exchange can be efficiently caused by the introduction of association interface-controlling modification even when using the hinge sequence of naturally occurring human IgG1.

First, K409R and D356K were introduced to MRAH-G1d to prepare MRAH-G1drP1 (SEQ ID NO: 15), and K409R and K439E were introduced to H54-G1d to prepare H54-G1drN1 (SEQ ID NO: 16). Antibody L chains MRAL-k0 and L28-k0 were used for the heavy chain variable regions MRAH and H54, respectively. MRAH-G1drP1/MRAL-k0 and H54-G1drN1/L28-k0 were expressed and purified according to the method of Reference Example 1. Next, two types of homologous forms thus obtained were mixed under reaction conditions given below, and the reaction products were evaluated according to the method of Reference Example 2.

Reaction condition: in TBS (Takara Bio Inc., pH 7.6), [each mAb]=0.2 mg/ml, 0.05% Tween 20 (Junsei Chemical Co., Ltd.), 37° C., 24 hours. The study was conducted under 3 conditions of a reducing agent [GSH (Sigma-Aldrich Corp.)]=0.5 mM or 5 mM or [2-MEA (Sigma-Aldrich Corp.)]=25 mM.

FIG. 2 shows the results of analyzing the reaction products according to the method of Reference Example 2. The rate of bispecific antibody formation under the same condition as in Example 1 (GSH=0.5 mM) was 21.8%, which was drastically reduced compared with the efficiency of the case where the amino acid residue at position 228 (EU numbering) was Ser. By contrast, the rate of bispecific antibody formation under the reducing condition of 2-MEA (25 mM) or GSH (5 mM) was 99% or more. These results demonstrated that the bispecific antibody can be prepared with high efficiency by introducing association interface-controlling modification and using an appropriate reducing condition even if the hinge sequence is the sequence of naturally occurring human IgG1.

[Example 3] Fab Arm Exchange in Variant Lacking Disulfide Bond Between Heavy and Light Chains As mentioned above, in the FAE reaction, HL molecules resulting from the cleavage of hinge region disulfide bonds by a reducing agent reassociate. Thus, if such HL molecules can be efficiently formed, it is estimated that the FAE reaction can proceed under a milder reducing condition. In naturally occurring human IgG4, a disulfide bond formed between H and L chains is reported to form between L chains by the introduction of C131S modification (Schuurman J et al., Mol. Immunol. 2001, 38, 1-8). This disulfide bond between L chains is formed at only one position and may therefore be reduced more easily than two disulfide bonds formed in the core hinges. If HL molecules can be efficiently formed through the cleavage of a disulfide bond between L chains by the addition of a reducing agent, there is the possibility that bispecific antibodies can be prepared with high efficiency, as shown in FIG. 3. Accordingly, this study was conducted to test whether or not Fab arm exchange reaction (rate of bispecific antibody formation) can be performed with high efficiency by introducing association interface-controlling modification to the CH3 regions of variants having C131S modification.

In human IgG1, a disulfide bond between H and L chains is formed between 220C of the H chain and the L chain. Accordingly, for the purpose of also conducting similar studies in human IgG1, this study was conducted to test whether or not Fab arm exchange reaction (bispecific antibody formation) can be performed with high efficiency by introducing association interface-controlling modification to the CH3 regions of variants having C220S modification.

S228P was introduced to the hinges of the heavy chain constant regions of MRAH-wtG4d and H54-wtG4d to prepare MRAH-G4d (SEQ ID NO: 17) and H54-G4d (SEQ ID NO: 18) having a G1-type hinge structure. Next, C131S as modification for deleting disulfide bonds between H and L chains was introduced to MRAH-G4d and H54-G4d to prepare MRAH-G4dv1 (SEQ ID NO: 19) and H54-G4dv1 (SEQ ID NO: 20). In addition, C226S and C229S as modifications for deleting hinge disulfide bonds, and E356K and K439E as respective CH3 interface-controlling modifications were introduced to MRAH-G4dv1 and H54-G4dv1 to prepare MRAH-G4dv2P1 (SEQ ID NO: 21) and H54-G4dv2N1 (SEQ ID NO: 22). As for naturally occurring human IgG4 as well, C131S as modification for deleting disulfide bonds between H and L chains, C226S and C229S as modifications for deleting hinge disulfide bonds, and E356K and K439E as respective CH3 interface-controlling modifications were introduced to MRAH-wtG4d and H54-wtG4d to prepare MRAH-wtG4dv2P1 (SEQ ID NO: 46) and H54-wtG4dv2N1 (SEQ ID NO: 47). For the studies using human IgG1, C220S as modification for deleting disulfide bonds between H and L chains was introduced to MRAH-G1d and H54-G1d to prepare MRAH-G1dv1 (SEQ ID NO: 23) and H54-G1dv1 (SEQ ID NO: 24). In addition, C226S and C229S as modifications for deleting hinge disulfide bonds, K409R as CH3 interface-controlling modification, and E356K and K439E as respective CH3 interface-controlling modifications were introduced to MRAH-G1dv1 and H54-G1dv1 to prepare MRAH-G1dv2rP1 (SEQ ID NO: 25) and H54-G1dv2rN1 (SEQ ID NO: 26). As shown in FIG. 4, naturally occurring human IgG1 has longer hinge regions than those of naturally occurring human IgG4, and therefore has a long distance between the C termini of the L chains, which probably makes a disulfide bond difficult to form. Hence, amino acids at positions 220 to 225 (EU numbering) in the hinge regions of G1dv2rP1 and G1dv2rN1 were substituted by a naturally occurring human IgG4 sequence YGPP to prepare MRAH-G1dv3rP1 (SEQ ID NO: 27) and H54-G1dv3rN1 (SEQ ID NO: 28). The prepared variants are shown in Tables 1 and 2 below. MRAH-wtG4dP1/MRAL-k0, H54-wtG4dN1/L28-k0, MRAH-wtG4dv2P1/MRAL-k0, H54-wtG4dv2N1/L28-k0, MRAH-G4dv2P1/MRAL-k0, H54-G4dv2N1/L28-k0, MRAH-G1 drP1/MRAL-k0, H54-G1drN1/L28-k0, MRAH-G1dv2rP1/MRAL-k0, H54-G1dv2rN1/L28-k0, MRAH-G1dv3rP1/MRAL-k0, and H54-G1dv3rN1/L28-k0 were expressed and purified according to the method of Reference Example 1.

Reaction condition: in TBS (Takara Bio Inc., pH 7.4), [each mAb]=2 mg/ml, [2-MEA (Sigma-Aldrich Corp.)]=25 mM, 37° C., 90 min.

The two types of antibody variable regions MRAH/MRAL and H54/L28 used in this study differ largely in pI. Therefore, peaks corresponding to their respective homologous forms and the resulting bispecific antibodies can be easily separated by capillary electrophoresis isoelectric focusing (CE-IEF), and the reaction efficiency can be evaluated. FIGS. 5-1 and 5-2 show the results of evaluating the reaction products by CE-IEF. The reaction product wtG4dP1//N1 of MRAH-wtG4dP1/MRAL-k0 and H54-wtG4dN1/L28-k0 and the reaction product G4dv2P1//N1 of MRAH-G4dv2P1/MRAL-k0 and H54-G4dv2N1/L28-k0 had 94.3% and 96.2% rates, respectively, of bispecific antibody formation. By contrast, the reaction product G1drP1//N1 of MRAH-G1drP1/MRAL-k0 and H54-G1drN1/L28-k0, the reaction product G1dv2rP1//N1 of MRAH-G1dv2rP1/MRAL-k0 and H54-G1dv2rN1/L28-k0, and the reaction product G1dv3rP1//N1 of MRAH-G1dv3rP1/MRAL-k0 and H54-G1dv3rN1/L28-k0 had 94.4%, 87.7%, and 84.1% rates, respectively, of bispecific antibody formation. The reaction product wtG4dv2P1//N1 of MRAH-wtG4dv2P1/MRAL-k0 and H54-wtG4dv2N1/L28-k0 exhibited a decreased rate of recovery in CE-IEF (data not shown). These results demonstrated that the bispecific antibody can also be prepared with exceedingly high efficiency by a method which involves mixing two types of homologous forms having a disulfide bond between L chains in the presence of a reducing agent.

TABLE 1

| Antibody H chain gene name | SEQ ID NO | Modification introduced to MRAH-wtG4d | Antibody H chain gene name | SEQ ID NO | Modification introduced to H54-wtG4d |
|---|---|---|---|---|---|
| MRAH-G4d | 17 | S228P | H54-G4d | 18 | S228P |
| MRAH-G4dv1 | 19 | C131S/S228P | H54-G4dv1 | 20 | C131S/S228P |
| MRAH-G4dv2P1 | 21 | C131S/C226S/S228P/C229S/E356K | H54-G4dv2N1 | 22 | C131S/C226S/S228P/C229S/K439E |
| MRAH-wtG4dv2P1 | 46 | C131S/C226S/C229S/E356K | H54-wtG4dv2N1 | 47 | C131S/C226S/C229S/K439E |

TABLE 2

| Antibody H chain gene name | SEQ ID NO | Modification introduced to MRAH-G1d | Antibody H chain gene name | SEQ ID NO | Modification introduced to H54-G1d |
|---|---|---|---|---|---|
| MRAH-G1dv1 | 23 | C220S | H54-G1dv1 | 24 | C220S |
| MRAH-G1dv2rP1 | 25 | C220S/C226S/C229S/E356K/K409R | H54-G1dv2rN1 | 26 | C220S/C226S/C229S/K409R/K439E |
| MRAH-G1dv3rP1 | 27 | 220-229:YGPPSPPS/E356K/K409R | H54-G1dv3rN1 | 28 | 220-229:YGPPSPPS/K409R/K439E |

Next, two types of homologous forms thus obtained were mixed in the combinations given below under the reaction condition given below, and the reaction products were evaluated according to the methods of Reference Examples 2 and 4.
(1) MRAH-wtG4dP1/MRAL-k0 and H54-wtG4dN1/L28-k0
(2) MRAH-wtG4dv2P1/MRAL-k0 and H54-wtG4dv2N1/MRAL-k0
(3) MRAH-G4dv2P1/MRAL-k0 and H54-G4dv2N1/L28-k0
(4) MRAH-G1drP1/MRAL-k0 and H54-G1drN1/L28-k0
(5) MRAH-G1dv2rP1/MRAL-k0 and H54-G1dv2rN1/L28-k0
(6) MRAH-G1dv3rP1/MRAL-k0 and H54-G1dv3rN1/L28-k0

Next, the FAE reaction products and their parent homologous forms were evaluated by non-reducing polyacrylamide gel electrophoresis (SDS-PAGE). The results are shown in FIG. 6. MRAH-wtG4dP1/MRAL-k0, H54-wtG4dN1/L28-k0, MRAH-G1drP1/MRAL-k0, and H54-G1drN1/L28-k0 were migrated as homodimers of HL molecules because of the presence of the disulfide bonds between H and L chains and in hinges. By contrast, H chains, L chains, and L chain dimers formed by the association of L chains through a disulfide bond (L2 in the diagram) were observed for MRAH-G4dv2P1/MRAL-k0, H54-G4dv2N1/L28-k0, MRAH-G1 dv2rP1/MRAL-k0, H54-G1dv2rN1/L28-k0, MRAH-G1dv3rP1/MRAL-k0, and H54-G1dv3rN1/L28-k0 lacking the disulfide bonds between H and L chains. The FAE reaction products wtG4dP1//N1 and G1drP1//N1 were observed as HL molecule dimers formed by the association of two H chains and two L chains, suggesting that hinge disulfide bonds cleaved by a reducing agent are reformed during heterodimerization associated with FAE reaction. By contrast, in the FAE reaction products G4dv2P1//N1, G1dv2rP1//N1, and G1dv3rP1//N1, only H and L chain monomers were observed, and no L chain dimer was observed.

These results can be interpreted as follows. MRAH-G4dv2P1/MRAL-k0, H54-G4dv2N1/L28-k0, MRAH-G1dv2rP1/MRAL-k0, H54-G1dv2rN1/L28-k0, MRAH-G1dv3rP1/MRAL-k0, and H54-G1dv3rN1/L28-k0 form a disulfide bond between L chains by the deletion of disulfide bonds between H and L chains and in hinges. The disulfide bond between L chains is cleaved by mixing these antibodies in the presence of a reducing agent. The resulting HL molecules associate to form bispecific antibodies. However, a disulfide bond between L chains does not seem to be reformed in association with this heterodimerization.

[Example 4] Study on Reducing Agent for Forming Disulfide Bond Between L Chains

Reducing agents differ in reduction potential or reaction mode depending on their types. In a reaction using 2-MEA or DTT, it is believed that the reducing agent is added to a thiol group of a protein upon cleavage of a disulfide bond, and then eliminated by solvent replacement. This easiness of elimination may differ depending on the structure or the concentration of the reducing agent. As a matter of course, a disulfide bond cannot be reformed in a state where the reducing agent has not yet been eliminated. In Example 3, no disulfide bond was formed between the L chains of G4dv2P1//N1, G1dv2rP1//N1, or G1dv3rP1//N1. This may be partly because of the influence of the reducing condition. Accordingly, the reducing condition was studied using 2-MEA, DTT, and TCEP.

Two types of homologous forms were mixed in the combinations given below under the reaction condition given below, and the reaction products were evaluated according to the methods of Reference Examples 2 and 4.
(1) MRAH-G1drP1/MRAL-k0 and H54-G1drN1/L28-k0
(2) MRAH-G1dv2rP1/MRAL-k0 and H54-G1dv2rN1/L28-k0
(3) MRAH-G1dv3rP1/MRAL-k0 and H54-G1dv3rN1/L28-k0
(4) MRAH-G4dv2P1/MRAL-k0 and H54-G4dv2N1/L28-k0

Reaction condition: in TBS (Takara Bio Inc.), [each mAb]=0.45 mg/ml, [2-MEA]=25 mM or [DTT]=1 mM or [TCEP]=1 mM, 37° C., 90 min.

The reaction products were evaluated by ion-exchange chromatography. The results are shown in FIGS. 7-1 and 7-2. As a result of performing the reaction with 25 mM 2-MEA, G1drP1//N1, G1dv2rP1//N1, G1dv3rP1//N1, and G4dv2P1//N1 exhibited reaction efficiency of 97.9%, 79.0%, 80.4%, and 91.40%, respectively. As a result of performing the reaction with 1 mM DTT, G1drP1//N1, G1dv2rP1//N1, G1dv3rP1//N1, and G4dv2P1//N1 exhibited reaction efficiency of 93.3%, 76.6%, 71.8%, and 87.3%, respectively. As a result of performing the reaction with 1 mM TCEP, G1drP1//N1, G1dv2rP1//N1, G1dv3rP1//N1, and G4dv2P1//N1 exhibited reaction efficiency of 91.9%, 80.0%, 71.2%, and 81.5%, respectively. Next, the homologous forms used in the reaction and the reaction products were each evaluated by non-reducing SDS-PAGE. The results are shown in FIG. 8. The reaction with 1 mM DTT or 1 mM TCEP increased the rate of disulfide bond formation between L chains in all of G1dv2rP1//N1, G1dv3rP1//N1, and G4dv2P1//N1 (G1dv2r, G1dv3r, and G4dv2, respectively, in the diagram), as compared with the reaction condition involving 25 mM 2-MEA. These results suggested that use of DTT or TCEP allows FAE reaction to proceed with high efficiency and can form a disulfide between the C termini of the L chains of G1dv2rP1//N1, G1dv3rP1//N1, and G4dv2P1//N1.

[Example 5] Fab Arm Exchange in Naturally Occurring Human IgG4 Lacking Hinge Region Referring to the crystallographic structure of human IgG1 hinges shown in FIG. 4, the C termini of the L chains are distant from each other due to the hinge structure. In Example 3, no disulfide bond was formed between the L chains of the FAE reaction product G4dv2P1//N1. This may be due to this distance. Accordingly, study was conducted to test whether or not a disulfide bond can be formed between the L chains of an FAE reaction product by bringing the C termini of the L chains close to each other by the deletion of the hinge regions.

The YGPPCPPC sequence or the YGPPSPPS sequence at positions 219 to 229 (EU numbering) in MRAH-G4dv1/MRAL-k0 and H54-G4dv1/L28-k0, MRAH-G4dv2P1/MRAL-k0 and H54-G4dv2N1/L28-k0 were deleted to prepare MRAH-G4dv4/MRAL-k0 (SEQ ID NO: 29), H54-G4dv4/L28-k0 (SEQ ID NO: 30), MRAH-G4dv4P1/MRAL-k0 (SEQ ID NO: 31), and H54-G4dv4N1/L28-k0 (SEQ ID NO: 32). MRAH-G4dv4/MRAL-k0, H54-G4dv4/L28-k0, MRAH-G4dv4P1/MRAL-k0, and H54-G4dv4N1/L28-k0 were expressed and purified according to the method of Reference Example 1, and mixed under the reaction condition given below, and the reaction products were evaluated according to the methods of Reference Examples 3 and 4.

Reaction condition: in TBS (Sigma-Aldrich Corp., pH 7.4), [each mAb]=0.45 mg/ml, [2-MEA (Sigma-Aldrich Corp.)]=25 mM, 37° C., 90 min.

The reaction products were evaluated by ion-exchange chromatography. The results are shown in FIG. 9. G4dv4P1//N1 obtained by mixing MRAH-G4dv4P1/MRAL-k0 and H54-G4dv4N1/L28-k0 exhibited reaction efficiency of 95.4%. Next, the homologous forms used in the reaction and the reaction products were each evaluated by non-reducing SDS-PAGE. The results are shown in FIG. 10. The amount of L chain dimers was increased for MRAH-G4dv4P1/MRAL-k0 lacking hinge regions, as compared with MRAH-G4dv2P1/MRAL-k0. As for the specimens after the reaction, the rate of disulfide bond formation between L chains was increased in G4dv4P1//N1 as compared with G4dv2P1//N1. These results suggest that by bringing the C-terminal portions of L chains close to each other by the deletion of the hinge regions, a disulfide bond was successfully formed between the L chains of the FAE reaction products.

[Example 6] Fab Arm Exchange in Human IgG4 Lacking Hinge Region

The preceding Examples showed that after reduction of a disulfide bond between the L chains of MRAH-G4dv4P1/MRAL-k0 and H54-G4dv4N1/L28-k0 lacking hinge regions by use of DTT or TCEP, the different HL molecules associate to reform the disulfide bond between the L chains. WO2011/131746 discloses that FAE reaction is performed using one antibody molecule having 405L and another antibody molecule having 409R as two types of antibody molecules and can thereby take place efficiently. Since the hinge regions of these molecules are of normal naturally occurring IgG1, the formation of HL molecules in the process of FAE reaction requires reducing two disulfide bonds. On the other hand, FAE reaction using MRAH-G4dv4P1/MRAL-k0 and H54-G4dv4N1/L28-k0 described above seemed to be able to proceed under a milder reducing condition, because the disulfide bond that needs to be reduced for HL molecule formation is one disulfide bond between L chains. Accordingly, the antibody molecules disclosed in WO2011/131746 were compared with MRAH-G4dv4P1/MRAL-k0 and H54-G4dv4N1/L28-k0 as to FAE reaction efficiency under a milder reducing condition.

Here, the existing Fab arm exchange technology was used as a control for comparison. Specifically, K409R was added to MRAH-G1d/MRAL-k0 to prepare MRAH-G1dr/MRAL-k0 (SEQ ID NO: 33). F405L was added to H54-G1d/L28-k0 to prepare H54-G1d1/MRAL-k0 (SEQ ID NO: 34). MRAH-G1dr/MRAL-k0, H54-G1d1/L28-k0, MRAH-G4dv4P1/MRAL-k0, and H54-G4dv4N1/L28-k0 were expressed and purified according to the method of Reference Example 1.

Two types of homologous forms were mixed in the combinations given below under the reaction condition given below, and the reaction products were evaluated according to the method of Reference Example 3.

because only one disulfide bond needs to be reduced and is fewer compared to when reducing normal hinge regions. This disulfide bond formation site is not limited to hinge regions and may be any region of an antibody. Accordingly, FAE reaction in a molecule with one disulfide bond formed between CH3 regions was subsequently studied.

C226S and C229S for deleting hinge region disulfide bonds were added to MRAH-G4d and H54-G4d/L28-k0, and CH3 interface-controlling charge modification and modification for forming an inter-CH3 disulfide bond were further added thereto to prepare MRAH-G4dNX010P (SEQ ID NO: 35), MRAH-G4dNX010N (SEQ ID NO: 36), MRAH-G4dNX011P (SEQ ID NO: 37), MRAH-G4dNX011N (SEQ ID NO: 38), MRAH-G4dNX012P (SEQ ID NO: 39), MRAH-G4dNX012N (SEQ ID NO: 40), MRAH-G4dNX013N (SEQ ID NO: 41), MRAH-G4dNX014P (SEQ ID NO: 42), MRAH-G4dNX014N (SEQ ID NO: 43), MRAH-G4dNX015P (SEQ ID NO: 44), and MRAH-G4dNX015N (SEQ ID NO: 45). The added modifications are shown in Table 3 below.

MRAH-G4dNX010P/MRAL-k0, H54-G4dNX010N/L28-k0, MRAH-G4dNX011P/MRAL-k0, H54-G4dNX011N/L28-k0, MRAH-G4dNX012P/MRAL-k0, H54-G4dNX012N/L28-k0, H54-G4dNX013N/L28-k0, MRAH-G4dNX014P/MRAL-k0, H54-G4dNX014N/L28-k0, MRAH-G4dNX015P/MRAL-k0, and H54-G4dNX015N/L28-k0 were expressed and purified according to the method of Reference Example 1.

TABLE 3

| Antibody H chain gene name | SEQ ID NO | Modification introduced to MRAH-G4d | Antibody H chain gene name | SEQ ID NO | Modification introduced to H54-G4d |
|---|---|---|---|---|---|
| MRAH-G4dNX010P | 35 | C226S/C229S/Y349C/E356K | H54-G4dNX010N | 36 | C226S/C229S/E356C/K439E |
| MRAH-G4dNX011P | 37 | C226S/C229S/Y349C/E356K/V397Y | H54-G4dNX011N | 38 | C226S/C229S/E356C/V397Y/K439E |
| MRAH-G4dNX012P | 39 | C226S/C229S/E356K/T394C | H54-G4dNX012N | 40 | C226S/C229S/T394C/K439E |
| MRAH-G4dNX014P | 42 | C226S/C229S/L351C/E356K | H54-G4dNX013N | 41 | C226S/C229S/S354C/K439E |
| MRAH-G4dNX015P | 44 | C226S/C229S/E356K/Y407C | H54-G4dNX014N | 43 | C226S/C229S/L351C/K439E |
|  |  |  | H54-G4dNX015N | 45 | C226S/C229S/Y407C/K439E |

(1) MRAH-G1dr/MRAL-k0 and H54-G1d1/L28-k0
(2) MRAH-G4dv4P1/MRAL-k0 and H54-G4dv4N1/L28-k0 Reaction condition: in TBS (Takara Bio Inc.), [each mAb]=0.45 mg/ml, [GSH]=5 mM or 0.5 mM, 37° C., 90 min.

The reaction products were evaluated by ion-exchange chromatography. The results are shown in FIG. 11. G1dr/d1 obtained by mixing MRAH-G1dr/MRAL-k0 and H54-G1d1/L28-k0 with 5 mM or 0.5 mM GSH exhibited reaction efficiency of 8.5% and 0.4%. By contrast, G4dv4P1//N1 obtained by mixing MRAH-G4dv4P1/MRAL-k0 and H54-G4dv4N1/L28-k0 with 5 mM or 0.5 mM GSH exhibited reaction efficiency of 94.5% and 65.6%. These results demonstrated that FAE reaction is performed by the reduction of a disulfide bond between L chains and can thereby proceed with high efficiency even under a milder reducing condition.

[Example 7] Fab Arm Exchange in Naturally Occurring Human IgG4 with Disulfide Bond Formed Between CH3 Regions As shown in Example 6, FAE reaction to form HL molecules by the reduction of a disulfide bond between L chains can proceed with high efficiency under a milder reducing condition, as compared with FAE reaction to form HL molecules by the reduction of the hinge region disulfide bonds of naturally occurring IgG1. This is believed to be Two types of homologous forms were mixed in the combinations given below under the reaction condition given below, and the reaction products were evaluated according to the methods of Reference Examples 4 and 5.
(1) MRAH-G4dNX010P/MRAL-k0 and H54-G4dNX010N/L28-k0
(2) MRAH-G4dNX011P/MRAL-k0 and H54-G4dNX011N/L28-k0
(3) MRAH-G4dNX012P/MRAL-k0 and H54-G4dNX012N/L28-k0
(4) MRAH-G4dNX010P/MRAL-k0 and H54-G4dNX013N/L28-k0
(5) MRAH-G4dNX014P/MRAL-k0 and H54-G4dNX014N/L28-k0
(6) MRAH-G4dNX015P/MRAL-k0 and H54-G4dNX015N/L28-k0

Reaction condition: in TBS (Sigma-Aldrich Corp., pH 7.4), [each mAb]=0.2 mg/ml or 0.225 mg/mL, [2-MEA (Sigma-Aldrich Corp.)]=25 mM, 37° C., 90 min.

The reaction products were evaluated by IEF. The results are shown in FIGS. 12-1 and 12-2. In the reaction product G4dNX010P//010N of MRAH-G4dNX010P/MRAL-k0 and H54-G4dNX010N/L28-k0, the reaction product G4dNX011P//011N of MRAH-G4dNX011P/MRAL-k0 and H54-G4dNX011N/L28-k0, the reaction product G4dNX010P//013N of G4dNX010P/MRAL-k0 and H54-

G4dNX013N/L28-k0, and the reaction product G4dNX014P//014N of MRAH-G4dNX014P/MRAL-k0 and H54-G4dNX014N/L28-k0, the pI of the reaction products were intermediate to that of each of the homologous forms, suggesting that the FAE reaction proceeded to form bispecific antibodies (biAb in the diagram).

The reaction products and their homologous forms were evaluated by non-reducing SDS-PAGE. The results are shown in FIGS. 13-1 and 13-2. In the FAE reaction products G4dNX010P//010N, G4dNX011P//011N, G4dNX010P//013N, and G4dNX014P//014N, the reacted antibody molecules formed HL molecule dimers (H2L2 in the diagram), suggesting that an inter-CH3 disulfide bond was reformed. In the homologous forms MRAH-G4dNX014P/MRAL-k0 and H54-G4dNX014N/L28-k0 of these molecules, the antibody molecules formed HL molecule dimers (H2L2 in the diagram). Thus, it was considered that an inter-CH3 disulfide bond was formed. However, MRAH-G4dNX010P/MRAL-k0, H54-G4dNX010N/L28-k0, MRAH-G4dNX011P/MRAL-k0, H54-G4dNX011N/L28-k0, and H54-G4dNX013N/L28-k0 were composed mainly of HL molecules. Thus, no inter-CH3 disulfide bond was believed to be formed.

These results can be interpreted as follows. MRAH-G4dNX014P/MRAL-k0 and H54-G4dNX014N/L28-k0 having formed the inter-CH3 disulfide bond became HL molecules by the reduction of the inter-CH3 disulfide bond by a reducing agent, and an inter-CH3 disulfide bond is believed to be reformed when these HL molecules associated. In MRAH-G4dNX010P/MRAL-k0 and H54-G4dNX010N/L28-k0, MRAH-G4dNX011P/MRAL-k0 and H54-G4dNX011N/L28-k0, or MRAH-G4dNX010P/MRAL-k0 and MRAH-G4dNX013N/MRAL-k0, which formed no inter-CH3 disulfide bond in a homologous form, the distance between the Y349C modifications or the E356C modifications added to each homologous form, or the distance between Y349C and S354C were too large to form a disulfide bond. By contrast, in the bispecific antibodies formed after association of HL molecules, it is believed that the distance between Y349C and E356C or the distance between Y349C and S354C was short enough to be able to form a disulfide bond. These results demonstrated that FAE reaction can also proceed by mixing two types of antibodies having an inter-CH3 disulfide bond in the presence of a reducing agent.

[Reference Example 1] Preparation of Antibody Expression Vector and Expression and Purification of Antibody The full-length genes having nucleotide sequences encoding the H chain and the L chain of each antibody were synthesized using assembly PCR or the like and prepared by a method generally known to those skilled in the art. Amino acid substitution was introduced by a method generally known to those skilled in the art using PCR or the like. The obtained plasmid fragments were inserted to expression vectors for animal cells to prepare H chain expression vectors and L chain expression vectors. The nucleotide sequences of the obtained expression vectors were determined by a method generally known to those skilled in the art. The prepared plasmids were transiently transfected to a human embryonic kidney cancer cell-derived HEK293H line (Invitrogen Corp.) or FreeStyle 293 cells (Invitrogen Corp.) for antibody expression. The obtained culture supernatant was recovered and then passed through a 0.22 μm filter MILLEX(R)-GV (Millipore Corp.) or a 0.45 μm filter MILLEX(R)-GV (Millipore Corp.) to obtain a culture supernatant. The antibody was purified from the obtained culture supernatant by a method generally known to those skilled in the art using rProtein A Sepharose Fast Flow (GE Healthcare Japan Corp.) or Protein G Sepharose 4 Fast Flow (GE Healthcare Japan Corp.). As for the concentration of the purified antibody, the absorbance was measured at 280 nm using a spectrophotometer, and the antibody concentration was calculated by use of an extinction coefficient calculated from the obtained value by a method such as PACE (Protein Science 1995; 4: 2411-2423).

[Reference Example 2] CE-IEF

The CE-IEF measurement was carried out by a method generally known to those skilled in the art using PA800 Plus (Beckman Coulter Inc.). Pharmalyte having a broad range of 5 to 8 and Pharmalyte having a broad range of 8 to 10.5 were mixed in equal amounts and analyzed in a pI range of 5 to 10.5. The analysis was conducted using a 4 mg/mL antibody solution, and the results were analyzed using 32 karat software (Beckman Coulter Inc.). A value determined by dividing the area value of the bispecific antibody by the area value of all antibodies present in the system, followed by multiplication by 100 was used as the rate of bispecific antibody formation (%).

[Reference Example 3] Evaluation of Rate of Bispecific Antibody Formation by Ion-Exchange Chromatography The separation of each specimen was evaluated by the ion-exchange chromatography purification method using Prominence UFLC (Shimadzu Corp.). The bispecific antibody was separated by the two-solution mixed gradient method using a 25 mM MES buffer solution (pH 5.0) and a 25 mM MES buffer solution (pH 5.0) containing 500 mM sodium chloride as mobile phases and ProPac WCX-10 (Thermo Fisher Scientific K.K.) as a column. The data was obtained at a wavelength of 215 nm. The elution results were evaluated using Empower 2 (Waters Corp.).

A value determined by dividing the area value of the bispecific antibody by the area value of all antibodies present in the system, followed by multiplication by 100 was used as the rate of bispecific antibody formation (%). If one of the homologous forms had a poor rate of recovery, the area value of the other homologous form was doubled and summed with the area value of the bispecific antibody, and the resulting value was used as the area value of all antibodies for the calculation.

[Reference Example 4] Non-Reducing SDS-PAGE

Each disulfide bond was evaluated by SDS polyacrylamide gel electrophoresis using Mini-PROTEAN Tetra system (Bio-Rad Laboratories, Inc.). The power supply used was Power Pac 3000 (Bio-Rad Laboratories, Inc.) or POWER SUPPLY KS-7510 (Marysol Sangyo Co., Ltd.), and the electrophoresis gel used was Mini-PROTEAN TGX Gel (4 to 20%, Bio-Rad Laboratories, Inc.). An antibody-containing solution was diluted with Tris-Glycine SDS Sample Buffer (2×, TEFCO) and then heat-treated at 95° C. for 2 minutes, and this sample was electrophoresed. The gel after the electrophoresis was stained using CBB Stain One (Nacalai Tesque, Inc.). The gel thus stained was visualized using Typhoon FLA 9500 (GE Healthcare Japan Corp.).

[Reference Example 5] IEF

Each FAE reaction product was evaluated by isoelectric focusing using Phastsystem (GE Healthcare Japan Corp.). PhastGel Dry IEF (GE Healthcare Japan Corp.) was swollen with an ampholyte solution containing Pharmalyte 5-8 (GE Healthcare Japan Corp.) and Pharmalyte 8-10.5 (GE Healthcare Japan Corp.) mixed in equal amounts, according to the protocol of the manufacturer. Then, the sample was electrophoresed. The gel after the electrophoresis was stained with silver using PlusOne Silver Staining Kit, Protein (GE Healthcare Japan Corp.). The gel thus stained was dried and then visualized using a scanner.

[Reference Example 6] Measurement of Tm

The Tm of CH3 domains was measured by a method generally known to those skilled in the art using Rotor-gene Q (Qiagen N.V.). A sample containing a mixture of each antibody at a concentration of 0.1 mg/mL and SYPRO orange at a concentration of 10× concentrate was heated from 30° C. to 99° C. The fluorescence intensity (excitation wavelength: 470 nm, fluorescence wavelength: 555 nm) was measured in every 0.4° C. This measurement was conducted in PBS (Sigma-Aldrich Corp., pH 7.4). The analysis was conducted using Rotor-gene Q series software. The point of inflection determined by the primary differential of the fluorescence intensity was defined as Tm. The Tm of the CH3 domains was calculated through the use of Tm of MRAH CH2 around 70° C., Tm of MRAH Fab around 95° C., Tm of H54 CH2 around 70° C., and Tm of H54 Fab around 90° C.

INDUSTRIAL APPLICABILITY

Bispecific antibodies can be prepared under a reducing condition with higher efficiency by use of the method of the present invention than that by conventional techniques.

---

The invention claimed is:

1. A method for producing a heteromultimer, the method comprising:
   (a) providing a first molecule comprising two copies of a first antibody heavy chain and two copies of a first antibody light chain,
   wherein the first antibody heavy chain comprises a heavy chain constant region of human IgG1 type that has no core hinge region Cys residues and does not have a Cys at position 220 (EU numbering),
   wherein the first antibody light chain comprises a light chain constant region comprising one or more Cys residues, including a Cys at position 214 (EU numbering),
   wherein the first molecule has a first antigen-binding activity, and
   wherein the two copies of the first antibody light chain are linked to each other by a Cys-Cys disulfide bond linking their respective positions 214 (EU numbering);
   (b) providing a second molecule comprising two copies of a second antibody heavy chain different from the first antibody heavy chain and two copies of a second antibody light chain different from the first antibody light chain,
   wherein the second antibody heavy chain comprises a heavy chain constant region of human IgG1 type that has no core hinge region Cys residues and does not have a Cys at position 220 (EU numbering),
   wherein the second antibody light chain comprises a light chain constant region comprising one or more Cys residues including a Cys at position 214 (EU numbering),
   wherein the second molecule has a second antigen-binding activity different from the first antigen-binding activity, and
   wherein the two copies of the second antibody light chain are linked to each other by a Cys-Cys disulfide bond linking their respective positions 214 (EU numbering);
   (c) incubating the first and second molecules together under a reducing condition that allows Cys-Cys disulfide bonds in the first molecule and second molecule to isomerize; and (d) obtaining a heteromultimer comprising a first arm comprising the first antibody heavy and light chains associated together and a second arm comprising the second antibody heavy and light chains associated together, wherein the only covalent bond linking the first and second arms together is a Cys-Cys disulfide bond linking position 214 (EU numbering) of the first antibody light chain and position 214 (EU numbering) of the second antibody light chain.

2. The method of claim 1, wherein the first and second antibody heavy chains both meet the criteria of one of the following (1) to (3) (all position numbers according to EU numbering):

(1) an amino acid residue other than Cys at position 220, an amino acid residue other than Cys at position 226, and an amino acid residue other than Cys at position 229; or (2) a deletion of all of positions 219 to 229; or (3) the sequence Tyr-Gly-Pro-Pro at positions 220 to 225, an amino acid residue other than Cys at position 226, and an amino acid residue other than Cys at position 229.

3. The method of claim 1, wherein the heavy chain constant regions of the first and second antibody heavy chains each comprise a CH3 region, and one or more of (A) to (F) is true:

(A) amino acid residues at positions 356 and 439 (EU numbering) in the CH3 region of the first antibody heavy chain have the same type of charge (+ or −), (B) amino acid residues at positions 357 and 370 (EU numbering) in the CH3 region of the first antibody heavy chain have the same type of charge (+ or −), (C) amino acid residues at positions 399 and 409 (EU numbering) in the CH3 region of the first antibody heavy chain have the same type of charge (+ or −), (D) amino acid residues at positions 356 and 439 (EU numbering) in the CH3 region of the second antibody heavy chain have the same type of charge (+ or −), (E) amino acid residues at positions 357 and 370 (EU numbering) in the CH3 region of the second antibody heavy chain have the same type of charge (+ or −), (F) amino acid residues at positions 399 and 409 (EU numbering) in the CH3 region of the second antibody heavy chain have the same type of charge (+ or −), provided that,
when both (A) and (D) are true, the type of charge in (A) is the opposite of the type of charge in (D), and
when both (B) and (E) are true, the type of charge in (B) is the opposite of the type of charge in (E), and
when both (C) and (F) are true, the type of charge in (C) is the opposite of the type of charge in (F).

4. The method of claim 3, wherein the amino acid residues at positions 356, 399, 409, and 439 (EU numbering) of the first antibody heavy chain are all positively charged, and the amino acid residues at positions 356, 399, 409, and 439 (EU numbering) of the second antibody heavy chain are all negatively charged.

5. The method of claim 1, wherein the first molecule has no disulfide bonds between the first antibody heavy chains and the second molecule has no disulfide bonds between the second antibody heavy chains.

6. The method of claim 1, wherein the heteromultimer is a bispecific antibody.

7. A method for producing a heteromultimer, the method comprising:

(a) providing a first molecule comprising two copies of a first antibody heavy chain and two copies of a first antibody light chain, wherein the first antibody heavy chain comprises a heavy chain constant region of human IgG4 type that has no core hinge region Cys residues and does not have a Cys at position 131 (EU numbering), wherein the first antibody light chain comprises a light chain constant region comprising one or more Cys residues, including a Cys at position 214 (EU numbering), wherein the first molecule has a first antigen-binding activity, and wherein the two copies of the first antibody light chain are linked to each other by a Cys-Cys disulfide bond linking their respective positions 214 (EU numbering);

(b) providing a second molecule comprising two copies of a second antibody heavy chain different from the first antibody heavy chain and two copies of a second antibody light chain different from the first antibody light chain, wherein the second antibody heavy chain comprises a heavy chain constant region of human IgG4 type that has no core hinge region Cys residues and does not have a Cys at position 131 (EU numbering), wherein the second antibody light chain comprises a light chain constant region comprising one or more Cys residues including a Cys at positions 214 (EU numbering), wherein the second molecule has a second antigen-binding activity different from the first antigen-binding activity, and wherein the two copies of the second antibody light chain are linked to each other by a Cys-Cys disulfide bond linking their respective positions 214 (EU numbering);

(c) incubating the first and second molecules together under a reducing condition that allows Cys-Cys disulfide bonds in the first molecule and second molecule to isomerize; and (d) obtaining a heteromultimer comprising a first arm comprising the first antibody heavy and light chains associated together and a second arm comprising the second antibody heavy and light chains associated together, wherein the only covalent bond linking the first and second arms together is a Cys-Cys disulfide bond linking position 214 (EU numbering) of the first antibody light chain and position 214 (EU numbering) of the second antibody light chain.

8. The method of claim 7, wherein the first and second antibody heavy chains both meet the criteria of one of the following (1) to (3) (all position numbers according to EU numbering):

(1) an amino acid residue other than Cys at position 131, an amino acid residue other than Cys at position 226, and an amino acid residue other than Cys at position 229; or (2) an amino acid residue other than Cys at position 131, an amino acid residue other than Cys at position 226, a Pro at position 228, and an amino acid residue other than Cys at position 229; or (3) a deletion of all of positions 219 to 229, and an amino acid residue other than Cys at position 131.

9. The method of claim 7, wherein the heavy chain constant regions of the first and second antibody heavy chains each comprise a CH3 region, and one or more of (A) to (F) is true:

(A) amino acid residues at positions 356 and 439 (EU numbering) in the CH3 region of the first antibody heavy chain have the same type of charge (+ or −),
(B) amino acid residues at positions 357 and 370 (EU numbering) in the CH3 region of the first antibody heavy chain have the same type of charge (+ or −),
(C) amino acid residues at positions 399 and 409 (EU numbering) in the CH3 region of the first antibody heavy chain have the same type of charge (+ or −),
(D) amino acid residues at positions 356 and 439 (EU numbering) in the CH3 region of the second antibody heavy chain have the same type of charge (+ or −),
(E) amino acid residues at positions 357 and 370 (EU numbering) in the CH3 region of the second antibody heavy chain have the same type of charge (+ or −),
(F) amino acid residues at positions 399 and 409 (EU numbering) in the CH3 region of the second antibody heavy chain have the same type of charge (+ or −),
provided that,
when both (A) and (D) are true, the type of charge in (A) is the opposite of the type of charge in (D), and
when both (B) and (E) are true, the type of charge in (B) is the opposite of the type of charge in (E), and
when both (C) and (F) are true, the type of charge in (C) is the opposite of the type of charge in (F).

10. The method of claim 9, wherein the amino acid residues at positions 356, 399, 409, and 439 (EU numbering) of the first antibody heavy chain are all positively charged, and the amino acid residues at positions 356, 399, 409, and 439 (EU numbering) of the second antibody heavy chain are all negatively charged.

11. The method of claim 7, wherein the first molecule has no disulfide bonds between the first antibody heavy chains and the second molecule has no disulfide bonds between the second antibody heavy chains.

12. The method of claim 7, wherein the heteromultimer is a bispecific antibody.

13. The method of claim 7, wherein step (c) comprises contacting the first and second molecules with a substance selected from the group consisting of glutathione, L-cysteine, dithiothreitol (DTT), β-mercapto-ethanol, tris(2-carboxyethyl)phosphine (TCEP), and 2-mercaptoethylamine (2-MEA).

14. The method of claim 1, wherein step (c) comprises contacting the first and second molecules with a substance selected from the group consisting of glutathione, L-cysteine, dithiothreitol (DTT), β-mercapto-ethanol, tris(2-carboxyethyl)phosphine (TCEP), and 2-mercaptoethylamine (2-MEA).

* * * * *